US010316021B2

(12) United States Patent
Kablaoui et al.

(10) Patent No.: US 10,316,021 B2
(45) Date of Patent: Jun. 11, 2019

(54) HETEROARYLPHENOXY BENZAMIDE KAPPA OPIOID LIGANDS

(71) Applicant: Pfizer Inc., New York, NY (US)

(72) Inventors: Natasha Mariam Kablaoui, Newton, MA (US); Michael Eric Green, Boston, MA (US); Justin Ian Montgomery, Ledyard, CT (US); Michael Aaron Brodney, Newton, MA (US); Patrick Robert Verhoest, Newton, MA (US); Gregory Wayne Kauffman, East Greenwich, RI (US); Danica Antonia Rankic, New London, CT (US); Scot Richard Mente, Arlington, MA (US); Bruce Nelsen Rogers, Belmont, MA (US); Kapildev Kashmirilal Arora, Niantic, CT (US); Matthew Francis Dunn, Middletown, CT (US)

(73) Assignee: Pfizer Inc., New York, NY (US)

( * ) Notice: Subject to any disclaimer, the term of this patent is extended or adjusted under 35 U.S.C. 154(b) by 50 days.

(21) Appl. No.: 15/820,679

(22) Filed: Nov. 22, 2017

(65) Prior Publication Data

US 2018/0148432 A1    May 31, 2018

Related U.S. Application Data

(60) Provisional application No. 62/585,016, filed on Nov. 13, 2017, provisional application No. 62/576,435, filed on Oct. 24, 2017, provisional application No. 62/426,980, filed on Nov. 28, 2016.

(51) Int. Cl.
*C07D 403/04* (2006.01)
*C07D 231/20* (2006.01)
*C07D 413/04* (2006.01)
*C07D 417/04* (2006.01)
*A61P 25/00* (2006.01)

(52) U.S. Cl.
CPC ............ *C07D 403/04* (2013.01); *A61P 25/00* (2018.01); *C07D 231/20* (2013.01); *C07D 413/04* (2013.01); *C07D 417/04* (2013.01); *C07B 2200/13* (2013.01)

(58) Field of Classification Search
CPC .. C07D 403/04; C07D 231/20; C07D 413/04; C07D 417/04
See application file for complete search history.

(56) References Cited

U.S. PATENT DOCUMENTS

| | | | |
|---|---|---|---|
| 6,953,789 B2 | 10/2005 | Yamashita et al. | |
| 6,969,724 B2 | 11/2005 | Barlocco et al. | |
| 7,365,209 B2 | 4/2008 | Letourneau et al. | |
| 7,381,719 B2 | 6/2008 | Blanco-Pillado et al. | |
| 7,396,943 B2 | 7/2008 | Benesh et al. | |
| 7,560,463 B2 | 7/2009 | Mitch et al. | |
| 7,709,552 B2 | 5/2010 | Buezo et al. | |
| 7,910,741 B2 | 3/2011 | Nishizawa et al. | |
| 8,003,642 B2 | 8/2011 | Kusuda et al. | |
| 8,048,895 B2 | 11/2011 | Carroll | |
| 8,063,059 B2 | 11/2011 | Hermann | |
| 8,173,695 B2 | 5/2012 | Buezo et al. | |
| 8,188,277 B2 | 5/2012 | Fukushima et al. | |
| 8,242,145 B2 | 8/2012 | Hutchinson et al. | |
| 8,450,335 B2 | 5/2013 | Singh et al. | |
| 8,609,696 B2 | 12/2013 | Cogan et al. | |

(Continued)

FOREIGN PATENT DOCUMENTS

| | | |
|---|---|---|
| CR | 11559 | 10/2010 |
| EP | 1132379 | 9/2001 |
| HN | 2010001319 | 1/2013 |

(Continued)

OTHER PUBLICATIONS

Bruchas, M.R., et al., "The Dynorphin-Kappa Opioid System as a Modulator of Stress-induced and Pro-addictive Behaviors", Brain Research, Feb. 16, 2010, pp. 44-55, vol. 1314.

(Continued)

*Primary Examiner* — Rebecca L Anderson
(74) *Attorney, Agent, or Firm* — Haley Guiliano LLP; James F. Haley, Jr.

(57) ABSTRACT

The present invention provides compounds of Formula I:

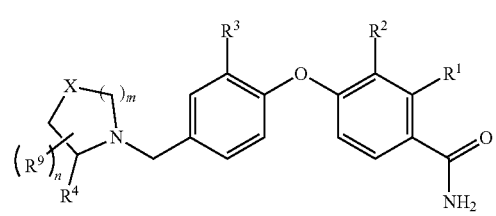

and pharmaceutically acceptable salts thereof wherein the variables $R^1$, $R^2$, $R^3$, $R^4$, $R^9$, X, m and n are as defined herein; processes for the preparation of; intermediates used in the preparation of; and compositions containing such compounds or salts, and their uses for treating kappa opioid (κ-opioid) associated disorders including, e.g., a neurological disorder, or psychiatric disorder such as a neurocognitive disorder, substance abuse disorder, depressive disorder, anxiety disorder, trauma and stressor related disorder and feeding and eating disorder.

25 Claims, 4 Drawing Sheets

(2 of 4 Drawing Sheet(s) Filed in Color)

(56) References Cited

U.S. PATENT DOCUMENTS

2009/0186873 A1    7/2009    Buezo et al.
2015/0274657 A1    10/2015    Montagne et al.

FOREIGN PATENT DOCUMENTS

| WO | 2009094260 | 7/2009 |
| WO | 2013059648 | 4/2013 |
| WO | 2015109080 | 7/2015 |
| WO | 2016086149 | 6/2016 |

OTHER PUBLICATIONS

Butelman, Eduardo, R., et al., "k-opioid receptor/dynorphin system: genetic and pharmacotherapeutic implications for addictions", Trends in Neurosciences, Oct. 2012, pp. 587-596, 35(10).

Carroll, F. Ivy, et al., "The Development of k Opioid Receptor Antagonists", Journal of Medicinal Chemistry, Mar. 28, 2013, pp. 2178-2195, 56(6).

Carroll, F. Ivy, et al., "The Discovery and Development of the N-Substituted trans-3,4-Dimethyl-4-(3'-hydroxyphenyl)piperidine Class of Pure Opioid Receptor Antagonists", ChemMedChem, 2014, pp. 1638-1654, vol. 9.

Chavkin, Charles, "The Therapeutic Potential of k-Opioids for Treatment of Pain and Addiction", Neuropsychopharmacology Reviews, Jan. 2011, pp. 369-370, 36(1).

Cueva, Juan Pablo, et al., "C7β-Methyl Analogues of the Orvinols: The Discovery of Kappa Opioid Antagonists with Nociceptin/Orphanin FQ Peptide (NOP) Receptor Partial Agonism and Low, or Zero, Efficacy at Mu Opioid Receptors", Journal of Medicinal Chemistry, May 28, 2015, pp. 4242-4249, 58(10).

Kissler, Jessica L., et al., "The One-Two Punch of Alcoholism: Role of Central Amygdala Dynorphins/Kappa-Opioid Receptors", Biological Psychiatry, May 15, 2014, pp. 774-782, 75(10).

Lalanne, Laurence, et al., "The kappa opioid receptor: from addiction to depression, and back", Frontiers in Psychiatry, Dec. 8, 2014, pp. 1-17, vol. 5, article 170.

Lowe, Stephen L., et al., "Safety, Tolerability, and Pharmacokinetic Evaluation of Single- and Multiple-Ascending Doses of a Novel Kappa Opioid Receptor Antagonist LY2456302 and Drug Interaction With Ethanol in Healthy Subjects", Journal of Clinical Pharmacology, 2014, pp. 968-978, 54(9).

Lutz, Pierre-Eric, et al., "Opioid receptors: distinct roles in mood disorders", Trends in Neurosciences, Mar. 2013, pp. 195-206, 36(3).

Mitch, Charles H., et al., "Discovery of Aminobenzyloxyarylamides as k Opioid Receptor Selective Antagonists: Application to Preclinical Development of a k Opioid Receptor Antagonist Receptor Occupancy Tracer", Journal of Medicinal Chemistry, Dec. 8, 2011, pp. 8000-8012, 54(23).

Munro, Thomas A., et al., "Selective Opioid Antagonists nor-BNI, GNTI and JDTic Have Low Affinities for Non-Opioid Receptors and Transporters", PLOS One, Aug. 2013, pp. 1-9, 8(8).

Nutt, David J., "The role of the opioid system in alcohol depenence", Journal of Psychopharmacology, 2014, pp. 8-22, 28(1).

Rorick-Kehn, Linda M., et al., "Determining Pharmacological Selectivity of the Kappa Opioid Receptor Antagonist LY2456302 Using Pupillometry as a Translational Biomarker in Rat and Human" International Journal of Neuropsychopharmacology, Feb. 2015, pp. 1-11, 18(2).

Rorick-Kehn, Linda M., et al., "LY2456302 is a novel, potent, orally-bioavailable small molecule kappa-selective antagonist with activity in animal models predictive of efficacy in mood and addictive disorders", Neuropharmacology, 2014, pp. 131-144, vol. 77.

Urbano, Mariangela, et al., "Antagonists of the kappa opioid receptor", Bioorganic & Medicinal Chemistry Letters, 2014, pp. 2021-2032, vol. 24.

Van't Veer, Ashlee, et al., "Ablation of Kappa-Opioid Receptors from Brain Dopamine Neurons has Anxiolytic-Like Effects and Enhances Cocaine-Induced Plasticity", Neuropsychopharmacology, 2013, pp. 1585-1597, 38(8).

Wu, Huixian, et al., "Structure of the human kappa opioid receptor in complex with JDTic", Nature, May 17, 2012, pp. 327-332, 485(7398).

Zheng, Ming-Qiang, et al., "Synthesis and Evaluation of 11C-LY2795050 as a k-Opioid Receptor Antagonist Radiotracer for PET Imaging", Journal of Nuclear Medicine, Jan. 25, 2013, pp. 455-463, vol. 54.

Kim, Su Jin, et al., "Determination of the in vivo selectivity of a new kappa-opioid receptor antagonist PET tracer 11C-LY2795050 in the rhesus monkey", Journal of Nuclear Medicine, 2013, pp. 1668-1674, 54(9).

Lee, Hong, et al., "Virtually Instantaneous, Room-Temperature [11C]-Cyanation Using Biaryl Phosphine Pd(0) Complexes" Journal of the American Chemical Society, 2015, pp. 648-651, 137(2).

Naganawa, Mika, et al., "Kinetic modeling of 11C-LY2795050, a novel antagonist radiotracer for PET imaging of the kappa opioid receptor in humans", Journal of Cerebral Blood Flow & Metabolism, 2014, pp. 1818-1825, 34(11).

Naganawa, Mika, et al., "Test-retest reproducibility of binding parameters in humans with 11C-LY2795050, an antagonist PET radiotracer fro the k opioid receptor", Journal of Nuclear Medicine, 2015, pp. 243-248, 56(2).

Zheng, Ming-Qiang, et al., "An improved antagonist radiotracer for the K-opioid receptor: synthesis and characterization of 11C-LY2459989", Journal of Nuclear Medicine, 2014, pp. 1185-1191, 55(7).

International Patent Application No. PCT/IB2017/057418, filed Nov. 27, 2017; International Search Report and Written Opinion dated Mar. 21, 2018, 12 pages.

| Compound | KOR Ki | MOR Ki | Selectivity over MOR | % RO for 50% PR reversal | HLM | >25% inhibition @3 µM |
|---|---|---|---|---|---|---|
| 11 | 1.2 | 51 | 42 | 30 | 20 | no |
| 8 | 2.6 | 99 | 37 | 25 | 12 | no |
| 12 | 1.5 | 42 | 31 | 30 | 8 | no |
| Comparator A | 3.1 | 0.01 | 0.03 | NT | 20 | no |
| Comparator B | 12 | 118 | 9.8 | NT | 89 | no |
| Comparator C | 1.2 | 21 | 17 | NT | 320 | yes |
| Comparator D | 5.8 | 163 | 28 | NT | 45 | yes |
| Comparator E | 0.2 | 7.8 | 39 | 70 | 30 | yes |
| Comparator F | 0.9 | 45 | 50 | NT | 36 | no |

FIG. 7

| Compound | SPTDI | THLE | HepG2 72hr | RST inhibitor | cLogP | SFLogD |
|---|---|---|---|---|---|---|
| 11 | 0.0055 | >300 | 267 | no effect | 3.3 | 1.9 |
| 8 | 0.0044 | >300 | >300 | no effect | 3.4 | 1.9 |
| 12 | 0.0042 | >300 | >300 | no effect | 3.3 | 1.4 |
| Comparator A | 0.0037 | >300 | 174 | no effect | 3.9 | 1.8 |
| Comparator B | 0.0041 | 224 | 112 | no effect | 4.7 | 2.7 |
| Comparator C | NT | 177 | 72 | 21 | 4.1 | 3.2 |
| Comparator D | 0.0065 | 179 | 69 | no effect | 4.1 | 2.3 |
| Comparator E | 0.0113 | 26 | 43 | 19 | 6.1 | 4.6 |
| Comparator F | 0.0133 | 37 | 56 | 66 | 5.2 | 3.7 |

HETEROARYLPHENOXY BENZAMIDE KAPPA OPIOID LIGANDS

This application is a Non-Provisional application which claims benefit under 35 U.S.C. § 119(e) of U.S. Provisional Patent Application No. 62/426,980, filed Nov. 28, 2016, U.S. Provisional Patent Application No. 62/576,435, filed Oct. 24, 2017 and U.S. Provisional Patent Application No. 62/585,016, filed on Nov. 13, 2017, the disclosures of which are hereby incorporated by reference in their entirety.

FIELD OF THE INVENTION

The present invention generally relates to compounds, which are kappa opioid ligands, for example kappa opioid antagonists, and to pharmaceutical compositions comprising the compounds and methods of treatment using the compounds.

BACKGROUND OF THE INVENTION

Opioid ligands act upon one or more of the four known opioid receptors, namely the μ (MOR), δ (DOR), κ (KOR) and opioid like (ORL) receptors. The opioid receptors belong to the class A (Rhodopsin-like) γ subfamily of G protein-coupled receptors (GPCRs) and have a common seven-transmembrane helical architecture. Of the four opioid receptors, the μ (MOR), δ (DOR) and κ (KOR) are more closely related, sharing approximately 70% sequence homology in their seven-transmembrane domains with more variation being present in their extracellular loops and even greater variation in their N and C termini. The crystal structure of the human KOR (hKOR) has been solved with the receptor in complex with the selective antagonist ligand JDTic, i.e. ((3R)-7-hydroxy-N-[(1 S)-1-(((3R,4R)-4-(3-hydroxyphenyl)-3,4-dimethyl-1-piperidinyl)methyl)-2-methylpropyl]-1,2,3,4-tetrahydro-3-isoquinoline-carboxamide. The hKOR binding pocket was found to be relatively large and partially capped by the extracellular loop 2 (ECL2) β-hairpin, with a relatively narrow and deep pocket containing an aspartate side chain (Asp138). The aspartate residue is conserved in all aminergic GPCRs, including the opioid receptors, and is critical in the selectivity of aminergic receptors towards protonated amine-containing ligands. Wu, H. et al. "Structure of the human kappa opioid receptor in complex with JDTic" Nature 2012 485(7398): 327-332.

Pharmacological studies have reported that the KOR is a $G_{i/o}$-coupled receptor which is selectively activated by endogenous dynorphin opioid peptides. The KOR has been found to be widely expressed in the brain, spinal cord and peripheral tissues. Particular areas of the brain in which the KOR is found have been associated with reward, cognitive function and stress responsiveness and include the ventral tegmental area (VTA), nucleus accumbens, prefrontal cortex, hippocampus, striatum, amygdala, locus coeruleus, substantia nigra, dorsal raphe nucleus and hypothalamus. Evidence has shown that dynorphin levels are increased under painful and stressful conditions and that disruption of the KOR can produce an anti-stress effect. Stress and drugs of abuse have been found to cross-modulate dynorphin-dependent molecular pathways, indicating that stress-induced dynorphin release and KOR activation are involved in pharmacological processes related to depression and substance abuse. Findings such as these have stimulated interest in seeking KOR antagonists as potential pharmacotherapies for disorders such as depression, anxiety, addictive disorders or other stress associated psychiatric conditions. For example, KOR antagonist compounds may be useful in the treatment of addiction, such as relapse addiction, to drug substances such as the psychostimulants cocaine, amphetamine, methamphetamine and the like; opioids such as heroin, morphine, oxycodone, hydrocodone, hydromorphone and the like; nicotine; cannabinoids, such as marijuana; and alcohol. In addition, KOR antagonists may also be useful for treatment of depression and other psychiatric disorders. (See e.g. Bruchas, M. R. et al. "The Dynorphin-Kappa Opioid System as a Modulator of Stress-induced and Pro-addictive Behaviors", Brain Res. 2010 Feb. 16; 1314C: 44;doi:10:1016/j.brainres.2009.08.062; Lalanne, L. et al. "The kappa opioid receptor: from addiction to depression, and back", Frontiers in Psychiatry 2014, 5, 170; doi: 10.3389/fpsyt.2014.00170; and Kissler, J. L. et al. "The One-Two Punch of Alcoholism: Role of Central Amygdala Dynorphins/Kappa-Opioid Receptors" Biol. Psychiatry 2014, 75, 774-782; doi: 10.1016/j.biopsych. 2013.03.014.)

New or improved agents that modulate (such as antagonize) kappa opioid receptors are needed to provide improved therapeutic options for the treatment of diseases or conditions associated with dysregulated activity of the kappa opioid receptor/dynorphin system, such as those described herein. It may also be desirable to devise new agents which exhibit selectivity for the kappa opioid receptor over the closely related mu and delta opioid receptors. See e.g. Urbano, M. et al. "Antagonists of the kappa opioid receptor", Bioorganic & Medicinal Chemistry Letters 2014, 24, 2021-2032; Munro, T. A. et al. "Selective K Opioid Antagonists nor-BNI, GNTI and JDTic Have Low Affinities for Non-Opioid Receptors and Transporters", Plos One 2013, 8(8) e70701; doi:10.1371/journal.pone.0070701; Mitch, C. H. et al. "Discovery of Aminobenzyloxyarylamides as K Opioid Receptor Selective Antagonists: Application to Preclinical Development of a K Opioid Receptor Antagonist Receptor Occupancy Tracer", J. Med. Chem. 2011, 54, 8000-8012; doi: 10.1021/jm2007789r; and Rorick-Kehn, L. M. et al. "Determining Pharmacological Selectivity of the Kappa Opioid Receptor Antagonist LY2456302 Using Pupillometry as a Translational Biomarker in Rat and Human", International Journal of Neuropsychopharmacology 2015, 1-11; doi: 10.1093/ijnp/pyu036.

SUMMARY OF THE INVENTION

A first embodiment of a first aspect of the present invention is a compound of Formula I

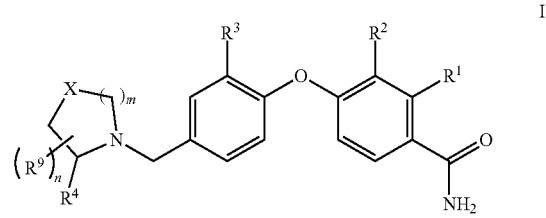

or a pharmaceutically acceptable salt thereof; wherein $R^1$ is hydrogen, fluoro or hydroxy; $R^2$ and $R^3$ are each independently hydrogen or fluoro; X is $CR^5R^6$ or O; m is 1 or 2; n is 0, 1 or 2; $R^4$ is selected from the group consisting of

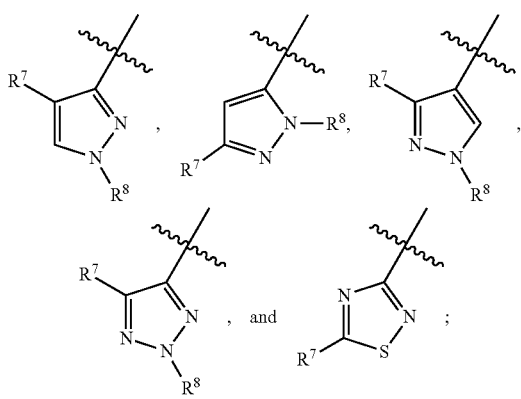

$R^5$ and $R^6$ are each independently selected from the group consisting of hydrogen, fluoro, hydroxy, $C_1$-$C_3$alkyl and $C_1$-$C_3$alkoxy; $R^7$ and $R^8$ are each independently selected from the group consisting of hydrogen, $C_1$-$C_6$alkyl and $C_1$-$C_6$alkoxy; wherein the $C_1$-$C_6$alkyl and $C_1$-$C_6$alkoxy are optionally substituted with one to three fluoro; and $R^9$ at each occurrence is independently selected from fluoro, $C_1$-$C_3$alkyl and $C_1$-$C_6$alkoxy, wherein the $C_1$-$C_3$alkyl and $C_1$-$C_6$alkoxy are optionally substituted with one to three fluoro.

Another embodiment of the present invention is a pharmaceutical composition comprising compounds of Formula I, or a pharmaceutically acceptable salt thereof together with a pharmaceutically acceptable vehicle, diluent or carrier. The pharmaceutical compositions described herein can be used for modulating the kappa opioid receptor (such as antagonizing the kappa opioid receptor) in a patient; and for treating diseases or disorders associated with the kappa opioid receptor, such as a neurological disorder, neurocognitive disorder, substance abuse disorder, depressive disorder, anxiety disorder, trauma and stressor related disorder or a feeding and eating disorder.

Another embodiment of the present invention is directed to crystalline forms of 4-(4-{[(2S)-2-(3-methoxy-1-methyl-1H-pyrazol-4-yl)pyrrolidin-1-yl]methyl}phenoxy)benzamide, wherein each solid form can be uniquely identified by several different analytical parameters, alone or in combination, such as, but not limited to: powder X-ray diffraction (PXRD) pattern peaks or combinations of two or more PXRD peaks; solid state NMR (ssNMR) 13C chemical shifts or combinations of two or more ssNMR chemical shifts; and Raman peak shifts or combinations of two or more Raman peak shifts.

Based on the disclosure provided herein, one of ordinary skill in the art would appreciate that a first and second crystalline form of 4-(4-{[(2S)-2-(3-methoxy-1-methyl-1H-pyrazol-4-yl)pyrrolidin-1-yl]methyl}phenoxy)benzamide (referred to herein as "Form 1" and "Form 2") can be uniquely identified by several different spectral peaks or patterns in varying combinations. For example, a crystalline form of 4-(4-{[(2S)-2-(3-methoxy-1-methyl-1H-pyrazol-4-yl)pyrrolidin-1-yl]methyl}phenoxy)benzamide (Form 2) can be characterized by the powder x-ray diffraction (PXRD) peak list described in Table 9, the Raman peak list described in Table 10, the solid state NMR (ssNMR) peak list described in Table 11 or combinations thereof. The crystalline form of 4-(4-{[(2S)-2-(3-methoxy-1-methyl-1H-pyrazol-4-yl)pyrrolidin-1-yl]methyl}phenoxy)benzamide (Form 1) can be characterized by the Raman peak list described in Table 16, or the solid state NMR (ssNMR) peak list described in Table 17 or combinations thereof.

Another embodiment of the present invention is directed to a crystalline form of 4-(4-{[(2S)-2-(3-methoxy-1-methyl-1H-pyrazol-4-yl)pyrrolidin-1-yl]methyl}phenoxy)benzamide (Form 2), wherein the crystalline form has an analytical parameter selected from the group consisting of: i) a solid state NMR spectrum comprising 13C chemical shifts (ppm) at 124.2±0.2, 126.4±0.2, and 152.6±0.2; ii) a powder X-ray diffraction pattern comprising peaks at diffraction angles (2θ) of 17.8±0.2, 10.1±0.2, and 15.1±0.2; and iii) a Raman spectrum comprising Raman peak shifts (cm-1) at 1660±2, 1597±2, and 815±2.

Another embodiment of the present invention is directed to a pharmaceutical composition comprising the crystalline form of 4-(4-{[(2S)-2-(3-methoxy-1-methyl-1H-pyrazol-4-yl)pyrrolidin-1-yl]methyl}phenoxy)benzamide (Form 2) in a therapeutically effective amount in admixture with at least one pharmaceutically acceptable excipient.

Another embodiment of the present invention is directed to a crystalline form of 4-(4-{[(2S)-2-(3-methoxy-1-methyl-1H-pyrazol-4-yl)pyrrolidin-1-yl]methyl}phenoxy)benzamide (Form 1), wherein the crystalline form has a solid state NMR spectrum comprising 13C chemical shifts (ppm) at 121.6±0.2, 127.9±0.2, and 153.7±0.2.

Another embodiment of the present invention is directed to a pharmaceutical composition comprising the crystalline form of 4-(4-{[(2S)-2-(3-methoxy-1-methyl-1H-pyrazol-4-yl)pyrrolidin-1-yl]methyl}phenoxy)benzamide (Form 1) in a therapeutically effective amount in admixture with at least one pharmaceutically acceptable excipient.

Another embodiment of the present invention is directed to a method of modulating kappa opioid receptors, the method comprising administering to a patient a therapeutically effective amount of a crystalline form of 4-(4-{[(2S)-2-(3-methoxy-1-methyl-1H-pyrazol-4-yl)pyrrolidin-1-yl]methyl}phenoxy)benzamide (Form 2).

Another embodiment of the present invention is directed to a method of modulating kappa opioid receptors, the method comprising administering to a patient a therapeutically effective amount of a crystalline form of 4-(4-{[(2S)-2-(3-methoxy-1-methyl-1H-pyrazol-4-yl)pyrrolidin-1-yl]methyl}phenoxy)benzamide (Form 1).

Another embodiment of the present invention is directed to a method of treating a neurological disorder or a psychiatric disorder in a patient, the method comprising administering to the patient a therapeutically effective amount of a crystalline form of 4-(4-{[(2S)-2-(3-methoxy-1-methyl-1H-pyrazol-4-yl)pyrrolidin-1-yl]methyl}phenoxy)benzamide (Form 2).

Another embodiment of the present invention is directed to a method of treating a neurological disorder or a psychiatric disorder in a patient, the method comprising administering to the patient a therapeutically effective amount of a crystalline form of 4-(4-{[(2S)-2-(3-methoxy-1-methyl-1H-pyrazol-4-yl)pyrrolidin-1-yl]methyl}phenoxy)benzamide (Form 1).

Further exemplary combinations of characteristic peak values that can be used to identify Form 1 and Form 2 are described below and in no way should these exemplary combinations be viewed as limiting other peak value combinations disclosed herein.

The present invention is also directed to methods of treatment employing the compounds of Formula I, such as:

(1) Methods of modulating the kappa opioid receptor (such as antagonizing the kappa opioid receptor), by administering a therapeutically effective amount of a compound of any of the embodiments of Formula I or a pharmaceutically acceptable salt thereof, and a pharmaceutically acceptable vehicle, diluent or carrier, to a patient in need thereof.

(2) Methods for treating disorders, conditions or diseases of the central nervous system and neurological disorders in which the kappa opioid receptor may be involved, such as cognitive disorders (including HIV-associated dementia, Alzheimer's disease and mild cognitive impairment ("MCI"), Lewy body dementia, vascular dementia, drug-related dementia); disorders associated with muscular spasticity, weakness, tremors, or chorea (Parkinson's disease, Lewy body dementia, Huntington's disease, tardive dyskinesia, frontotemporal dementia, Creutzfeldt-Jacob disease, myoclonus, dystonia, delirium, Gilles de la Tourette's syndrome, epilepsy, muscular spasms); sleep disorders (including hypersomnia, circadian rhythm sleep disorder, insomnia, parasomnia) and psychiatric disorders as associated with anxiety (including acute stress disorder, generalized anxiety disorder, social anxiety disorder, panic disorder, post-traumatic stress disorder, agoraphobia, and obsessive-compulsive disorder); impulse control disorders (including compulsive gambling and intermittent explosive disorder); mood disorders (including bipolar I disorder, bipolar II disorder, mania, mixed affective state, major depression, chronic depression, seasonal depression, psychotic depression, seasonal depression, premenstrual syndrome (PMS), premenstrual dysphoric disorder (PDD), and postpartum depression); psychomotor disorder; psychotic disorders (including schizophrenia, schizoaffective disorder, schizophreniform, and delusional disorder); substance abuse disorders including drug dependence/addiction (i.e., addiction, including relapse addiction), such as narcotic dependence (including addiction to opioids such as heroin, oxycodone, morphine, hydrocodone, hydromorphone and the like), alcoholism, amphetamine dependence, methamphetamine dependence, cocaine dependence, nicotine dependence, cannabinoid dependence (such as marijuana (THC) dependence), and drug withdrawal syndrome); eating disorders (including anorexia, bulimia, binge eating disorder, hyperphagia, obesity, compulsive eating disorders and pagophagia); sexual dysfunction disorders, such as premature ejaculation; and pediatric psychiatric disorders (including attention deficit disorder, attention deficit/hyperactivity disorder, conduct disorder, and autism spectrum disorders) in a mammal, preferably a human, comprising administering to said mammal a therapeutically effective amount of a compound of Formula I or pharmaceutically acceptable salt thereof. The compounds of Formula I may also be useful for improving cognitive deficits and memory (both short-term and long-term) and learning ability. The text revision of the fourth edition of the Diagnostic and Statistical Manual of Mental Disorders (DSM-IV-TR) (2000, American Psychiatric Association, Washington, D.C.) provides a diagnostic tool for identifying many of the disorders described herein. The skilled artisan will recognize that there are alternative nomenclatures, nosologies, and classification systems for disorders described herein, including those as described in the DMS-IV-TR, and that terminology and classification systems evolve with medical scientific progress;

(3) Methods for treating a neurological disorder (such as spinocerebellar ataxia syndromes, Parkinson's disease (i.e. levodopa induced dyskinesia in Parkinson's disease; cognitive disorder; or a sleep disorder) or a psychiatric disorder (such as anxiety; factitious disorder; impulse control disorder; mood disorder; psychomotor disorder; psychotic disorder; drug dependence; eating disorder; and pediatric psychiatric disorder) in a mammal, preferably a human, comprising administering to said mammal a therapeutically effective amount of a compound of Formula I or pharmaceutically acceptable salt thereof;

(4) Methods for the treatment of feeding and or eating disorders (e.g. avoidant/restrictive food intake disorder, anorexia nervosa, bulimia nervosa, binge-eating disorders) or obesity; and (5) Methods for the treatment of substance abuse disorders including addiction, such as negative affect states during withdrawal as well as relapse addiction, wherein the substance addiction includes, but is not limited to, alcohol, cocaine, amphetamine, methamphetamine, opioid, cannabinoid (marijuana), sedative, hypnotics, anxiolytic or nicotine (tobacco) addiction.

The present invention is also directed to combination therapies wherein the compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided.

All patents, patent applications and references referred to herein are hereby incorporated by reference in their entirety.

Other features and advantages of this invention will be apparent from this specification and the appendant claims which describe the invention. It is to be understood that both the foregoing and the following detailed description are exemplary only and are not restrictive of the invention as claimed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7 is a table summarizing the in vitro cell toxicity data for Examples 11, 8 and 12 and Comparators AF. The data provided are from the single point time dependent inhibition (SPTDI) at CYP3A assay, the transformed human liver endothelial assay (THLE), the HepG2 72 hour assay (HepG2), and the respirometric screening technology assay (RST). The hydrophilicity (cLogP) and lipophilicity (SFLogD) of the compounds is also provided. Cells containing data that are not in the ideal range for a given assay are highlighted in gray. "NT"=not tested.

DETAILED DESCRIPTION OF THE INVENTION

Figure 1:
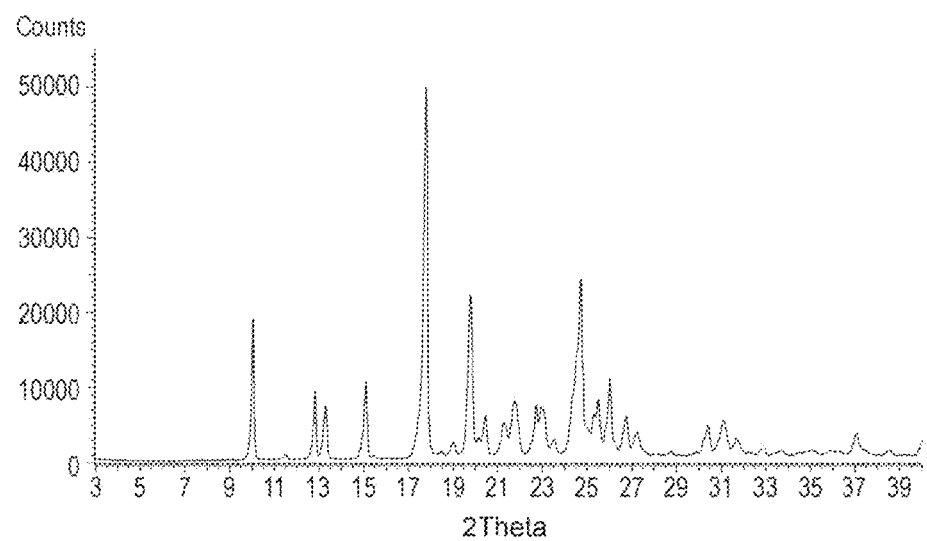
FIG. 1 depicts a characteristic PXRD pattern of Form 2 carried out on a Bruker AXS D4 Endeavor diffractometer equipped with a Cu radiation source. The divergence slit was set at 0.6 mm while the secondary optics used variable slits. Diffracted radiation was detected by a PSD-Lynx Eye detector.

The present invention may be understood more readily by reference to the following detailed description of exemplary embodiments of the invention and the examples included therein. It is to be understood that this invention is not limited to specific methods of synthesis, which may of course vary. It is also to be understood that the terminology used herein is for the purpose of describing particular embodiments only and is not intended to be limiting.

In this specification and in the claims that follow, reference will be made to a number of terms that shall be defined to have the following meanings:

As used herein, "feeding and eating disorders" refer to illnesses in which the patient suffers disturbances in his/her eating behaviors and related thoughts and emotions. Representative examples of feeding and eating disorders include overeating, bulimia nervosa, manorexia nervosa, an avoidant/restrictive food intake disorder, binge-eating disorder, compulsive dieting, nocturnal sleep-related eating disorder, pica, Prader-Willi syndrome, and night-eating syndrome.

"Patient" refers to warm-blooded animals such as, for example, guinea pigs, mice, rats, gerbils, cats, rabbits, dogs, cattle, goats, sheep, horses, monkeys, chimpanzees, and humans.

The term "pharmaceutically acceptable" means the substance or composition must be compatible, chemically and/or toxicologically, with the other ingredients comprising a formulation, and/or the mammal being treated therewith.

The term "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In reference to the treatment of a kappa opioid mediated disease or disorder (e.g., a neurological disorder, neurocognitive disorder, substance abuse disorder, depressive disorder, anxiety disorder, trauma and stressor related disorder and feeding and eating disorder), a therapeutically effective amount refers to that amount which has the effect of relieving to some extent (or, for example, eliminating) one or more symptoms associated with a kappa opioid mediated disease or disorder (e.g., a neurological disorder selected from spinocerebellar ataxia syndrome and levodopa induced dyskinesia in Parkinson's disease; a neurocognitive disorder selected from neuropsychiatric symptoms due to Alzheimer's disease (e.g., apathy, anxiety, and depression) and frontotemporal dementia; a substance abuse disorder selected from stimulant use disorder, stimulant withdrawal, alcohol use disorder, alcohol withdrawal, tobacco use disorder, tobacco withdrawal, opioid use disorder, opioid withdrawal, cannabis use disorder, sedative use disorder, hypnotic use disorder and anxiolytic use disorder; a depressive disorder selected from major depressive disorder, persistent depressive disorder, bipolar disorder and premenstrual dysphoric disorder; an anxiety disorder selected from social anxiety disorder, obsessive-compulsive disorder, specific phobia disorder, panic disorder and generalized anxiety disorder; a trauma and stressor related disorder which is posttraumatic stress disorder; a feeding and eating disorder selected from an avoidant/restrictive food intake disorder, anorexia nervosa, bulimia nervosa and binge eating disorder).

The term "treating", as used herein, unless otherwise indicated, means reversing, alleviating, inhibiting the progress of, delaying the progression of, delaying the onset of, or preventing the disease, disorder or condition to which such term applies, or one or more symptoms of such disease, disorder or condition. The term "treatment", as used herein, unless otherwise indicated, refers to the act of treating as "treating" is defined immediately above. The term "treating" also includes adjuvant and neo-adjuvant treatment of a subject. For the avoidance of doubt, reference herein to "treatment" includes reference to curative, palliative and prophylactic treatment, and to the administration of a medicament for use in such treatment.

The term "alkyl" refers to a linear or branched-chain saturated hydrocarbyl substituent (i.e., a substituent obtained from a hydrocarbon by removal of a hydrogen); in one embodiment containing from one to six carbon atoms (a $C_1$-$C_6$alkyl). Non-limiting examples of such substituents include methyl, ethyl, propyl (including n-propyl and isopropyl), butyl (including n-butyl, isobutyl, sec-butyl and tert-butyl), pentyl, isoamyl, hexyl and the like. Another embodiment is an alkyl containing from one to three carbons (a $C_1$-$C_3$alkyl), which includes methyl, ethyl, propyl and isopropyl.

The term "alkoxy" refers to a linear or branched-chain saturated hydrocarbyl substituent attached to an oxygen radical (i.e., a substituent obtained from a hydrocarbon alcohol by removal of the hydrogen from the OH); in one embodiment containing from one to six carbon atoms (a $C_1$-$C_6$alkoxy). Non-limiting examples of such substituents include methoxy, ethoxy, propoxy (including n-propoxy and isopropoxy), butoxy (including n-butoxy, isobutoxy, sec-butoxy and tert-butoxy), pentoxy, hexoxy and the like. Another embodiment is an alkoxy containing from one to three carbons (a $C_1$-$C_3$alkoxy) including methoxy, ethoxy, propoxy and isopropoxy.

In some instances, the number of carbon atoms in a hydrocarbyl substituent (i.e., alkyl) is indicated by the prefix "$C_x$-$C_y$-" or "$C_{x-y}$," wherein x is the minimum and y is the maximum number of carbon atoms in the substituent. Thus, for example, "$C_1$-$C_6$-alkyl" or "$C_{1-6}$alkyl" refers to an alkyl substituent containing from 1 to 6 carbon atoms. Illustrating further, "$C_1$-$C_3$alkyl" refers to an alkyl substituent containing from 1 to 3 carbon atoms.

The term "hydroxy" or "hydroxyl" refers to —OH. When used in combination with another term(s), the prefix "hydroxy" indicates that the substituent to which the prefix is attached is substituted with one or more hydroxy substituents. Compounds bearing a carbon to which one or more hydroxy substituents include, for example, alcohols, enols and phenol. The term "fluoro" refers to fluorine (which may be depicted as —F).

If substituents are described as "independently" having more than one variable, each instance of a substituent is selected independent of the other(s) from the list of variables available. Each substituent therefore may be identical to or different from the other substituent(s).

If substituents are described as being "independently selected" from a group, each instance of a substituent is selected independent of the other(s). Each substituent therefore may be identical to or different from the other substituent(s).

As used herein, the term "Formula I" may be hereinafter referred to as a "compound(s) of the invention," "the present invention," and "compound of Formula I." Such terms are also defined to include all forms of the compound of Formula I, including hydrates, solvates, isomers, crystalline and non-crystalline forms, isomorphs, polymorphs, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist as clathrates or other complexes (including co-crystals). Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components, which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975). Co-crystals are typically defined as crystalline complexes of neutral molecular constituents that are bound together through non-covalent interactions, but could also be a complex of a neutral molecule with a salt. Co-crystals may be prepared by melt crystallization, by recrystallization from solvents, or by physically grinding the components together; see O. Almarsson and M. J. Zaworotko, *Chem. Commun.* 2004, 17, 1889-1896. For a general review of multi-component complexes, see J. K. Haleblian, *J. Pharm. Sci.* 1975, 64, 1269-1288.

The compounds of the invention (including salts thereof) may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —$COO^-Na^+$, —$COO^-K$, or —$SO_3^-Na^+$) or non-ionic (such as —$N^-N^+(CH_3)_3$) polar head group. For more information, see *Crystals and the Polarizing Microscope* by N. H. Hartshorne and A. Stuart, 4$^{th}$ Edition (Edward Arnold, 1970).

Also included within the scope of the invention are metabolites of compounds of Formula I, that is, compounds formed in vivo upon administration of the drug.

The compounds of the invention may have asymmetric carbon atoms. The carbon-carbon bonds of the compounds of the invention may be depicted herein using a solid line (———), a solid wedge (◥■), or a dotted wedge (⋯⋯). The use of a solid line to depict bonds to asymmetric carbon atoms is meant to indicate that all possible stereoisomers (e.g., specific enantiomers, racemic mixtures, etc.) at that carbon atom are included, unless otherwise specified. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included, unless otherwise specified. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

Certain of the compounds of Formula I may exhibit the phenomenon of tautomerism; it is to be understood that such tautomers are also regarded as compounds of the invention.

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of Formula I with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention, when possible, include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclic, carboxylic, and sulfonic classes of organic acids.

Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, p-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include the lighter alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long-chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulfate and hemicalcium salts.

Also within the scope of the present invention are so-called "prodrugs" of the compound of the invention. Thus, certain derivatives of the compound of the invention which may have little or no pharmacological activity themselves can, when administered into or onto the body, be converted into the compound of the invention having the desired activity, for example, by hydrolytic cleavage. Such derivatives are referred to as "prodrugs." Further information on the use of prodrugs may be found in "Pro-drugs as Novel Delivery Systems, Vol. 14, ACS Symposium Series (T. Higuchi and V. Stella) and "Bioreversible Carriers in Drug Design," Pergamon Press, 1987 (ed. E. B. Roche, American Pharmaceutical Association). Prodrugs in accordance with the invention can, for example, be produced by replacing appropriate functionalities present in the compounds of any of Formula I with certain moieties known to those skilled in the art as "pro-moieties" as described, for example, in "Design of Prodrugs" by H. Bundgaard (Elsevier, 1985).

The present invention also includes isotopically labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, sulfur, fluorine and chlorine, such as $^2$H, $^3$H, $^{13}$, $^{11}$, $^{14}$, $^{15}$N, $^{18}$O, $^{17}$O, $^{32}$P, $^{35}$S, $^{18}$F, and $^{36}$Cl, respectively. Compounds of the present invention, prodrugs thereof, and pharmaceutically acceptable salts of said compounds or of said prodrugs that contain the aforementioned isotopes and/or other isotopes of other atoms are within the scope of this invention. Certain isotopically labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Substitution with positron-emitting isotopes, such as $^{11}$C, $^{18}$F, $^{15}$O and $^{13}$N, can be useful in Positron Emission Tomography (PET) studies for examining substrate receptor occupancy.

Isotopically labeled compounds of Formula I of this invention and prodrugs thereof can generally be prepared by carrying out the procedures disclosed in the Schemes and/or in the Examples and Preparations below, by substituting a readily available isotopically labeled reagent for a non-isotopically labeled reagent.

Compounds of Formula I (including salts thereof) may exist in a continuum of solid states ranging from fully amorphous to fully crystalline. The term 'amorphous' refers to a state in which the material lacks long-range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from apparent solid to a material with liquid properties occurs, which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The term "polymorph" refers to different crystalline forms of the same compound and includes, but is not limited to, other solid state molecular forms including hydrates (e.g., bound water present in the crystalline structure) and solvates (e.g., bound solvents other than water) of the same compound.

The term "solvate" describes a molecular complex comprising the drug substance and a stoichiometric or non-stoichiometric amount of one or more solvent molecules (e.g., ethanol). When the solvent is tightly bound to the drug the resulting complex will have a well-defined stoichiometry that is independent of humidity. When, however, the solvent is weakly bound, as in channel solvates and hygroscopic compounds, the solvent content will be dependent on humidity and drying conditions. In such cases, the complex will often be non-stoichiometric.

The term "hydrate" describes a solvate comprising the drug substance and a stoichiometric or non-stoichiometric amount of water.

The term "powder X-ray diffraction pattern" or "PXRD pattern" refers to the experimentally observed diffractogram or parameters derived therefrom. Powder X-ray diffraction patterns are characterized by peak position (abscissa) and peak intensities (ordinate).

The term "2 theta value" or "2θ" refers to the peak position in degrees based on the experimental setup of the X-ray diffraction experiment and is a common abscissa unit in diffraction patterns. The experimental setup requires that if a reflection is diffracted when the incoming beam forms an angle theta (θ) with a certain lattice plane, the reflected beam is recorded at an angle 2 theta (2θ). It should be understood that reference herein to specific 2θ values for a specific solid form is intended to mean the 2θ values (in degrees) as measured using the X-ray diffraction experimental conditions as described herein.

The term "Form 1" as described herein is a single crystal of the compound 4-(4-{[(2S)-2-(3-methoxy-1-methyl-1H-pyrazol-4-yl)pyrrolidin-1-yl]methyl}phenoxy)benzamide, single enantiomer (Example 12), formerly referenced as "Form B" in U.S. Provisional Patent Application No. 62/426,980, filed on Nov. 28, 2016, and U.S. Provisional Patent Application No. 62/576,435, filed on Oct. 26, 2017.

The term "Form 2" as described herein is a single crystal of the compound 4-(4-{[(2S)-2-(3-methoxy-1-methyl-1H-pyrazol-4-yl)pyrrolidin-1-yl]methyl}phenoxy)benzamide, single enantiomer (Example 12), formerly referenced as Form A in U.S. Provisional Patent Application No. 62/426,980, filed on Nov. 28, 2016, and U.S. Provisional Patent Application No. 62/576,435, filed on Oct. 26, 2017.

A second embodiment of a first aspect of the present invention is the compound of the first aspect wherein m is 1; X is $CR^5R^6$; $R^5$ and $R^6$ are each independently selected from the group consisting of hydrogen, fluoro and methyl; $R^7$ is selected from the group consisting of hydrogen, methyl and methoxy; and $R^8$ is methyl or hydrogen; or a pharmaceutically acceptable salt thereof.

A third embodiment of a first aspect of the present invention is the compound of the second embodiment of the first aspect which is a compound of the Formula Ia

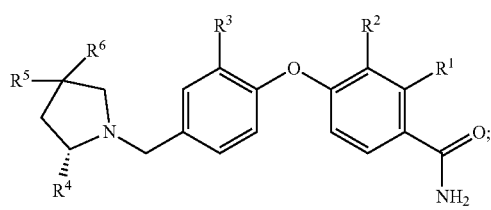

Ia or a pharmaceutically acceptable salt thereof.

A fourth embodiment of a first aspect of the present invention is the compound of the third embodiment of the first aspect wherein $R^4$ is

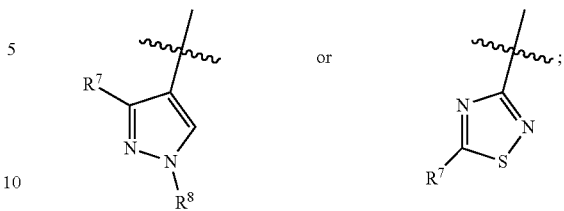

$R^5$ and $R^6$ are each hydrogen and $R^7$ is methyl or methoxy; or a pharmaceutically acceptable salt thereof.

A fifth embodiment of a first aspect of the present invention is the compound of the first embodiment of the first aspect wherein m is 2; or a pharmaceutically acceptable salt thereof.

A sixth embodiment of a first aspect of the present invention is the compound of the fifth embodiment of the first aspect wherein X is O; or a pharmaceutically acceptable salt thereof.

A seventh embodiment of a first aspect of the present invention is the compound of the sixth embodiment of the Formula Ib

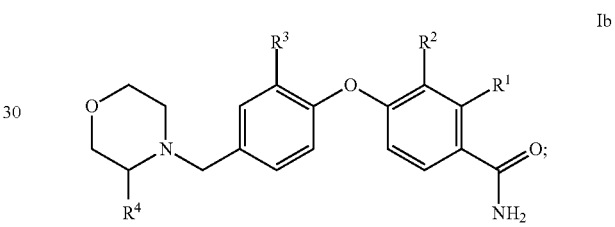

Ib wherein $R^4$ is

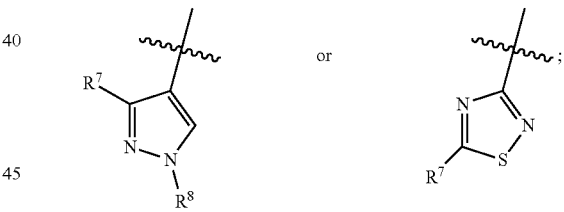

$R^7$ is methyl or methoxy; and $R^8$ is methyl or hydrogen; or a pharmaceutically acceptable salt thereof.

An eighth embodiment of a first aspect of the present invention is the compound of the fifth embodiment of the first aspect wherein X is $CR^5R^6$; or a pharmaceutically acceptable salt thereof.

A ninth embodiment of a first aspect of the present invention is the compound of the eighth embodiment of the first aspect of the Formula Ic

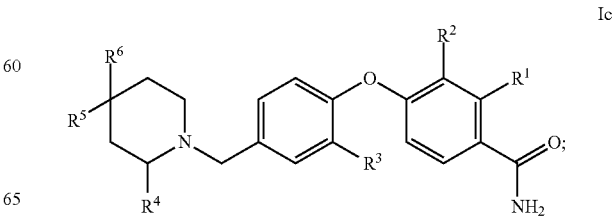

Ic wherein $R^4$ is

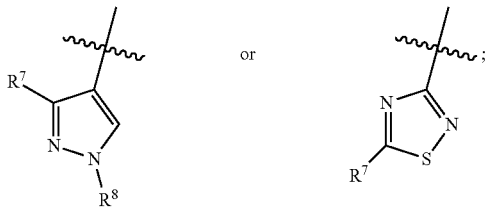

$R^5$ and $R^6$ are each hydrogen; $R^7$ is methyl or methoxy; and $R^8$ is methyl or hydrogen; or a pharmaceutically acceptable salt thereof.

A tenth embodiment of a first aspect of the present invention is a compound of the first embodiment of the first aspect selected from the group consisting of: (+/−)-4-(4-{[2-(1,3-dimethyl-1H-pyrazol-4-yl)pyrrolidin-1-yl]methyl}-2-fluorophenoxy)benzamide; (+)-4-(4-{[2-(1,3-dimethyl-1H-pyrazol-4-yl)pyrrolidin-1-yl]methyl}-2-fluorophenoxy) benzamide; (−)-4-(4-{[2-(1,3-dimethyl-1H-pyrazol-4-yl)pyrrolidin-1-yl]methyl}-2-fluorophenoxy)benzamide; (+/−)-4-(4-{[2-(1,3-dimethyl-1H-pyrazol-4-yl)pyrrolidin-1-yl]methyl}phenoxy)-3-fluorobenzamide; 4-(4-{[2-(1,3-dimethyl-1H-pyrazol-4-yl)pyrrolidin-1-yl]methyl}phenoxy)-3-fluorobenzamide, ENT-1; 4-(4-{[2-(1,3-dimethyl-1H-pyrazol-4-yl)pyrrolidin-1-yl]methyl}phenoxy)-3-fluorobenzamide, ENT-2; (+/−)-3-fluoro-4-(4-{[2-(3-methoxy-1-methyl-1H-pyrazol-4-yl)pyrrolidin-1-yl]methyl} phenoxy)benzamide; (−)-3-fluoro-4-(4-{[2-(3-methoxy-1-methyl-1H-pyrazol-4-yl)pyrrolidin-1-yl]methyl}phenoxy) benzamide; (+)-3-fluoro-4-(4-{[2-(3-methoxy-1-methyl-1H-pyrazol-4-yl)pyrrolidin-1-yl]methyl} phenoxy)benzamide; 4-(4-{[(2S)-2-(5-methyl-1,2,4-thiadiazol-3-yl)pyrrolidin-1-yl]methyl}phenoxy)benzamide; 4-(4-{[(2S)-2-(1,3-dimethyl-1H-pyrazol-4-yl)pyrrolidin-1-yl]methyl}phenoxy) benzamide; 4-(4-{[2-(3-methoxy-1-methyl-1H-pyrazol-4-yl)pyrrolidin-1-yl]methyl}phenoxy) benzamide, single enantiomer; (+/−)-4-(4-{[2-(3-methoxy-1H-pyrazol-4-yl)pyrrolidin-1-yl]methyl}phenoxy) benzamide; (−)-4-(4-{[2-(3-methoxy-1H-pyrazol-4-yl)pyrrolidin-1-yl]methyl}phenoxy) benzamide; (+)-4-(4-{[2-(3-methoxy-1H-pyrazol-4-yl)pyrrolidin-1-yl]methyl}phenoxy) benzamide; (+/−)-4-(4-{[2-(1,3-dimethyl-1H-pyrazol-4-yl)pyrrolidin-1-yl]methyl}phenoxy)-2-hydroxybenzamide; (+)-4-(4-{[2-(1,3-dimethyl-1H-pyrazol-4-yl)pyrrolidin-1-yl]methyl}phenoxy)-2-hydroxybenzamide; (−)-4-(4-{[2-(1,3-dimethyl-1H-pyrazol-4-yl)pyrrolidin-1-yl]methyl}phenoxy)-2-hydroxybenzamide; 3-fluoro-4-(4-{[(2S)-2-(1-methyl-1H-pyrazol-3-yl)pyrrolidin-1-yl]methyl}phenoxy) benzamide; 3-fluoro-4-(4-{[3-(3-methoxy-1-methyl-1H-pyrazol-4-yl)morpholin-4-yl]methyl} phenoxy)benzamide, ENT-1; 4-(4-{[2-(3-methoxy-1-methyl-1H-pyrazol-4-yl)piperidin-1-yl]methyl}phenoxy) benzamide, ENT-1; 4-(2-fluoro-4-{[3-(3-methoxy-1-methyl-1H-pyrazol-4-yl)morpholin-4-yl]methyl} phenoxy)benzamide, ENT-1; 4-(4-{[3-(3-methoxy-1-methyl-1H-pyrazol-4-yl)morpholin-4-yl]methyl}phenoxy) benzamide, ENT-1; 4-(4-{[4-fluoro-2-(3-methoxy-1-methyl-1H-pyrazol-4-yl)pyrrolidin-1-yl]methyl}phenoxy)benzamide, Isomer 2, assumed racemic, either cis or trans; 4-(4-{[2-(1,3-dimethyl-1H-pyrazol-4-yl)-4-fluoropyrrolidin-1-yl]methyl}phenoxy) benzamide, Isomer 1; 4-(4-{[2-(1,3-dimethyl-1H-pyrazol-4-yl)-4-fluoropyrrolidin-1-yl]methyl}phenoxy) benzamide, Isomer 2; 4-(4-{[(2S)-2-(1,3-dimethyl-1H-pyrazol-5-yl)pyrrolidin-1-yl]methyl}phenoxy)-2-hydroxybenzamide; 3-fluoro-4-(4-{[2-(3-methoxy-1-methyl-1H-pyrazol-4-yl)-4-methylpyrrolidin-1-yl]methyl}phenoxy)benzamide, Isomer 1; 3-fluoro-4-(4-{[2-(3-methoxy-1-methyl-1H-pyrazol-4-yl)-4-methylpyrrolidin-1-yl]methyl}phenoxy) benzamide, Isomer 2; 3-fluoro-4-(4-{[2-(3-methoxy-1-methyl-1H-pyrazol-4-yl)-4-methylpyrrolidin-1-yl]methyl}phenoxy)benzamide, Isomer 3; 3-fluoro-4-(4-{[2-(3-methoxy-1-methyl-1H-pyrazol-4-yl)-4-methylpyrrolidin-1-yl]methyl}phenoxy)benzamide, Isomer 4; 4-(2-fluoro-4-{[2-(3-methoxy-1-methyl-1H-pyrazol-4-yl)pyrrolidin-1-yl]methyl}phenoxy)benzamide, ENT-2; 2-hydroxy-4-(4-{[2-(3-methoxy-1-methyl-1H-pyrazol-4-yl)pyrrolidin-1-yl]methyl} phenoxy)benzamide, ENT-2; 2-hydroxy-4-(4-{[(2S)-2-(1-methyl-1H-pyrazol-3-yl)pyrrolidin-1-yl]methyl}phenoxy) benzamide; 4-(4-{[2-(2,5-dimethyl-2H-1,2,3-triazol-4-yl)pyrrolidin-1-yl]methyl}phenoxy) benzamide, ENT-2; 4-(4-{[2-(2,5-dimethyl-2H-1,2,3-triazol-4-yl)pyrrolidin-1-yl]methyl}-2-fluorophenoxy)benzamide, ENT-2; 4-(4-{[(2S)-2-(1,3-dimethyl-1H-pyrazol-5-yl)pyrrolidin-1-yl]methyl}phenoxy)-3-fluorobenzamide; and; or a pharmaceutically acceptable salt thereof.

An eleventh embodiment of the first aspect of the present invention is the compound (−)-4-(4-{[2-(1,3-dimethyl-1H-pyrazol-4-yl)pyrrolidin-1-yl]methyl}-2-fluorophenoxy)benzamide; or a pharmaceutically acceptable salt thereof. A twelfth embodiment of a first aspect of the present invention is the compound 4-(4-{[2-(1,3-dimethyl-1H-pyrazol-4-yl)pyrrolidin-1-yl]methyl} phenoxy)-3-fluorobenzamide, ENT-1; or a pharmaceutically acceptable salt thereof. A thirteenth embodiment of a first aspect of the present invention is the compound 4-(4-{[(2S)-2-(1,3-dimethyl-1H-pyrazol-4-yl)pyrrolidin-1-yl]methyl}phenoxy)benzamide; or a pharmaceutically acceptable salt thereof. A fourteenth embodiment of a first aspect of the present invention is the compound 4-(4-{[2-(3-methoxy-1-methyl-1H-pyrazol-4-yl)pyrrolidin-1-yl]methyl}phenoxy)benzamide, single enantiomer; or a pharmaceutically acceptable salt thereof. A fifteenth embodiment of a first aspect of the present invention is the compound (−)-4-(4-{[2-(1,3-dimethyl-1H-pyrazol-4-yl)pyrrolidin-1-yl]methyl}phenoxy)-2-hydroxybenzamide; or a pharmaceutically acceptable salt thereof. A sixteenth embodiment of a first aspect of the present invention is the compound 3-fluoro-4-(4-{[2-(3-methoxy-1-methyl-1H-pyrazol-4-yl)pyrrolidin-1-yl]methyl}phenoxy) benzamide, ENT-1; or a pharmaceutically acceptable salt thereof. A seventeenth embodiment of a first aspect of the present invention is the compound 4-(4-{[(2S)-2-(5-methyl-1,2,4-thiadiazol-3-yl)pyrrolidin-1-yl]methyl}phenoxy)benzamide; or a pharmaceutically acceptable salt thereof.

In another embodiment, the crystalline form of 4-(4-{[(2S)-2-(3-methoxy-1-methyl-1H-pyrazol-4-yl)pyrrolidin-1-yl]methyl}phenoxy)benzamide (Form 2) has a solid state NMR spectrum further comprising a 13C chemical shift (ppm) at 37.9±0.2.

In yet another embodiment, the crystalline form of 4-(4-{[(2S)-2-(3-methoxy-1-methyl-1H-pyrazol-4-yl)pyrrolidin-1-yl]methyl}phenoxy)benzamide (Form 2) has a solid state NMR spectrum further comprising a 13C chemical shift (ppm) at 119.6±0.2.

In another embodiment of the present invention, the crystalline form of 4-(4-{[(2S)-2-(3-methoxy-1-methyl-1H-pyrazol-4-yl)pyrrolidin-1-yl]methyl}phenoxy)benzamide (Form 2) has a powder X-ray diffraction pattern further comprising a peak at a diffraction angle (2θ) of 13.3±0.2.

In another embodiment, the crystalline form of 4-(4-{[(2S)-2-(3-methoxy-1-methyl-1H-pyrazol-4-yl)pyrrolidin-1-yl]methyl}phenoxy)benzamide (Form 2) has powder X-ray diffraction pattern further comprising a peak at a diffraction angle (2θ) of 24.7±0.2.

In another embodiment, the crystalline form of 4-(4-{[(2S)-2-(3-methoxy-1-methyl-1H-pyrazol-4-yl)pyrrolidin-1-yl]methyl}phenoxy)benzamide (Form 2) has a Raman spectrum further comprising a Raman peak shift (cm-1) at 639±2.

In another embodiment, the crystalline form of 4-(4-{[(2S)-2-(3-methoxy-1-methyl-1H-pyrazol-4-yl)pyrrolidin-1-yl]methyl}phenoxy)benzamide (Form 2) has a Raman spectrum further comprising a Raman peak shift (cm-1) at 1174±2.

In yet another embodiment, the crystalline form of 4-(4-{[(2S)-2-(3-methoxy-1-methyl-1H-pyrazol-4-yl)pyrrolidin-1-yl]methyl}phenoxy)benzamide (Form 1) has a solid state NMR spectrum further comprising a 13C chemical shift (ppm) at 39.0±0.2.

In yet another embodiment, the crystalline form of 4-(4-{[(2S)-2-(3-methoxy-1-methyl-1H-pyrazol-4-yl)pyrrolidin-1-yl]methyl}phenoxy)benzamide (Form 1) has a solid state NMR spectrum further comprising a 13C chemical shift (ppm) at 119.0±0.2.

Another embodiment of the present invention is directed to a method of treating a neurological disorder or a psychiatric disorder in a patient by administering to the patient a therapeutically effective amount of the crystalline Form 1 and/or crystalline Form 2, wherein the neurological disorder is selected from spinocerebellar ataxia syndrome and levodopa induced dyskinesia in Parkinson's disease, and the psychiatric disorder is selected from neurocognitive disorder, substance abuse disorder, depressive disorder, anxiety disorder, trauma and stressor related disorder and feeding and eating disorder.

Another embodiment of the present invention is directed to a method of treating a neurological disorder or a psychiatric disorder in a patient by administering to the patient a therapeutically effective amount of the crystalline Form 1 and/or crystalline Form 2, wherein the neurological disorder selected from spinocerebellar ataxia syndrome and levodopa induced dyskinesia in Parkinson's disease.

Another embodiment of the present invention is directed to a method of treating a neurocognitive disorder in a patient by administering to the patient a therapeutically effective amount of the crystalline Form 1 and/or crystalline Form 2, wherein the neurocognitive disorder selected from neuropsychiatric symptoms due to Alzheimer's disease and frontotemporal dementia.

Another embodiment of the present invention is directed to a method of treating cognitive decline associated with Alzheimer's disease in a patient by administering to the patient a therapeutically effective amount of the crystalline Form 1 and/or crystalline Form 2.

Another embodiment of the present invention is directed to a method of treating a substance abuse disorder in a patient by administering to the patient a therapeutically effective amount of the crystalline Form 1 and/or crystalline Form 2, wherein the substance abuse disorder selected from stimulant use disorder, stimulant withdrawal, alcohol use disorder, alcohol withdrawal, tobacco use disorder, tobacco withdrawal, opioid use disorder, opioid withdrawal, cannabis use disorder, sedative use disorder, hypnotic use disorder and anxiolytic use disorder.

Another embodiment of the present invention is directed to a method of treating a depressive disorder in a patient by administering to the patient a therapeutically effective amount of the crystalline Form 1 and/or crystalline Form 2, wherein the depressive disorder selected from major depressive disorder, persistent depressive disorder, bipolar disorder and premenstrual dysphoric disorder.

Another embodiment of the present invention is directed to a method of treating an anxiety disorder in a patient by administering to the patient a therapeutically effective amount of the crystalline Form 1 and/or crystalline Form 2, wherein the anxiety disorder selected from social anxiety disorder, obsessive-compulsive disorder, specific phobia disorder, panic disorder, generalized anxiety disorder and post-traumatic stress disorder.

Another embodiment of the present invention is directed to a method of treating a feeding and eating disorder or a psychiatric disorder in a patient by administering to the patient a therapeutically effective amount of the crystalline Form 1 and/or crystalline Form 2, wherein the feeding and eating disorder selected from an avoidant/restrictive food intake disorder, anorexia nervosa, bulimia nervosa and binge eating disorder.

A first embodiment of a second aspect of the present invention is a pharmaceutical composition comprising a therapeutically effective amount of a compound of any one of the first through seventeenth embodiments of the first aspect or a pharmaceutically acceptable salt thereof and a pharmaceutically acceptable vehicle, diluent or carrier.

A first embodiment of a third aspect of the present invention is a method of treating a disorder selected from the group consisting of a neurological disorder, neurocognitive disorder, substance abuse disorder, depressive disorder, anxiety disorder, trauma and stressor related disorder and feeding and eating disorder in a patient, the method comprising administering a therapeutically effective amount of a compound of any one of the first through seventeenth embodiments of the first aspect, or a pharmaceutically acceptable salt thereof to the patient in need of treatment of the disorder.

A second embodiment of a third aspect of the present invention is the method of the first embodiment of the third aspect wherein the disorder being treated is a neurological disorder selected from spinocerebellar ataxia syndrome and levodopa induced dyskinesia in Parkinson's disease.

A third embodiment of a third aspect of the present invention is the method of the first embodiment of the third aspect wherein the disorder being treated is a neurocognitive disorder selected from neuropsychiatric symptoms due to Alzheimer's disease and frontotemporal dementia.

A fourth embodiment of a third aspect of the present invention is the method of the first embodiment of the third aspect wherein the disorder being treated is a substance abuse disorder selected from stimulant use disorder, stimulant withdrawal, alcohol use disorder, alcohol withdrawal, tobacco use disorder, tobacco withdrawal, opioid use disorder, opioid withdrawal, cannabis use disorder, sedative use disorder, hypnotic use disorder and anxiolytic use disorder.

A fifth embodiment of a third aspect of the present invention is the method of the first embodiment of the third aspect wherein the disorder being treated is a depressive disorder selected from major depressive disorder, persistent depressive disorder, bipolar disorder and premenstrual dysphoric disorder.

A sixth embodiment of a third aspect of the present invention is the method of the first embodiment of the third aspect wherein the disorder being treated is an anxiety disorder selected from social anxiety disorder, obsessive-compulsive disorder, specific phobia disorder, panic disorder and generalized anxiety disorder.

A seventh embodiment of a third aspect of the present invention is the method of the first embodiment of the third aspect wherein the disorder being treated is a trauma and stressor related disorder which is posttraumatic stress disorder.

An eighth embodiment of a third aspect of the present invention is the method of the first embodiment of the third aspect wherein the disorder being treated is a feeding and eating disorder selected from an avoidant/restrictive food intake disorder, anorexia nervosa, bulimia nervosa and binge eating disorder.

A first embodiment of a fourth aspect of the present invention is a compound according to any one of the first through seventeenth embodiments of the first aspect, or a pharmaceutically acceptable salt thereof for use in treatment of a disorder selected from the group consisting of a neurological disorder, neurocognitive disorder, substance abuse disorder, depressive disorder, anxiety disorder, trauma and stressor related disorder and feeding and eating disorder.

A second embodiment of a fourth aspect of the present invention is the use of the first embodiment of the fourth aspect wherein the disorder is a neurological disorder selected from spinocerebellar ataxia syndrome and levodopa induced dyskinesia in Parkinson's disease.

A third embodiment of a fourth aspect of the present invention is the use of the first embodiment of the fourth aspect wherein the disorder is a neurocognitive disorder selected from neuropsychiatric symptoms due to Alzheimer's disease and frontotemporal dementia.

A fourth embodiment of a fourth aspect of the present invention is the use of the first embodiment of the fourth aspect wherein the disorder is a substance abuse disorder selected from stimulant use disorder, stimulant withdrawal, alcohol use disorder, alcohol withdrawal, tobacco use disorder, tobacco withdrawal, opioid use disorder, opioid withdrawal, cannabis use disorder, sedative use disorder, hypnotic use disorder and anxiolytic use disorder.

A fifth embodiment of a fourth aspect of the present invention is the use of the first embodiment of the fourth aspect wherein the disorder is a depressive disorder selected from major depressive disorder, persistent depressive disorder, bipolar disorder and premenstrual dysphoric disorder.

A sixth embodiment of a fourth aspect of the present invention is the use of the first embodiment of the fourth aspect wherein the disorder is an anxiety disorder selected from social anxiety disorder, obsessive-compulsive disorder, specific phobia disorder, panic disorder and generalized anxiety disorder.

A seventh embodiment of a fourth aspect of the present invention is the use of the first embodiment of the fourth aspect wherein the disorder being treated is a trauma and stressor related disorder which is posttraumatic stress disorder.

The present invention also provides compositions (e.g., pharmaceutical compositions) comprising a novel compound of Formula I (including a pharmaceutically acceptable salt thereof) as described in the second aspect of the invention. Accordingly, in one embodiment, the invention provides a pharmaceutical composition comprising a therapeutically effective amount of a novel compound of Formula I (or a pharmaceutically acceptable salt thereof) and optionally comprising a pharmaceutically acceptable carrier. In one further embodiment, the invention provides a pharmaceutical composition comprising a therapeutically effective amount of a compound of Formula I (or a pharmaceutically acceptable salt thereof), optionally comprising a pharmaceutically acceptable carrier and, optionally, at least one additional medicinal or pharmaceutical agent (such as a medication used in the treatment of addiction, a medication used in the treatment of an impulse control disorder or an antipsychotic agent or anti-schizophrenia agent or an anti-Parkinson's agent or an anti-Alzheimer's agent as described herein). In one embodiment, the additional medicinal or pharmaceutical agent is a medication used in the treatment of addiction. In another embodiment the additional medicinal or pharmaceutical agent is a medication used in the treatment of an impulse control disorder. In yet another embodiment the additional medicinal or pharmaceutical agent is an anti-schizophrenia agent as described herein. In yet another embodiment the additional medicinal or pharmaceutical agent is a medication used in the treatment or prevention of cognitive decline or an agent used to aid cognition.

The pharmaceutically acceptable carrier may comprise any conventional pharmaceutical carrier or excipient. Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid, may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration, the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulation, solution or suspension, for parenteral injection as a sterile solution, suspension or emulsion, for topical administration as an ointment or cream, or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages. One of ordinary skill in the art would appreciate that the composition may be formulated in sub-therapeutic dosage such that multiple doses are envisioned.

In one embodiment the composition comprises a therapeutically effective amount of a compound of Formula I (or a pharmaceutically acceptable salt thereof) and a pharmaceutically acceptable carrier.

Compounds of Formula I (including pharmaceutically acceptable salts thereof) are kappa opioid modulators. In some embodiments, a compound of Formula I is a kappa opioid antagonist [i.e., binding (having affinity for) and deactivating kappa opioid receptors]. As used herein, when referencing to a compound, the term "kappa opioid modulator" or "kappa opioid antagonist" refers to a compound that is a kappa opioid receptor modulator or a kappa opioid receptor antagonist, respectively (i.e., not necessarily entirely selective between/among subtypes of opioid receptors; for example, the compound may be selective, or even highly selective, for the kappa opioid receptor but may not be entirely so, particularly with respect to the closely related mu opioid receptor).

Administration of the compounds of Formula I may be affected by any method that enables delivery of the compounds to the site of action. These methods include, for example, enteral routes (e.g., oral routes, buccal routes, sublabial routes, sublingual routes), intranasal routes, inhaled routes, intraduodenal routes, parenteral injection (including intravenous, subcutaneous, intramuscular, intravascular or infusion), intrathecal routes, epidural routes, intracerebral routes, intracerebroventricular routes, topical routes, and rectal administration.

In one embodiment of the present invention, the compounds of Formula I may be administered by oral routes.

Dosage regimens may be adjusted to provide the optimum desired response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specifications for the dosage unit forms of the invention are dictated by a variety of factors, such as the unique characteristics of the therapeutic agent and the particular therapeutic or prophylactic effect to be achieved. In one embodiment of the present invention, the compounds of Formula I may be used to treat humans.

It is to be noted that dosage values may vary with the type and severity of the condition to be alleviated, and may include single or multiple doses. It is to be further understood that for any particular subject, specific dosage regimens should be adjusted over time according to the individual's need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose escalation as determined by the skilled artisan. Determining appropriate dosages and regimens for administration of the chemotherapeutic agent is well known in the relevant art and would be understood to be encompassed by the skilled artisan once provided the teachings disclosed herein.

The amount of the compound of Formula I or a pharmaceutically acceptable salt thereof administered will be dependent on the subject being treated, the severity of the disorder or condition, the rate of administration, the disposition of the compound and the discretion of the prescribing physician. Generally, an effective dosage is in the range of about 0.0001 to about 50 mg per kg body weight per day, for example about 0.01 to about 10 mg/kg/day, in single or divided doses. For a 70 kg human, this would amount to about 0.007 mg to about 3500 mg/day, for example about 0.7 mg to about 700 mg/day. In some instances, dosage levels below the lower limit of the aforesaid range may be more than adequate, while in other cases still larger doses may be employed without causing any harmful side effect, provided that such larger doses are first divided into several small doses for administration throughout the day.

As used herein, the term "combination therapy" refers to the administration of a compound of Formula I or a pharmaceutically acceptable salt thereof together with at least one additional pharmaceutical or medicinal agent (e.g., a medication used in the treatment of drug addiction, Parkinson's disease, Alzheimer's disease or an anti-schizophrenia agent), either sequentially or simultaneously.

The present invention includes the use of a combination of a compound of Formula I (or a pharmaceutically acceptable salt thereof) and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formula I or a pharmaceutically acceptable salt of the compound; (b) a second pharmaceutically active agent; and (c) a pharmaceutically acceptable carrier, vehicle or diluent.

The compound of Formula I (including a pharmaceutically acceptable salt thereof) is optionally used in combination with another active agent. Such an active agent may be, for example, a compound to treat addiction, an atypical antipsychotic or an anti-Parkinson's disease agent or an anti-Alzheimer's agent. Accordingly, another embodiment of the invention provides methods of treating a kappa opioid mediated disorder (e.g., a neurological and psychiatric disorder associated with the kappa opioid receptor), comprising administering to a mammal an effective amount of a compound of Formula I (including a pharmaceutically acceptable salt of the compound) and further comprising administering another active agent. Various pharmaceutically active agents may be selected for use in conjunction with the compounds of Formula I (including pharmaceutically acceptable salts thereof), depending on the disease, disorder, or condition to be treated. Pharmaceutically active agents that may be used in combination with the compositions of the present invention include, without limitation:

(i) acetylcholinesterase inhibitors such as donepezil hydrochloride (ARICEPT, MEMAC); or Adenosine $A_{2A}$ receptor antagonists such as Preladenant (SCH 420814) or SCH 412348;

(ii) amyloid-β (or fragments thereof), such as $A\beta_{1-15}$ conjugated to pan HLA DR-binding epitope (PADRE) and ACC-001 (Elan/Wyeth);

(iii) antibodies to amyloid-β (or fragments thereof), such as bapineuzumab (also known as AAB-001) and AAB-002 (Wyeth/Elan);

(iv) amyloid-lowering or -inhibiting agents (including those that reduce amyloid production, accumulation and fibrillization) such as colostrinin and bisnorcymserine (also known as BNC);

(v) alpha-adrenergic receptor agonists such as clonidine (CATAPRES);

(vi) beta-adrenergic receptor blocking agents (beta blockers) such as carteolol;

(vii) anticholinergics such as amitriptyline (ELAVIL, ENDEP);

(viii) anticonvulsants such as carbamazepine (TEGRETOL, CARBATROL);

(ix) antipsychotics, such as lurasidone (also known as SM-13496; Dainippon Sumitomo);
(x) calcium channel blockers such as nilvadipine (ESCOR, NIVADIL);
(xi) catechol O-methyltransferase (COMT) inhibitors such as tolcapone (TASMAR);
(xii) central nervous system stimulants such as caffeine;
(xiii) corticosteroids such as prednisone (STERAPRED, DELTASONE);
(xiv) dopamine receptor agonists such as apomorphine (APOKYN);
(xv) dopamine receptor antagonists such as tetrabenazine (NITOMAN, XENAZINE, dopamine D2 antagonists such as Quetiapine); dopamine D3 antagonists or partial agonists such as BP 897, PG 619, YQA14, RGH 188 (cariprazine), [$^3$H]LS-3-134, SB277011A, GSK598809, Buspirone (Buspar®), NGB 2904, CJB 090, PG01037, PG 622, R-PG 648, BAK 2-66, S33138, BP1.4979, SR 21502;
(xvi) dopamine reuptake inhibitors such as nomifensine maleate (MERITAL);
(xvii) gamma-aminobutyric acid (GABA) receptor agonists such as baclofen (LIORESAL, KEMSTRO);
(xviii) histamine 3 ($H_3$) antagonists such as ciproxifan;
(xix) immunomodulators such as glatiramer acetate (also known as copolymer-1; COPAXONE);
(xx) immunosuppressants such as methotrexate (TREXALL, RHEUMATREX);
(xxi) interferons, including interferon beta-1a (AVONEX, REBIF) and interferon beta-1b (BETASERON, BETAFERON);
(xxii) levodopa (or its methyl or ethyl ester), alone or in combination with a DOPA decarboxylase inhibitor (e.g., carbidopa (SINEMET, CARBILEV, PARCOPA));
(xxiii) N-methyl-D-aspartate (NMDA) receptor antagonists such as memantine (NAMENDA, AXURA, EBIXA);
(xxiv) monoamine oxidase (MAO) inhibitors such as selegiline (EMSAM);
(xxv) muscarinic receptor (particularly M1 subtype) agonists such as bethanechol chloride (DUVOID, URECHOLINE);
(xxvi) neuroprotective drugs such as 2,3,4,9-tetrahydro-1H-carbazol-3-one oxime;
(xxvii) nicotinic receptor agonists such as epibatidine;
(xxviii) norepinephrine (noradrenaline) reuptake inhibitors such as atomoxetine (STRATTERA);
(xxix) phosphodiesterase (PDE) inhibitors, for example, PDE9 inhibitors such as BAY 73-6691 (Bayer AG) and PDE 10 (e.g., PDE10A) inhibitors such as papaverine;
(xxx) other PDE inhibitors including (a) PDE1 inhibitors (e.g., vinpocetine), (b) PDE2 inhibitors (e.g., erythro-9-(2-hydroxy-3-nonyl)adenine (EHNA)), (c) PDE4 inhibitors (e.g., rolipram), and (d) PDE5 inhibitors (e.g., sildenafil (VIAGRA, REVATIO));
(xxxi) quinolines such as quinine (including its hydrochloride, dihydrochloride, sulfate, bisulfate and gluconate salts);
(xxxii) β-secretase inhibitors such as WY-25105;
(xxxiii) γ-secretase inhibitors such as LY-411575 (Lilly);
(xxxiv) serotonin (5-hydroxytryptamine) 1A ($5-HT_{1A}$) receptor antagonists such as spiperone;
(xxxv) serotonin (5-hydroxytryptamine) 4 ($5-HT_4$) receptor agonists such as PRX-03140 (Epix);
(xxxvi) serotonin (5-hydroxytryptamine) 6 ($5-HT_6$) receptor antagonists such as mianserin (TORVOL, BOLVIDON, NORVAL);
(xxxvii) serotonin (5-HT) reuptake inhibitors such as alaproclate, citalopram (CELEXA, CIPRAMIL);
(xxxviii) trophic factors, such as nerve growth factor (NGF), basic fibroblast growth factor (bFGF; ERSOFERMIN), neurotrophin-3 (NT-3), cardiotrophin-1, brain-derived neurotrophic factor (BDNF), neublastin, meteorin, and glial-derived neurotrophic factor (GDNF), and agents that stimulate production of trophic factors, such as propentofylline;
and the like.
(xxxix) medications used in the treatment of various drug addictions such as methadone, buprenorphine (Suboxone® and Subutex®), naloxone (Narcan®, Evzio®), naltrexone (ReVia®), Levo-alpha Acetyl Methadol (LAAM), bupropion (Wellbutrin®, Buproban®, Aplenzin®, Budeprion®, Zyban®), varenicline (Chantix®), nicotine patches or gums, acamprosate (Campral®), disulfiram (Antabuse®) and topiramate (Topamax®).

In addition to the description provided above, particular classes of antidepressants that can be used in combination with the compounds of the invention include norepinephrine reuptake inhibitors, selective serotonin reuptake inhibitors (SSRIs), NK-1 receptor antagonists, monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, and atypical antidepressants. Suitable norepinephrine reuptake inhibitors include tertiary amine tricyclics and secondary amine tricyclics. Examples of suitable tertiary amine tricyclics and secondary amine tricyclics include amitriptyline, clomipramine, doxepin, imipramine, trimipramine, dothiepin, butriptyline, iprindole, lofepramine, nortriptyline, protriptyline, amoxapine, desipramine and maprotiline. Examples of suitable selective serotonin reuptake inhibitors include fluoxetine, fluvoxamine, paroxetine, and sertraline. Examples of monoamine oxidase inhibitors include isocarboxazid, phenelzine, and tranylcyclopramine. Examples of suitable reversible inhibitors of monoamine oxidase include moclobemide. Examples of suitable serotonin and noradrenaline reuptake inhibitors of use in the present invention include venlafaxine. Examples of suitable atypical antidepressants include bupropion, lithium, nefazodone, trazodone and viloxazine. Examples of anti-Alzheimer's agents include Dimebon, NMDA receptor antagonists such as memantine; and cholinesterase inhibitors such as donepezil and galantamine. Examples of suitable classes of anti-anxiety agents that can be used in combination with the compounds of the invention include benzodiazepines and serotonin 1A ($5-HT_{1A}$) agonists or antagonists, especially 5-HT1A partial agonists, and corticotropin releasing factor (CRF) antagonists. Suitable benzodiazepines include alprazolam, chlordiazepoxide, clonazepam, chlorazepate, diazepam, halazepam, lorazepam, oxazepam, and prazepam. Suitable $5-HT_{1A}$ receptor agonists or antagonists include buspirone, flesinoxan, gepirone, and ipsapirone. Suitable atypical antipsychotics include paliperidone, bifeprunox, ziprasidone, risperidone, aripiprazole, olanzapine, and quetiapine. Suitable nicotine acetylcholine agonists include ispronicline, varenicline and MEM 3454. Anti-pain agents include pregabalin, gabapentin, clonidine, neostigmine, baclofen, midazolam, ketamine and ziconotide. Examples of suitable anti-Parkinson's disease agents include L-DOPA (or its methyl or ethyl ester), a DOPA decarboxylase inhibitor (e.g., carbidopa (SINEMET, CARBILEV, PARCOPA), an Adenosine $A_{2A}$ receptor antagonist [e.g., Preladenant (SCH 420814) or SCH 412348], benserazide (MADOPAR), α-methyldopa, monofluoromethyldopa, difluoromethyldopa, brocresine, or m-hydroxybenzylhydrazine), a dopamine agonist [such as apomorphine (APOKYN), bromocriptine (PARLODEL), cabergoline (DOSTINEX), dihydrexidine, dihydroergocryptine, fenoldopam (CORLOPAM), lisuride (DOPERGIN), pergolide (PERMAX), piribedil (TRIVASTAL, TRASTAL), pramipexole (MIRAPEX), quinpirole, ropinirole (REQUIP), rotigotine (NEUPRO), SKF-82958 (GlaxoSmithKline), and sarizotan], a monoamine oxidase (MAO) inhibitor [such as selegiline (EMSAM), selegiline hydrochloride (L-deprenyl, ELDEPRYL, ZELAPAR), dimethylselegilene, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), CHF-3381 (Chiesi Farmaceutici), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL)], a catechol O-methyltransferase (COMT) inhibitor [such as tolcapone (TASMAR), entacapone (COMTAN), and tropolone], an N-methyl-D-aspartate (NMDA) receptor antagonist [such as amantadine (SYMMETREL)], anticholinergics [such as amitriptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANSDERM-SCOP), scopolamine methylbromide (PARMINE), dicycloverine (BENTYL, BYCLOMINE, DIBENT, DILOMINE, tolterodine (DETROL), oxybutynin (DITROPAN, LYRINEL XL, OXYTROL), penthienate bromide, propantheline (PRO-BANTHINE), cyclizine, imipramine hydrochloride (TOFRANIL), imipramine maleate (SURMONTIL), lofepramine, desipramine (NORPRAMIN), doxepin (SINEQUAN, ZONALON), trimipramine (SURMONTIL), and glycopyrrolate (ROBINUL)], or a combination thereof. Examples of anti-schizophrenia agents include ziprasidone, risperidone, olanzapine, quetiapine, aripiprazole, asenapine, blonanserin, or iloperidone. Some additional active agent examples include rivastigmine (Exelon), Clozapine, Levodopa, Rotigotine, Aricept, Methylphenidate, memantine, milnacipran, guanfacine, bupropion, and atomoxetine.

As noted above, the compounds of Formula I (including pharmaceutically acceptable salts thereof) may be used in combination with one or more additional agents which are described herein. When a combination therapy is used, the one or more additional agents may be administered sequentially or simultaneously with the compound of the invention. In one embodiment, the additional agent is administered to a mammal (e.g., a human) prior to administration of the compound of the invention. In another embodiment, the additional agent is administered to the mammal after administration of the compound of the invention. In another embodiment, the additional agent is administered to the mammal (e.g., a human) simultaneously with the administration of the compound of the invention or a pharmaceutically acceptable salt thereof.

The invention also provides a pharmaceutical composition for the treatment of a substance abuse disorder (such as an addiction) in a mammal, including a human, which comprises an amount of a compound of Formula I (or a pharmaceutically acceptable salt thereof), as defined above (including hydrates, solvates and polymorphs of said compound or pharmaceutically acceptable salts thereof), in combination with one or more (for example one to three) medications used in the treatment of addiction such as methadone, buprenorphine, naloxone, naltrexone, levo-alpha-acetylmethadol (LAAM), bupropion, varenicline, nicotine patches or gums, acamprosate, disulfiram and topiramate, wherein the amounts of the active agent and the combination when taken as a whole are therapeutically effective for treating the addiction. The selection of the additional agents used in the pharmaceutical composition may be targeted to the particular substance disorder (such as addiction(s)) being treated.

The invention also provides a pharmaceutical composition for the treatment of impulse control disorders (including disorders such as intermittent explosive disorder, kleptomania, pathological gambling, pyromania, trichotillomania and dermatillomania) in a mammal, including a human, which comprises an amount of a compound of Formula I (or a pharmaceutically acceptable salt thereof), as defined above (including hydrates, solvates and polymorphs of said compound or pharmaceutically acceptable salts thereof), in combination with one or more (for example one to three) agents used to treat impulse control disorders such as clomipramine, selective serotonin reuptake inhibitors (SSRIs), pimozide, anticonvulsants such as topiramate, anti-psychotics and anti-anxiolytics such as benzodiazepines, wherein the amounts of the active agent and the combination when taken as a whole are therapeutically effective for treating the particular impulse control disorder(s).

It will be understood that the compounds of Formula I depicted above are not limited to a particular stereoisomer (e.g., enantiomer or atropisomer) shown, but also include all stereoisomers and mixtures thereof.

The compounds of the invention, or their pharmaceutically acceptable salts, may be prepared by a variety of methods that are analogously known in the art. The reaction Schemes described below, together with synthetic methods known in the art of organic chemistry, or modifications and derivatizations that are familiar to those of ordinary skill in the art, illustrate methods for preparing the compounds. Others, including modifications thereof, will be readily apparent to one skilled in the art.

The starting materials used herein are commercially available or may be prepared by routine methods known in the art (such as those methods disclosed in standard reference books such as the COMPENDIUM OF ORGANIC SYNTHETIC METHODS, Vol. I-XIII (published by Wiley-Interscience)). Preferred methods include, but are not limited to, those described below.

The reactions for preparing compounds of the invention can be carried out in suitable solvents, which can be readily selected by one of skill in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Via consideration of the particular reaction step, suitable solvents for a particular reaction step can be selected by the skilled artisan.

During any of the following synthetic sequences, it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999; and T. W. Greene and P. G. M. Wuts, Protective Groups in Organic Chemistry, John Wiley & Sons, 2007, which are hereby incorporated by reference.

Compounds of the present invention or the pharmaceutically acceptable salts of said compounds or tautomers and radioisotopes, can be prepared according to the reaction Schemes discussed herein below. Unless otherwise indicated, the substituents in the Schemes are defined as above. Isolation and purification of the products is accomplished by standard procedures, which are known to a chemist of ordinary skill.

One skilled in the art will recognize that in some cases, the compounds in Schemes 1 through 5 will be generated as a mixture of diastereomers and/or enantiomers; these may be separated at various stages of the synthetic Scheme using conventional techniques or a combination of such techniques, such as, but not limited to, crystallization, normal-phase chromatography, reversed-phase chromatography and chiral chromatography, to afford the single enantiomers of the invention.

It will be understood by one skilled in the art that the various symbols, superscripts and subscripts used in the Scheme, methods and examples are used for convenience of representation and/or to reflect the order in which they are introduced in the Scheme, and are not intended to necessarily correspond to the symbols, superscripts or subscripts in the appended claims. The Schemes are representative of methods useful in synthesizing the compounds of the present invention. It is to be understood that they are not to constrain the scope of the invention in any way.

It is understood to those skilled in the art that some protecting groups cannot withstand some of the reaction conditions described in the reaction schemes below. Therefore, some protecting group manipulations may be required in order to adequately complete the syntheses. Due to the multitude of protection-deprotection possibilities, these manipulations will not be expressly described.

General Synthetic Schemes

The compounds of Formula I may be prepared by the methods described below, together with synthetic methods known in the art of organic chemistry, or modifications and transformations that are familiar to those of ordinary skill in the art. The starting materials used herein are commercially available or may be prepared by routine methods known in the art [such as those methods disclosed in standard reference books such as the *Compendium of Organic Synthetic Methods*, Vol. I-XII (published by Wiley-Interscience)]. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of Formula I, or their pharmaceutically acceptable salts, can be prepared according to the reaction Schemes discussed herein below. Unless otherwise indicated, the substituents in the Schemes are defined as above.

Isolation and purification of the products is accomplished by standard procedures, which are known to a chemist of ordinary skill.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. Additionally, one skilled in the art will recognize that in many cases, these compounds will be mixtures and enantiomers that may be separated at various stages of the synthetic schemes using conventional techniques, such as, but not limited to, crystallization, normal-phase chromatography, reverse phase chromatography and chiral chromatography, to afford single enantiomers. The schemes are representative of methods useful in synthesizing the compounds of the present invention. They are not to constrain the scope of the invention in any way.

Scheme 1 refers to the preparation of compounds of Formula I. Referring to Scheme 1a, compounds II and III can be combined via a standard reductive amination procedure using a standard reductant, for example but not limited to sodium triacetoxyborohydride, in a standard solvent, for example but not limited to dichloromethane, to form compounds of Formula I. In certain instances, compounds of Formula II are single enantiomers IIa (Scheme 1b) or IIb (Scheme 1b), and lead to the preparation of single enantiomers of compounds of Formula I, either Ia or Ib. In certain instances the racemic compounds of Formula I are separated into single enantiomers Ia or Ib in an additional chiral separation step.

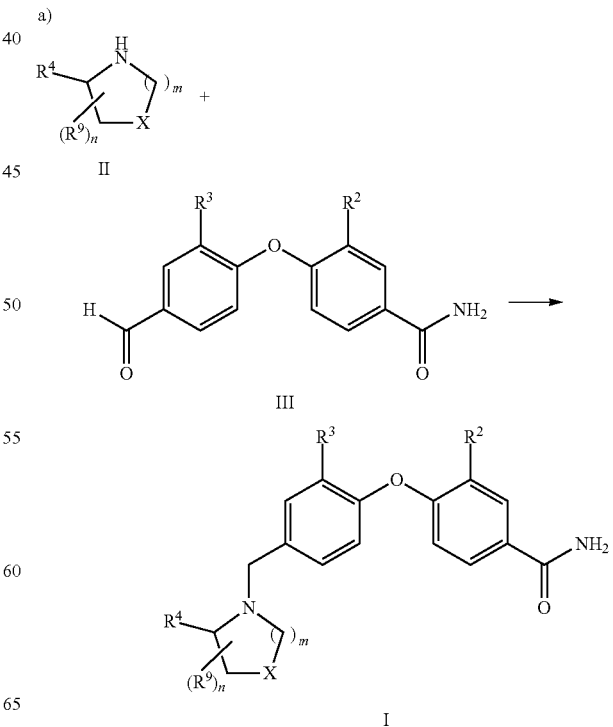

Scheme 1

-continued

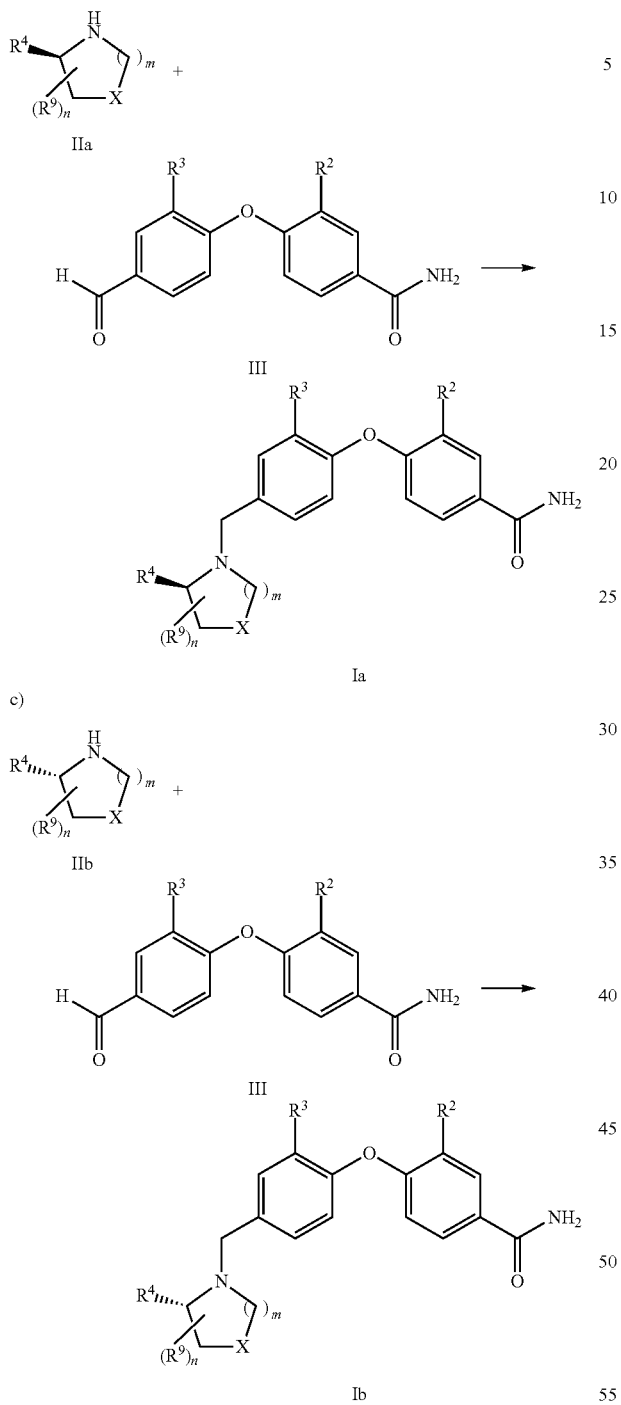

Ia

Ib

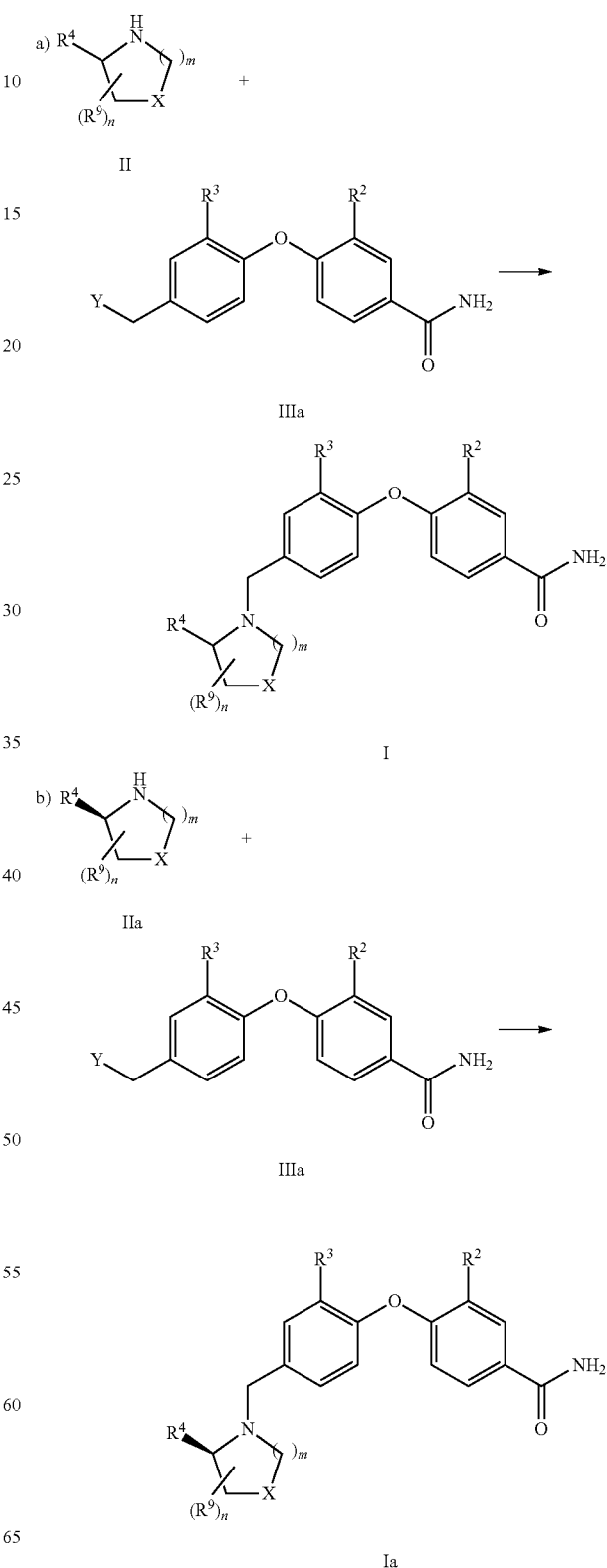

Scheme 2

I

Ia of Formula I, either Ia or Ib. In certain instances the racemic compounds of Formula I are separated into single enantiomers Ia or Ib in an additional chiral separation step.

Scheme 2 represents an alternative synthesis for the preparation of compounds of Formula I. Referring to Scheme 2a, compounds II and IIIa, where Y=Cl, Br, I, mesolyate or tosylate can be combined via a standard amine alkylation procedure using a standard base, for example but not limited to potassium carbonate, in a standard solvent, for example but not limited to DMF, to form compounds of Formula I. In certain instances, compounds of Formula II are single enantiomers IIa (Scheme 2b) or IIb (Scheme 2b), and lead to the preparation of single enantiomers of compounds -continued

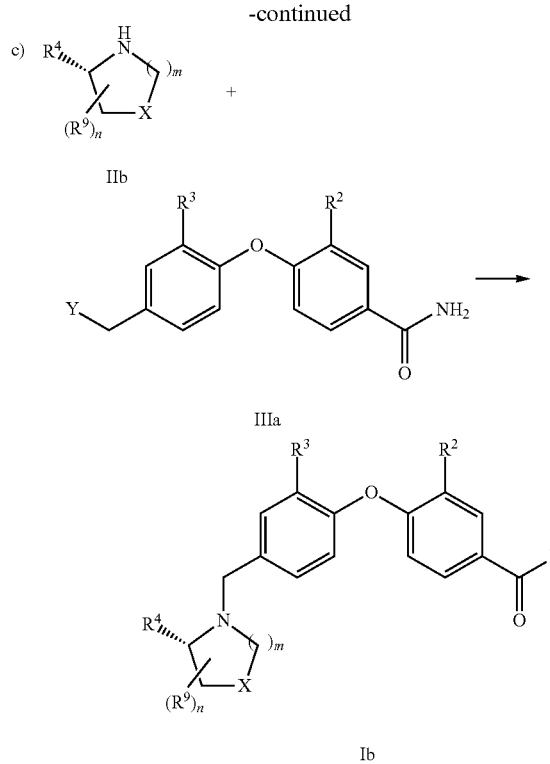

Ib

Scheme 3 refers to the preparation of compounds Ic. Compounds II and VI can be combined to form compounds of Formula V via a standard reductive amination procedure using a standard reductant, for example but not limited to sodium triacetoxyborohydride, in a standard solvent, for example but not limited to dichloromethane. Treatment of the benzodioxanone compounds V with a solution of ammonia in a suitable solvent, such as but not limited to methanol, forms compounds of Formula Ic. In some instances compounds of Formula Ic were separated into single enantiomers in an additional chiral separation step. In an analogous manner to Scheme 2, compounds of Formula Ic can also be constructed via a standard amine alkylation procedure.

Scheme 3

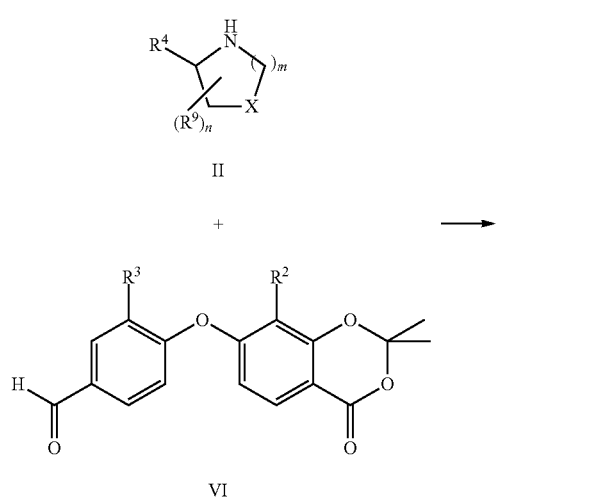

-continued

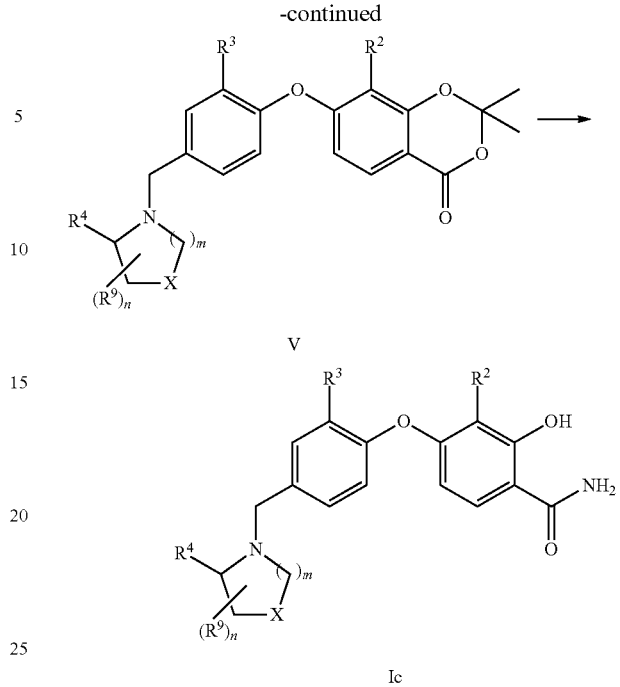

Ic

Compounds of Formula II are made through several different processes. Scheme 4 refers to the preparation of a subset of compounds of Formula II, including specifically compounds of Formula IIc. Compounds of the Formula VII, wherein Y=Br or I, and $R^{7'}$ can be defined herein as $R^7$, can be metallated via, for example but not limited to, treatment with n-butyllithium or isopropyl magnesium chloride, to afford an appropriately metallated pyrazole of Formula VIII. Treatment with appropriately selected protected gamma lactam of Formula IX affords compounds of Formula X. Protecting group $P^1$ in this case refers to groups well known to those skilled in the art for amine protection. For example, $P^1$ may be a tert-butoxycarbonyl (BOC), which can be cleaved via acidic conditions in an appropriate solvent, including but not limited to treatment with a solution of HCl in dioxane. Alternatively $P^1$ may be one of many other protecting groups suitable for amines, including carboxybenzyl (Cbz) or benzoyl group (Bz) and can be cleaved under standard conditions known to one skilled in the art. Deprotection of compounds of Formula X affects cyclization to 3,4-dihydropyrroles of Formula XI. Compounds of Formula IIc are then prepared by reduction of compound XI with a reducing agent, such as, but not limited to, sodium borohydride, in a solvent such as, but not limited to, methanol.

Scheme 4

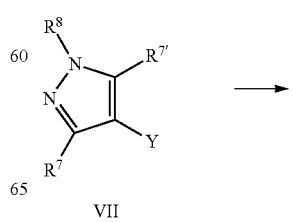

VII

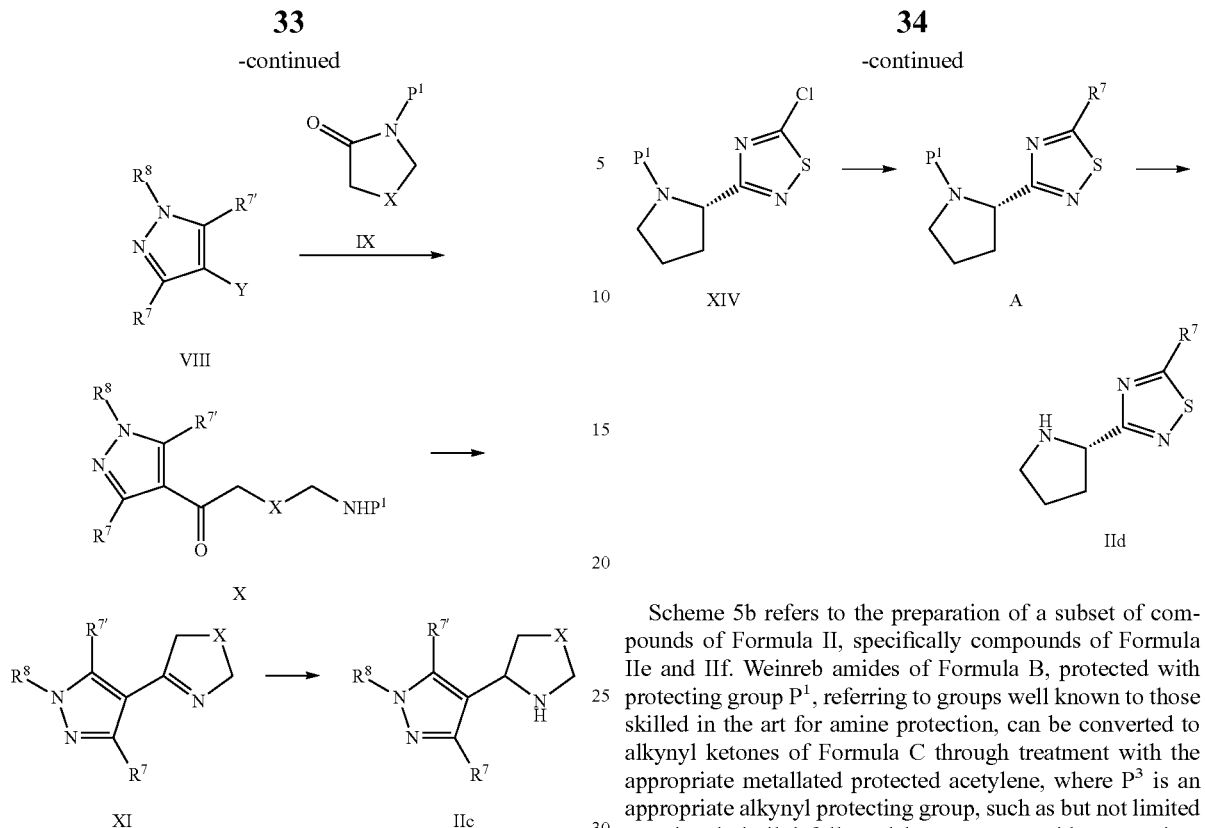

Scheme 5a refers to the preparation of a subset of compounds of Formula II, specifically compounds of Formula IId. Cyano-substituted pyrrolidines of Formula XII, protected with protecting group $P^1$, referring to groups well known to those skilled in the art for amine protection (see above), can be converted to carboximidamides of Formula XIII through treatment with sodium methoxide followed by treatment with ammonium chloride. Condensation of compounds of Formula XIII with trichloro(chlorosulfanyl) methane under basic conditions, for example but not limited to a mixture of N,N-diisopropylethlamine in DCM, affords chloro thiadiazoles of Formula XIV. Conversion of chloro thiadiazoles of Formula XIV to the corresponding protected alkyl thiadiazole of Formula A can be affected via a transition metal-catalyzed cross-coupling reaction, such as but not limited to the palladium-catalyzed Suzuki reaction. Protected alkyl thiadiazole of Formula A can then be appropriately deprotected by methods well known to those skilled in the art of amine deprotection to afford pyrazoles of the Formula IId.

Scheme 5b refers to the preparation of a subset of compounds of Formula II, specifically compounds of Formula IIe and IIf. Weinreb amides of Formula B, protected with protecting group $P^1$, referring to groups well known to those skilled in the art for amine protection, can be converted to alkynyl ketones of Formula C through treatment with the appropriate metallated protected acetylene, where $P^3$ is an appropriate alkynyl protecting group, such as but not limited to, trimethyl silyl followed by treatment with ammonium chloride. Condensation of compounds of Formula C with an appropriate alkyl hydrazine affords both pyrazole isomers of protected pyrrolidines of Formula D. Conversion of compounds of Formula D to the corresponding pyrrolidines of Formula IIe and IIf can be affected via deprotection methods well known to those skilled in the art of amine deprotection.

Scheme 5b

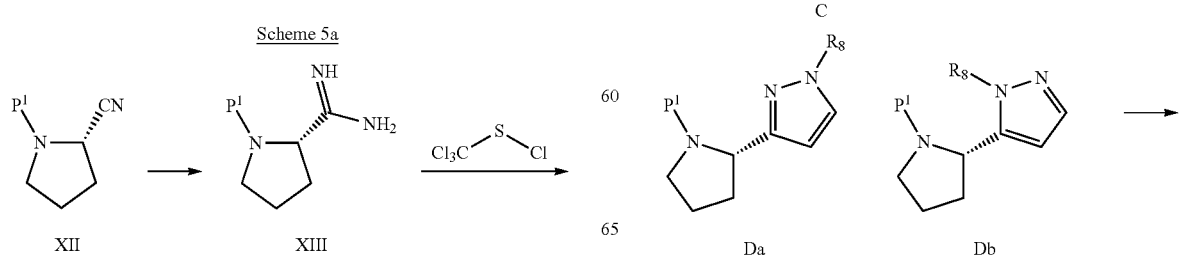

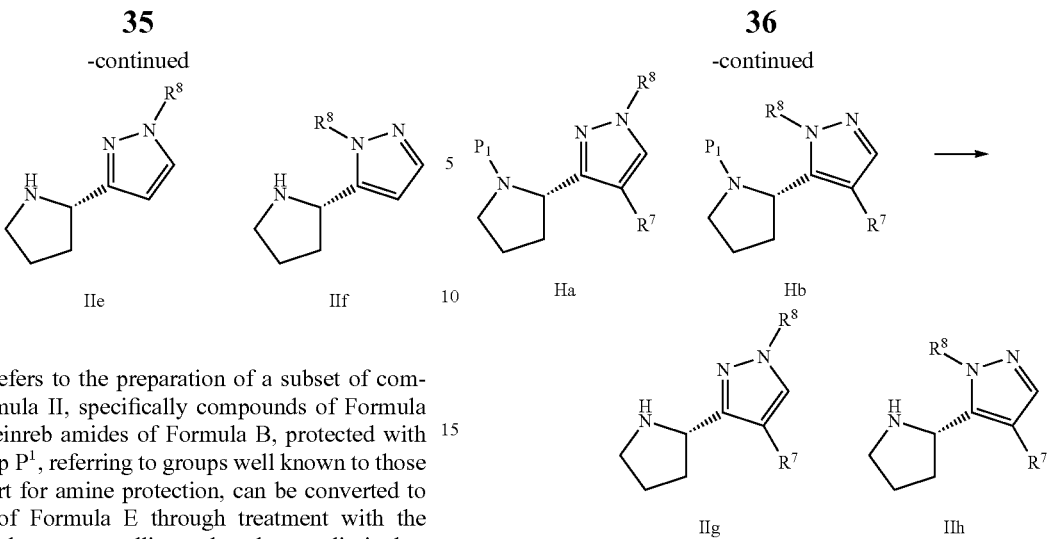

Scheme 5c refers to the preparation of a subset of compounds of Formula II, specifically compounds of Formula IIg and IIh. Weinreb amides of Formula B, protected with protecting group $P^1$, referring to groups well known to those skilled in the art for amine protection, can be converted to alkyl ketones of Formula E through treatment with the appropriate ethyl organometallic, such as but not limited to, alkyl Grignard reagents, followed by treatment with ammonium chloride. Treatment of compounds of Formula E with N,N-dimethyl formamide dimethyl acetal affords enamines of Formula F. Condensation of enamines of Formula F with hydrazine affords protected pyrrolidines of Formula G. Alkylation of compounds of Formula G, using standard alkylating agents, such as but not limited to alkyl iodides, in the presence of a base, such as but not limited to sodium hydride, affords isomeric protected pyrrolidines of Formula H. In some instances this step may be omitted when compounds where $R^8$ is H are desired. Deprotection of pyrrolidines of Formula H can be affected via deprotection methods well known to those skilled in the art of amine deprotection to afford pyrrolidines of Formula IIg and IIh.

Scheme 6 refers to the preparation of a subset of compounds of Formula II, specifically compounds of Formula IIc. The scheme starts with a pyrazole aldehyde of Formula XV, where $R^{8'}$ is either a $C_1$-$C_6$ alkyl group or a protecting group $P^2$, for example but not limited to, benzyl, which can be removed using palladium on carbon in the presence of hydrogen gas, for example. Imines of Formula XVI can be generated by reaction of aldehydes of Formula XV with prop-2-en-1-amine (allyl amine) in an appropriate solvent such as dichloromethane. Addition of a vinyl Grignard reagent and trapping with an appropriate amine protecting group $P^1$, referring to groups well known to those skilled in the art for amine protection, results in a bis-olefinic amine of Formula XVII. Ring closing metathesis, utilizing for example but not limited to Grubbs' second generation catalyst benzylidene[1,3-bis(2,4,6-trimethylphenyl)imidazolidin-2-ylidene]dichloro(tricyclohexylphosphine)ruthenium, affords the 2,5-dihydropyrrole pyrazole of Formula XVIII. Pyrrolidines of Formula XIX can be prepared via the reduction of compound XVIII with a reducing agent such as, but not limited to, palladium on carbon in the presence of triethylsilane. Final deprotection either of $P^1$ alone affords compounds of Formula IIc; in the instances where $R^{8'}$ is a protecting group, $R^8$ in compound IIe is a hydrogen once a second deprotection step is performed.

Scheme 5c

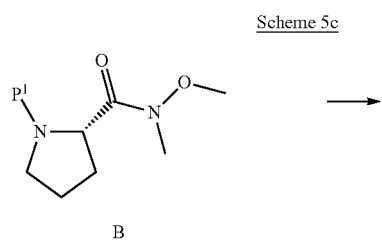

B

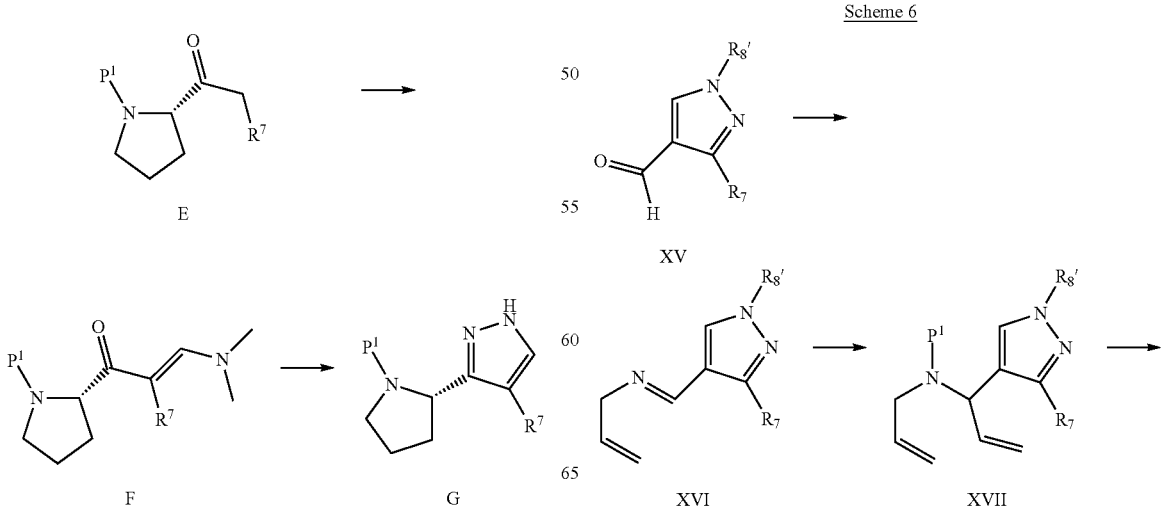

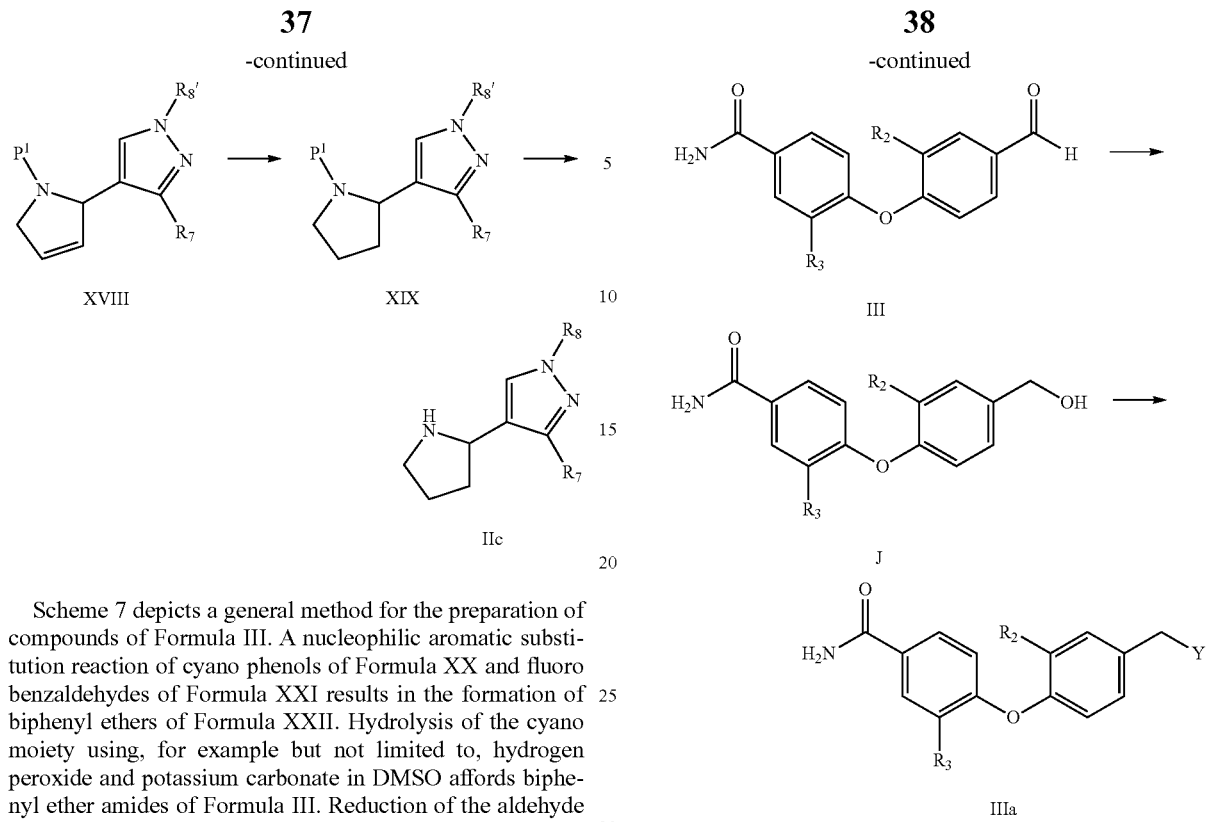

Scheme 7 depicts a general method for the preparation of compounds of Formula III. A nucleophilic aromatic substitution reaction of cyano phenols of Formula XX and fluoro benzaldehydes of Formula XXI results in the formation of biphenyl ethers of Formula XXII. Hydrolysis of the cyano moiety using, for example but not limited to, hydrogen peroxide and potassium carbonate in DMSO affords biphenyl ether amides of Formula III. Reduction of the aldehyde in amides of Formula III can be accomplished using standard reducing agents such as but not limited to sodium borohydride to afford alcohols of Formula J. In some instances, treatment of alcohols of Formula J with a halogenating agent such as but not limited to thionyl chloride in the case where Y=Cl, provides benzyl halides (Y=Cl, Br or I) of Formula IIIa. Alternatively, treatment of alcohols of Formula J with the appropriate sulfonyl chloride or anhydride in the presence of a base, such as but not limited to diisopropyl ethyl amine, can provide sulfonates (Y=mesolate or tolsylate) of Formula IIIb.

Scheme 8 refers to the general method for the preparation of compounds of Formula VI. Protection of the a 2,4-dihydroxycarboxylic acid of Formula XXIII to generate compounds of Formula XXIV can be afforded through treatment with, for example, acetone and trifluoroacetic anhydride in the presence of trifluoroacetic acid. A nucleophilic aromatic substitution reaction of compounds of Formulae XXIV and XXV results in the formation of biphenyl ethers of the Formula VI.

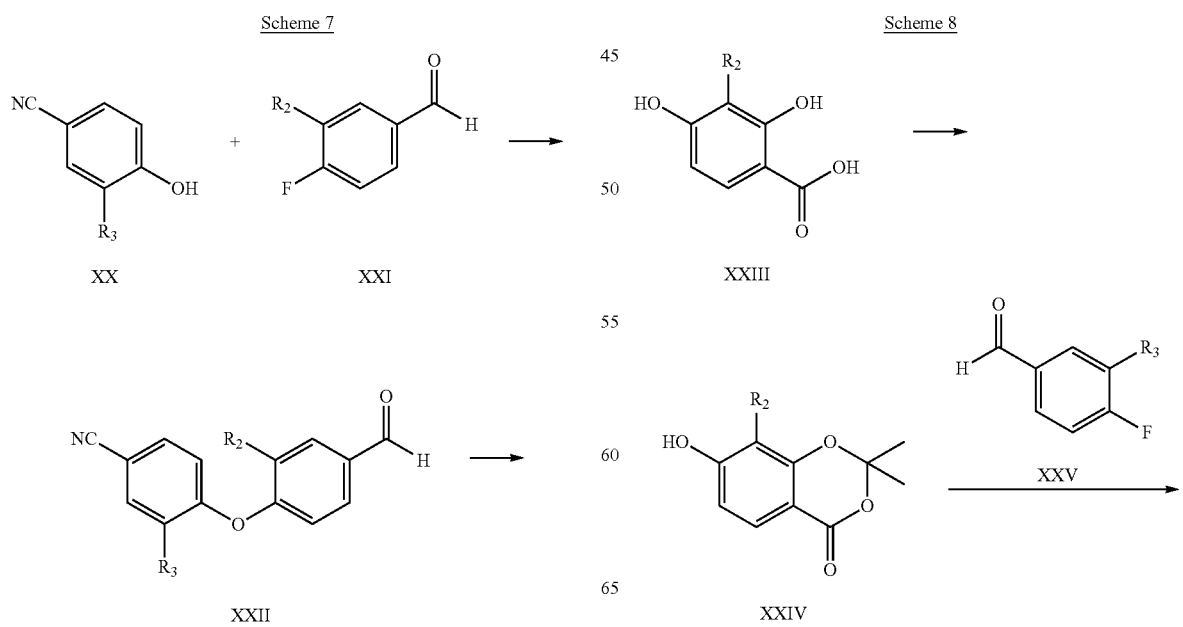

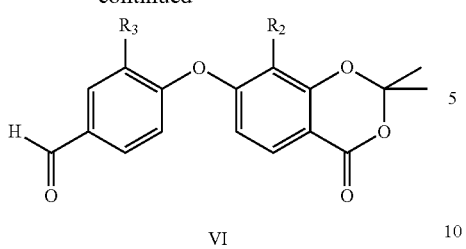

VI

Alternatively, one skilled in the art could envision preparing compounds of Formula I via the solvolysis of compounds of Formula K as depicted in Scheme 9, where water would be the appropriate nucleophile for the synthesis of compounds of Formula Ka and Kb, and ammonia would be the appropriate nucleophile for the synthesis of compounds of Formula Kc.

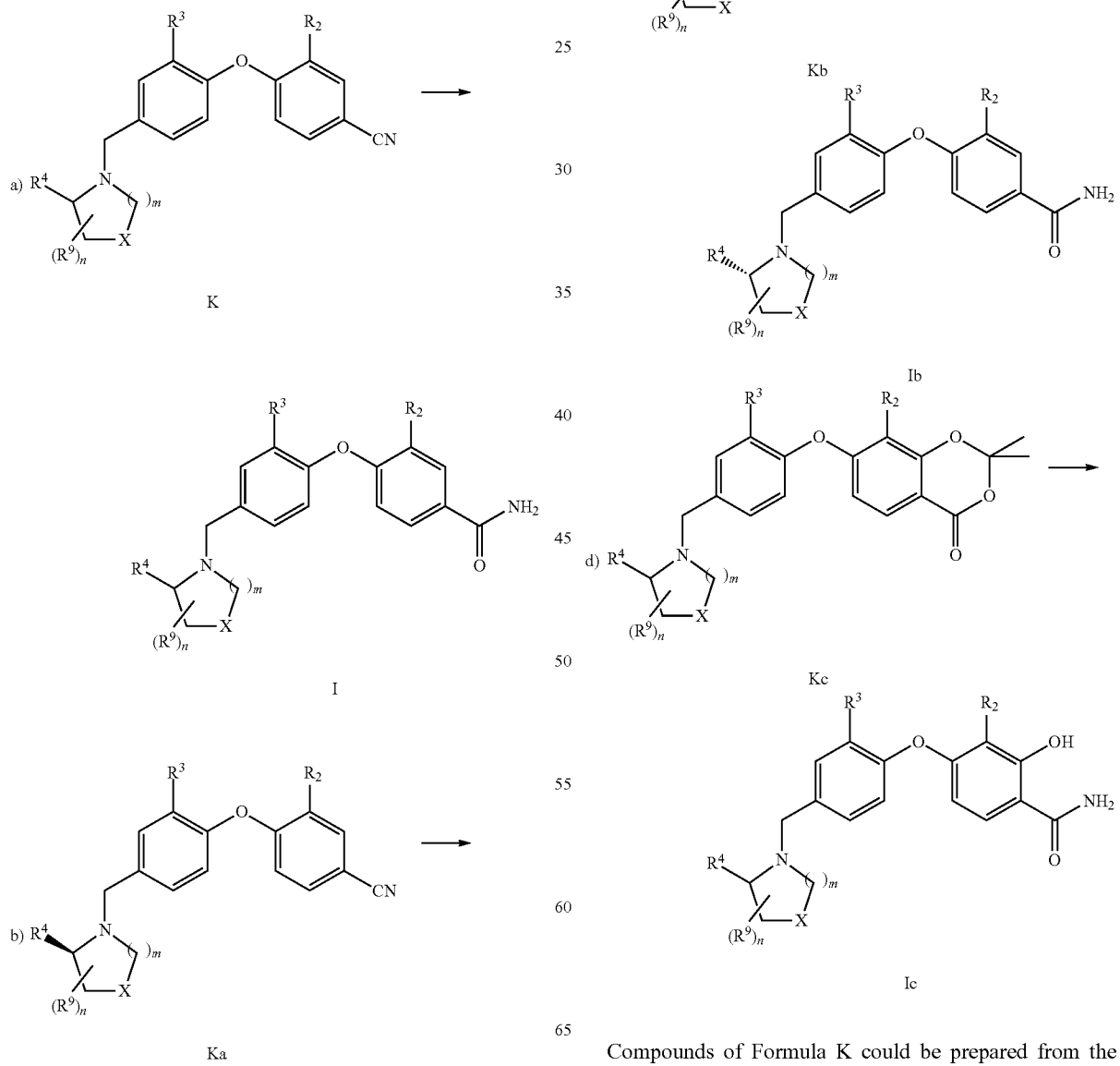

Compounds of Formula K could be prepared from the base-promoted nucleophilic aromatic substitution of fluorobenzylnitriles of Formula L and hydroxy benzlamines of Formulae IV as depicted in Scheme 10. Also compounds of Formula Kc could be prepared from the nucleophilic aromatic substitution of substituted fluororsalicyclic acid derivatives of Formula M with hydroxy benzylamines of Formula IV as depicted in Scheme 11. In either of these cases, the nucleophilic substitution reaction can take place in a solvent such as, but not limited to, DMF and in the presence of a base such as, but not limited to, potassium carbonate.

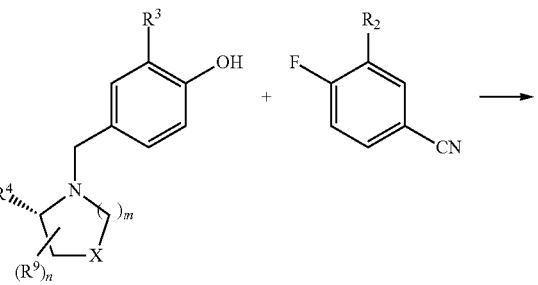

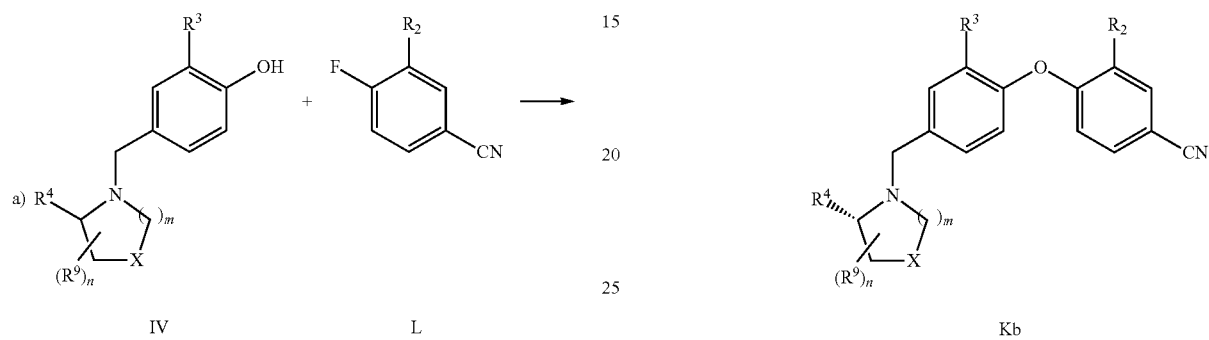

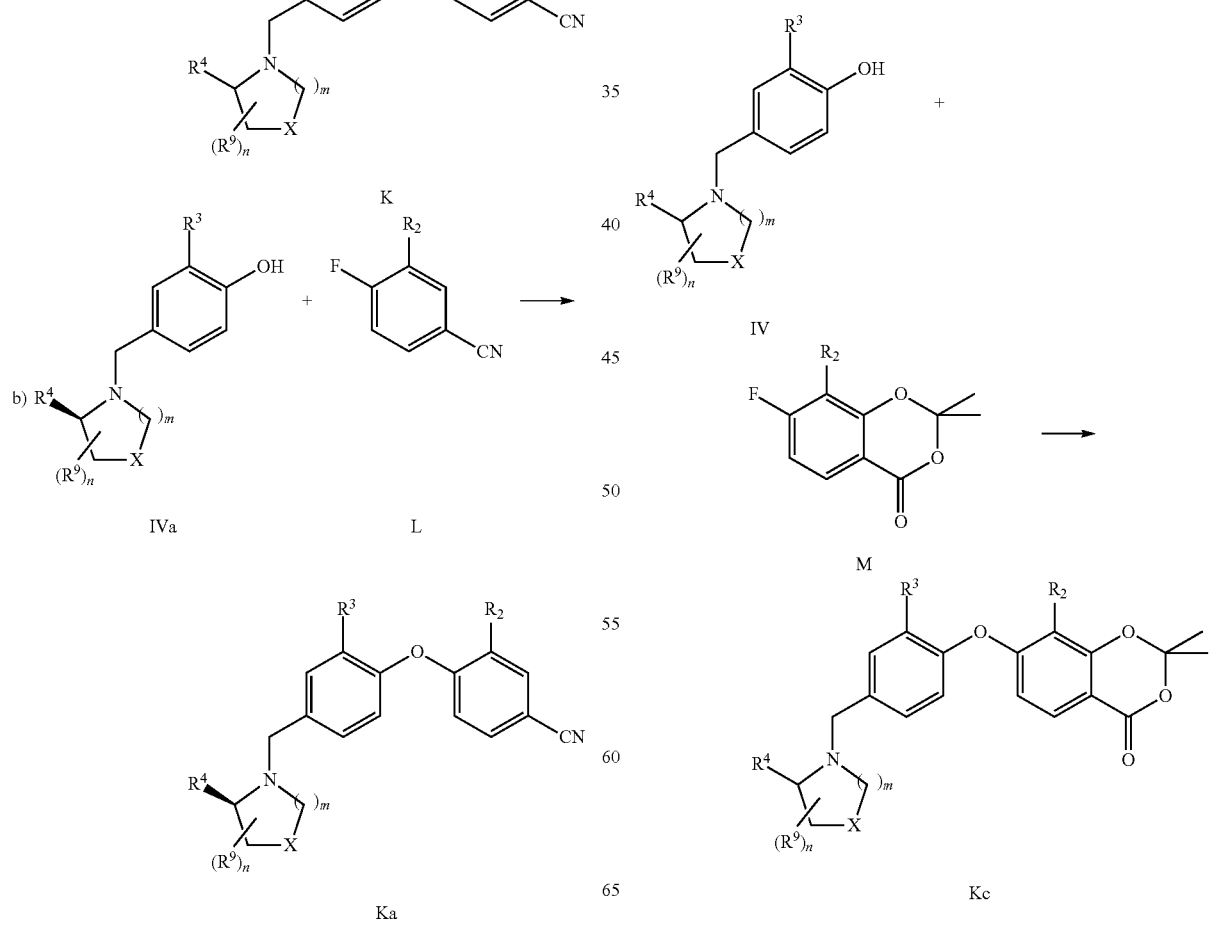

Hydroxybenzyl aminde of Formula IV could be prepared by an individual skilled in the art via reductive amination of amines of Formula II with hydroxybenzaldehydes of Formula N as depicted in Scheme 12. These reactions could take place under standard reductive amination conditions using a reducing agent such as, but not limited to, sodium triacetoxyborohydride, in a solvent such as, but not limited to, dichloromethane.

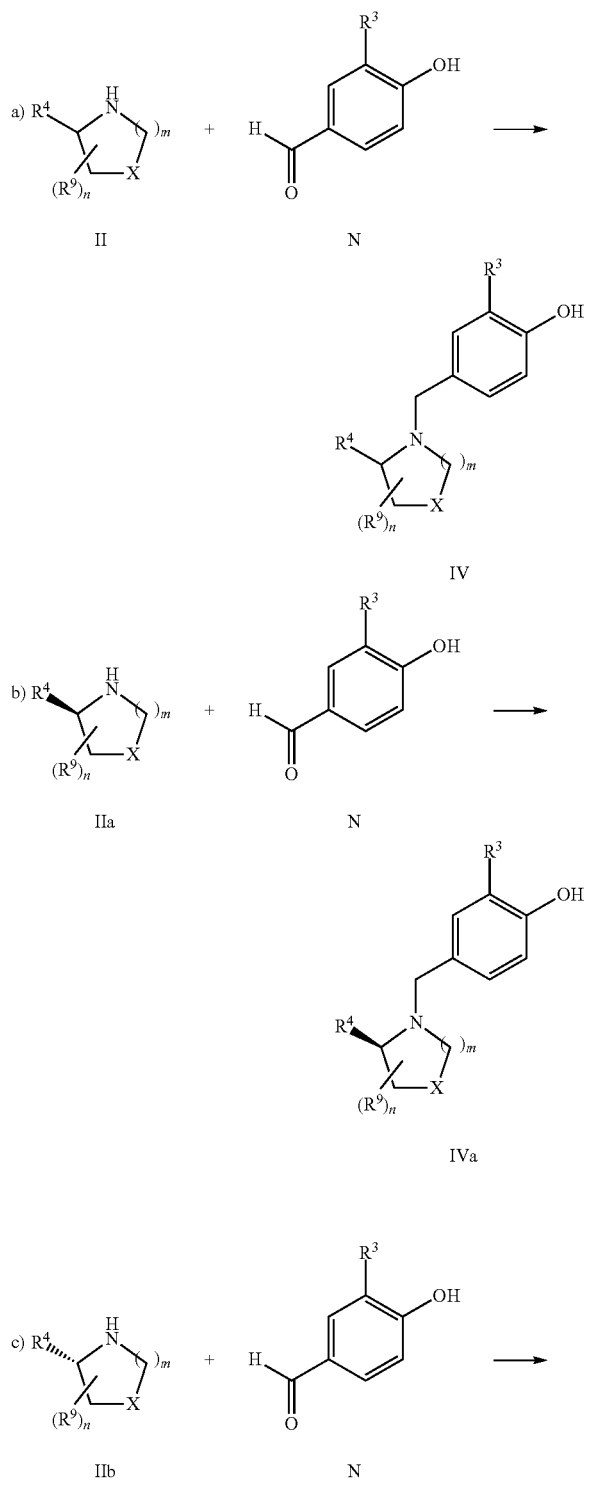

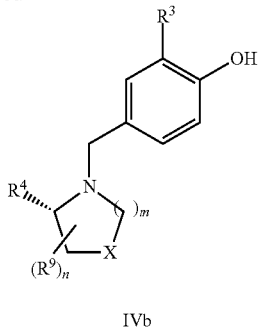

As used herein, the term "reacting" (or "reaction" or "reacted") refers to the bringing together of designated chemical reactants such that a chemical transformation takes place generating a compound different from any initially introduced into the system. Reactions can take place in the presence or absence of solvent.

Compounds of Formula I may exist as stereoisomers, such as atropisomers, racemates, enantiomers, or diastereomers. Conventional techniques for the preparation/isolation of individual enantiomers include chiral synthesis from a suitable optically pure precursor or resolution of the racemate using, for example, chiral high-performance liquid chromatography (HPLC) or chiral supercritical fluid chromatography. Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of Formula I (and chiral precursors thereof) may be obtained in enantiomerically enriched form using chromatography, typically HPLC, on an asymmetric resin with a mobile phase consisting of a hydrocarbon, typically heptane or hexane, containing from 0% to 50% 2-propanol, typically from 2% to 20%, and from 0% to 5% of an alkylamine, typically 0.1% diethylamine. Concentration of the eluate affords the enriched mixture. Stereoisomeric conglomerates may be separated by conventional techniques known to those skilled in the art. See, e.g., *Stereochemistry of Organic Compounds* by E. L. Eliel and S. H. Wilen (Wiley, New York, 1994), the disclosure of which is incorporated herein by reference in its entirety. Suitable stereoselective techniques are well known to those of ordinary skill in the art.

Where a compound of Formula I contains an alkenyl or alkenylene (alkylidene) group, geometric cis/trans (or Z/E) isomers are possible. Cis/trans isomers may be separated by conventional techniques well known to those skilled in the art, for example, chromatography and fractional crystallization. Salts of the present invention can be prepared according to methods known to those of skill in the art.

The compounds of Formula I that are basic in nature are capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the basic compounds of this invention can be prepared by treating the basic compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, isonicotinic acid, lactic acid, pantothenic acid, ascorbic acid, 2,5-dihydroxybenzoic acid, gluconic acid, saccharic acid, formic acid, methanesulfonic acid, ethanesulfonic acid, benzenesulfonic acid, p-toluenesulfonic acid, and pamoic [i.e., 4,4'-methanediylbis(3-hydroxynaphthalene-2-carboxylic acid)] acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as ethanesulfonic acid, or the like.

Those compounds of Formula I that are acidic in nature are capable of forming base salts with various pharmacologically acceptable cations. Examples of such salts include the alkali metal or alkaline earth metal salts, and particularly the sodium and potassium salts. These salts are all prepared by conventional techniques. The chemical bases which are used as reagents to prepare the pharmaceutically acceptable base salts of this invention are those which form non-toxic base salts with the acidic compounds of Formula I. These salts may be prepared by any suitable method, for example, treatment of the free acid with an inorganic or organic base, such as an amine (primary, secondary or tertiary), an alkali metal hydroxide or alkaline earth metal hydroxide, or the like. These salts can also be prepared by treating the corresponding acidic compounds with an aqueous solution containing the desired pharmacologically acceptable cations, and then evaporating the resulting solution to dryness, for example under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are, for example, employed in order to ensure completeness of reaction and maximum yields of the desired final product.

Pharmaceutically acceptable salts of compounds of Formula I may be prepared by one or more of three methods:
(i) by reacting the compound of Formula I with the desired acid or base;
(ii) by removing an acid- or base-labile protecting group from a suitable precursor of the compound of Formula I or by ring-opening a suitable cyclic precursor, for example, a lactone or lactam, using the desired acid or base; or
(iii) by converting one salt of the compound of Formula I to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionized to almost non-ionized.

Polymorphs can be prepared according to techniques well-known to those skilled in the art, for example, by crystallization.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture may have almost identical physical properties, they may have different physical properties compared to the true racemate. Racemic mixtures may be separated by conventional techniques known to those skilled in the art—see, for example, *Stereochemistry of Organic Compounds* by E. L. Eliel and S. H. Wilen (Wiley, New York, 1994).

The invention also includes isotopically labeled compounds of Formula I wherein one or more atoms is replaced by an atom having the same atomic number, but an atomic mass or mass number different from the atomic mass or mass number usually found in nature. Isotopically labeled compounds of Formula I (or pharmaceutically acceptable salts thereof or N-oxides thereof) can generally be prepared by conventional techniques known to those skilled in the art or by processes analogous to those described herein, using an appropriate isotopically labeled reagent in place of the non-labeled reagent otherwise employed.

The compounds of Formula I should be assessed for their biopharmaceutical properties, such as solubility and solution stability (across pH), permeability, etc., in order to select the most appropriate dosage form and route of administration for treatment of the proposed indication. Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form. Pharmaceutical compositions suitable for the delivery of compounds of the present invention (or pharmaceutically acceptable salts thereof) and methods for their preparation will be readily apparent to those skilled in the art. Such compositions and methods for their preparation may be found, for example, in *Remington's Pharmaceutical Sciences,* 19th Edition (Mack Publishing Company, 1995).

The compounds of the invention (including pharmaceutically acceptable salts thereof and N-oxides thereof) may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast-dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropyl methylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet. The compounds of the invention may also be used in fast-dissolving, fast-disintegrating dosage forms such as those described by Liang and Chen, *Expert Opinion in Therapeutic Patents* 2001, 11, 981-986.

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methylcellulose, microcrystalline cellulose, lower alkyl-substituted hydroxypropyl cellulose, starch, pregelatinized starch and sodium alginate. Generally, the disintegrant will comprise from 1 weight % to 25 weight %, for example, from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulfate. Lubricants generally comprise from 0.25 weight % to 10 weight %, for example, from 0.5 weight % to 3 weight % of the tablet.

Other possible ingredients include anti-oxidants, colorants, flavoring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt-congealed, or extruded before tabletting. The final formulation may comprise one or more layers and may be coated or uncoated; it may even be encapsulated.

The formulation of tablets is discussed in *Pharmaceutical Dosage Forms: Tablets*, Vol. 1, by H. Lieberman and L. Lachman (Marcel Dekker, New York, 1980).

Consumable oral films for human or veterinary use are typically pliable water-soluble or water-swellable thin-film dosage forms which may be rapidly dissolving or mucoadhesive and typically comprise a compound of Formula I, a film-forming polymer, a binder, a solvent, a humectant, a plasticizer, a stabilizer or emulsifier, a viscosity-modifying agent and a solvent. Some components of the formulation may perform more than one function.

The compound of Formula I (or pharmaceutically acceptable salts thereof) may be water-soluble or insoluble. A water-soluble compound typically comprises from 1 weight % to 80 weight %, more typically from 20 weight % to 50 weight %, of the solutes. Less soluble compounds may comprise a smaller proportion of the composition, typically up to 30 weight % of the solutes. Alternatively, the compound of Formula I may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavorings and flavor enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high-energy dispersions and osmotic and coated particles are to be found in Verma et al., *Pharmaceutical Technology On-line*, 25(2), 1-14 (2001). The use of chewing gum to achieve controlled release is described in WO 00/35298.

The compounds of the invention (including pharmaceutically acceptable salts thereof) may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (for example to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of Formula I (including pharmaceutically acceptable salts thereof) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(DL-lactic-coglycolic acid) (PLGA) microspheres.

The compounds of the invention (including pharmaceutically acceptable salts thereof) may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated. See e.g., Finnin and Morgan, *J. Pharm. Sci.* 1999, 88, 955-958.

Other means of topical administration include delivery by electroporation, iontophoresis, phonophoresis, sonophoresis and microneedle or needle-free (e.g., Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention (including pharmaceutically acceptable salts thereof) can also be administered intranasally or by inhalation, typically in the form of a dry powder (either alone; as a mixture, for example, in a dry blend with lactose; or as a mixed component particle, for example, mixed with phospholipids, such as phosphatidylcholine) from a dry powder inhaler, as an aerosol spray from a pressurized container, pump, spray, atomizer (for example an atomizer using electrohydrodynamics to produce a fine mist), or nebulizer, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or hydroxypropyl methylcellulose), blisters and cartridges for use in an inhaler or insufflator may be formulated to contain a powder mix of the compound of the invention, a suitable powder base such as lactose or starch and a performance modifier such as L-leucine, mannitol, or magnesium stearate. The lactose may be anhydrous or in the form of the monohydrate. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 μg to 20 mg of the compound of the invention per actuation and the actuation volume may vary from 1 μL to 100 μL. A typical formulation may comprise a compound of Formula I or a pharmaceutically acceptable salt thereof, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 0.01 to 100 mg of the compound of Formula I. The overall daily dose will typically be in the range 1 μg to 200 mg, which may be administered in a single dose or, more usually, as divided doses throughout the day.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention (including pharmaceutically acceptable salts thereof) may also be administered directly to the eye or ear, typically in the form of drops of a micronized suspension or solution in isotonic, pH-adjusted, sterile saline. Other formulations suitable for ocular and aural administration include ointments, gels, biodegradable (e.g., absorbable gel sponges, collagen) and non-biodegradable (e.g., silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropyl methylcellulose, hydroxyethyl cellulose, or methylcellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention (including pharmaceutically acceptable salts thereof) may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e., as a carrier, diluent, or solubilizer. Most commonly used for these purposes are alpha-, beta- and gamma-cyclodextrins, examples of which may be found in International Patent Applications Nos. WO 91/11172, WO 94/02518 and WO 98/55148.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of Formula I, a prodrug thereof, or a salt of such compound or prodrug, and a second compound as described above. The kit comprises means for containing the separate compositions such as a container, a divided bottle or a divided foil packet. Typically the kit comprises directions for the administration of the separate components. The kit form is particularly advantageous when the separate components are for example administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. In some embodiments, the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, etc. . . . Second Week, Monday, Tuesday, . . . " etc. Other variations of memory aids will be readily apparent. A "daily dose" can be a single tablet or capsule or several pills or capsules to be taken on a given day. Also, a daily dose of the Formula I compound can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. For example, the dispenser is equipped with a memory aid, so as to further facilitate compliance with the regimen. An example of such a memory aid is a mechanical counter which indicates the number of daily doses that has been dispensed. Another example of such a memory aid is a battery-powered microchip memory coupled with a liquid crystal readout, or audible reminder signal which, for example, reads out the date that the last daily dose has been taken and/or reminds one when the next dose is to be taken.

Experimental Procedures

The following illustrate the synthesis of various compounds of the present invention. Additional compounds within the scope of this invention may be prepared using the methods illustrated in these Examples, either alone or in combination with techniques generally known in the art. Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate, generally AcroSeal® products from Acros Organics, Aldrich® Sure/Seal™ from Sigma-Aldrich, or DriSolv® products from EMD Chemicals. In other cases, commercial solvents were passed through columns packed with 4 Å molecular sieves, until the following QC standards for water were attained: a) <100 ppm for dichloromethane, toluene, N,N-dimethylformamide and tetrahydrofuran; b) <180 ppm for methanol, ethanol, 1,4-dioxane and diisopropylamine. For very sensitive reactions, solvents were further treated with metallic sodium, calcium hydride or molecular sieves, and distilled just prior to use. Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. In some examples, chiral separations were carried out to separate enantiomers of certain compounds of the invention (in some examples, the separated enantiomers are designated as ENT-1 and ENT-2, according to their order of elution). In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer. Racemic compounds are indicated by the presence of (+/−) adjacent to the structure; in these cases, any indicated stereochemistry represents the relative (rather than absolute) configuration of the compound's substituents.

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary. In general, reactions were followed by thin-layer chromatography or mass spectrometry, and subjected to work-up when appropriate. Purifications may vary between experiments: in general, solvents and the solvent ratios used for eluents/gradients were chosen to provide appropriate $R_f$s or retention times. All starting materials in these Preparations and Examples are either commercially available or can be prepared by methods known in the art or as described herein.

The following are abbreviations which may appear in the experimental procedures described herein:

9-BBN=9-borabicyclo[3.3.1]nonane; BF$_3$.Et$_2$O=boron trifluoride diethyl etherate; BINAP=1,1'-binaphthalene-2,2'-diylbis(diphenylphosphane); Boc=tert-butoxycarbonyl; br=broad; n-BuLi=n-butyllithium; t-BuONa=sodium tert-butoxide; t-ButylXPhos=di-tert-butyl[2',4',6'-tri(propan-2-yl)biphenyl-2-yl]phosphane; Bz=benzoyl; CDCl$_3$=deuterochloroform; CD$_3$OD=deuteromethanol; CF$_3$COOH=trifluoroacetic acid; d=doublet; dd=doublet of doublets; ddd=doublet of doublet of doublets; DBU=1,8-diazabicyclo[5.4.0]undec-7-ene; DCM=dichloromethane; DEPT=distortionless enhancement of polarization transfer; DMB=(2,4-dimethoxyphenyl)methyl; dppf=1,1'-bis(diphenylphosphino)ferrocene; EDC or EDCI=1-[3-(dimethylamino)propyl]-3-ethylcarbodiimide hydrochloride; EtOAc=ethyl acetate; EtOH=ethanol; g=gram; GCMS=gas chromatography-mass spectrometry; h=hour; H$_2$O=water; HATU=O-(7-azabenzotriazol-1-yl)-N,N,N',N'-tetramethyluronium hexafluorophosphate; HCl=hydrochloric acid or hydrogen chloride; HPLC=high-performance liquid chromatography; Hz=hertz; K$_2$CO$_3$=potassium carbonate; KF=potassium fluoride; kg=kilogram; L=liter; LCMS=liquid chromatography mass spectrometry; m=multiplet; M=molar; m-CPBA=3-chloroperoxybenzoic acid; MeOH=methanol; mg=milligram; MHz=megahertz; min=minutes; mL=milliliter; μL=microliter; mmol=millimole; pmol=micromole; Mo(CO)$_6$=molybdenum hexacarbonyl; mol=mole; MPa=megapascal; N=normal; N$_2$=nitrogen; NaH=sodium hydride; NaHCO$_3$=sodium bicarbonate; NaOAc=sodium acetate; NaOt-Bu=sodium tert-butoxide; NaOCl=sodium hypochlorite; NaOH=sodium hydroxide; NaOMe=sodium methoxide; Na$_2$SO$_4$=sodium sulfate; NEt$_3$=triethylamine; NH$_4$Cl=ammonium chloride; NH$_2$OH.HCl=hydroxylamine hydrochloride; NMR=nuclear magnetic resonance; NOE=nuclear Overhauser effect; Pd(Amphos)$_2$Cl$_2$=bis[di-tert-butyl(4-dimethylaminophenyl)phosphine] dichloropalladium(II); Pd$_2$(dba)$_3$ tris(dibenzylideneacetone)dipalladium(0); Pd(dppf)Cl$_2$=[1,1'-bis(diphenylphosphino)-ferrocene]dichloropalladium(II); Pd(dtbpf)Cl$_2$=[1,1'-bis(di-tert-butylphosphino)-ferrocene]dichloropalladium(II); Pd(PCy$_3$)$_2$Cl$_2$=dichlorobis(tricyclohexyl-phosphine)palladium(II); PPh$_3$=triphenylphosphine; psi=pounds per square inch; q=quartet; rt=room temperature; s=singlet; T3P=2,4,6-tripropyl-1,3,5,2,4,6-trioxatriphosphinane 2,4,6-trioxide; TBAF=tetrabutylammonium fluoride; TEA=triethylamine; TEA.3HF=triethylamine trihydrofluoride; TFA=trifluoroacetic acid; THF=tetrahydrofuran; TLC=thin-layer chromatography; t=triplet; Xantphos=4,5-bis(diphenylphosphino)-9,9-dimethylxanthene.

Preparation P1: 1,3-Dimethyl-4-(pyrrolidin-2-yl)-1H-pyrazole (P1)

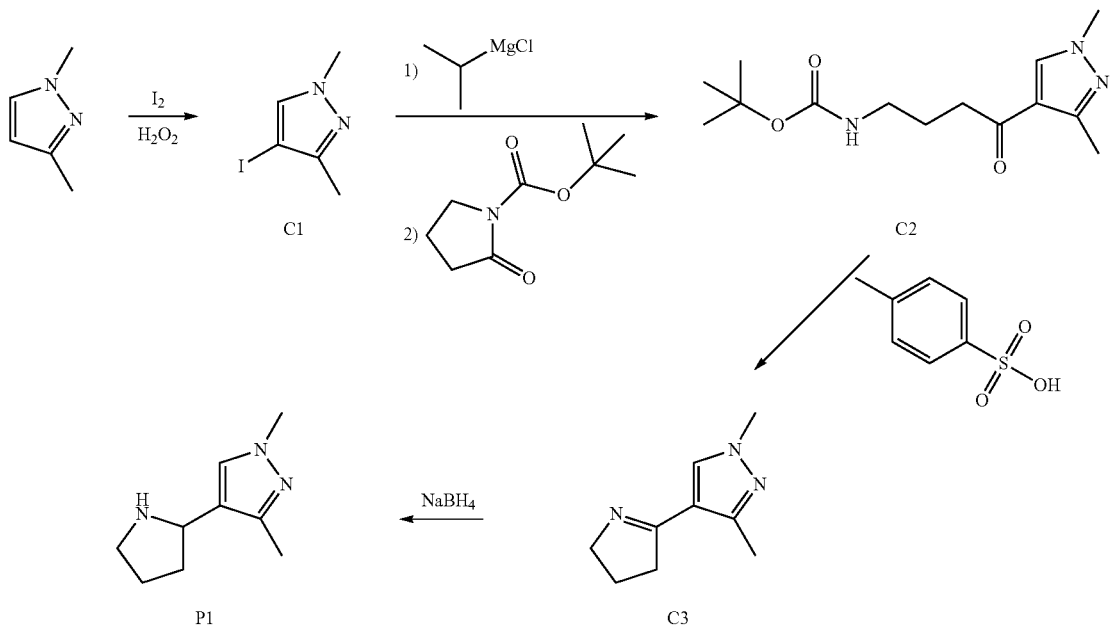

Step 1. Synthesis of 4-iodo-1,3-dimethyl-1H-pyrazole (C1)

Iodine (66 g, 260 mmol) and hydrogen peroxide (30% in water, 35.4 g, 312 mmol) were added to a solution of 1,3-dimethyl-1H-pyrazole (50 g, 520 mmol) in water (500 mL), and the reaction mixture was stirred at 20° C. for 20 hours. Saturated aqueous sodium sulfite solution (100 mL) was then added, and the resulting suspension was extracted with ethyl acetate (2×300 mL). The combined organic layers were washed with saturated aqueous sodium chloride solution (400 mL), dried over sodium sulfate, filtered, and concentrated in vacuo to provide the product as a yellow oil.

Yield: 100 g, 450 mmol, 87%. ¹H NMR (400 MHz, CDCl₃) δ 7.32 (s, 1H), 3.85 (s, 3H), 2.24 (s, 3H).

Step 2. Synthesis of tert-butyl [4-(1,3-dimethyl-1H-pyrazol-4-yl)-4-oxobutyl]carbamate (C2)

A solution of isopropylmagnesium chloride in tetrahydrofuran (2 M, 29.7 mL, 59.4 mmol) was added in a drop-wise manner to a 5° C. solution of C1 (12 g, 54.0 mmol) in tetrahydrofuran (60 mL), at a rate that maintained the internal temperature of the reaction mixture below 10° C. The reaction was allowed to proceed at 5° C., and aliquots were quenched into methanol and analyzed by HPLC to monitor the extent of Grignard formation; once full conversion was observed (~5 to 10 minutes), a solution of tert-butyl 2-oxopyrrolidine-1-carboxylate (11.0 g, 59.4 mmol) in tetrahydrofuran (60 mL) was added drop-wise, again at a rate which maintained the reaction temperature below 10° C. The reaction was monitored by HPLC, and when no additional conversion was observed (~1 hour), it was quenched via careful addition of aqueous acetic acid (10%, 60 mL) and ethyl acetate (100 mL). The organic layer was separated and washed with saturated aqueous sodium chloride solution (2×100 mL), dried over magnesium sulfate, filtered, and concentrated to a mass of 35 g. Heptane (40 mL) was added, to a total volume of approximately 80 mL, and approximately 20 mL of solvent was removed via heating at atmospheric pressure. The mixture was slowly cooled to 20° C., and the resulting thick slurry was allowed to stir overnight at 20° C., whereupon it was filtered. The filter cake was rinsed with cold heptane (0° C., 30 mL) to afford the product as a white solid. Yield: 9.59 g, 34.1 mmol, 63%. ¹H NMR (400 MHz, CDCl₃) δ 7.79 (s, 1H), 4.72-4.58 (br s, 1H), 3.86 (s, 3H), 3.24-3.14 (m, 2H), 2.74 (dd, J=7.3, 7.0 Hz, 2H), 2.48 (s, 3H), 1.95-1.83 (m, 2H), 1.42 (s, 9H).

Step 3. Synthesis of 4-(3,4-dihydro-2H-pyrrol-5-yl)-1,3-dimethyl-1H-pyrazole (C3)

p-Toluenesulfonic acid monohydrate (10.29 g, 54.1 mmol) was added to a solution of C2 (10.0 g, 35.6 mmol) in tetrahydrofuran (100 mL), and the reaction mixture was stirred at 55° C. for 18 hours. It was then treated with aqueous sodium hydroxide solution (3 M, 100 mL) and diluted with dichloromethane (50 mL). The aqueous layer was extracted with dichloromethane (30 mL), and the combined organic layers were dried over magnesium sulfate, filtered, and concentrated in vacuo to provide the product as a colorless oil. Yield: 5.80 g, 35.5 mmol, quantitative. ¹H NMR (400 MHz, CDCl₃) δ 7.58 (s, 1H), 3.99 (tt, J=7.3, 1.8 Hz, 2H), 3.85 (s, 3H), 2.83-2.75 (m, 2H), 2.49 (s, 3H), 2.00-1.90 (m, 2H).

Step 4. Synthesis of 1,3-dimethyl-4-(pyrrolidin-2-yl)-1H-pyrazole (P1)

A solution of C3 (5.80 g, 35.5 mmol) in methanol (58 mL) was cooled to 5° C. and treated with sodium borohydride (1.6 g, 42 mmol). Acetic acid (0.20 mL, 3.5 mmol) was then added {Caution: exotherm} and the reaction mixture was stirred at 5° C. for 1.75 hours, at which time more sodium borohydride (0.40 g, 11 mmol) was added. After a total of 3 hours of reaction time, aqueous sodium hydroxide solution (3 M, 50 mL) was added, followed by dichloromethane (50 mL). The aqueous layer was extracted with dichloromethane (25 mL), and the combined organic layers were dried over magnesium sulfate, filtered, and concentrated in vacuo to afford the product as a pale yellow oil. Yield: 5.45 g, 33.0 mmol, 93%. ¹H NMR (400 MHz, CDCl₃) δ 7.20 (s, 1H), 3.98 (dd, J=8.3, 7.0 Hz, 1H), 3.79 (s, 3H), 3.14 (ddd, J=10.4, 7.9, 5.3 Hz, 1H), 2.94 (ddd, J=10.4, 8.4, 6.8 Hz, 1H), 2.25 (s, 3H), 2.17-2.07 (m, 1H), 1.93-1.8 (m, 2H, assumed; partially obscured by water peak), 1.64-1.53 (m, 1H).

Preparation P2: 1,3-Dimethyl-4-[(2S)-pyrrolidin-2-yl]-1H-pyrazole, Hydrochloride Salt (P2)

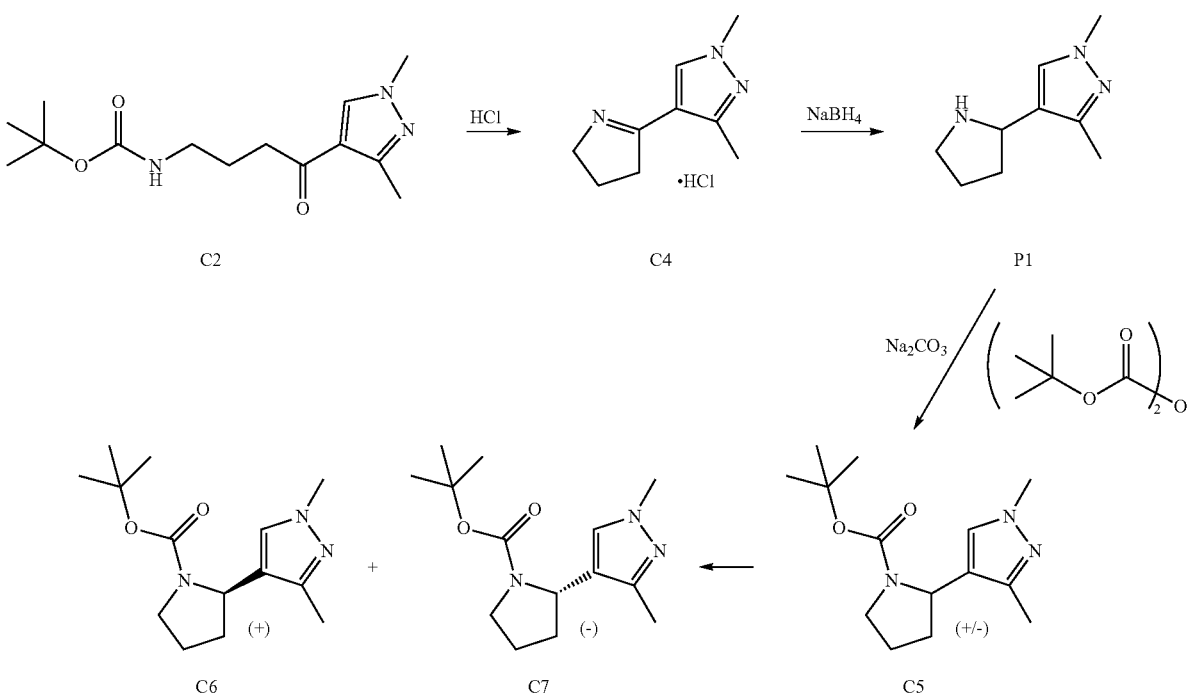

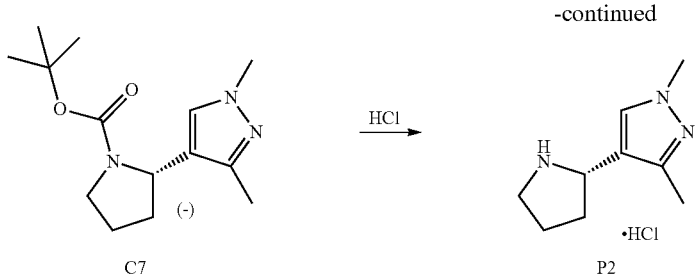

Step 1. Synthesis of 4-(3,4-dihydro-2H-pyrrol-5-yl)-1,3-dimethyl-1H-pyrazole, Hydrochloride Salt (C4)

Three identical reactions were carried out. A solution of hydrogen chloride in 1,4-dioxane (4 M, 1.5 L, 6 mol) was added in a drop-wise manner to a 0° C. solution of C2 (100 g, 0.355 mol) in dichloromethane (500 mL). The reaction mixture was stirred at 25° C. for 6 hours, whereupon the reaction mixtures were combined and concentrated in vacuo, affording the crude product (300 g). This material was taken directly to the following step.

Step 2. Synthesis of 1,3-dimethyl-4-(pyrrolidin-2-yl)-1H-pyrazole (P1)

To a 0° C. solution of C4 (from the previous step; 300 g, 51.06 mol) in methanol (3 L) was added sodium borohydride (299 g, 7.90 mol) over 30 minutes. After the reaction mixture had stirred at 25° C. for 5 hours, it was quenched via addition of saturated aqueous ammonium chloride solution (5 L). The resulting mixture was concentrated under reduced pressure to afford the crude product as a solution, which was used directly in the following step.

Step 3. Synthesis of tert-butyl 2-(1,3-dimethyl-1H-pyrazol-4-yl)pyrrolidine-1-carboxylate (C5)

To a solution of P1 (from the previous step; 51.06 mol) in methanol (1.5 L) was added sodium carbonate (349 g, 3.29 mol). Di-tert-butyl dicarbonate (476 g, 2.18 mol) was then introduced, and the reaction mixture was stirred at 25° C. for 16 hours. Removal of solvent in vacuo provided a yellow oil, which was purified by silica gel chromatography (Eluent: 3:1 petroleum ether/ethyl acetate) to afford the product as a white solid. From analysis of the $^1$H NMR, this material was presumed to exist as a mixture of rotamers. Yield: 125 g, 471 mmol, 44% over 3 steps. LCMS m/z 265.9 [M+H]$^+$. $^1$H NMR (400 MHz, CDCl$_3$) δ 7.02 (s, 1H), 4.97-4.65 (br m, 1H), 3.78 (s, 3H), 3.58-3.37 (br m, 2H), 2.23-2.07 (br m, 1H), 2.21 (s, 3H), 1.98-1.81 (m, 2H), 1.80-1.71 (m, 1H), [1.45 (br s) and 1.30 (br s), total 9H].

Step 4. Isolation of tert-butyl (2R)-2-(1,3-dimethyl-1H-pyrazol-4-yl)pyrrolidine-1-carboxylate (C6) and tert-butyl (2S)-2-(1,3-dimethyl-1H-pyrazol-4-yl)pyrrolidine-1-carboxylate (C7)

Separation of C5 (130 g, 490 mmol) into its component enantiomers was carried out via supercritical fluid chromatography [Column: Phenomenex Lux Cellulose-2, 5 μm; Mobile phase: 85:15 carbon dioxide/(1:1 methanol/acetonitrile)]. The first-eluting product, obtained as a white solid that exhibited a positive (+) rotation, was designated as C6. From analysis of the $^1$H NMR, this material was presumed to exist as a mixture of rotamers. Yield: 55.0 g, 207 mmol, 42%. LCMS m/z 266.5 [M+H]$^+$. $^1$H NMR (400 MHz, CDCl$_3$) δ 7.02 (s, 1H), 4.96-4.64 (br m, 1H), 3.78 (s, 3H), 3.58-3.37 (br m, 2H), 2.22 (s, 3H), 2.2-2.08 (br m, 1H), 1.97-1.81 (m, 2H), 1.80-1.71 (m, 1H), [1.45 (br s) and 1.30 (br s), total 9H].

The second-eluting product, also obtained as a white solid, exhibited a negative (−) rotation, and was designated as C7. From analysis of the $^1$H NMR, this material was presumed to exist as a mixture of rotamers. Yield: 57.8 g, 218 mmol, 44%. LCMS m/z 266.3 [M+H]$^+$. $^1$H NMR (400 MHz, CDCl$_3$) δ 7.00 (s, 1H), 4.94-4.63 (br m, 1H), 3.75 (s, 3H), 3.56-3.35 (br m, 2H), 2.19 (s, 3H), 2.18-2.06 (br m, 1H), 1.96-1.78 (m, 2H), 1.78-1.68 (m, 1H), [1.43 (br s) and 1.28 (br s), total 9H].

By analytical HPLC (Column: Phenomenex Lux Cellulose-2, 4.6×250 mm, 5 μm; Mobile phase A: carbon dioxide; Mobile phase B: 1:1 methanol/acetonitrile; Gradient: 5% B from 0 to 1.00 minute, 5% to 60% B over 8.00 minutes; Flow rate: 3.0 mL/minute), C6 exhibited a retention time of 4.02 minutes. Using the same analytical system, C7 exhibited a retention time of 4.33 minutes. The indicated absolute configurations for C6 and C7 were assigned on the basis of an X-ray structural determination carried out on C6 (see below). Slow crystallization of a sample of C6 from heptane provided the crystal used for the structural determination.

Single-Crystal X-Ray Structural Determination of C6

Single Crystal X-Ray Analysis

Data collection was performed on a Bruker APEX diffractometer at room temperature. Data collection consisted of omega and phi scans.

The structure was solved by direct methods using the SHELX software suite in the orthorhombic class space group P2$_1$2$_1$2$_1$. The structure was subsequently refined by the full-matrix least squares method. All non-hydrogen atoms were found and refined using anisotropic displacement parameters.

The hydrogen atoms were placed in calculated positions and were allowed to ride on their carrier atoms. The final refinement included isotropic displacement parameters for all hydrogen atoms.

Analysis of the absolute structure using likelihood methods (Hooft 2008) was performed using PLATON (Spek 2010). The results indicate that the absolute structure has been correctly assigned. The method calculates that the probability that the structure is correctly assigned is 1.0000 and the probability that the structure is incorrect to be 0.000. The Hooft parameter is reported as −0.11 with an esd of 0.10.

The final R-index was 3.7%. A final difference Fourier revealed no missing or misplaced electron density.

Pertinent crystal, data collection and refinement information is summarized in Table 1. Atomic coordinates, bond lengths, bond angles, and displacement parameters are listed in Tables 2-4.

SOFTWARE AND REFERENCES

SHELXTL, Version 5.1, Bruker AXS, 1997.

PLATON, A. L. Spek, *J. Appl. Cryst.* 2003, 36, 7-13.

MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.

OLEX2, O. V. Dolomanov, L. J. Bourhis, R. J. Gildea, J. A. K. Howard, and H. Puschmann, *J. Appl. Cryst.* 2009, 42, 339-341.

R. W. W. Hooft, L. H. Straver, and A. L. Spek, *J. Appl. Cryst.* 2008, 41, 96-103.

H. D. Flack, *Acta Cryst.* 1983, A39, 867-881.

TABLE 1

Crystal data and structure refinement for C6.

| | |
|---|---|
| Empirical formula | C$_{14}$H$_{23}$N$_3$O$_2$ |
| Formula weight | 265.36 |
| Temperature | 296(2) K |
| Wavelength | 1.54178 Å |
| Crystal system | Orthorhombic |
| Space group | P2$_1$2$_1$2$_1$ |
| Unit cell dimensions | a = 5.7468(2) Å   α = 90° |
| | b = 13.2277(5) Å   β = 90° |
| | c = 20.1470(8) Å   γ = 90° |
| Volume | 1531.51(10) Å$^3$ |
| Z | 4 |
| Density (calculated) | 1.151 Mg/m$^3$ |
| Absorption coefficient | 0.627 mm$^{-1}$ |
| F(000) | 576 |
| Crystal size | 0.600 × 0.160 × 0.100 mm$^3$ |
| Theta range for data collection | 3.998 to 70.206° |
| Index ranges | −6 <= h <= 6, −16 <= k <= 16, −24 <= l <= 24 |
| Reflections collected | 23490 |
| Independent reflections | 2911 [R$_{int}$ = 0.0663] |
| Completeness to theta = 67.679° | 100.0% |
| Absorption correction | Empirical |
| Refinement method | Full-matrix least-squares on F$^2$ |
| Data/restraints/parameters | 2911/0/178 |
| Goodness-of-fit on F$^2$ | 1.028 |
| Final R indices [I > 2σ(I)] | R1 = 0.0370, wR2 = 0.1011 |
| R indices (all data) | R1 = 0.0391, wR2 = 0.1030 |
| Absolute structure parameter | 0.03(8) |
| Extinction coefficient | 0.0092(13) |
| Largest diff. peak and hole | 0.162 and −0.115 e · Å$^{-3}$ |

TABLE 2

Atomic coordinates (×10$^4$) and equivalent isotropic displacement parameters (Å$^2$ × 10$^3$) for C6. U(eq) is defined as one-third of the trace of the orthogonalized U$^{ij}$ tensor.

| | x | y | z | U(eq) |
|---|---|---|---|---|
| N(1) | 2738(3) | 5998(1) | 1378(1) | 55(1) |
| N(2) | 3971(3) | 6326(2) | 848(1) | 59(1) |
| N(3) | 6635(3) | 7262(1) | 2962(1) | 49(1) |
| O(1) | 9134(3) | 5944(1) | 2923(1) | 67(1) |
| O(2) | 7510(3) | 6475(1) | 3896(1) | 59(1) |
| C(1) | 3576(3) | 6365(2) | 1951(1) | 49(1) |

TABLE 2-continued

Atomic coordinates (×10$^4$) and equivalent isotropic displacement parameters (Å$^2$ × 10$^3$) for C6. U(eq) is defined as one-third of the trace of the orthogonalized U$^{ij}$ tensor.

| | x | y | z | U(eq) |
|---|---|---|---|---|
| C(2) | 777(5) | 5323(2) | 1287(1) | 73(1) |
| C(3) | 5608(4) | 6920(2) | 1104(1) | 51(1) |
| C(4) | 7310(5) | 7457(2) | 666(1) | 73(1) |
| C(5) | 5447(3) | 6963(1) | 1801(1) | 44(1) |
| C(6) | 6962(4) | 7559(1) | 2264(1) | 49(1) |
| C(7) | 6318(5) | 8683(2) | 2289(1) | 66(1) |
| C(8) | 4384(5) | 8718(2) | 2798(1) | 72(1) |
| C(9) | 5173(5) | 7972(2) | 3329(1) | 63(1) |
| C(10) | 7879(3) | 6505(2) | 3232(1) | 48(1) |
| C(11) | 8685(3) | 5723(2) | 4313(1) | 55(1) |
| C(12) | 11290(4) | 5813(3) | 4269(2) | 91(1) |
| C(13) | 7865(6) | 4681(2) | 4136(2) | 84(1) |
| C(14) | 7851(6) | 6016(2) | 5003(1) | 83(1) |

TABLE 3

Bond lengths [Å] and angles [°] for C6.

| | |
|---|---|
| N(1)—C(1) | 1.341(2) |
| N(1)—N(2) | 1.353(2) |
| N(1)—C(2) | 1.450(3) |
| N(2)—C(3) | 1.330(3) |
| N(3)—C(10) | 1.346(2) |
| N(3)—C(9) | 1.461(3) |
| N(3)—C(6) | 1.472(2) |
| O(1)—C(10) | 1.207(2) |
| O(2)—C(10) | 1.355(2) |
| O(2)—C(11) | 1.467(2) |
| C(1)—C(5) | 1.368(3) |
| C(1)—H(1) | 0.9300 |
| C(2)—H(2A) | 0.9600 |
| C(2)—H(2B) | 0.9600 |
| C(2)—H(2C) | 0.9600 |
| C(3)—C(5) | 1.410(2) |
| C(3)—C(4) | 1.496(3) |
| C(4)—H(4A) | 0.9600 |
| C(4)—H(4B) | 0.9600 |
| C(4)—H(4C) | 0.9600 |
| C(5)—C(6) | 1.499(3) |
| C(6)—C(7) | 1.533(3) |
| C(6)—H(6) | 0.9800 |
| C(7)—C(8) | 1.513(4) |
| C(7)—H(7A) | 0.9700 |
| C(7)—H(7B) | 0.9700 |
| C(8)—C(9) | 1.525(3) |
| C(8)—H(8A) | 0.9700 |
| C(8)—H(8B) | 0.9700 |
| C(9)—H(9A) | 0.9700 |
| C(9)—H(9B) | 0.9700 |
| C(11)—C(13) | 1.499(4) |
| C(11)—C(12) | 1.504(3) |
| C(11)—C(14) | 1.521(3) |
| C(12)—H(12A) | 0.9600 |
| C(12)—H(12B) | 0.9600 |
| C(12)—H(12C) | 0.9600 |
| C(13)—H(13A) | 0.9600 |
| C(13)—H(13B) | 0.9600 |
| C(13)—H(13C) | 0.9600 |
| C(14)—H(14A) | 0.9600 |
| C(14)—H(14B) | 0.9600 |
| C(14)—H(14C) | 0.9600 |
| C(1)—N(1)—N(2) | 112.04(16) |
| C(1)—N(1)—C(2) | 127.65(18) |
| N(2)—N(1)—C(2) | 120.31(18) |
| C(3)—N(2)—N(1) | 104.73(15) |
| C(10)—N(3)—C(9) | 125.32(16) |

TABLE 3-continued

Bond lengths [Å] and angles [°] for C6.

| | |
|---|---|
| C(10)—N(3)—C(6) | 121.13(16) |
| C(9)—N(3)—C(6) | 112.77(15) |
| C(10)—O(2)—C(11) | 120.84(16) |
| N(1)—C(1)—C(5) | 107.57(16) |
| N(1)—C(1)—H(1) | 126.2 |
| C(5)—C(1)—H(1) | 126.2 |
| N(1)—C(2)—H(2A) | 109.5 |
| N(1)—C(2)—H(2B) | 109.5 |
| H(2A)—C(2)—H(2B) | 109.5 |
| N(1)—C(2)—H(2C) | 109.5 |
| H(2A)—C(2)—H(2C) | 109.5 |
| H(2B)—C(2)—H(2C) | 109.5 |
| N(2)—C(3)—C(5) | 111.31(18) |
| N(2)—C(3)—C(4) | 121.01(18) |
| C(5)—C(3)—C(4) | 127.7(2) |
| C(3)—C(4)—H(4A) | 109.5 |
| C(3)—C(4)—H(4B) | 109.5 |
| H(4A)—C(4)—H(4B) | 109.5 |
| C(3)—C(4)—H(4C) | 109.5 |
| H(4A)—C(4)—H(4C) | 109.5 |
| H(4B)—C(4)—H(4C) | 109.5 |
| C(1)—C(5)—C(3) | 104.35(18) |
| C(1)—C(5)—C(6) | 128.59(16) |
| C(3)—C(5)—C(6) | 127.04(18) |
| N(3)—C(6)—C(5) | 112.28(15) |
| N(3)—C(6)—C(7) | 101.27(16) |
| C(5)—C(6)—C(7) | 113.00(17) |
| N(3)—C(6)—H(6) | 110.0 |
| C(5)—C(6)—H(6) | 110.0 |
| C(7)—C(6)—H(6) | 110.0 |
| C(8)—C(7)—C(6) | 103.33(18) |
| C(8)—C(7)—H(7A) | 111.1 |
| C(6)—C(7)—H(7A) | 111.1 |
| C(8)—C(7)—H(7B) | 111.1 |
| C(6)—C(7)—H(7B) | 111.1 |
| H(7A)—C(7)—H(7B) | 109.1 |
| C(7)—C(8)—C(9) | 103.7(2) |
| C(7)—C(8)—H(8A) | 111.0 |
| C(9)—C(8)—H(8A) | 111.0 |
| C(7)—C(8)—H(8B) | 111.0 |
| C(9)—C(8)—H(8B) | 111.0 |
| H(8A)—C(8)—H(8B) | 109.0 |
| N(3)—C(9)—C(8) | 103.34(17) |
| N(3)—C(9)—H(9A) | 111.1 |
| C(8)—C(9)—H(9A) | 111.1 |
| N(3)—C(9)—H(9B) | 111.1 |
| C(8)—C(9)—H(9B) | 111.1 |
| H(9A)—C(9)—H(9B) | 109.1 |
| O(1)—C(10)—N(3) | 124.52(17) |
| O(1)—C(10)—O(2) | 125.74(18) |
| N(3)—C(10)—O(2) | 109.74(16) |
| O(2)—C(11)—C(13) | 110.06(18) |
| O(2)—C(11)—C(12) | 111.8(2) |
| C(13)—C(11)—C(12) | 111.8(3) |
| O(2)—C(11)—C(14) | 101.85(19) |
| C(13)—C(11)—C(14) | 110.6(2) |
| C(12)—C(11)—C(14) | 110.3(2) |
| C(11)—C(12)—H(12A) | 109.5 |
| C(11)—C(12)—H(12B) | 109.5 |
| H(12A)—C(12)—H(12B) | 109.5 |
| C(11)—C(12)—H(12C) | 109.5 |
| H(12A)—C(12)—H(12C) | 109.5 |
| H(12B)—C(12)—H(12C) | 109.5 |
| C(11)—C(13)—H(13A) | 109.5 |
| C(11)—C(13)—H(13B) | 109.5 |
| H(13A)—C(13)—H(13B) | 109.5 |
| C(11)—C(13)—H(13C) | 109.5 |
| H(13A)—C(13)—H(13C) | 109.5 |
| H(13B)—C(13)—H(13C) | 109.5 |
| C(11)—C(14)—H(14A) | 109.5 |
| C(11)—C(14)—H(14B) | 109.5 |
| H(14A)—C(14)—H(14B) | 109.5 |
| C(11)—C(14)—H(14C) | 109.5 |
| H(14A)—C(14)—H(14C) | 109.5 |
| H(14B)—C(14)—H(14C) | 109.5 |

Symmetry transformations used to generate equivalent atoms.

TABLE 4

Anisotropic displacement parameters (Å$^2$ × 10$^3$) for C6. The anisotropic displacement factor exponent takes the form: $-2\pi^2[h^2 a^{*2} U^{11} + \ldots + 2 h k a^* b^* U^{12}]$.

| | U11 | U22 | U33 | U23 | U13 | U12 |
|---|---|---|---|---|---|---|
| N(1) | 52(1) | 66(1) | 47(1) | 0(1) | −4(1) | −2(1) |
| N(2) | 65(1) | 74(1) | 39(1) | 1(1) | −4(1) | 2(1) |
| N(3) | 57(1) | 60(1) | 30(1) | 3(1) | 3(1) | 5(1) |
| O(1) | 68(1) | 86(1) | 46(1) | 10(1) | 11(1) | 22(1) |
| O(2) | 67(1) | 76(1) | 32(1) | 10(1) | 3(1) | 10(1) |
| C(1) | 50(1) | 60(1) | 37(1) | 1(1) | 4(1) | 1(1) |
| C(2) | 63(1) | 76(1) | 79(2) | −6(1) | −14(1) | −10(1) |
| C(3) | 56(1) | 63(1) | 35(1) | 6(1) | 2(1) | 6(1) |
| C(4) | 85(2) | 93(2) | 42(1) | 14(1) | 12(1) | −6(1) |
| C(5) | 47(1) | 52(1) | 34(1) | 7(1) | 2(1) | 5(1) |
| C(6) | 52(1) | 62(1) | 33(1) | 10(1) | 1(1) | −4(1) |
| C(7) | 88(2) | 56(1) | 54(1) | 8(1) | −7(1) | −13(1) |
| C(8) | 86(2) | 54(1) | 75(2) | 1(1) | 1(1) | 9(1) |
| C(9) | 74(1) | 62(1) | 53(1) | −1(1) | 14(1) | 7(1) |
| C(10) | 47(1) | 65(1) | 32(1) | 5(1) | 2(1) | 0(1) |
| C(11) | 47(1) | 77(1) | 41(1) | 16(1) | −8(1) | −6(1) |
| C(12) | 52(1) | 141(3) | 79(2) | 32(2) | −12(1) | −16(2) |
| C(13) | 91(2) | 79(2) | 82(2) | 16(1) | −14(2) | −11(2) |
| C(14) | 94(2) | 118(2) | 38(1) | 17(1) | −3(1) | 0(2) |

Step 5. Synthesis of 1,3-dimethyl-4-[(2S)-pyrrolidin-2-yl]-1H-pyrazole, Hydrochloride Salt (P2)

A solution of C7 (1.80 g, 6.78 mmol) in diethyl ether (25 mL) was treated with a solution of hydrogen chloride in 1,4-dioxane (4 M, 8.5 mL, 34 mmol). After the reaction mixture had been stirred at room temperature overnight, it was concentrated in vacuo, providing the product as a thick oil. Yield: 1.10 g, 5.45 mmol, 80%. LCMS m/z 166.1 [M+H]$^+$. $^1$H NMR (500 MHz, CD$_3$OD) [the sample used for the NMR was derived from deprotection of a different lot of C7, using the same method] δ 8.07 (s, 1H), 4.66 (dd, J=9.4, 6.8 Hz, 1H), 3.96 (s, 3H), 3.46-3.41 (m, 2H), 2.50-2.42 (m, 1H), 2.39 (s, 3H), 2.32-2.24 (m, 1H), 2.24-2.11 (m, 2H).

Preparation P3: 3-Methoxy-1-methyl-4-(pyrrolidin-2-yl)-1H-pyrazole, Hydrochloride Salt (P3)

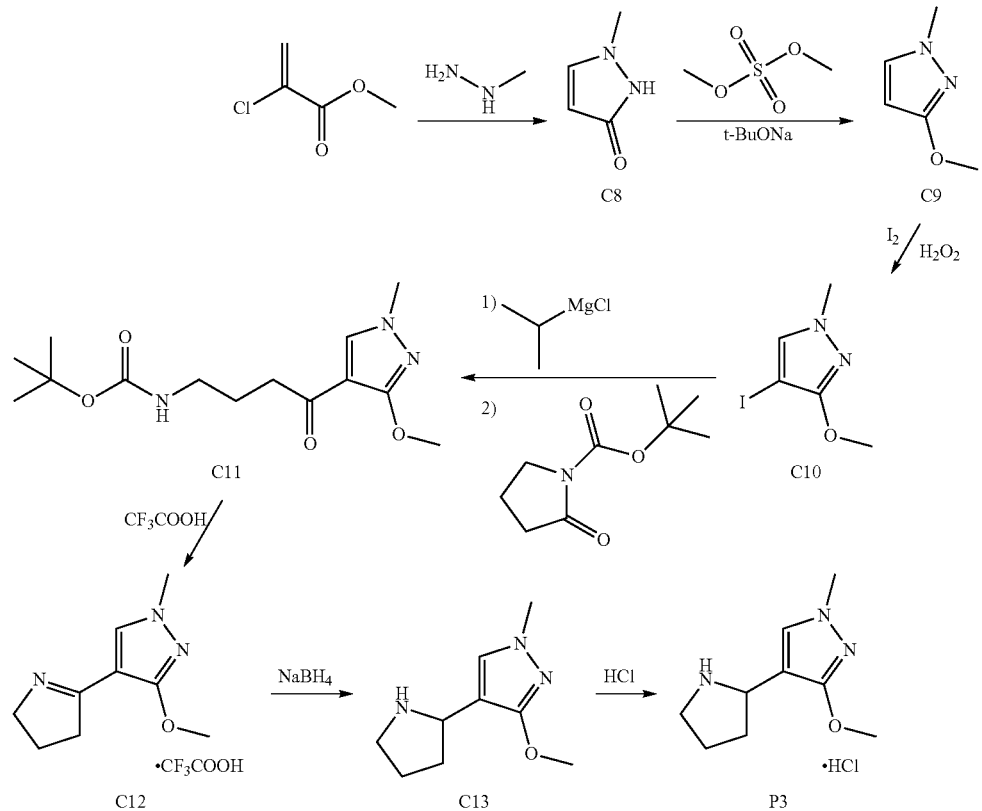

Step 1. Synthesis of 1-methyl-1,2-dihydro-3H-pyrazol-3-one (C8)

A solution of methyl 2-chloroprop-2-enoate (1.36 kg, 11.3 mol) in tetrahydrofuran (10.9 L) was cooled to 0° C. to 5° C. Methylhydrazine (670 g, 14.5 mol) was added in a drop-wise manner at 0° C. to 5° C.; at the completion of the addition, the reaction mixture was warmed to 15° C. to 25° C. and allowed to stir for 10 hours, whereupon 20% aqueous sodium carbonate solution was added until the pH reached 8-9. After removal of tetrahydrofuran via concentration under reduced pressure, the pH of the remaining material was adjusted to 9-10 via addition of 20% aqueous sodium carbonate solution. The resulting mixture was cooled to 0° C. to 5° C., and stirred for 1-2 hours while crystallization occurred. Collection of the precipitate via filtration afforded the product as a solid (910 g). The filtrate was extracted with ethyl acetate (3×2.5 volumes), and the combined organic layers were concentrated in vacuo to provide additional product (60 g). Combined yield: 970 g, 9.89 mol, 88%. $^1$H NMR (500 MHz, CDCl$_3$) δ 7.07 (s, 1H), 5.57 (s, 1H), 3.69 (s, 3H).

Step 2. Synthesis of 3-methoxy-1-methyl-1H-pyrazole (C9)

Sodium tert-butoxide (940 g, 9.78 mol) was added portion-wise to a solution of C8 (750 g, 7.64 mol) in tetrahydrofuran (7.5 L), and the resulting suspension was warmed to 45° C. to 55° C. Dimethyl sulfate (1.14 Kg, 9.04 mol) was added drop-wise over 60 minutes at 45° C. to 55° C., and the reaction mixture was stirred for 5 hours, whereupon it was cooled to 10° C. to 20° C. and treated drop-wise with water (3.75 L). The resulting mixture was concentrated to remove tetrahydrofuran, and then extracted with ethyl acetate (3×3.75 L). The combined organic layers were washed sequentially with water (2.25 L) and with saturated aqueous sodium chloride solution (2.25 L), and concentrated to afford the product as a brown oil. Yield: 530 g, 4.73 mol, 62%. LCMS m/z 113.2 [M+H]$^+$. $^1$H NMR (500 MHz, CDCl$_3$) δ 7.08 (d, J=2.2 Hz, 1H), 5.57 (d, J=2.3 Hz, 1H), 3.84 (s, 3H), 3.69 (s, 3H).

Step 3. Synthesis of 4-iodo-3-methoxy-1-methyl-1H-pyrazole (C10)

Iodine (510 g, 2.01 mol) was added in one portion to a 20° C. to 25° C. mixture of C9 (450 g, 4.01 mol) in water (4.5 L), and the reaction mixture was allowed to stir for 30 minutes. Hydrogen peroxide (84 g, 2.5 mol) was then added drop-wise into the reaction mixture over approximately 1.5 hours, at a rate sufficient to maintain the reaction temperature below 30° C. After completion of the addition, stirring was continued for 4 hours, whereupon the reaction mixture was treated with aqueous sodium sulfite solution (10%, 900 mL). The resulting mixture was extracted with tert-butyl methyl ether (2×4.5 L), and the combined organic layers were concentrated under reduced pressure at 30° C. to 35° C., to a volume of approximately 900 mL. Heptane (2.25 L) was slowly added, and the mixture was cooled to 10° C. to 15° C. and stirred for 3 hours. The solid was collected via filtration to afford the product as a pale yellow solid. Yield: 706 g, 2.97 mol, 74%. LCMS m/z 239.0 [M+H]$^+$. $^1$H NMR (500 MHz, CDCl$_3$) δ 7.16 (s, 1H), 3.92 (s, 3H), 3.74 (s, 3H).

Step 4. Synthesis of tert-butyl [4-(3-methoxy-1-methyl-1H-pyrazol-4-yl)-4-oxobutyl]carbamate (C11)

A solution of C10 (300 g, 1.26 mol) in tetrahydrofuran (1.8 L) was degassed and purged with nitrogen five times. After the solution had been cooled to −30° C. to −40° C., a solution of isopropylmagnesium chloride in tetrahydrofuran (2 M, 830 mL, 1.66 mol) was added drop-wise over 1 hour, whereupon stirring was continued at −30° C. to −40° C. for 40 minutes. A solution of tert-butyl 2-oxopyrrolidine-1-carboxylate (260 g, 1.40 mol) in tetrahydrofuran (600 mL) was then added drop-wise over 1 hour, at a rate that maintained the reaction temperature below −30° C. The reaction mixture was maintained at −30° C. to −40° C. for 40 minutes, whereupon it was treated with aqueous citric acid solution (10%, 1.5 L) and extracted with ethyl acetate (2.4 L). The organic layer was washed with saturated aqueous sodium chloride solution (2×2.4 L), and concentrated to a volume of 600 to 900 mL. Heptane (1.5 L) was added over 30 minutes, and the resulting mixture was cooled to 10° C. to 20° C. over 30 minutes and then stirred for 5 hours. The solid was collected via filtration and washed with cold heptane (600 mL) to provide the product as a white solid. Yield: 320 g, 1.08 mol, 86%. LCMS m/z 298.2 [M+H]$^+$. $^1$H NMR (400 MHz, CDCl$_3$) δ 7.69 (s, 1H), 4.81-4.67 (br s, 1H), 3.97 (s, 3H), 3.74 (s, 3H), 3.21-3.11 (m, 2H), 2.76 (t, J=7.0 Hz, 2H), 1.88-1.78 (m, 2H), 1.42 (s, 9H).

Step 5. Synthesis of 4-(3,4-dihydro-2H-pyrrol-5-yl)-3-methoxy-1-methyl-1H-pyrazole, Trifluoroacetic Acid Salt (C12)

A solution of C11 (550 g, 1.85 mol) in dichloromethane (3.3 L) was warmed to 35° C. to 39° C. Trifluoroacetic acid (1.05 kg, 9.21 mol) was added drop-wise, and stirring was continued at 35° C. to 39° C. for 16 hours, whereupon the reaction mixture was concentrated to a final volume of approximately 1 L. Methanol (1.65 L) was added, and the resulting mixture was concentrated to afford the product as an oil, which was generally used directly for the next step, without additional purification. LCMS m/z 180.1 [M+H]$^+$. $^1$H NMR (500 MHz, CDCl$_3$) δ 8.43 (br s, 1H), 4.06-3.99 (m, 2H), 4.02 (s, 3H), 3.84 (s, 3H), 3.32 (dd, J=8.2, 7.9 Hz, 2H), 2.35-2.26 (m, 2H).

Step 6. Synthesis of 3-methoxy-1-methyl-4-(pyrrolidin-2-yl)-1H-pyrazole (C13)

A solution of C12 (280 g, 1.56 mol) in methanol (2.24 L) was cooled to 0° C. to 5° C., and sodium borohydride (50 g, 1.3 mol) was added in portions, at a rate sufficient to maintain the reaction temperature below 5° C. After the reaction mixture had stirred at 0° C. to 5° C. for 2 hours, it was treated with aqueous sodium hydroxide solution (3 M, approximately 1.6 L) until the pH reached 10 to 11. The resulting mixture was concentrated to a volume of approximately 2.5 L, diluted with water (1.4 L), and extracted with dichloromethane (3×1.68 L). The combined organic layers were concentrated to provide the product. Yield: 243 g, 1.34 mol, 86%. LCMS m/z 182.1 [M+H]$^+$. $^1$H NMR (500 MHz, CDCl$_3$) δ 7.03 (s, 1H), 3.93-3.86 (m, 1H), 3.87 (s, 3H), 3.66 (s, 3H), 3.07 (ddd, J=10.3, 8.0, 5.2 Hz, 1H), 2.90-2.82 (m, 1H), 2.08 (br s, 1H), 2.05-1.96 (m, 1H), 1.88-1.71 (m, 2H), 1.69-1.59 (m, 1H).

Step 7. Synthesis of 3-methoxy-1-methyl-4-(pyrrolidin-2-yl)-1H-pyrazole, Hydrochloride Salt (P3)

A solution of hydrogen chloride in 1,4-dioxane (13% by weight; 260 g, 0.93 mol) was added drop-wise to a solution of C13 (170 g, 0.938 mol) in 1,4-dioxane (1.7 L), held at 25° C. to 30° C. The reaction mixture was stirred at 25° C. to 30° C. for 3 hours, whereupon it was slowly cooled to 15° C. to 20° C. and stirred for an additional 3 hours. The accumulated solid was isolated via filtration and rinsed with 1,4-dioxane (340 mL), affording the product as a white solid. Yield: 150 g, 0.689 mol, 73%. $^1$H NMR (500 MHz, DMSO-d$_6$) δ 9.73-9.58 (br s, 1H), 8.78-8.64 (br s, 1H), 7.73 (s, 1H), 4.40-4.30 (m, 1H), 3.82 (s, 3H), 3.68 (s, 3H), 3.22-3.13 (m, 2H), 2.25-2.16 (m, 1H), 2.09-1.86 (m, 3H).

Preparation P4: 3-Methoxy-1-methyl-4-(pyrrolidin-2-yl)-1H-pyrazole (Single Enantiomer, from Dibenzoyl-L-Tartaric Acid Resolution) (P4)

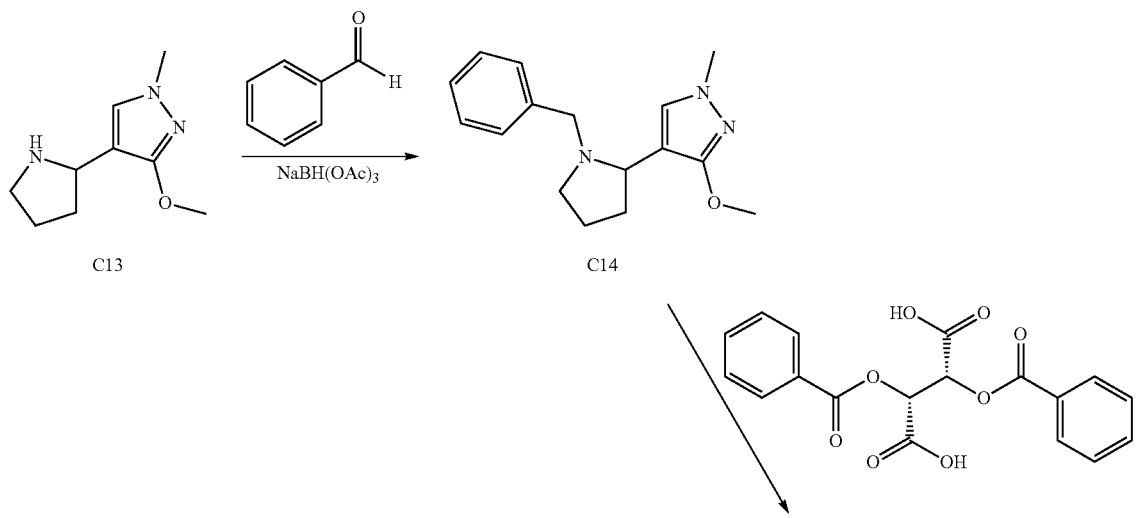

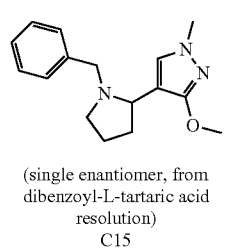
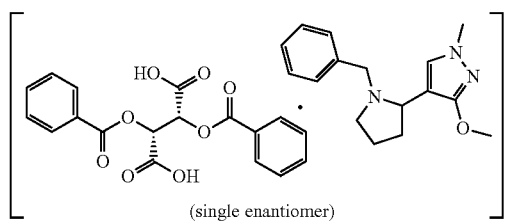

(single enantiomer, from dibenzoyl-L-tartaric acid resolution)
P4

(single enantiomer, from dibenzoyl-L-tartaric acid resolution)
C15

(single enantiomer)

Step 1. Synthesis of 4-(1-benzylpyrrolidin-2-yl)-3-methoxy-1-methyl-1H-pyrazole (C14)

Benzaldehyde (6.39 mL, 62.9 mmol) was added to a solution of C13 (9.5 g, 52 mmol) in dichloromethane (200 mL). Sodium triacetoxyborohydride (98%, 11.3 g, 52.3 mmol) was introduced, and the reaction mixture was stirred at room temperature for 1 hour, whereupon it was partitioned between 1 M aqueous sodium hydroxide solution and dichloromethane. After the organic layer had been dried over sodium sulfate, filtered, and concentrated in vacuo, the residue was purified using silica gel chromatography (Gradient: 0% to 10% methanol in dichloromethane) to provide the product as an oil. Yield: 13.0 g, 47.9 mmol, 92%. LCMS m/z 272.2 [M+H]$^+$. $^1$H NMR (400 MHz, CDCl$_3$) δ 7.30-7.26 (m, 4H, assumed; partially obscured by solvent peak), 7.25-7.19 (m, 1H), 7.17 (s, 1H), 3.95 (d, J=13 Hz, 1H, assumed; partially obscured by peak at 3.93 ppm), 3.93 (s, 3H), 3.73 (s, 3H), 3.32 (dd, J=8.0, 7.6 Hz, 1H), 3.10 (d, J=13.1 Hz, 1H), 3.03-2.97 (m, 1H), 2.18-2.07 (m, 2H), 1.90-1.68 (m, 3H).

Step 2. Resolution of C14 to obtain 4-(1-benzylpyrrolidin-2-yl)-3-methoxy-1-methyl-1H-pyrazole (Single Enantiomer, from Dibenzoyl-L-Tartaric Acid Resolution) (C15)

(2R,3R)-2,3-Bis(benzoyloxy)butanedioic acid (dibenzoyl-L-tartaric acid; 15.6 g, 43.5 mmol) was dissolved in ethanol (125 mL). A solution of C14 (11.8 g, 43.5 mmol) in ethanol (25 mL) was added, and the resulting mixture was stirred overnight at room temperature. The precipitate was isolated via filtration and rinsing with ethanol; the resulting solid (13.7 g) was recrystallized from ethanol (425 mL). A small sample of the recrystallized material was partitioned between 1 M aqueous sodium hydroxide solution and diethyl ether. The organic layer of this pilot was concentrated to an oil, which was shown to consist of a single enantiomer via analysis for enantiomeric excess. The bulk material was therefore partitioned between aqueous sodium hydroxide solution (1 M, 100 mL) and diethyl ether. The organic layer was washed with aqueous sodium hydroxide solution (1 M, 2×100 mL), dried over magnesium sulfate, filtered, and concentrated in vacuo to provide the product as an oil. Yield: 6.0 g, 22 mmol, 51%. LCMS m/z 272.2 [M+H]$^+$. $^1$H NMR (400 MHz, CDCl$_3$) δ 7.30-7.26 (m, 4H, assumed; partially obscured by solvent peak), 7.25-7.19 (m, 1H), 7.17 (s, 1H), 3.95 (d, J=13 Hz, 1H, assumed; partially obscured by peak at 3.93 ppm), 3.93 (s, 3H), 3.73 (s, 3H), 3.32 (dd, J=8.0, 7.6 Hz, 1H), 3.09 (d, J=13.1 Hz, 1H), 3.03-2.97 (m, 1H), 2.18-2.07 (m, 2H), 1.90-1.68 (m, 3H).

Step 3. Synthesis of 3-methoxy-1-methyl-4-(pyrrolidin-2-yl)-1H-pyrazole (Single Enantiomer, from Dibenzoyl-L-Tartaric Acid Resolution) (P4)

Palladium on carbon (3.11 g) was added to a solution of C15 (6.0 g, 22 mmol) in methanol (100 mL). Ammonium formate (7.11 g, 113 mmol) was introduced, and the reaction mixture was stirred at room temperature for 1 hour. It was then diluted with ethyl acetate, treated with diatomaceous earth, filtered, and concentrated in vacuo to ⅓ of the original volume. Filtration and concentration of the filtrate under reduced pressure provided the product as a thick oil. Yield: 4.0 g, 22 mmol, quantitative. LCMS m/z 182.1 [M+H]$^+$.

Preparation P5: Benzyl (2S)-2-(5-methyl-1,2,4-thiadiazol-3-yl)pyrrolidine-1-carboxylate (P5)

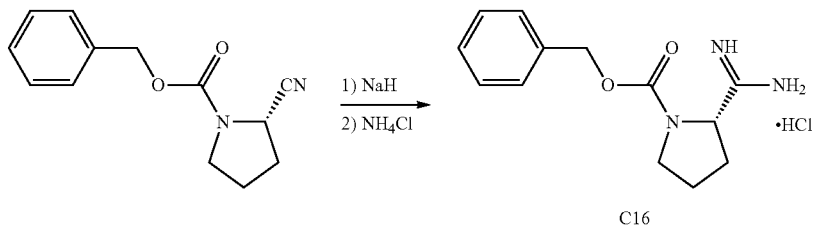

C16

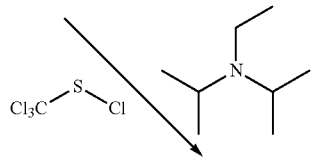

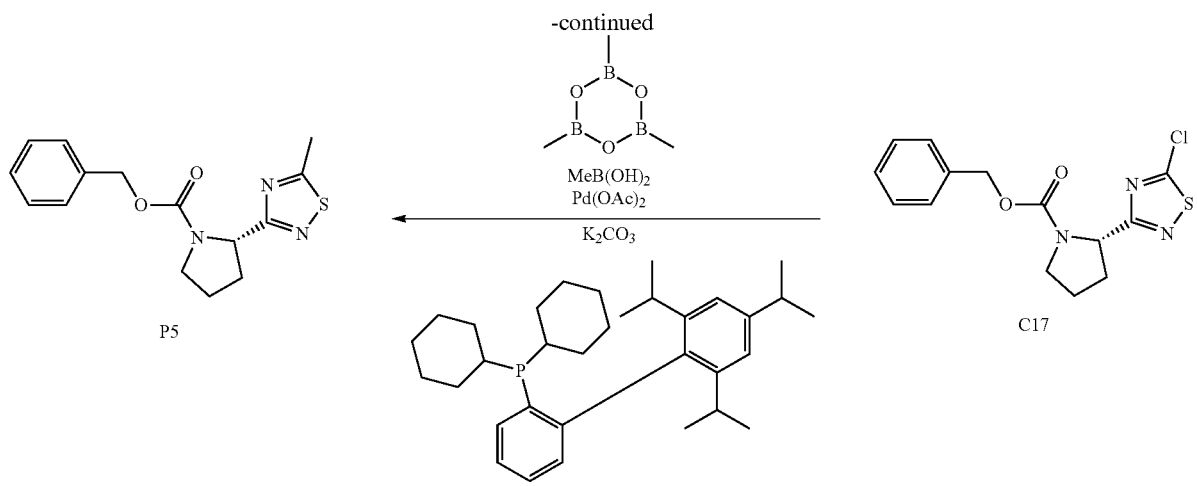

Step 1. Synthesis of benzyl (2S)-2-carbamimidoylpyrrolidine-1-carboxylate, Hydrochloride Salt (C16)

This experiment was carried out in 2 identical batches. Sodium hydride (60% in mineral oil; 782 mg, 19.6 mmol) was added to methanol (75 mL) to prepare a solution of sodium methoxide. This solution was added to a solution of benzyl (2S)-2-cyanopyrrolidine-1-carboxylate (9.0 g, 39 mmol) in methanol (75 mL), and the reaction mixture was stirred at 40° C. for 16 hours. Ammonium chloride (4.18 g, 78.1 mmol) was added to the reaction mixture in one portion at 40° C., and stirring was continued at that temperature for an additional 24 hours. At this point, the two reaction batches were combined and concentrated in vacuo. The residue was mixed with dichloromethane (500 mL) and filtered; concentration of the filtrate in vacuo afforded the product as a yellow gum. From analysis of the $^1$H NMR, this material may exist as a mixture of rotamers. Yield: 17.0 g, 59.9 mmol, 77%. $^1$H NMR (400 MHz, CDCl$_3$) δ 7.45-7.25 (m, 5H), 5.25-5.04 (m, 2H), 4.84-4.53 (m, 1H), 3.80-3.36 (m, 2H), 2.55-1.84 (m, 5H).

Step 2. Synthesis of benzyl (2S)-2-(5-chloro-1,2,4-thiadiazol-3-yl)pyrrolidine-1-carboxylate (C17)

This reaction was run in two identical batches. Trichloro (chlorosulfanyl)methane (6.12 g, 32.9 mmol) was added to a 0° C. solution of C16 (8.5 g, 30 mmol) and N,N-diisopropylethylamine (19.4 g, 150 mmol) in dichloromethane (200 mL). The reaction mixture was stirred at 0° C. for 1 hour, whereupon the two batches were combined and concentrated in vacuo. Silica gel chromatography (Gradient: 0% to 25% ethyl acetate in petroleum ether) afforded the product as a yellow oil. From analysis of the $^1$H NMR, this material was presumed to exist as a mixture of rotamers. Yield: 8.0 g, 25 mmol, 42%. LCMS m/z 323.9 (chlorine isotope pattern observed) [M+H]$^+$. $^1$H NMR (400 MHz, CDCl$_3$) δ 7.41-7.23 (m, 4H, assumed; partially obscured by solvent peak), 7.14-7.07 (m, 1H), 5.24-5.12 (m, 2H), [5.09 (d, half of AB quartet, J=12.6 Hz) and 4.92 (d, half of AB quartet, J=12.6 Hz), total 1H], 3.82-3.72 (m, 1H), 3.68-3.54 (m, 1H), 2.42-2.26 (m, 1H), 2.14-2.02 (m, 2H), 2.02-1.90 (m, 1H).

Step 3. Synthesis of benzyl (2S)-2-(5-methyl-1,2,4-thiadiazol-3-yl)pyrrolidine-1-carboxylate (P5)

This reaction was run in two identical batches. A mixture of C17 (1.70 g, 5.25 mmol), methylboronic acid (943 mg, 15.8 mmol), trimethylboroxin (1.98 g, 15.8 mmol), palladium(II) acetate (118 mg, 0.526 mmol), 2-dicyclohexylphosphino-2',4',6'-triisopropylbiphenyl (501 mg, 1.05 mmol), and potassium carbonate (2.18 g, 15.8 mmol) in tetrahydrofuran (20 mL) and water (2 mL) was stirred at 67° C. for 20 hours. A major peak in the LCMS of the reaction mixture was appropriate for the product (LCMS m/z 303.9 [M+H]$^+$). The two reactions were combined and concentrated in vacuo; two purifications using silica gel chromatography (Gradient: 0% to 30% ethyl acetate in petroleum ether) provided the product as an orange gum. From analysis of the $^1$H NMR, this material was presumed to exist as a mixture of rotamers. Yield: 1.71 g, 5.64 mmol, 54%. $^1$H NMR (400 MHz, CDCl$_3$) δ 7.41-7.20 (m, 4H), 7.11-7.03 (m, 1H), [5.30-5.04 (m) and 4.92 (d, half of AB quartet, J=12.6 Hz), total 3H], 3.84-3.73 (m, 1H), 3.69-3.54 (m, 1H), [2.78 (s) and 2.70 (s), total 3H], 2.42-2.25 (m, 1H), 2.14-2.01 (m, 2H), 2.01-1.88 (m, 1H).

Preparation P6: 3-Methoxy-4-(pyrrolidin-2-yl)-1H-pyrazole (P6)

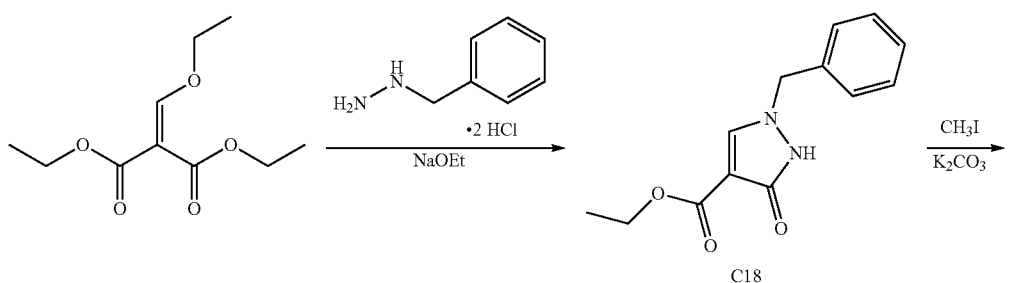

-continued
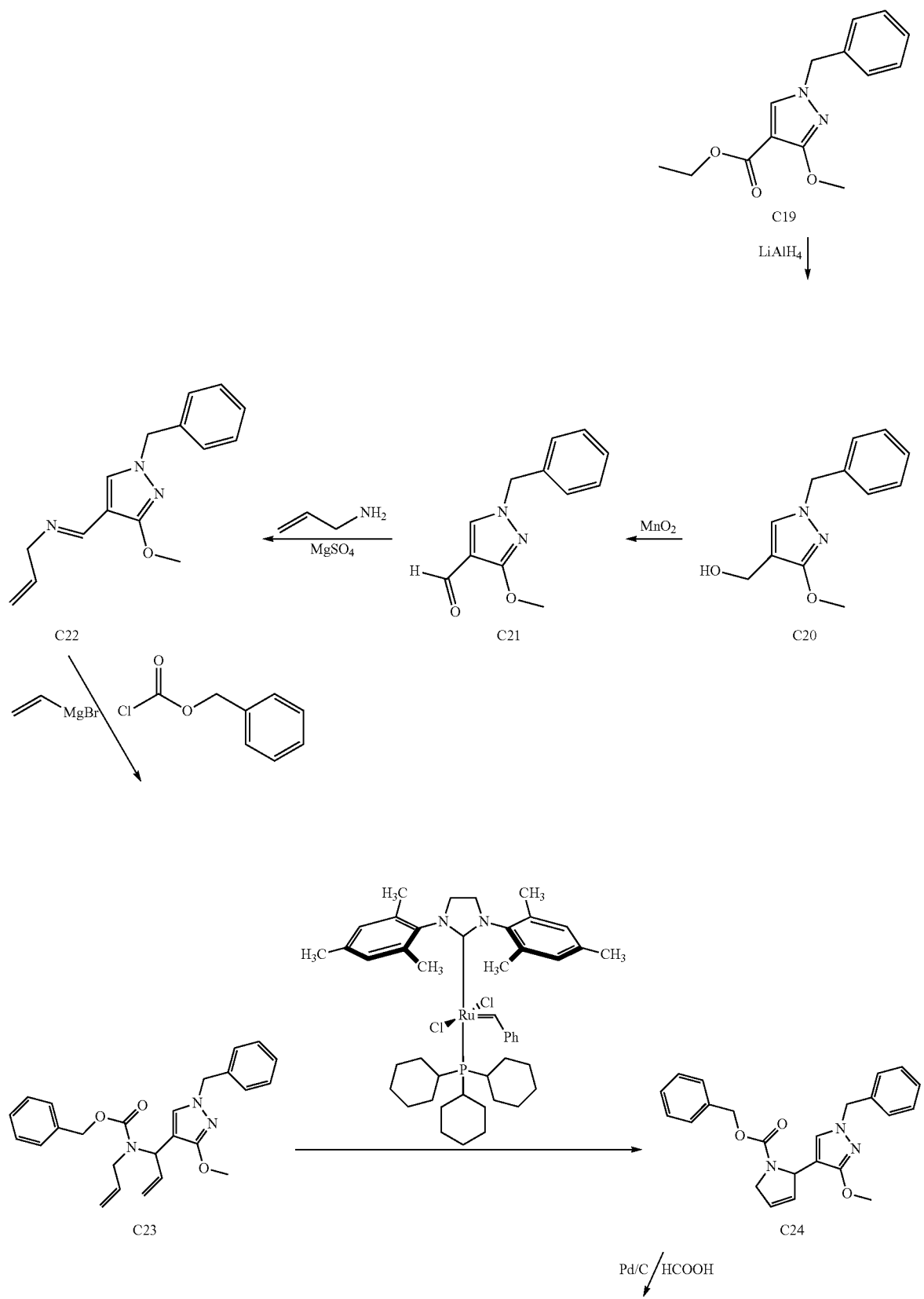

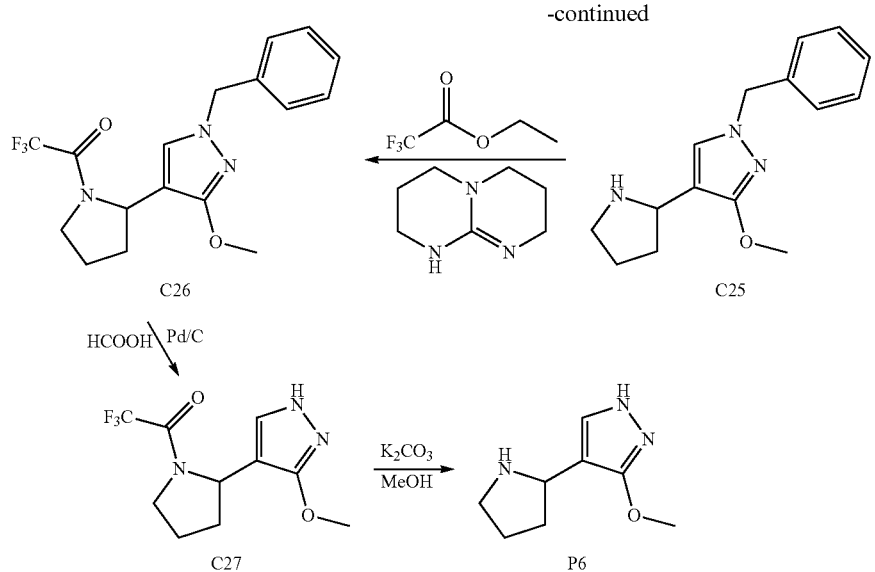

Step 1. Synthesis of ethyl 1-benzyl-3-oxo-2,3-di-hydro-1H-pyrazole-4-carboxylate (C18)

A solution of sodium ethoxide in ethanol (2.6 M, 44 mL, 114 mmol) was diluted with 100 mL ethanol (100 mL) and cooled in an ice bath. Diethyl (ethoxymethylidene)propane-dioate (4.99 g, 23.1 mmol) was added, followed by portion-wise addition of benzylhydrazine dihydrochloride (4.50 g, 23.1 mmol); during these additions, the internal reaction temperature was maintained below 10° C. Upon completion of the additions, the reaction mixture was warmed to room temperature and stirred for 2 hours, whereupon it was poured into cold hydrochloric acid (1 M, 250 mL). After the resulting mixture had stirred overnight, the solid was collected via filtration to afford the product as a solid. Yield: 3.6 g, 14.6 mmol, 63%. LCMS m/z 247.4 [M+H]+. $^1$H NMR (400 MHz, CDCl$_3$) δ 8.06 (br s, 1H), 7.51 (s, 1H), 7.41-7.33 (m, 3H), 7.31-7.27 (m, 2H), 5.13 (s, 2H), 4.31 (q, J=7.2 Hz, 2H), 1.34 (t, J=7.1 Hz, 3H).

Step 2. Synthesis of ethyl 1-benzyl-3-methoxy-1H-pyrazole-4-carboxylate (C19)

A solution of C18 (3.60 g, 14.6 mmol) in N,N-dimethyl-formamide (40 mL) was treated with potassium carbonate (4.04 g, 29.2 mmol), followed by iodomethane (1.09 mL, 17.5 mmol). The reaction mixture, which displayed a major peak in the LCMS consistent with the product (LCMS m/z 261.4 [M+H]+), was stirred at room temperature for 3 hours, whereupon it was partitioned between water and diethyl ether. The aqueous layer was extracted with diethyl ether, and the combined organic layers were dried over sodium sulfate, filtered and concentrated in vacuo. The product was obtained as a solid, which was used without additional purification. Yield: 3.8 g, 14.6 mmol, 100%. $^1$H NMR (400 MHz, CDCl$_3$) δ 7.63 (s, 1H), 7.41-7.32 (m, 3H), 7.27-7.22 (m, 2H), 5.13 (s, 2H), 4.26 (q, J=7.1 Hz, 2H), 4.00 (s, 3H), 1.31 (t, J=7.1 Hz, 3H).

Step 3. Synthesis of (1-benzyl-3-methoxy-1H-pyra-zol-4-yl)methanol (C20)

A solution of C19 (5.40 g, 20.7 mmol) in tetrahydrofuran (100 mL) was cooled in an ice bath and treated drop-wise with a solution of lithium aluminum hydride in tetrahydro-furan (1 M, 41 mL, 41 mmol). After the reaction mixture had been stirred at 0° C. for 30 minutes, it was warmed to room temperature and allowed to stir for an additional 30 minutes before being cooled in an ice bath. The reaction was quenched via sequential addition of water (1.5 mL), aqueous sodium hydroxide solution (15%, 1.5 mL), and water (4.5 mL), whereupon it was warmed to room temperature and stirred overnight. The resulting mixture was filtered, and the collected solids were washed with tetrahydrofuran. Concentration of the combined filtrates under reduced pressure afforded the product as a thick oil. Yield: 3.60 g, 16.5 mmol, 80%. $^1$H NMR (400 MHz, CDCl$_3$) δ 7.38-7.28 (m, 3H), 7.25-7.20 (m, 2H), 7.14 (s, 1H), 5.11 (s, 2H), 4.47 (d, J=5.5 Hz, 2H), 3.95 (s, 3H), 1.56 (t, J=5.7 Hz, 1H, assumed, partially obscured by water peak).

Step 4. Synthesis of 1-benzyl-3-methoxy-1H-pyrazole-4-carbaldehyde (C21)

Manganese(IV) oxide (99%, 7.24 g, 82.4 mmol) was added to a solution of C20 (3.60 g, 16.5 mmol) in tetrahy-drofuran (50 mL). The reaction mixture was heated at reflux for 2 hours, whereupon it was cooled to room temperature, treated with diatomaceous earth, and concentrated in vacuo. Purification via silica gel chromatography (Gradient: 5% to 30% ethyl acetate in heptane) provided the product as a white solid. Yield: 3.0 g, 14 mmol, 85%. $^1$H NMR (400 MHz, CDCl$_3$) δ 9.73 (s, 1H), 7.62 (s, 1H), 7.43-7.35 (m, 3H), 7.30-7.25 (m, 2H, assumed; partially obscured by solvent peak), 5.14 (s, 2H), 4.01 (s, 3H).

Step 5. Synthesis of (E)-1-(1-benzyl-3-methoxy-1H-pyrazol-4-yl)-N-(prop-2-en-1-yl)methanimine (C22)

A solution of C21 (3.0 g, 14 mmol) in dichloromethane (100 mL) was treated with magnesium sulfate (16.9 g, 140 mmol), followed by prop-2-en-1-amine (3.12 mL, 41.6 mmol), and the reaction mixture was stirred at room temperature overnight. It was then filtered, and the filtrate was concentrated in vacuo, affording the product as an oil. Yield:

3.60 g, 14 mmol, quantitative. $^1$H NMR (400 MHz, CDCl$_3$) δ 8.11 (br s, 1H), 7.58 (s, 1H), 7.39-7.30 (m, 3H), 7.27-7.23 (m, 2H), 6.05-5.94 (m, 1H), 5.21-5.14 (m, 1H), 5.14-5.08 (m, 1H), 5.12 (s, 2H), 4.13-4.09 (m, 2H), 3.98 (s, 3H).

Step 6. Synthesis of benzyl [1-(1-benzyl-3-methoxy-1H-pyrazol-4-yl)prop-2-en-1-yl]prop-2-en-1-ylcarbamate (C23)

Benzyl chloroformate (1.99 mL, 13.9 mmol) was added to a solution of C22 (3.56 g, 13.9 mmol) in tetrahydrofuran (50 mL). The reaction mixture was heated to 60° C. for 1 hour, whereupon it was cooled to room temperature and then placed in a dry ice/acetone bath. A solution of vinylmagnesium bromide in tetrahydrofuran (0.7 M, 21.9 mL, 15.3 mmol) was added drop-wise over approximately 15 minutes; upon completion of the addition, the reaction mixture was allowed to warm to room temperature for 1 hour. Saturated aqueous ammonium chloride solution was added, and the resulting mixture was extracted with ethyl acetate. The combined organic layers were dried over sodium sulfate, filtered, concentrated in vacuo, and purified via silica gel chromatography (Gradient: 5% to 30% ethyl acetate in heptane). The product was obtained as an oil. Yield: 3.29 g, 7.88 mmol, 57%. LCMS m/z 418.5 [M+H]$^+$. $^1$H NMR (400 MHz, CDCl$_3$) δ 7.39-7.28 (m, 8H), 7.20-7.14 (m, 2H), 7.2-6.9 (v br s, 1H), 6.11-5.97 (m, 1H), 5.74-5.58 (m, 2H), 5.22-5.10 (m, 4H), 5.08 (s, 2H), 5.00-4.88 (m, 2H), 3.96-3.86 (m, 1H), 3.88 (s, 3H), 3.76-3.68 (m, 1H).

Step 7. Synthesis of benzyl 2-(I-benzyl-3-methoxy-1H-pyrazol-4-yl)-2,5-dihydro-1H-pyrrole-1-carboxylate (C24)

A solution of C23 (3.20 g, 7.66 mmol) in dichloromethane (100 mL) was treated with benzylidene[1,3-bis(2,4,6-trimethylphenyl)imidazolidin-2-ylidene]dichloro (tricyclohexylphosphine)ruthenium (second-generation Grubb's catalyst; 350 mg, 0.412 mmol). After the reaction flask had been protected from light, the reaction mixture was stirred at room temperature for 1.5 hours, whereupon diatomaceous earth was added, and the mixture was concentrated in vacuo. Silica gel chromatography (Gradient: 10% to 50% ethyl acetate in heptane) afforded the product as an oil. From analysis of the $^1$H NMR, this material was presumed to exist as a mixture of rotamers. Yield: 2.60 g, 6.68 mmol, 87%. LCMS m/z 390.4 [M+H]$^+$. $^1$H NMR (400 MHz, CDCl$_3$) δ [7.39-7.24 (m), 7.23-7.09 (m), and 6.90 (s), total 11H, assumed; partially obscured by solvent peak], 5.85-5.70 (m, 2H), 5.55-5.44 (m, 1H), [5.19 (d, half of AB quartet, J=12.5 Hz) and 5.13-5.00 (m), total 4H], 4.36-4.19 (m, 2H), [3.89 (s) and 3.79 (s), total 3H].

Step 8. Synthesis of 1-benzyl-3-methoxy-4-(pyrrolidin-2-yl)-1H-pyrazole (C25)

A solution of C24 (2.00 g, 5.14 mmol) in ethanol (25 mL) was treated with palladium on carbon (1.00 g), followed by formic acid (10 mL). After 4 hours, the reaction mixture was filtered, and the filtrate was concentrated under reduced pressure. The residue was partitioned between 1 M aqueous sodium hydroxide solution and dichloromethane. The organic layer was dried over sodium sulfate, filtered, and concentrated in vacuo to provide the product as a thick oil. Yield: 1.27 g, 4.94 mmol, 96%. LCMS m/z 258.5 [M+H]$^+$.

Step 9. Synthesis of 1-[2-(1-benzyl-3-methoxy-1H-pyrazol-4-yl)pyrrolidin-1-yl]-2,2,2-trifluoroethanone (C26)

Ethyl trifluoroacetate (1.76 mL, 14.8 mmol), C25 (1.27 g, 4.94 mmol), and 1,3,4,6,7,8-hexahydro-2H-pyrimido[1,2-a] pyrimidine (97%, 708 mg, 4.93 mmol) were combined in acetonitrile (25 mL). The reaction mixture was stirred overnight at room temperature, whereupon it was partitioned between 1 M hydrochloric acid and ethyl acetate. The organic layer was dried over sodium sulfate, filtered, concentrated in vacuo, and subjected to silica gel chromatography (Gradient: 10% to 50% ethyl acetate in heptane), affording the product as an oil. From analysis of the $^1$H NMR, this material was presumed to exist as a mixture of rotamers. Yield: 872 mg, 2.47 mmol, 50%. LCMS m/z 354.4 [M+H]$^+$. $^1$H NMR (400 MHz, CDCl$_3$) δ 7.38-7.28 (m, 3H), 7.22-7.12 (m, 2H), [7.08 (s) and 6.90 (s), total 1H], [5.20-5.16 (m) and 5.12-5.03 (m), total 3H], [3.91 (s) and 3.90 (s), total 3H], 3.82-3.61 (m, 2H), 2.22-2.06 (m, 3H), 2.01-1.88 (m, 1H).

Step 10. Synthesis of 2,2,2-trifluoro-1-[2-(3-methoxy-1H-pyrazol-4-yl)pyrrolidin-1-yl]ethanone (C27)

A solution of C26 (1.0 g, 2.8 mmol) in ethanol (25 mL) was treated with palladium on carbon (1.0 g), followed by formic acid (5 mL), and the reaction mixture was heated at reflux for 3 hours. It was then cooled to room temperature and filtered. The filtrate was concentrated in vacuo to provide the product as a thick oil, which was carried directly to the following step. LCMS m/z 264.3 [M+H]$^+$.

Step 11. Synthesis of 3-methoxy-4-(pyrrolidin-2-yl)-1H-pyrazole (P6)

Potassium carbonate (3.0 g, 22 mmol) was added to a solution of C27 (from the previous step, ≤2.8 mmol) in methanol (10 mL). The reaction mixture was stirred at room temperature overnight and then filtered; the filtrate was partitioned between water and dichloromethane. The aqueous layer was extracted with dichloromethane, and the combined organic layers were concentrated in vacuo to afford the product as an oil. Yield: 228 mg, 1.36 mmol, 49% over 2 steps. $^1$H NMR (400 MHz, CDCl$_3$) δ 7.21 (s, 1H), 3.99 (dd, J=8, 7 Hz, 1H), 3.92 (s, 3H), 3.14 (ddd, J=10.6, 7.9, 5.2 Hz, 1H), 2.93 (ddd, J=10.5, 8.3, 6.7 Hz, 1H), 2.12-2.02 (m, 1H), 1.95-1.66 (m, 3H).

Preparation P7: 1-Methyl-3-[(2S)-pyrrolidin-2-yl]-1H-pyrazole (P7)

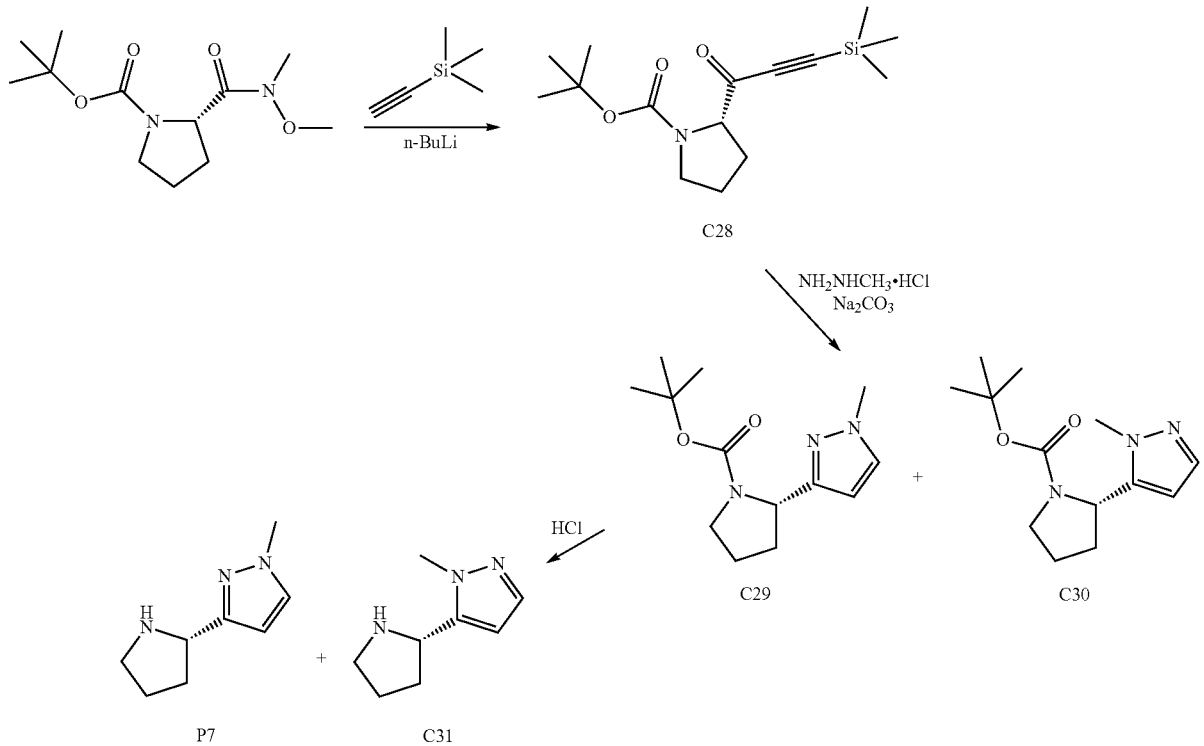

Step 1. Synthesis of tert-butyl (2S)-2-[3-(trimethylsilyl)prop-2-ynoyl]pyrrolidine-1-carboxylate (C28)

A solution of n-butyllithium in hexanes (2.5 M, 16.7 mL, 41.8 mmol) was added in a drop-wise manner to a −70° C. solution of ethynyl(trimethyl)silane (4.11 g, 41.8 mmol) in tetrahydrofuran (150 mL). After the reaction mixture had been stirred at −70° C. for 1 hour, a solution of tert-butyl (2S)-2-[methoxy(methyl)carbamoyl]pyrrolidine-1-carboxylate (6.0 g, 23 mmol) in tetrahydrofuran (20 mL) was added. Stirring was continued at −70° C. for 1 hour, whereupon the reaction mixture was warmed to 0° C. and allowed to stir for 2 hours. Saturated aqueous ammonium chloride solution (200 mL) was added, and the resulting mixture was extracted with ethyl acetate (2×300 mL). The combined organic layers were dried over sodium sulfate, filtered, concentrated in vacuo, and purified via chromatography on silica gel (Gradient: 9% to 20% ethyl acetate in petroleum ether), affording the product as a pale yellow oil. From analysis of the $^1$H NMR, this material was presumed to exist as a mixture of rotamers. Yield: 3.80 g, 12.9 mmol, 56%. $^1$H NMR (400 MHz, CDCl$_3$) δ [4.41 (dd, J=8.8, 4.3 Hz) and 4.23 (dd, J=8.5, 5.0 Hz), total 1H], 3.58-3.40 (m, 2H), 2.30-2.14 (m, 1H), 2.08-1.81 (m, 3H), [1.48 (s) and 1.43 (s), total 9H], [0.24 (s) and 0.24 (s), total 9H].

Step 2. Synthesis of tert-butyl (2S)-2-(1-methyl-1H-pyrazol-3-yl)pyrrolidine-1-carboxylate (C29) and tert-butyl (2S)-2-(1-methyl-1H-pyrazol-5-yl)pyrrolidine-1-carboxylate (C30)

Sodium carbonate (10.9 g, 103 mmol) and methylhydrazine hydrochloride (6.37 g, 77.2 mmol) were added to a solution of C28 (3.80 g, 12.9 mmol) in ethanol (100 mL), and the reaction mixture was heated at reflux for 2 hours. It was then cooled to 28° C. and concentrated under reduced pressure to remove ethanol; the residue was partitioned between water (50 mL) and ethyl acetate (100 mL). The organic layer was dried over sodium sulfate, filtered, concentrated in vacuo, and purified via silica gel chromatography (Gradient: 17% to 25% ethyl acetate in petroleum ether) to provide a mixture of the products as a yellow oil. Yield: 2.20 g, 8.75 mmol, 68%. LCMS m/z 252.1 [M+H]$^+$.

Step 3. Synthesis of 1-methyl-3-[(2S)-pyrrolidin-2-yl]-1H-pyrazole (P7) and 1-methyl-5-[(2S)-pyrrolidin-2-yl]-1H-pyrazole (C31)

To a 28° C. mixture of C29 and C30 (2.20 g, 8.75 mmol) was added a solution of hydrogen chloride in ethyl acetate (4.0 M, 50 mL). The reaction mixture was stirred at 28° C. for 16 hours, whereupon it was concentrated in vacuo. The residue was separated into its component regioisomers using supercritical fluid chromatography (Column: Chiral Technologies Chiralpak IC-3, 3 μm; Mobile phase A: carbon dioxide; Mobile phase B: ethanol containing 0.05% diethylamine; Gradient: 5% to 40% B). The regiochemistry of the products was assigned on the basis of nuclear Overhauser effects (NOE) in NMR studies. Compound P7 was isolated as a brown oil. Yield: 650 mg, 4.30 mmol, 49%. $^1$H NMR (400 MHz, CD$_3$OD) δ 7.55 (d, J=2.5 Hz, 1H), 6.29 (d, J=2.5 Hz, 1H), 4.41-4.35 (m, 1H), 3.87 (s, 3H), 3.3-3.21 (m, 1H), 3.17-3.08 (m, 1H), 2.35-2.23 (m, 1H), 2.11-1.94 (m, 3H).

Compound C31 was obtained as a yellow solid. Yield: 610 mg, 4.03 mmol, 46%. $^1$H NMR (400 MHz, CD$_3$OD) δ

7.51 (d, J=2.0 Hz, 1H), 6.55 (d, J=2.0 Hz, 1H), 4.95-4.9 (m, 1H, assumed; largely obscured by water peak), 3.95 (s, 3H), 3.49-3.42 (m, 2H), 2.58-2.48 (m, 1H), 2.33-2.13 (m, 3H).

Preparation P8: 4-(4-Fluoropyrrolidin-2-yl)-1,3-dimethyl-1H-pyrazole (P8)

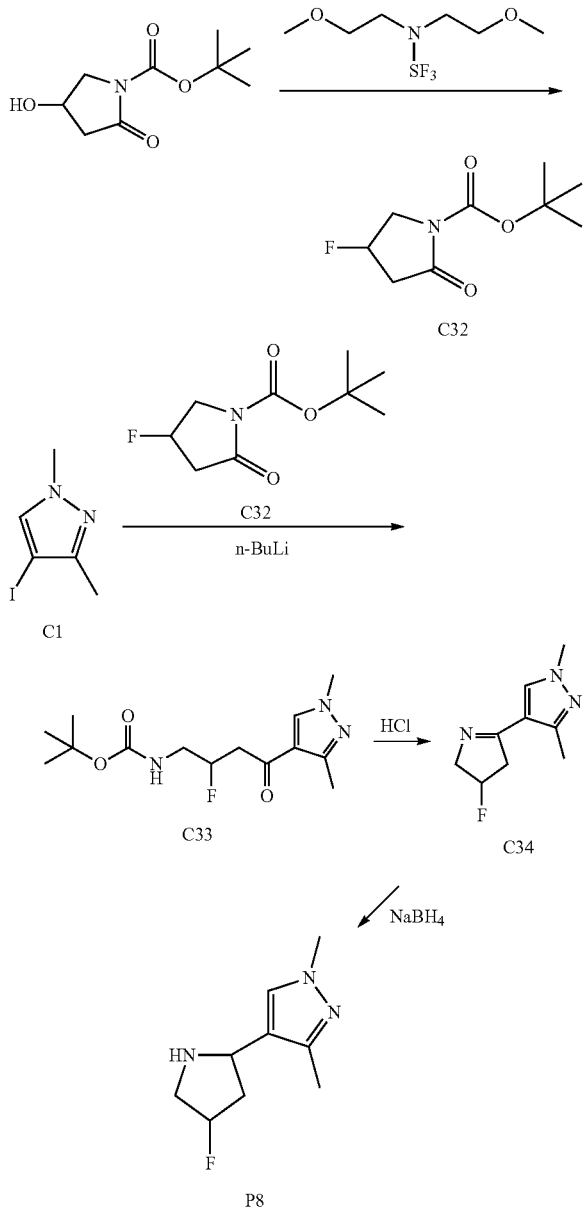

Step 1. Synthesis of tert-butyl 4-fluoro-2-oxopyrrolidine-1-carboxylate (C32)

A solution of tert-butyl 4-hydroxy-2-oxopyrrolidine-1-carboxylate (2.00 g, 9.94 mmol) in dichloromethane (25 mL) was cooled in a dry ice/acetone bath and then treated with [bis(2-methoxyethyl)amino]sulfur trifluoride (Deoxo-Fluor; 2.5 mL, 14 mmol). The reaction mixture was allowed to warm slowly to room temperature over 16 hours, whereupon it was partitioned between dichloromethane and aqueous sodium bicarbonate solution. The organic layer was dried over sodium sulfate, filtered, and concentrated in vacuo. Silica gel chromatography (Gradient: 10% to 50% ethyl acetate in heptane) afforded the product as a white solid. Yield: 966 mg, 4.75 mmol, 48%. $^1$H NMR (400 MHz, CDCl$_3$) δ 5.08 (ddd, J=51.6, 7.8, 7.6 Hz, 1H), 3.89 (dddd, J=11.2, 8.8, 3.5, 0.8 Hz, 1H), 3.65-3.57 (m, 1H), 2.54-2.41 (m, 1H), 2.29-2.13 (m, 1H), 1.55 (s, 9H).

Step 2. Synthesis of tert-butyl [4-(1,3-dimethyl-1H-pyrazol-4-yl)-2-fluoro-4-oxobutyl]carbamate (C33)

A solution of n-butyllithium in hexanes (2.5 M, 0.92 mL, 2.3 mmol) was added to a −78° C. solution of C1 (510 mg, 2.30 mmol) and C32 (485 mg, 2.39 mmol) in tetrahydrofuran (20 mL), and stirring was continued at −78° C. for 30 minutes. Acetic acid (670 μL) was added at −78° C., and stirring was allowed to proceed for an additional 30 minutes at that temperature, at which point the cooling bath was removed. Water (10 mL) was added to the reaction mixture, which was then extracted with ethyl acetate (3×100 mL). The combined organic layers were dried over magnesium sulfate, filtered, and concentrated in vacuo. After purification via silica gel chromatography (Gradient: 30% to 75% ethyl acetate in heptane), the product was isolated as a gum. Yield: 370 mg, 1.24 mmol, 54%. GCMS m/z 299.1 [M+]. $^1$H NMR (500 MHz, CDCl$_3$) δ 8.03 (d, J=3.4 Hz, 1H), 5.12 (ddd, J=49.9, 8.0, 4.2 Hz, 1H), 4.75-4.67 (br s, 1H), 3.86 (s, 3H), 3.38-3.29 (m, 2H), 2.48 (s, 3H), 2.24-2.05 (m, 2H), 1.42 (s, 9H).

Step 3. Synthesis of 4-(3-fluoro-3,4-dihydro-2H-pyrrol-5-yl)-1,3-dimethyl-1H-pyrazole (C34)

A solution of C33 (370 mg, 1.24 mmol) in dichloromethane (10 mL) was treated with a solution of hydrogen chloride in 1,4-dioxane (4.0 M, 3.1 mL, 12.4 mmol). The reaction mixture was stirred at room temperature for 18 hours, whereupon it was concentrated under reduced pressure, affording the product as a white gum. This material contained some impurities by $^1$H NMR. Yield: 210 mg, 1.16 mmol, 94%. GCMS m/z 181.1 [M+]. $^1$H NMR (500 MHz, CD$_3$OD), characteristic product peaks: δ 8.38 (d, J=2.7 Hz, 1H), 5.43 (ddd, J=48.7, 8.2, 4.0 Hz, 1H), 3.89 (s, 3H), 3.22-3.10 (m, 2H), 2.44 (s, 3H).

Step 4. Synthesis of 4-(4-fluoropyrrolidin-2-yl)-1,3-dimethyl-1H-pyrazole (P8)

Sodium borohydride (88 mg, 2.3 mmol) was added to a solution of C34 (210 mg, 1.16 mmol) in methanol (8 mL). After the reaction mixture had been stirred for 1 hour at room temperature, it was diluted with saturated aqueous ammonium chloride solution (4 mL) and water (4 mL). The resulting mixture was extracted with ethyl acetate (3×100 mL), and the combined organic layers were dried over magnesium sulfate, filtered, and concentrated under reduced pressure. The product was obtained as a light tan gum, which was presumed to consist of a mixture of the cis and trans products, and contained some impurities by $^1$H NMR analysis. Yield: 182 mg, 0.993 mmol, 86%. GCMS m/z 183.1 [M+]. $^1$H NMR (500 MHz, CD$_3$OD), characteristic product peaks: δ 7.62 (d, J=2.9 Hz, 1H), [5.24-5.21 (m) and 5.14-5.10 (m), J$_{HF}$=53 Hz, 1H], [4.27-4.23 (m) and 4.20-4.17 (m), total 1H], 3.81 (s, 3H), 2.25 (s, 3H).

Preparation P9: 1,5-Dimethyl-4-(pyrrolidin-2-yl)-1H-pyrazole, Hydrochloride Salt (P9)

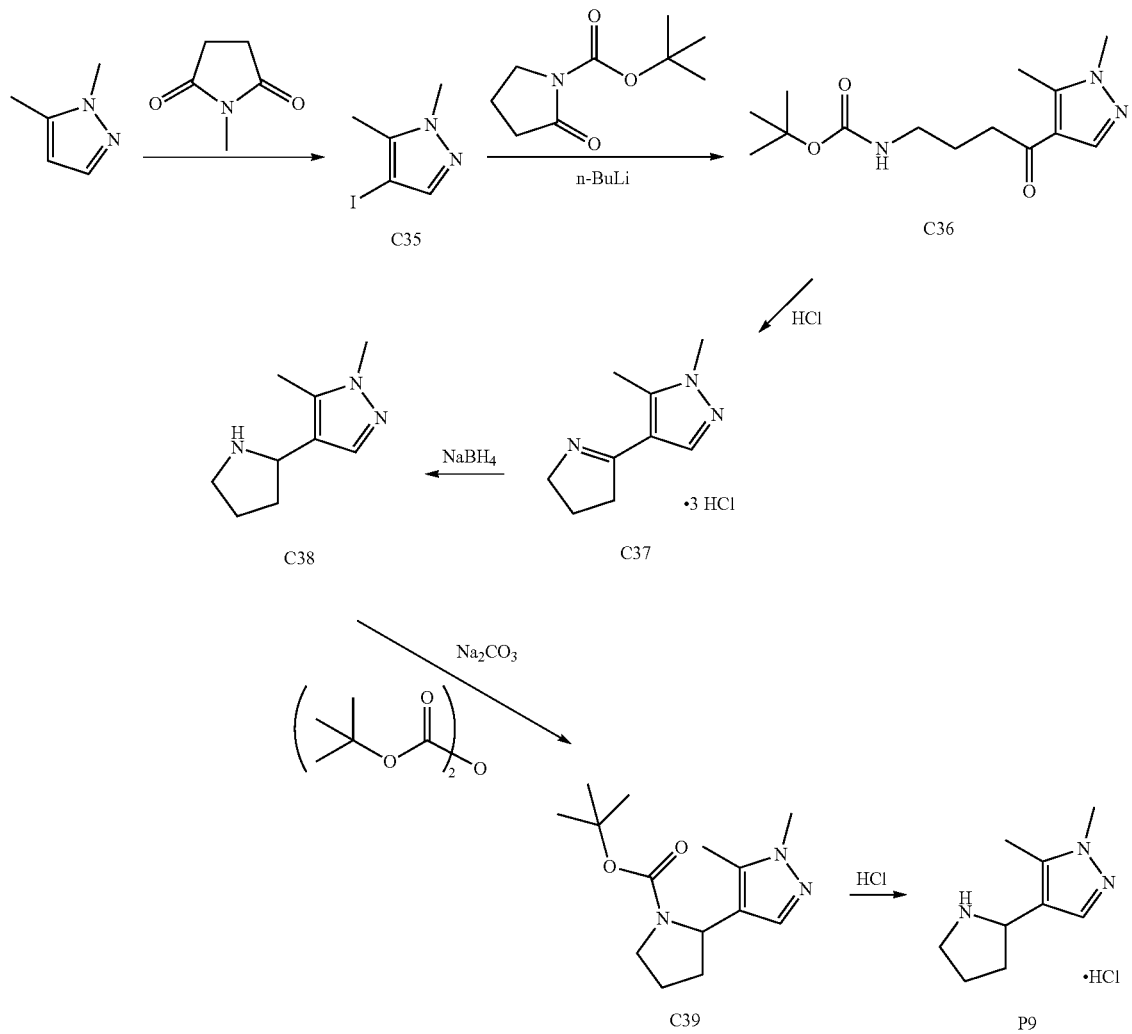

Step 1. Synthesis of 4-iodo-1,5-dimethyl-1H-pyrazole (C35)

N-Iodosuccinimide (35.8 g, 159 mmol) was added to a 10° C. solution of 1,5-dimethyl-1H-pyrazole (15.3 g, 159 mmol) in N,N-dimethylformamide (20 mL). The reaction mixture was stirred at 10° C. for 16 hours, and at 15° C. for 48 hours, whereupon it was diluted with ethyl acetate (500 mL) and washed sequentially with water (3×100 mL), aqueous sodium sulfite solution (100 mL), and saturated aqueous sodium chloride solution (50 mL). The organic layer was dried over sodium sulfate, filtered, and concentrated in vacuo to afford the product as a white solid. Yield: 28.0 g, 126 mmol, 79%. $^1$H NMR (400 MHz, CDCl$_3$) δ 7.41 (s, 1H), 3.85 (s, 3H), 2.29 (s, 3H).

Step 2. Synthesis of tert-butyl [4-(1,5-dimethyl-1H-pyrazol-4-yl)-4-oxobutyl]carbamate (C36)

A solution of n-butyllithium in hexanes (2.5 M, 49.8 mL, 124 mmol) was added to a −65° C. solution of C35 (26.3 g, 118 mmol) in tetrahydrofuran (300 mL), and the reaction mixture was stirred at −60° C. to −70° C. for 1 hour. A solution of tert-butyl 2-oxopyrrolidine-1-carboxylate (23.0 g, 124 mmol) in tetrahydrofuran (50 mL) was then added drop-wise, while the temperature of the reaction mixture was maintained at −60° C. to −70° C. Stirring was continued at that temperature for 2 hours, whereupon the reaction was quenched by addition of aqueous ammonium chloride solution (50 mL) and water (100 mL). The resulting mixture was extracted with ethyl acetate (3×150 mL), and the combined organic layers were washed with saturated aqueous sodium chloride solution (100 mL), dried over sodium sulfate, filtered, and concentrated in vacuo. Silica gel chromatography (Gradient: 20% to 33% ethyl acetate in petroleum ether) provided the product as a light yellow solid. Yield: 8.55 g, 30.4 mmol, 26%. $^1$H NMR (400 MHz, CDCl$_3$) δ 7.81 (s, 1H), 4.73-4.60 (br s, 1H), 3.80 (s, 3H), 3.24-3.14 (m, 2H), 2.80 (dd, J=7.5, 7.0 Hz, 2H), 2.56 (s, 3H), 1.93-1.84 (m, 2H), 1.43 (s, 9H).

Step 3. Synthesis of 4-(3,4-dihydro-2H-pyrrol-5-yl)-1,5-dimethyl-1H-pyrazole, Trihydrochloride Salt (C37)

A solution of hydrogen chloride in 1,4-dioxane (4 M, 60 mL) was added to a solution of C36 (8.55 g, 30.4 mmol) in dichloromethane (100 mL) and the reaction mixture was stirred at 20° C. for 16 hours. It was then concentrated under reduced pressure to provide the product as a yellow solid, which was used directly in the following step. LCMS m/z 164.1 [M+H]$^+$. $^1$H NMR (400 MHz, DMSO-d$_6$) δ 8.2-8.0 (br s, 3H), 7.98 (s, 1H), 3.75 (s, 3H), 2.89 (dd, J=7.3, 7.3 Hz, 2H), 2.85-2.75 (m, 2H), 2.48 (s, 3H), 1.89-1.79 (m, 2H).

Step 4. Synthesis of 1,5-dimethyl-4-(pyrrolidin-2-yl)-1H-pyrazole (C38)

Sodium borohydride (5.55 g, 147 mmol) was added in a portion-wise manner to a 0° C. solution of C37 (from the previous step, ≤30.4 mmol) in methanol (250 mL) {Caution: gas evolution.} The reaction mixture was then allowed to stir at 18° C. for 18 hours, whereupon sodium borohydride (2.22 g, 58.7 mmol) was again added and stirring was continued at 15° C. for 3 hours. Aqueous ammonium chloride solution (150 mL) was added, and the resulting mixture was concentrated in vacuo to provide an aqueous solution (approximately 150 mL), which was used directly in the next step.

Step 5. Synthesis of tert-butyl 2-(1,5-dimethyl-1H-pyrazol-4-yl)pyrrolidine-1-carboxylate (C39)

Sodium carbonate (7.77 g, 73.3 mmol) and di-tert-butyl dicarbonate (12.8 g, 58.6 mmol) were added to a 15° C. mixture of the aqueous solution of C38 (from the previous step; ≤30.4 mmol) and methanol (200 mL). The reaction mixture was stirred at 18° C. for 16 hours, whereupon it was diluted with water (200 mL) and extracted with ethyl acetate (3×150 mL). The combined organic layers were washed with saturated aqueous sodium chloride solution (60 mL), dried over sodium sulfate, filtered, and concentrated in vacuo. Silica gel chromatography (Gradient: 17% to 50% ethyl acetate in petroleum ether) afforded the product as a colorless oil. From analysis of the $^1$H NMR, this material was presumed to exist as a mixture of rotamers. Yield: 3.50 g, 13.2 mmol, 43% over three steps. LCMS m/z 266.2 [M+H]$^+$. $^1$H NMR (400 MHz, CDCl$_3$) δ 7.19 (s, 1H), 4.90-4.62 (br m, 1H), 3.74 (br s, 3H), 3.59-3.36 (br m, 2H), 2.25-2.08 (br m, 1H), 2.21 (br s, 3H), 2.04-1.81 (m, 2H), 1.79-1.67 (m, 1H), [1.43 (br s) and 1.28 (br s), total 9H].

Step 6. Synthesis of 1,5-dimethyl-4-(pyrrolidin-2-yl)-1H-pyrazole, Hydrochloride Salt (P9)

To a solution of C39 (3.50 g, 13.2 mmol) in dichloromethane (40 mL) was added a solution of hydrogen chloride in 1,4-dioxane (4 M, 20 mL) and the reaction mixture was stirred at 20° C. for 5 hours. Concentration in vacuo provided a solid, which was combined with the product of a similar reaction carried out on C39 (500 mg, 1.9 mmol) and washed with hexanes (30 mL), providing the product as an off-white solid. Combined yield: 2.80 g, 13.9 mmol, 92%. LCMS m/z 166.1 [M+H]$^+$. $^1$H NMR (400 MHz, DMSO-d$_6$) δ 10.23-10.09 (br s, 1H), 8.96-8.81 (br s, 1H), 7.64 (s, 1H), 4.46-4.35 (m, 1H), 3.73 (s, 3H), 3.29-3.11 (m, 2H), 2.29 (s, 3H), 2.23-2.15 (m, 1H), 2.11-1.88 (m, 3H).

Preparation P10: Mixture of tert-Butyl 2-(1,4-dimethyl-1H-pyrazol-5-yl)pyrrolidine-1-carboxylate and tert-Butyl 2-(1,4-dimethyl-1H-pyrazol-3-yl)pyrrolidine-1-carboxylate (P10)

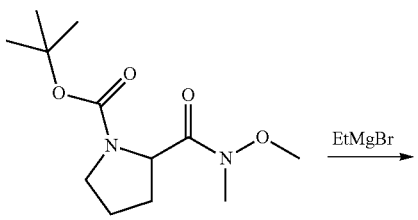

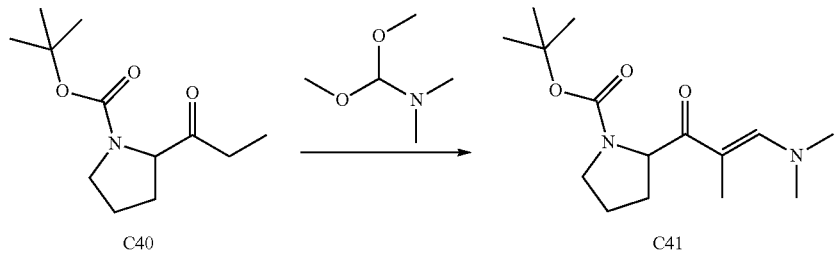

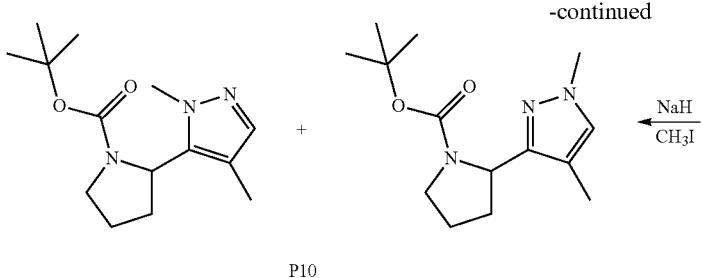 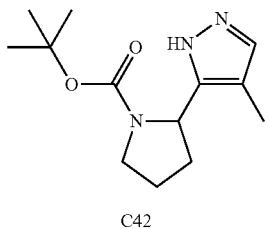

Step 1. Synthesis of tert-butyl 2-propanoylpyrrolidine-1-carboxylate (C40)

A solution of ethylmagnesium bromide in diethyl ether (3.0 M, 14.2 mL, 42.6 mmol) was added drop-wise to a 0° C. solution of tert-butyl 2-[methoxy(methyl)carbamoyl]pyrrolidine-1-carboxylate (10.0 g, 38.7 mmol) in tetrahydrofuran (100 mL). The reaction mixture was stirred at room temperature for 2 hours, whereupon saturated aqueous ammonium chloride solution was added. The aqueous layer was extracted with ethyl acetate (2×200 mL), and the combined organic layers were washed with saturated aqueous sodium chloride solution, dried over sodium sulfate, filtered, and concentrated in vacuo. Purification via silica gel chromatography (Gradient: 0% to 30% ethyl acetate in petroleum ether) afforded the product as a light oil. From analysis of the $^1$H NMR, this material was presumed to exist as a mixture of rotamers. Yield: 6.10 g, 26.8 mmol, 69%. $^1$H NMR (400 MHz, CDCl$_3$) δ [4.35 (dd, J=8.5, 4.0 Hz) and 4.24 (dd, J=8.5, 5.0 Hz), total 1H], 3.59-3.38 (m, 2H), 2.57-2.35 (m, 2H), 2.25-2.06 (m, 1H), 1.94-1.75 (m, 3H), [1.46 (s) and 1.40 (s), total 9H], [1.08 (t, J=7.3 Hz) and 1.06 (t, J=7.5 Hz), total 3H].

Step 2. Synthesis of tert-butyl 2-[3-(dimethylamino)-2-methylprop-2-enoyl]pyrrolidine-1-carboxylate (C41)

A solution of C40 (500 mg, 2.20 mmol) in N,N-dimethylformamide dimethyl acetal (20 mL) was heated at reflux for 16 hours. The reaction mixture was concentrated in vacuo to afford the product as a black oil. Yield: 550 mg, 1.95 mmol, 89%.

Step 3. Synthesis of tert-butyl 2-(4-methyl-1H-pyrazol-5-yl)pyrrolidine-1-carboxylate (C42)

To a solution of C41 (550 mg, 1.95 mmol) in ethanol (15 mL) was added a solution of hydrazine hydrate (2 mL). The reaction mixture was heated at reflux for 16 hours, whereupon it was concentrated in vacuo to provide the product as a yellow oil. Yield: 450 mg, 1.79 mmol, 92%.

Step 4. Synthesis of a mixture of tert-butyl 2-(1,4-dimethyl-1H-pyrazol-5-yl)pyrrolidine-1-carboxylate and tert-butyl 2-(1,4-dimethyl-1H-pyrazol-3-yl)pyrrolidine-1-carboxylate (P10)

To a solution of C42 (450 mg, 1.79 mmol) in tetrahydrofuran (20 mL) was added sodium hydride (129 mg, 5.38 mmol). After the reaction mixture had stirred for 1 hour, it was treated with iodomethane (2.54 g, 17.9 mmol), and the reaction was allowed to proceed until it was shown to be complete by LCMS, which exhibited a major peak for the product (LCMS m/z 265.9 [M+H]$^+$). At this point, water (50 mL) was added, and the resulting mixture was extracted with ethyl acetate (3×50 mL). The combined organic layers were washed with saturated aqueous sodium chloride solution (50 mL), dried over sodium sulfate, filtered, and concentrated in vacuo. Chromatography on silica gel (Eluent: 1:1 petroleum ether/ethyl acetate) afforded the product (presumed to be a mixture of two regioisomers) as a colorless oil. Yield: 210 mg, 0.791 mmol, 44%.

Examples 1, 2, and 3

(+/−)-4-(4-{[2-(1,3-Dimethyl-1H-pyrazol-4-yl)pyrrolidin-1-yl]methyl}-2-fluorophenoxy) benzamide (1), (+)-4-(4-{[2-(1,3-Dimethyl-1H-pyrazol-4-yl)pyrrolidin-1-yl]methyl}-2-fluorophenoxy)benzamide (ENT-1) (2), and (−)-4-(4-{[2-(1,3-Dimethyl-1H-pyrazol-4-yl)pyrrolidin-1-yl]methyl}-2-fluorophenoxy)benzamide (ENT-2) (3)

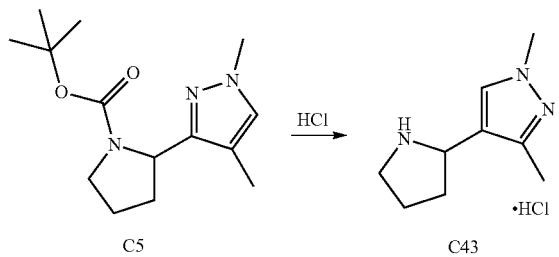

-continued

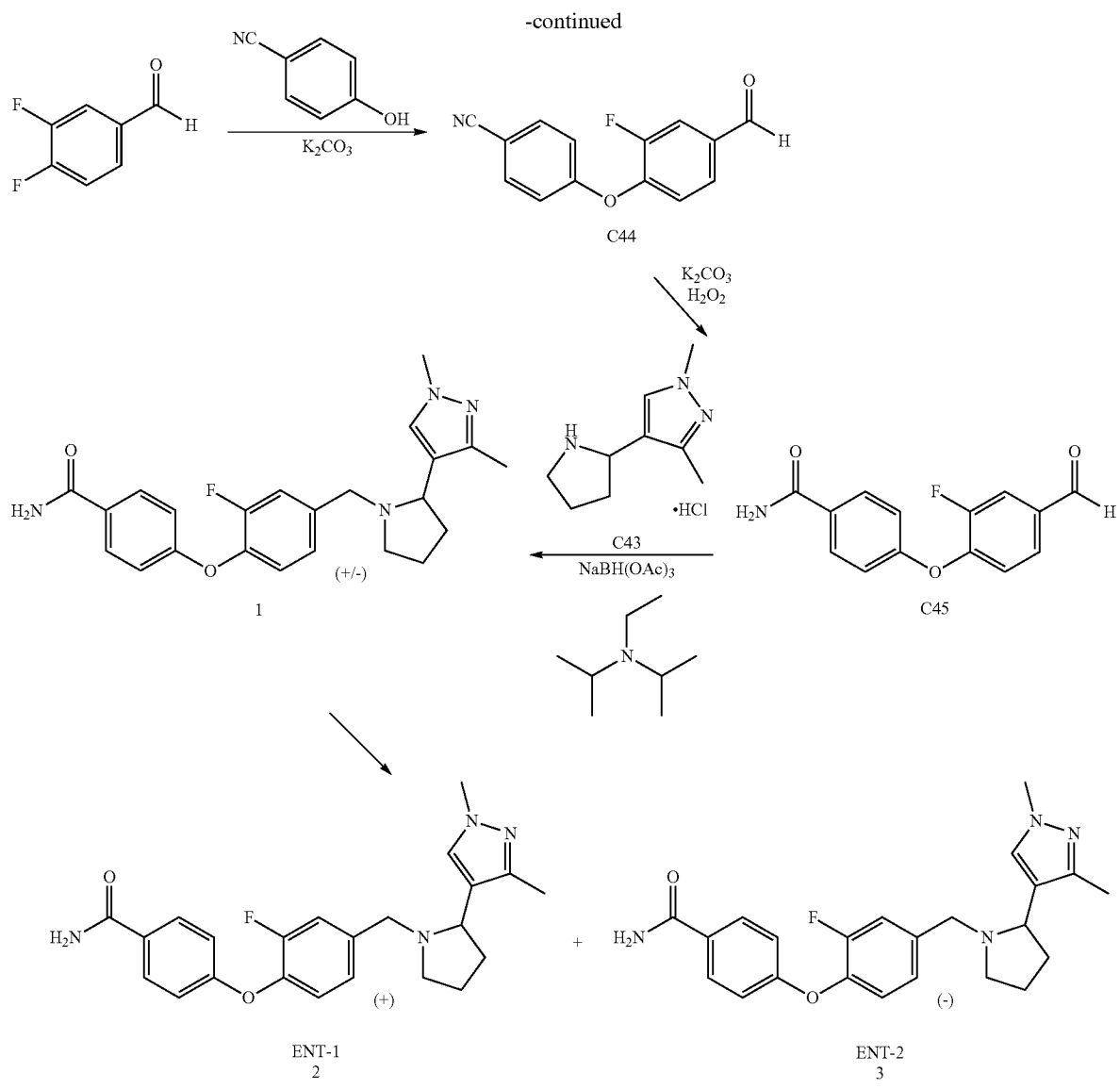

Step 1. Synthesis of 1,3-dimethyl-4-(pyrrolidin-2-yl)-1H-pyrazole, Hydrochloride Salt (C43)

A solution of C5 (1.85 g, 6.97 mmol) in ethyl acetate (25 mL) was treated with a solution of hydrogen chloride in ethyl acetate (1 M, 35 mL). The reaction mixture was stirred at room temperature overnight, whereupon it was concentrated in vacuo to afford the product as a thick oil. This material was used without further purification. Yield: 1.10 g, 5.45 mmol, 78%. LCMS m/z 166.1 [M+H]$^+$.

Step 2. Synthesis of 4-(2-fluoro-4-formylphenoxy)benzonitrile (C44)

3,4-Difluorobenzaldehyde (3.00 g, 21.1 mmol) was added to a mixture of 4-hydroxybenzonitrile (3.02 g, 25.4 mmol) and potassium carbonate (5.84 g, 42.2 mmol) in N,N-dimethylformamide (42 mL), and the reaction mixture was allowed to stir at 100° C. overnight. It was then cooled to room temperature and poured into water (300 mL) with stirring; after 15 minutes, the solid was collected via filtration to provide the product as an off-white solid. Yield: 4.52 g, 18.7 mmol, 89%. $^1$H NMR (500 MHz, CDCl$_3$) δ 9.98 (d, J=2.0 Hz, 1H), 7.77 (dd, half of ABX pattern, J=10.2, 1.8 Hz, 1H), 7.73 (ddd, half of ABXY pattern, J=8.3, 1.7, 1.0 Hz, 1H), 7.68 (br d, J=9.0 Hz, 2H), 7.29-7.25 (m, 1H, assumed; partially obscured by solvent peak), 7.09 (br d, J=8.8 Hz, 2H).

Step 3. Synthesis of 4-(2-fluoro-4-formylphenoxy)benzamide (C45)

Hydrogen peroxide (30% solution in water, 0.6 mL) was slowly added to a mixture of C44 (280 mg, 1.16 mmol) and potassium carbonate (481 mg, 3.48 mmol) in dimethyl sulfoxide (3 mL), at a rate that maintained the reaction temperature below 20° C. After the reaction mixture had been stirred at 20° C. for 3 hours, it was poured into an aqueous sodium sulfite solution (5 mL), while the temperature was kept below 20° C. The resulting mixture was extracted with dichloromethane (2×10 mL) containing sufficient methanol to enable extraction of the product, and the combined organic layers were washed with saturated aqueous sodium chloride solution (5 mL), dried over sodium sulfate, filtered, and concentrated in vacuo to afford the product as a solid. Yield: 300 mg, 1.16 mmol, quantitative. $^1$H NMR (400 MHz, CDCl$_3$) δ 9.95 (d, J=2.0 Hz, 1H), 7.87 (br d, J=8.8 Hz, 2H), 7.74 (dd, J=10.3, 1.8 Hz, 1H), 7.67 (br ddd, J=8.3, 1.8, 1.0 Hz, 1H), 7.18 (dd, J=8, 8 Hz, 1H), 7.10 (br d, J=8.8 Hz, 2H).

Step 4. Synthesis of (+/−)-4-(4-{[2-(1,3-dimethyl-1H-pyrazol-4-yl)pyrrolidin-1-yl]methyl}-2-fluorophenoxy)benzamide (1), (+)-4-(4-{[2-(1,3-dimethyl-1H-pyrazol-4-yl)pyrrolidin-1-yl]methyl}-2-fluorophenoxy)benzamide (ENT-1) (2), and (−)-4-(4-{[2-(1,3-dimethyl-1H-pyrazol-4-yl)pyrrolidin-1-yl]methyl}-2-fluorophenoxy)benzamide (ENT-2) (3)

A solution of C43 (303 mg, 1.50 mmol) in dichloromethane (6 mL) was treated with N,N-diisopropylethylamine (0.97 mL, 5.57 mmol) and stirred for 15 minutes, whereupon C45 (475 mg, 1.83 mmol) was added and stirring was continued for 20 minutes. Sodium triacetoxyborohydride (98%, 1.19 g, 5.50 mmol) was added and the reaction mixture was stirred overnight at room temperature. It was then partitioned between dichloromethane (50 mL) and saturated aqueous sodium bicarbonate solution (50 mL), and the aqueous layer was extracted twice with dichloromethane. The combined organic layers were dried over magnesium sulfate, filtered, concentrated in vacuo, and purified via silica gel chromatography (Gradient: 0% to 5% methanol in dichloromethane), affording the racemic product 1 as an off-white foam. Yield of racemic material: 510 mg, 1.25 mmol, 83%. LCMS m/z 409.4 [M+H]$^+$. $^1$H NMR (400 MHz, CDCl$_3$) δ 7.78 (brd, J=8.6 Hz, 2H), 7.29 (brs, 1H), 7.16 (d, J=11.7 Hz, 1H), 7.08-7.01 (m, 2H), 6.97 (br d, J=9.0 Hz, 2H), 6.15-5.85 (v br s, 2H), 3.89 (d, J=13.3 Hz, 1H), 3.83 (s, 3H), 3.39-3.27 (m, 1H), 3.15-3.00 (m, 2H), 2.28 (s, 3H), 2.22-2.10 (m, 2H), 1.97-1.69 (m, 3H).

Racemate 1 was separated into its enantiomers via supercritical fluid chromatography (Column: Phenomenex Lux Cellulose-2, 5 μm; Mobile phase A: carbon dioxide; Mobile phase B: methanol containing 0.2% ammonium hydroxide; Gradient: 5% to 60% B). The first-eluting product, obtained as a tan solid, exhibited a positive (+) rotation, and was designated as 2. Yield: 219 mg, 0.536 mmol, 43% for the separation. LCMS m/z 409.6 [M+H]$^+$. $^1$H NMR (400 MHz, CDCl$_3$) δ 7.79 (br d, J=8.6 Hz, 2H), 7.29-7.26 (1H, assumed; obscured by solvent peak), 7.16 (br d, J=11.3 Hz, 1H), 7.08-7.02 (m, 2H), 6.97 (br d, J=8.6 Hz, 2H), 6.3-5.4 (v br m, 2H), 3.90 (br d, J=13.3 Hz, 1H), 3.83 (s, 3H), 3.38-3.27 (m, 1H), 3.15-2.98 (m, 2H), 2.28 (s, 3H), 2.22-2.07 (m, 2H), 1.98-1.63 (m, 3H). This NMR data was obtained a number of months after isolation of 2, and exhibited broadened signals. A smaller-scale synthesis provided the following data immediately after isolation: LCMS m/z 431.0 [M+Na]$^+$. $^1$H NMR (400 MHz, CDCl$_3$) δ 7.78 (br d, J=9.0 Hz, 2H), 7.3-7.25 (1H, assumed; obscured by solvent peak), 7.16 (d, J=11 Hz, 1H), 7.07-7.03 (m, 2H), 6.98 (br d, J=8.0 Hz, 2H), 3.90 (d, J=13.0 Hz, 1H), 3.83 (s, 3H), 3.32 (dd, J=8.5, 8.0 Hz, 1H), 3.12-3.06 (m, 1H), 3.04 (d, J=13.0 Hz, 1H), 2.29 (s, 3H), 2.20-2.09 (m, 2H), 1.95-1.69 (m, 3H).

The second-eluting product (210 mg), which exhibited a negative (−) rotation, was suspended in ethyl acetate (5 mL) and filtered; the collected solid was designated as 3. Yield: 155 mg, 0.379 mmol, 30% for the separation. LCMS m/z 409.4 [M+H]$^+$. $^1$H NMR (400 MHz, CDCl$_3$) δ 7.78 (br d, J=8.6 Hz, 2H), 7.29-7.25 (1H, assumed; obscured by solvent peak), 7.16 (d, J=11.7 Hz, 1H), 7.08-7.02 (m, 2H), 6.97 (br d, J=8.6 Hz, 2H), 6.2-5.3 (v br m, 2H), 3.90 (d, J=13.3 Hz, 1H), 3.83 (s, 3H), 3.32 (dd, J=8.2, 8.2 Hz, 1H), 3.13-3.05 (m, 1H), 3.04 (d, J=13.3 Hz, 1H), 2.29 (s, 3H), 2.21-2.09 (m, 2H), 1.97-1.69 (m, 3H).

By analytical HPLC (Column: Phenomenex Lux Cellulose-2, 4.6×250 mm, 5 μm; Mobile phase A: carbon dioxide; Mobile phase B: methanol containing 0.2% ammonium hydroxide; Gradient: 5% B from 0 to 1.00 minute, 5% to 60% B over 8.00 minutes; Flow rate: 3.0 mL/minute), 2 exhibited a retention time of 8.95 minutes. Using the same analytical system, 3 exhibited a retention time of 10.00 minutes.

Examples 4, 5, and 6

(+/−)-4-(4-{[2-(1,3-Dimethyl-1H-pyrazol-4-yl)pyrrolidin-1-yl]methyl}phenoxy)-3-fluorobenzamide (4), 4-(4-{[2-(1,3-Dimethyl-1H-pyrazol-4-yl)pyrrolidin-1-yl]methyl}phenoxy)-3-fluorobenzamide, ENT-1 (5), and 4-(4-{[2-(1,3-Dimethyl-1H-pyrazol-4-yl)pyrrolidin-1-yl]methyl}phenoxy)-3-fluorobenzamide, ENT-2 (6)

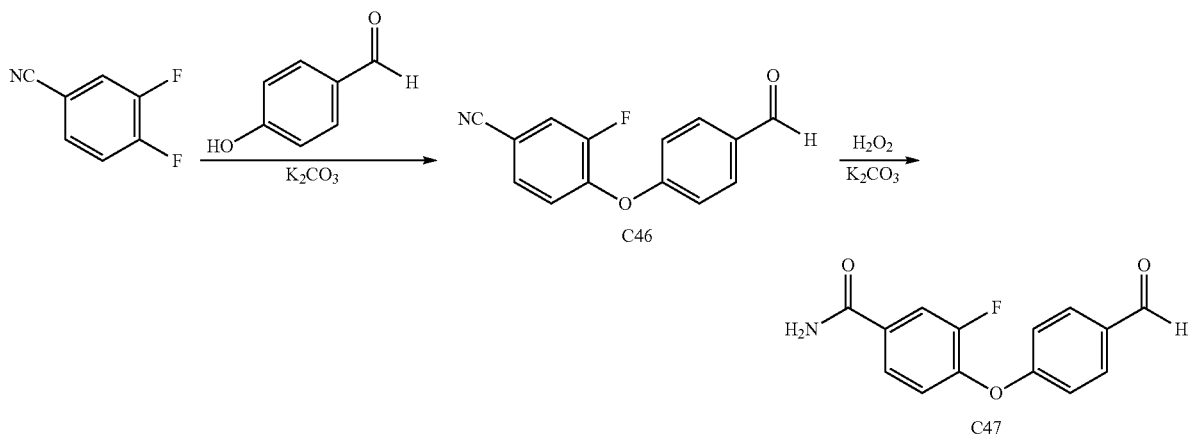

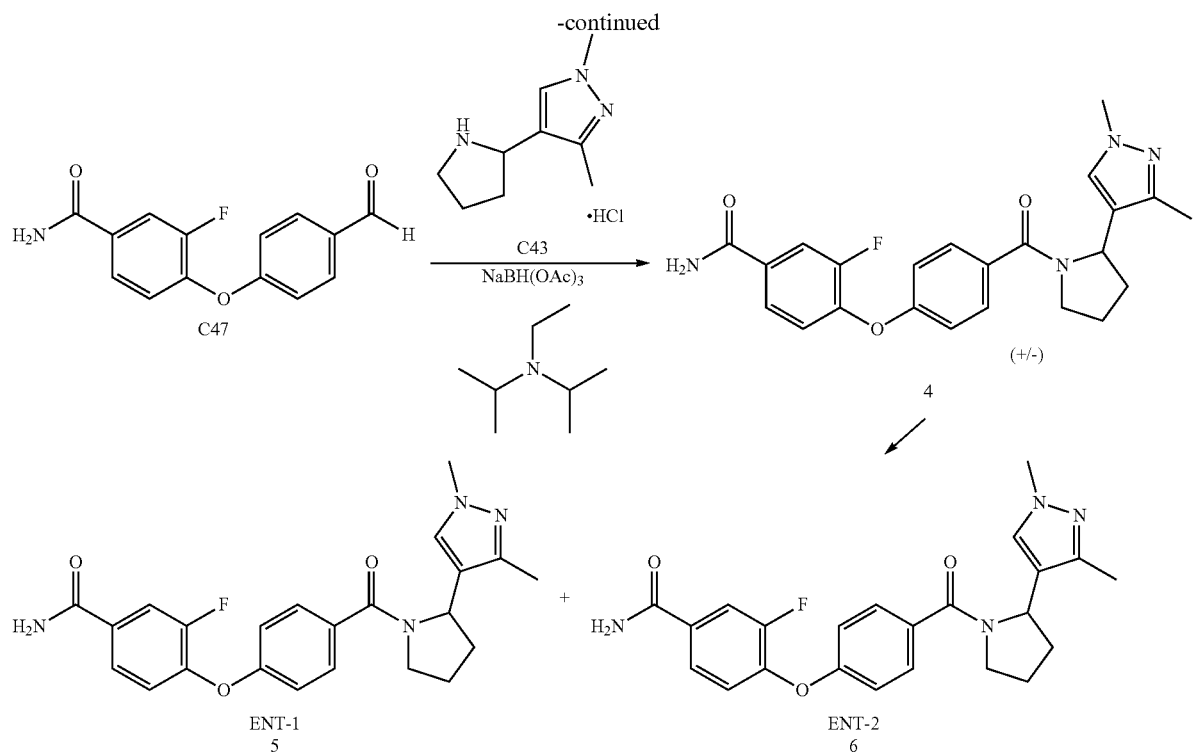

Step 1. Synthesis of 3-fluoro-4-(4-formylphenoxy)benzonitrile (C46)

Potassium carbonate (19.9 g, 144 mmol) was added to a mixture of 3,4-difluorobenzonitrile (10.0 g, 71.9 mmol) and 4-hydroxybenzaldehyde (8.78 g, 71.9 mmol) in N,N-dimethylformamide (200 mL). The reaction mixture was heated to 100° C. for 4 hours, whereupon it was cooled to room temperature and partitioned between water and ethyl acetate. The organic layer was washed with water (3×200 mL), dried over sodium sulfate, filtered, and concentrated in vacuo, affording the product as a yellow solid (17.7 g). By $^1$H NMR, this material contained some N,N-dimethylformamide. Yield, corrected for N,N-dimethylformamide: 16.8 g, 69.6 mmol, 97%. $^1$H NMR (400 MHz, CDCl$_3$) δ 9.99 (s, 1H), 7.93 (br d, J=8.6 Hz, 2H), 7.58-7.48 (m, 2H), 7.21 (dd, J=8.4, 8.0 Hz, 1H), 7.14 (br d, J=8.6 Hz, 2H).

Step 2. Synthesis of 3-fluoro-4-(4-formylphenoxy)benzamide (C47)

A solution of C46 (from the previous step; 16.8 g, 69.6 mmol) in dimethyl sulfoxide (100 mL) was cooled in an ice bath and treated with potassium carbonate (5.007 g, 36.7 mmol). An aqueous solution of hydrogen peroxide (30%, 8.24 mL, 80.7 mmol) was added drop-wise, and the reaction mixture was stirred at 0° C. for 5 minutes, and then warmed to room temperature. After 2 hours, it was poured into water (500 mL) and stirred at room temperature for 30 minutes. Collection of the solid via filtration and rinsing of the solid with water provided the product. Yield: 16.3 g, 62.9 mmol, 90%. $^1$H NMR (400 MHz, CDCl$_3$) δ 9.96 (s, 1H), 7.90 (br d, J=8.6 Hz, 2H), 7.74 (dd, J=10.7, 1.8 Hz, 1H), 7.63 (br d, J=8.2 Hz, 1H), 7.22 (dd, J=8.2, 8.2 Hz, 1H), 7.10 (br d, J=8.6 Hz, 2H), 6.2-5.5 (v br m, 2H).

Step 3. Synthesis of (+/−)-4-(4-{[2-(1,3-dimethyl-1H-pyrazol-4-yl)pyrrolidin-1-yl]methyl}phenoxy)-3-fluorobenzamide (4), 4-(4-{[2-(1,3-dimethyl-1H-pyrazol-4-yl) pyrrolidin-1-yl]methyl}phenoxy)-3-fluorobenzamide, ENT-1 (5), and 4-(4-{[2-(1,3-dimethyl-1H-pyrazol-4-yl)pyrrolidin-1-yl] methyl}phenoxy)-3-fluorobenzamide, ENT-2 (6)

A solution of C43 (760 mg, 3.77 mmol) and N,N-diisopropylethylamine (3.3 mL, 19 mmol) in dichloromethane (12.5 mL) was stirred for 15 minutes, whereupon C47 (975 mg, 3.76 mmol) was added and stirring was continued for 2 hours. Sodium triacetoxyborohydride (98%, 4.07 g, 18.8 mmol) was then added and the reaction mixture was stirred overnight at room temperature. After addition of saturated aqueous sodium bicarbonate solution (50 mL), the aqueous layer was extracted three times with dichloromethane, and the combined organic layers were dried over magnesium sulfate, filtered, and concentrated in vacuo. Chromatography on silica gel (Gradient: 0% to 5% methanol in dichloromethane) provided the racemic product as a glass. Yield of racemate 4: 1.12 g, 2.74 mmol, 73%. LCMS m/z 409.2 [M+H]$^+$. $^1$H NMR (400 MHz, CDCl$_3$) δ 7.68 (dd, J=11.1, 2.1 Hz, 1H), 7.51 (ddd, J=8.6, 2.0, 1.2 Hz, 1H), 7.30-7.24 (m, 3H, assumed; partially obscured by solvent peak), 7.00-6.93 (m, 3H), 6.2-5.8 (v br m, 2H), 3.90 (d, J=13.3 Hz, 1H), 3.82 (s, 3H), 3.30 (dd, J=8.2, 7.8 Hz, 1H), 3.09-3.00 (m, 2H), 2.28 (s, 3H), 2.20-2.09 (m, 2H), 1.93-1.67 (m 3H).

Racemate 4 was separated into its enantiomers via supercritical fluid chromatography [Column: Chiral Technologies Chiralcel OJ-H, 5 μm; Mobile phase: 85:15 carbon dioxide/ (methanol containing 0.2% ammonium hydroxide)]. The first-eluting enantiomer was dissolved in dichloromethane, filtered through a nylon Acrodisc®, concentrated in vacuo, and subjected to silica gel chromatography (Gradient: 50% to 100% ethyl acetate in heptane), providing 5 as an off-white foam. Yield: 378 mg, 0.925 mmol, 34% for the separation. LCMS m/z 409.3 [M+H]$^+$. $^1$H NMR (400 MHz, CDCl$_3$) δ 7.68 (dd, J=10.9, 2.0 Hz, 1H), 7.51 (br d, J=8 Hz, 1H), 7.29-7.24 (m, 3H, assumed; partially obscured by solvent peak), 7.00-6.94 (m, 3H), 6.2-5.5 (v br m, 2H), 3.90 (d, J=13.3 Hz, 1H), 3.82 (s, 3H), 3.30 (dd, J=8.6, 7.8 Hz, 1H), 3.09-3.02 (m, 1H), 3.03 (d, J=13.3 Hz, 1H), 2.28 (s, 3H), 2.20-2.09 (m, 2H), 1.93-1.67 (m, 3H).

The second-eluting enantiomer from the supercritical fluid chromatography was repurified in the same manner as 5, providing 6 as an off-white foam. Yield: 371 mg, 0.908 mmol, 33% for the separation. LCMS m/z 409.3 [M+H]$^+$. $^1$H NMR (400 MHz, CDCl$_3$) δ 7.68 (dd, J=10.9, 2.0 Hz, 1H), 7.51 (br d, J=8.6 Hz, 1H), 7.29-7.24 (m, 3H, assumed; partially obscured by solvent peak), 7.00-6.94 (m, 3H), 6.2-5.6 (v br m, 2H), 3.90 (d, J=12.9 Hz, 1H), 3.82 (s, 3H), 3.30 (dd, J=8.6, 7.8 Hz, 1H), 3.08-3.01 (m, 1H), 3.02 (d, J=13.3 Hz, 1H), 2.28 (s, 3H), 2.20-2.08 (m, 2H), 1.93-1.67 (m, 3H).

By analytical HPLC (Column: Chiral Technologies Chiralcel OJ-H, 4.6×250 mm, 5 µm; Mobile phase A: carbon dioxide; Mobile phase B: methanol containing 0.2% ammonium hydroxide; Gradient: 5% B from 0 to 1.00 minute, 5% to 60% B over 8.00 minutes; Flow rate: 3.0 mL/minute), 5 exhibited a retention time of 5.68 minutes. Using the same analytical system, 6 exhibited a retention time of 6.08 minutes.

Examples 7, 8, and 9

(+/−)-3-Fluoro-4-(4-{[2-(3-methoxy-1-methyl-1H-pyrazol-4-yl)pyrrolidin-1-yl]methyl}phenoxy)benzamide (7), (−)-3-Fluoro-4-(4-{[2-(3-methoxy-1-methyl-1H-pyrazol-4-yl) pyrrolidin-1-yl] methyl}phenoxy)benzamide (ENT-1) (8), and (+)-3-Fluoro-4-(4-{[2-(3-methoxy-1-methyl-1H-pyrazol-4-yl)pyrrolidin-1-yl]methyl}phenoxy)benzamide (ENT-2) (9)

Sodium triacetoxyborohydride (98%, 3.46 g, 16.0 mmol) was added to a mixture of C13 (1.45 g, 8.00 mmol) and C47 (2.07 g, 7.98 mmol) in dichloromethane (50 mL), and the reaction mixture was stirred at room temperature for 3 days. It was then partitioned between saturated aqueous sodium bicarbonate solution and dichloromethane, and the aqueous layer was extracted with dichloromethane. The combined organic layers were dried over sodium sulfate, filtered, and concentrated in vacuo. Silica gel chromatography (Gradient: 0% to 10% methanol in ethyl acetate) provided racemate 7 as an off-white foam. Yield of racemate 7: 2.60 g, 6.13 mmol, 77%. LCMS m/z 425.3 [M+H]$^+$.

Separation of 7 into its component enantiomers was carried out via supercritical fluid chromatography [Column: Chiral Technologies Chiralpak AD-H, 5 µm; Mobile phase: 85:15 carbon dioxide/(ethanol containing 0.2% ammonium hydroxide)]. The first-eluting product, which exhibited a negative (−) rotation, was repurified via silica gel chromatography (Gradient: 0% to 10% methanol in ethyl acetate) to afford a foamy solid, designated as 8. Yield: 1.12 g, 2.64 mmol, 43% for the separation. LCMS m/z 425.4 [M+H]$^+$. $^1$H NMR (400 MHz, CDCl$_3$) δ 7.67 (dd, J=11.1, 1.8 Hz, 1H), 7.50 (br d, J=8 Hz, 1H), 7.30-7.25 (m, 2H, assumed; partially obscured by solvent peak), 7.16 (s, 1H), 7.00-6.94 (m, 3H), 6.2-5.4 (v br m, 2H), 3.94-3.88 (m, 1H), 3.93 (s, 3H), 3.73 (s, 3H), 3.32 (dd, J=7.8, 7.4 Hz, 1H), 3.10 (d, J=12.9 Hz, 1H), 3.06-2.98 (m, 1H), 2.20-2.09 (m, 2H), 1.92-1.70 (m, 3H).

The second-eluting product, obtained as a tan foamy solid, exhibited a positive (+) rotation, and was designated as 9. Yield: 1.18 g, 2.78 mmol, 45% for the separation. LCMS m/z 425.6 [M+H]$^+$. $^1$H NMR (400 MHz, CDCl$_3$) δ 7.68 (dd, J=10.9, 2.0 Hz, 1H), 7.51 (br d, J=8 Hz, 1H), 7.34-7.25 (m, 2H, assumed; partially obscured by solvent peak), 7.17 (br s, 1H), 7.02-6.93 (m, 3H), 6.3-5.4 (v br m, 2H), 3.97-3.89 (m, 1H), 3.93 (s, 3H), 3.74 (s, 3H), 3.43-3.25

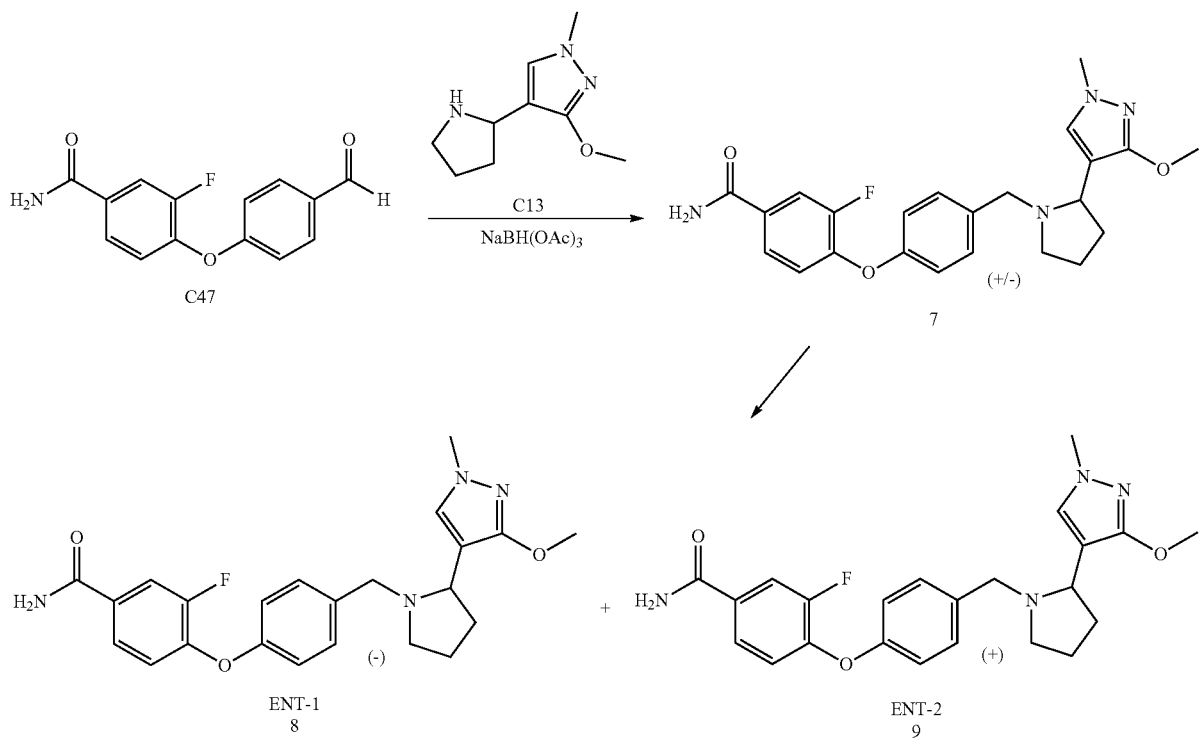

(m, 1H), 3.22-2.94 (m, 2H), 2.27-2.06 (m, 2H), 1.97-1.70 (m, 3H). This NMR data was obtained a number of months after isolation of 9, and exhibited broadened signals. A smaller-scale synthesis provided the following data immediately after isolation: LCMS m/z 425.1 [M+H]$^+$; $^1$H NMR (400 MHz, CDCl$_3$) δ 7.67 (dd, J=11.0, 2.0 Hz, 1H), 7.50 (ddd, J=8.5, 2.3, 1.2 Hz, 1H), 7.30-7.25 (m, 2H, assumed; partially obscured by solvent peak), 7.17 (br s, 1H), 7.00-6.93 (m, 3H), 6.15-5.5 (v br m, 2H), 3.95-3.87 (m, 1H), 3.92 (s, 3H), 3.73 (s, 3H), 3.33 (dd, J=8, 7 Hz, 1H), 3.11 (d, J=13.0 Hz, 1H), 3.06-2.98 (m, 1H), 2.22-2.07 (m, 2H), 1.92-1.7 (m, 3H).

By analytical HPLC (Column: Chiral Technologies Chiralpak AD-H, 4.6×250 mm, 5 μm; Mobile phase A: carbon dioxide; Mobile phase B: ethanol containing 0.2% ammonium hydroxide; Gradient: 5% B from 0 to 1.00 minute, 5% to 60% B over 8.00 minutes; Flow rate: 3.0 mL/minute), 8 exhibited a retention time of 6.55 minutes. Using the same analytical system, 9 exhibited a retention time of 7.05 minutes.

Example 8, (L)-Lactate Salt

3-Fluoro-4-(4-{[2-(3-methoxy-1-methyl-1H-pyrazol-4-yl)pyrrolidin-1-yl]methyl}phenoxy)benzamide, ENT-1, (L)-Lactate Salt (8, (L)-Lactate Salt)

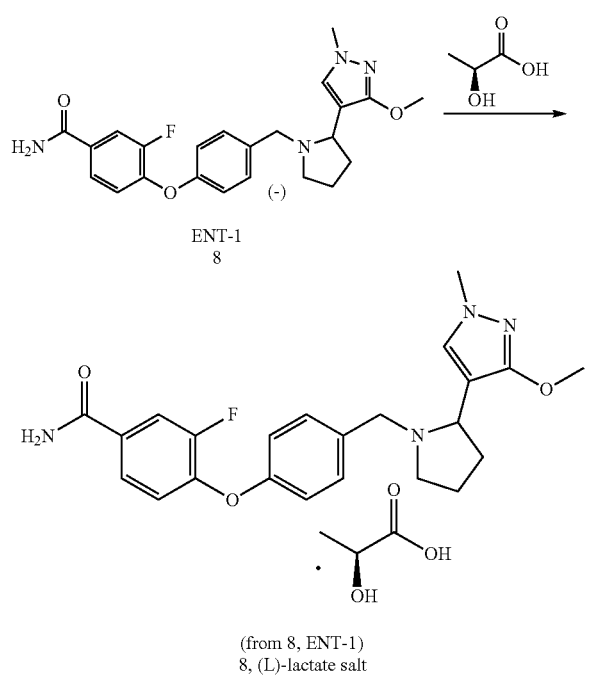

A solution of 8 (1.00 g, 2.36 mmol) in ethyl acetate (10 mL) was treated with a solution of L-(+)-lactic acid [(2S)-2-hydroxypropanoic acid; 98%, 282 mg, 3.07 mmol) in ethyl acetate (2 mL) and stirred at room temperature. After 30 minutes, the solution was seeded with the product, and stirring was continued for 3 days. Collection via filtration afforded the product as a solid, which proved to be crystalline via powder X-ray diffraction. Yield: 1.05 g, 2.04 mmol, 86%. LCMS m/z 425.3 [M+H]$^+$. $^1$H NMR (400 MHz, CD$_3$OD) δ 7.79 (dd, J=11.5, 2.2 Hz, 1H), 7.72 (ddd, J=8.5, 2.0, 1.1 Hz, 1H), 7.50 (s, 1H), 7.38 (br d, J=8.6 Hz, 2H), 7.15 (dd, J=8.2, 8.2 Hz, 1H), 7.04 (br d, J=8.8 Hz, 2H), 4.25-4.14 (m, 2H), 4.05 (q, J=6.8 Hz, 1H), 3.95-3.86 (m, 1H), 3.92 (s, 3H), 3.74 (s, 3H), 3.3-3.24 (m, 1H, assumed; partially obscured by solvent peak), 3.10-2.98 (m, 1H), 2.41-2.31 (m, 1H), 2.24-2.14 (m, 1H), 2.14-2.03 (m, 2H), 1.33 (d, J=6.8 Hz, 3H).

Example 10

4-(4-{[(2S)-2-(5-Methyl-1,2,4-thiadiazol-3-yl)pyrrolidin-1-yl]methyl}phenoxy)benzamide (10)

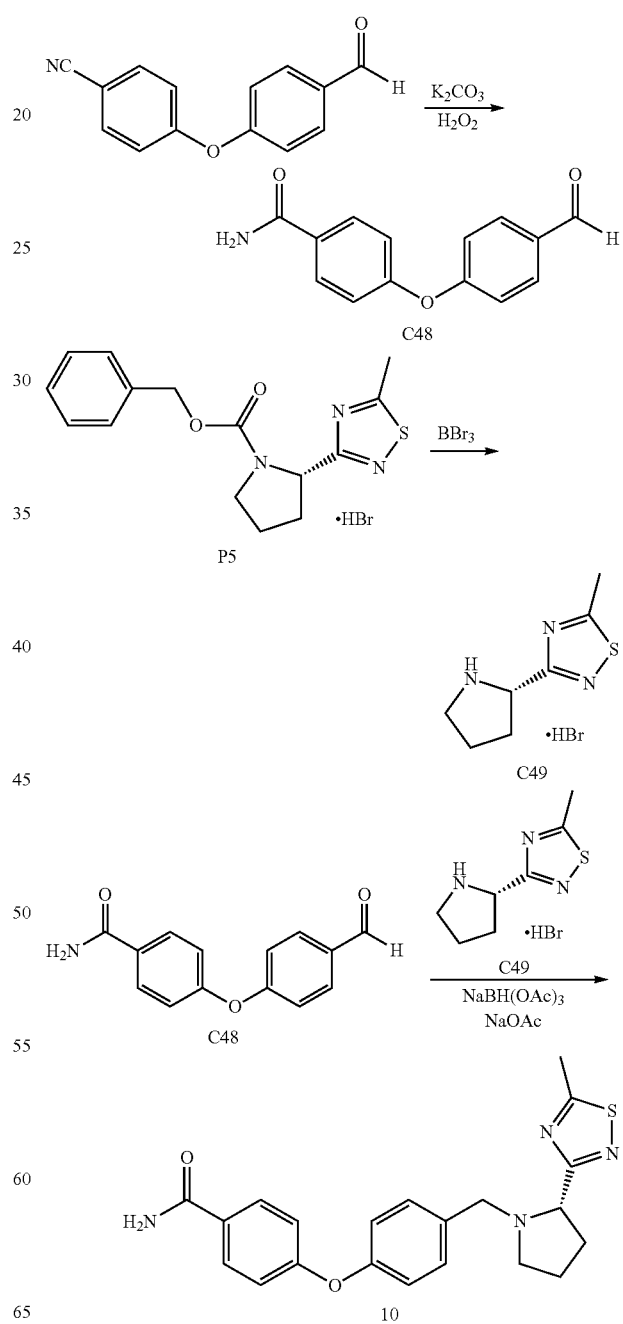

Step 1. Synthesis of 4-(4-formylphenoxy)benzamide (C48)

This experiment was carried out in two identical batches. An aqueous solution of hydrogen peroxide (30%, 21.2 g, 187 mmol) was added drop-wise to a 0° C. mixture of 4-(4-formylphenoxy)benzonitrile (38.0 g, 170 mmol) and potassium carbonate (11.8 g, 85.4 mmol) in dimethyl sulfoxide (380 mL). The reaction mixture was then stirred at 29° C. for 2 hours, whereupon the two batches were combined and poured into aqueous sodium sulfite solution (2.4 L). Filtration was used to isolate the resulting solid, which was washed with water and then partitioned between water and dichloromethane. The organic layer was dried over sodium sulfate, filtered, and concentrated in vacuo, affording the product as a white solid. Yield: 51.0 g, 211 mmol, 62%. LCMS m/z 241.9 [M+H]$^+$. $^1$H NMR (400 MHz, CDCl$_3$) δ 9.97 (s, 1H), 7.91 (br d, J=8.5 Hz, 2H), 7.88 (br d, J=8.5 Hz, 2H), 7.14 (br d, J=8.5 Hz, 4H).

Step 2. Synthesis of 5-methyl-3-[(2S)-pyrrolidin-2-yl]-1,2,4-thiadiazole (C49)

Boron tribromide (3.51 g, 14.0 mmol) was slowly added in a drop-wise manner to a −20° C. solution of P5 (1.70 g, 5.60 mmol) in dichloromethane (20 mL). The reaction mixture was allowed to stir at 24° C. for 3 hours, whereupon it was cooled to −20° C. and quenched with methanol (20 mL). The resulting solution was stirred at 20° C. for 30 minutes, and then concentrated in vacuo, providing the product as an orange solid (1.6 g), which was used in the next step without additional purification.

Step 3. Synthesis of 4-(4-{[(2S)-2-(5-methyl-1,2,4-thiadiazol-3-yl)pyrrolidin-1-yl]methyl}phenoxy)benzamide (10)

A mixture of C48 (1.50 g, 6.22 mmol), C49 (from the previous step; 1.6 g, 55.60 mmol), and sodium acetate (918 mg, 11.2 mmol) in 1,2-dichloroethane (30 mL) was stirred at 23° C. for 2.5 hours. Sodium triacetoxyborohydride (3.56 g, 16.8 mmol) was added to the reaction mixture and stirring was continued for 16 hours, whereupon the resulting solid was collected via filtration. This solid was partitioned between ethyl acetate (100 mL) and water (100 mL). The aqueous layer was extracted with ethyl acetate (2×50 mL), and the combined organic layers were dried over sodium sulfate, filtered, and concentrated under reduced pressure. Purification was effected first via supercritical fluid chromatography [Column: Chiral Technologies Chiralpak AD, 5 μm; Mobile phase: 3:2 carbon dioxide/(2-propanol containing 0.1% ammonium hydroxide)], followed by reversed-phase HPLC (Column: Agela Durashell, 5 μm; Mobile phase A: 0.05% ammonium hydroxide in water; Mobile phase B: acetonitrile; Gradient: 33% to 53% B), to afford the product as a pale yellow solid. Yield: 701 mg, 1.78 mmol, 32% over 2 steps. LCMS m/z 394.9 [M+H]$^+$. $^1$H NMR (400 MHz, CDCl$_3$) δ 7.77 (d, J=8.5 Hz, 2H), 7.32-7.25 (m, 2H, assumed; partially obscured by solvent peak), 6.97 (d, J=9.0 Hz, 2H), 6.94 (d, J=8.5 Hz, 2H), 6.2-5.6 (br m, 2H), 3.90 (dd, J=8.0, 7.5 Hz, 1H), 3.82 (d, J=13.0 Hz, 1H), 3.47 (d, J=13.0 Hz, 1H), 3.25-3.17 (m, 1H), 2.80 (s, 3H), 2.47-2.38 (m, 1H), 2.33-2.21 (m, 1H), 2.19-1.98 (m, 2H), 1.92-1.81 (m, 1H).

Example 11

4-(4-{[(2S)-2-(1,3-Dimethyl-1H-pyrazol-4-yl)pyrrolidin-1-yl]methyl}phenoxy)benzamide (11)

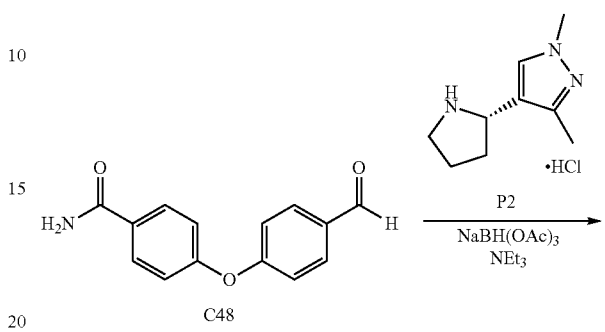

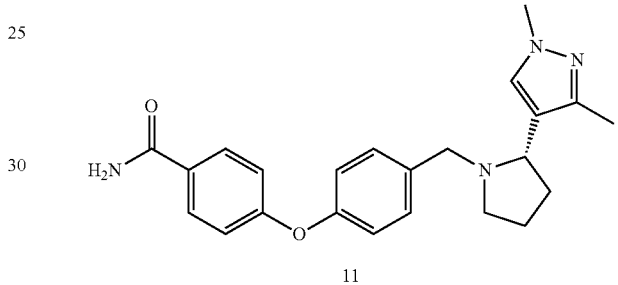

Triethylamine (2.70 mL, 19.4 mmol) was added to a solution of P2 (1.30 g, 6.44 mmol) and C48 (1.87 g, 7.75 mmol) in dichloromethane (25 mL), and the mixture was stirred for 30 minutes at room temperature. Sodium triacetoxyborohydride (98%, 2.79 g, 12.9 mmol) was added, and the reaction mixture was allowed to stir at room temperature for 2 hours, whereupon it was partitioned between saturated aqueous sodium bicarbonate solution and dichloromethane. The organic layer was dried over sodium sulfate, filtered, concentrated in vacuo, and subjected to silica gel chromatography (Gradient: 0% to 5% methanol in dichloromethane). The resulting material was recrystallized from ethyl acetate (65 mL) to provide a white solid (1.6 g). The mother liquor was concentrated and purified via silica gel chromatography (Gradient: 0% to 10% methanol in ethyl acetate); the resulting material was combined with the white solid isolated above to provide 2.0 g of impure product. This material was recrystallized from ethyl acetate (60 mL) to afford the product as a solid, which was shown to be crystalline via powder X-ray diffraction. Yield: 1.69 g, 4.33 mmol, 67%. LCMS m/z 391.4 [M+H]$^+$. $^1$H NMR (400 MHz, CDCl$_3$) δ 7.78 (br d, J=8.8 Hz, 2H), 7.30-7.25 (m, 3H, assumed; partially obscured by solvent peak), 7.00 (br d, J=8.6 Hz, 2H), 6.98 (br d, J=8.4 Hz, 2H), 6.2-5.3 (v br m, 2H), 3.91 (d, J=13.1 Hz, 1H), 3.83 (s, 3H), 3.30 (dd, J=8.4, 7.6 Hz, 1H), 3.10-3.03 (m, 1H), 3.03 (d, J=13.1 Hz, 1H), 2.29 (s, 3H), 2.20-2.09 (m, 2H), 1.94-1.68 (m, 3H).

Example 12

4-(4-{[(2S)-2-(3-methoxy-1-methyl-1H-pyrazol-4-yl)pyrrolidin-1-yl]methyl}phenoxy)benzamide (Single Enantiomer, Synthesized from P4) (12)

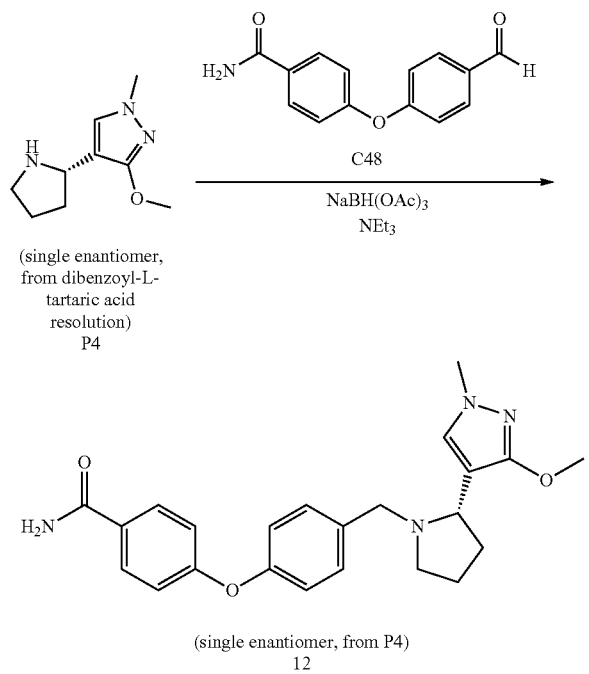

Sodium triacetoxyborohydride (98%, 7.16 g, 33.1 mmol) was added to a solution of P4 (5.00 g, 27.6 mmol) and C48 (6.99 g, 29.0 mmol) in dichloromethane (100 mL). The reaction mixture was stirred at room temperature overnight, whereupon it was partitioned between 1 M aqueous sodium hydroxide solution and dichloromethane. The resulting mixtu00re was filtered through diatomaceous earth, and the aqueous layer was extracted with dichloromethane. The combined organic layers were washed with water, dried over sodium sulfate, filtered, and concentrated in vacuo. After the resulting thick oil (12.6 g) had been dissolved in ethyl acetate (25 mL), it was seeded with a sample of the product and stirred overnight at room temperature. The solid was collected via filtration to afford a slightly pasty solid (9 g), and the filtrate was concentrated under reduced pressure and purified using silica gel chromatography (Gradient: 0% to 20% methanol in ethyl acetate). The material from the column was combined with the solid isolated above (combined weight: 10 g) and recrystallized from ethyl acetate (total volume, 50 mL) to afford 5 g of material.

The product from a similar reaction carried out using P4 (2.0 g, 11.0 mmol) was combined with the mother liquors from this recrystallization and concentrated; silica gel chromatography (Gradient: 0% to 10% methanol in ethyl acetate) provided a sticky foam (5 g). The two batches of 5 g were combined and recrystallized from ethyl acetate (total volume, 75 mL) to afford the product as a solid after rinsing with diethyl ether. Combined yield: 7.0 g, 17 mmol, 44%. LCMS m/z 407.6 [M+H]$^+$. $^1$H NMR (400 MHz, CDCl$_3$) δ 7.78 (br d, J=8.8 Hz, 2H), 7.31-7.25 (m, 2H, assumed; partially obscured by solvent peak), 7.16 (s, 1H), 7.02-6.95 (m, 4H), 6.2-5.5 (v br m, 2H), 3.94-3.88 (m, 1H), 3.93 (s, 3H), 3.74 (s, 3H), 3.32 (dd, J=7.8, 7.6 Hz, 1H), 3.11 (d, J=13.1 Hz, 1H), 3.07-3.00 (m, 1H), 2.21-2.07 (m, 2H), 1.93-1.70 (m, 3H).

Alternatively, Example 12 can be prepared using the following procedure:

A solution of P4 (2.5 g, 14 mmol, 1.15 equiv) in isopropyl alcohol (49 mL) was diluted with isopropyl alcohol (30 mL). The solution was concentrated to 30 mL total volume at atmospheric pressure in order to remove any residual water from the previous step. This solution was analyzed and found to contain acetic acid (2.13% v/v) and water (0.12%). The temperature was lowered to 15° C. and C48 (2.9 g, 12 mmol, 1.0 equiv) was added to the solution of P4 resulting in a slurry. Tetrahydrofuran (15 mL) was added followed by the addition of a single portion of sodium triacetoxyborohydride (3.8 g, 18 mmol, 1.5 equiv). The reaction was stirred at 15° C. for 90 minutes, whereupon it was quenched with a 2 M aqueous sodium hydroxide solution and the subsequent mixture stirred for 30 min. The mixture was concentrated under reduced pressure (45° C., 75 mbar) until most of the organic solvent was removed. To the remaining mixture (43 mL) was added dichloromethane (38 mL), transferred to a separatory funnel and the layers were separated. The aqueous layer was extracted with additional dichloromethane (38 mL). The combined organic layers were washed with water (38 mL) resulting in a cloudy organic layer which was filtered through celite. The filtrate was concentrated to ~30 mL under atmospheric pressure and then dilute with ethyl acetate (29 mL). Again, the solution was concentrated to ~30 mL under atmospheric pressure and then diluted with ethyl acetate (29 mL). The process of concentrating the solution to ~30 mL total volume was repeated again with the solution warmed to 78° C. Ethyl acetate was added until a total volume of ~40 mL was reached and the temperature was lowered to 58° C. over 10 min. Product seed (0.049 g, 0.12 mmol) was added and the temperature was maintained at 58° C. for 30 min before cooling to 20° C. over 2 h. The mixture was held at 20° C. overnight. The slurry was filtered and flask and cake were rinsed with ethyl acetate (8.7 mL). The filter cake was dried in a vacuum oven for 4 h to provide the product as a white solid. Yield: 4.18 g, 10.3 mmol, 86%.

Single Crystal X-ray Experimental: Form 2

A single crystal of the compound 4-(4-{[(2S)-2-(3-methoxy-1-methyl-1H-pyrazol-4-yl)pyrrolidin-1-yl]methyl}phenoxy)benzamide, single enantiomer (Example 12) was obtained by crystallization from acetone (designated Form 2) as follows:

Approximately 20 mg of Form 1, was weighed into a reaction vial followed by addition of approximately 1 mL of acetone. A clear solution was obtained. The reaction vial was then capped loosely, and the solvent was left to slowly evaporate. After two days, formation of high quality crystals was observed. The crystalline product was then viewed under polarized light microscope (PLM) to confirm crystallinity and large enough crystals were obtained for single crystal X-ray diffraction (SXRD) analysis.

Data collection was performed on a Bruker APEX diffractometer at room temperature. Data collection consisted of omega and phi scans. The structure was solved by direct methods using SHELX software suite in the Monoclinic class space group P2$_1$. The structure was subsequently refined by the full-matrix least squares method. All non-hydrogen atoms were found and refined using anisotropic displacement parameters. The hydrogen atoms located on nitrogen were found from the Fourier difference map and refined with distances restrained. The remaining hydrogen atoms were placed in calculated positions and were allowed to ride on their carrier atoms. The final refinement included isotropic displacement parameters for all hydrogen atoms. Analysis of the absolute structure using likelihood methods (Hooft 2008) was performed using PLATON (Spek 2010). Assuming the sample submitted is enantiopure, the results indicate that the absolute structure has been correctly assigned. The method calculates that the probability that the structure is correctly assigned is 1.000. The Hooft parameter is reported as 0.04 with an esd of 0.005. The final R-index was 3.0%. A final difference Fourier revealed no missing or misplaced electron density. Pertinent crystal, data collection and refinement are summarized in X-ray table 5. Atomic coordinates, bond lengths, bond angles and displacement parameters are listed in X-ray tables 6-8. The absolute stereochemistry of crystalline Form 2 was found to be (S) at the 2 position of the pyrrolidine ring. The single enantiomer of Example 12 is thus 4-(4-{[(2S)-2-(3-methoxy-1-methyl-1H-pyrazol-4-yl)pyrrolidin-1-yl]methyl}phenoxy)benzamide.

SOFTWARE AND REFERENCES

SHELXTL, Version 5.1, Bruker AXS, 1997
PLATON, A. L. Spek, J. Appl. Cryst. 2003, 36, 7-13.
MERCURY, C. F. Macrae, P. R. Edington, P. McCabe, E. Pidcock, G. P. Shields, R. Taylor, M. Towler and J. van de Streek, J. Appl. Cryst. 39, 453-457, 2006.
OLEX2, Dolomanov, O. V.; Bourhis, L. J.; Gildea, R. J.; Howard, J. A. K.; Puschmann, H., (2009). J. Appl. Cryst., 42, 339-341.
R. W. W. Hooft et al. J. Appl. Cryst. (2008). 41. 96-103.
H. D. Flack, Acta Cryst. 1983, A39, 867-881.

X-RAY TABLE 5

Crystal data and structure refinement for Form 2.

| | |
|---|---|
| Identification code | Z740 |
| Crystallization | Acetone |
| Empirical formula | C23 H26 N4 O3 |
| Formula weight | 406.48 |
| Temperature | 296(2) K |
| Wavelength | 1.54178 Å |
| Crystal system | Monoclinic |
| Space group | $P2_1$ |
| Unit cell dimensions | a = 8.8154(3) Å   α = 90°. |
| | b = 10.1601(3) Å  β = 92.4570(10)°. |
| | c = 11.7413(4) Å  γ = 90°. |
| Volume | 1050.65(6) Å$^3$ |
| Z | 2 |
| Density (calculated) | 1.285 Mg/m$^3$ |
| Absorption coefficient | 0.702 mm$^{-1}$ |
| F(000) | 432 |
| Crystal size | 0.320 × 0.200 × 0.100 mm$^3$ |
| Theta range for data collection | 3.768 to 70.092°. |
| Index ranges | −10 <= h <= 10, −12 <= k <= 12, −14 <= l <= 13 |
| Reflections collected | 20883 |
| Independent reflections | 3986 [R(int) = 0.0289] |
| Completeness to theta = 67.679° | 99.9% |
| Absorption correction | Empirical |
| Refinement method | Full-matrix least-squares on F$^2$ |
| Data/restraints/parameters | 3986/3/279 |
| Goodness-of-fit on F$^2$ | 1.039 |
| Final R indices [I > 2sigma(I)] | R1 = 0.0297, wR2 = 0.0748 |
| R indices (all data) | R1 = 0.0309, wR2 = 0.0758 |
| Absolute structure parameter | 0.04(5) |
| Extinction coefficient | n/a |
| Largest diff. peak and hole | 0.122 and −0.111 e · Å$^{-3}$ |

X-RAY TABLE 6

Atomic coordinates (×10$^4$) and equivalent isotropic displacement parameters (Å$^2$ × 10$^3$) for Form 2. U(eq) is defined as one third of the trace of the orthogonalized U$^{ij}$ tensor.

| | x | y | z | U(eq) |
|---|---|---|---|---|
| N(1) | −1199(3) | 8972(2) | 5078(2) | 71(1) |
| N(2) | 7879(2) | 2886(2) | 8975(1) | 45(1) |
| N(3) | 4316(2) | 4132(2) | 6385(1) | 46(1) |
| N(4) | 5496(2) | 4610(2) | 5780(1) | 52(1) |
| O(1) | −808(2) | 6796(2) | 5100(2) | 80(1) |
| O(2) | 4831(2) | 8572(1) | 8267(1) | 56(1) |
| O(3) | 4224(2) | 2694(2) | 7941(1) | 59(1) |
| C(1) | 2613(3) | 9431(2) | 7395(2) | 52(1) |
| C(2) | 1323(2) | 9309(2) | 6700(2) | 52(1) |
| C(3) | 896(2) | 8104(2) | 6233(2) | 45(1) |
| C(4) | −437(3) | 7901(2) | 5423(2) | 52(1) |
| C(5) | 1791(3) | 7024(2) | 6513(2) | 55(1) |
| C(6) | 3094(3) | 7131(2) | 7196(2) | 54(1) |
| C(7) | 3515(2) | 8349(2) | 7625(2) | 44(1) |
| C(8) | 5765(2) | 7483(2) | 8509(2) | 46(1) |
| C(9) | 5401(3) | 6610(2) | 9344(2) | 54(1) |
| C(10) | 6316(3) | 5535(2) | 9557(2) | 55(1) |
| C(11) | 7618(2) | 5337(2) | 8961(2) | 49(1) |
| C(12) | 7991(3) | 6253(2) | 8158(2) | 59(1) |
| C(13) | 7058(3) | 7328(2) | 7914(2) | 57(1) |
| C(14) | 8605(3) | 4151(2) | 9219(2) | 63(1) |
| C(15) | 8755(3) | 1805(2) | 9504(2) | 57(1) |
| C(16) | 8145(3) | 564(3) | 8924(2) | 68(1) |
| C(17) | 7404(3) | 1045(2) | 7813(2) | 61(1) |
| C(18) | 7736(2) | 2527(2) | 7766(2) | 48(1) |
| C(19) | 6579(2) | 3301(2) | 7071(2) | 44(1) |
| C(20) | 6824(2) | 4121(2) | 6173(2) | 52(1) |
| C(21) | 5000(2) | 3354(2) | 7156(2) | 42(1) |
| C(22) | 2711(3) | 3110(3) | 8095(3) | 79(1) |
| C(23) | 5210(4) | 5578(3) | 4890(2) | 80(1) |

X-RAY TABLE 7

Bond lengths [Å] and angles [°] for Form 2.

| | | | |
|---|---|---|---|
| N(1)—C(4) | 1.332(3) | C(12)—C(13) | 1.390(3) |
| N(1)—H(1X) | 0.91(2) | C(12)—H(12) | 0.9300 |
| N(1)—H(1Y) | 0.93(2) | C(13)—H(13) | 0.9300 |
| N(2)—C(14) | 1.459(3) | C(14)—H(14A) | 0.9700 |
| N(2)—C(15) | 1.466(3) | C(14)—H(14B) | 0.9700 |
| N(2)—C(18) | 1.466(3) | C(15)—C(16) | 1.520(4) |
| N(3)—C(21) | 1.328(2) | C(15)—H(15A) | 0.9700 |
| N(3)—N(4) | 1.373(3) | C(15)—H(15B) | 0.9700 |
| N(4)—C(20) | 1.335(3) | C(16)—C(17) | 1.515(4) |
| N(4)—C(23) | 1.450(3) | C(16)—H(16A) | 0.9700 |
| O(1)—C(4) | 1.224(3) | C(16)—H(16B) | 0.9700 |
| O(2)—C(7) | 1.374(2) | C(17)—C(18) | 1.534(3) |
| O(2)—C(8) | 1.401(2) | C(17)—H(17A) | 0.9700 |

X-RAY TABLE 7-continued

Bond lengths [Å] and angles [°] for Form 2.

| | | | |
|---|---|---|---|
| O(3)—C(21) | 1.349(2) | C(17)—H(17B) | 0.9700 |
| O(3)—C(22) | 1.418(3) | C(18)—C(19) | 1.500(3) |
| C(1)—C(7) | 1.376(3) | C(18)—H(18) | 0.9800 |
| C(1)—C(2) | 1.376(3) | C(19)—C(20) | 1.369(3) |
| C(1)—H(1) | 0.9300 | C(19)—C(21) | 1.401(3) |
| C(2)—C(3) | 1.388(3) | C(20)—H(20) | 0.9300 |
| C(2)—H(2) | 0.9300 | C(22)—H(22A) | 0.9600 |
| C(3)—C(5) | 1.383(3) | C(22)—H(22B) | 0.9600 |
| C(3)—C(4) | 1.494(3) | C(22)—H(22C) | 0.9600 |
| C(5)—C(6) | 1.377(3) | C(23)—H(23A) | 0.9600 |
| C(5)—H(5) | 0.9300 | C(23)—H(23B) | 0.9600 |
| C(6)—C(7) | 1.382(3) | C(23)—H(23C) | 0.9600 |
| C(6)—H(6) | 0.9300 | | |
| C(8)—C(9) | 1.370(3) | C(4)—N(1)—H(1X) | 119(2) |
| C(8)—C(13) | 1.371(3) | C(4)—N(1)—H(1Y) | 125(2) |
| C(9)—C(10) | 1.374(3) | H(1X)—N(1)—H(1Y) | 117(3) |
| C(9)—H(9) | 0.9300 | C(14)—N(2)—C(15) | 111.01(16) |
| C(10)—C(11) | 1.384(3) | C(14)—N(2)—C(18) | 115.38(18) |
| C(10)—H(10) | 0.9300 | C(15)—N(2)—C(18) | 104.22(16) |
| C(11)—C(12) | 1.374(3) | C(21)—N(3)—N(4) | 103.38(15) |
| C(11)—C(14) | 1.509(3) | C(20)—N(4)—N(3) | 111.26(16) |
| C(20)—N(4)—C(23) | 128.6(2) | C(12)—C(11)—C(10) | 118.4(2) |
| N(3)—N(4)—C(23) | 120.0(2) | C(12)—C(11)—C(14) | 121.7(2) |
| C(7)—O(2)—C(8) | 117.16(15) | C(10)—C(11)—C(14) | 119.8(2) |
| C(21)—O(3)—C(22) | 116.50(17) | C(11)—C(12)—C(13) | 121.1(2) |
| C(7)—C(1)—C(2) | 120.01(18) | C(11)—C(12)—H(12) | 119.5 |
| C(7)—C(1)—H(1) | 120.0 | C(13)—C(12)—H(12) | 119.5 |
| C(2)—C(1)—H(1) | 120.0 | C(8)—C(13)—C(12) | 118.9(2) |
| C(1)—C(2)—C(3) | 121.15(19) | C(8)—C(13)—H(13) | 120.6 |
| C(1)—C(2)—H(2) | 119.4 | C(12)—C(13)—H(13) | 120.6 |
| C(3)—C(2)—H(2) | 119.4 | N(2)—C(14)—C(11) | 114.81(16) |
| C(5)—C(3)—C(2) | 117.65(19) | N(2)—C(14)—H(14A) | 108.6 |
| C(5)—C(3)—C(4) | 117.85(19) | C(11)—C(14)—H(14A) | 108.6 |
| C(2)—C(3)—C(4) | 124.48(19) | N(2)—C(14)—H(14B) | 108.6 |
| O(1)—C(4)—N(1) | 122.0(2) | C(11)—C(14)—H(14B) | 108.6 |
| O(1)—C(4)—C(3) | 121.0(2) | H(14A)—C(14)—H(14B) | 107.5 |
| N(1)—C(4)—C(3) | 116.97(19) | N(2)—C(15)—C(16) | 105.18(16) |
| C(6)—C(5)—C(3) | 121.94(19) | N(2)—C(15)—H(15A) | 110.7 |
| C(6)—C(5)—H(5) | 119.0 | C(16)—C(15)—H(15A) | 110.7 |
| C(3)—C(5)—H(5) | 119.0 | N(2)—C(15)—H(15B) | 110.7 |
| C(7)—C(6)—C(5) | 119.19(19) | C(16)—C(15)—H(15B) | 110.7 |
| C(7)—C(6)—H(6) | 120.4 | H(15A)—C(15)—H(15B) | 108.8 |
| C(5)—C(6)—H(6) | 120.4 | C(17)—C(16)—C(15) | 104.5(2) |
| C(1)—C(7)—O(2) | 116.31(17) | C(17)—C(16)—H(16A) | 110.9 |
| C(1)—C(7)—C(6) | 120.00(18) | C(15)—C(16)—H(16A) | 110.9 |
| O(2)—C(7)—C(6) | 123.68(18) | C(17)—C(16)—H(16B) | 110.9 |
| C(9)—C(8)—C(13) | 121.0(2) | C(15)—C(16)—H(16B) | 110.9 |
| C(9)—C(8)—O(2) | 120.24(19) | H(16A)—C(16)—H(16B) | 108.9 |
| C(13)—C(8)—O(2) | 118.76(18) | C(16)—C(17)—C(18) | 105.8(2) |
| C(8)—C(9)—C(10) | 119.5(2) | C(16)—C(17)—H(17A) | 110.6 |
| C(8)—C(9)—H(9) | 120.3 | C(18)—C(17)—H(17A) | 110.6 |
| C(10)—C(9)—H(9) | 120.3 | C(16)—C(17)—H(17B) | 110.6 |
| C(9)—C(10)—C(11) | 121.1(2) | C(18)—C(17)—H(17B) | 110.6 |
| C(9)—C(10)—H(10) | 119.5 | H(17A)—C(17)—H(17B) | 108.7 |
| C(11)—C(10)—H(10) | 119.5 | N(2)—C(18)—C(19) | 115.08(17) |
| N(2)—C(18)—C(17) | 102.61(18) | | |
| C(19)—C(18)—C(17) | 114.03(19) | | |
| N(2)—C(18)—H(18) | 108.3 | | |
| C(19)—C(18)—H(18) | 108.3 | | |
| C(17)—C(18)—H(18) | 108.3 | | |
| C(20)—C(19)—C(21) | 102.77(17) | | |
| C(20)—C(19)—C(18) | 127.75(18) | | |
| C(21)—C(19)—C(18) | 129.47(18) | | |
| N(4)—C(20)—C(19) | 109.15(18) | | |
| N(4)—C(20)—H(20) | 125.4 | | |
| C(19)—C(20)—H(20) | 125.4 | | |
| N(3)—C(21)—O(3) | 122.22(17) | | |
| N(3)—C(21)—C(19) | 113.44(18) | | |
| O(3)—C(21)—C(19) | 124.34(17) | | |
| O(3)—C(22)—H(22A) | 109.5 | | |
| O(3)—C(22)—H(22B) | 109.5 | | |
| H(22A)—C(22)—H(22B) | 109.5 | | |
| O(3)—C(22)—H(22C) | 109.5 | | |
| H(22A)—C(22)—H(22C) | 109.5 | | |
| H(22B)—C(22)—H(22C) | 109.5 | | |
| N(4)—C(23)—H(23A) | 109.5 | | |
| N(4)—C(23)—H(23B) | 109.5 | | |
| H(23A)—C(23)—H(23B) | 109.5 | | |

X-RAY TABLE 7-continued

Bond lengths [Å] and angles [°] for Form 2.

| | |
|---|---|
| N(4)—C(23)—H(23C) | 109.5 |
| H(23A)—C(23)—H(23C) | 109.5 |
| H(23B)—C(23)—H(23C) | 109.5 |

Symmetry transformations used to generate equivalent atoms:

X-RAY TABLE 8

Anisotropic displacement parameters ($Å^2 \times 10^3$) for Form 2. The anisotropic displacement factor exponent takes the form: $-2\pi^2[h^2 a^{*2}U^{11} + \ldots + 2 h k a^* b^* U^{12}]$

| | $U^{11}$ | $U^{22}$ | $U^{33}$ | $U^{23}$ | $U^{13}$ | $U^{12}$ |
|---|---|---|---|---|---|---|
| N(1) | 75(1) | 62(1) | 73(1) | 1(1) | −27(1) | 6(1) |
| N(2) | 38(1) | 46(1) | 51(1) | 1(1) | −12(1) | 3(1) |
| N(3) | 45(1) | 48(1) | 46(1) | −1(1) | −8(1) | 5(1) |
| N(4) | 58(1) | 60(1) | 39(1) | 7(1) | −3(1) | 7(1) |
| O(1) | 82(1) | 57(1) | 99(1) | −3(1) | −32(1) | −13(1) |
| O(2) | 59(1) | 40(1) | 67(1) | −9(1) | −12(1) | 1(1) |
| O(3) | 41(1) | 59(1) | 76(1) | 20(1) | 7(1) | 4(1) |
| C(1) | 64(1) | 33(1) | 60(1) | −8(1) | −4(1) | 3(1) |
| C(2) | 57(1) | 39(1) | 59(1) | −1(1) | −3(1) | 7(1) |
| C(3) | 50(1) | 42(1) | 43(1) | 2(1) | 4(1) | −1(1) |
| C(4) | 56(1) | 50(1) | 50(1) | 1(1) | −1(1) | −5(1) |
| C(5) | 68(1) | 36(1) | 61(1) | −9(1) | −10(1) | −2(1) |
| C(6) | 62(1) | 35(1) | 63(1) | −6(1) | −9(1) | 8(1) |
| C(7) | 51(1) | 38(1) | 43(1) | −2(1) | 1(1) | −1(1) |
| C(8) | 49(1) | 40(1) | 48(1) | −6(1) | −6(1) | −1(1) |
| C(9) | 52(1) | 61(1) | 49(1) | −1(1) | 7(1) | 0(1) |
| C(10) | 59(1) | 60(1) | 46(1) | 8(1) | −3(1) | −3(1) |
| C(11) | 44(1) | 45(1) | 57(1) | −5(1) | −13(1) | −4(1) |
| C(12) | 45(1) | 53(1) | 79(2) | −2(1) | 15(1) | −4(1) |
| C(13) | 63(1) | 46(1) | 63(1) | 4(1) | 12(1) | −4(1) |
| C(14) | 44(1) | 57(1) | 86(2) | −4(1) | −24(1) | −1(1) |
| C(15) | 49(1) | 60(1) | 61(1) | 7(1) | −14(1) | 8(1) |
| C(16) | 76(2) | 54(1) | 72(2) | −1(1) | −14(1) | 17(1) |
| C(17) | 63(1) | 52(1) | 67(1) | −10(1) | −12(1) | 15(1) |
| C(18) | 34(1) | 61(1) | 47(1) | 1(1) | −1(1) | 8(1) |
| C(19) | 40(1) | 50(1) | 41(1) | −2(1) | −3(1) | 5(1) |
| C(20) | 44(1) | 66(1) | 46(1) | 3(1) | 5(1) | 4(1) |
| C(21) | 39(1) | 40(1) | 45(1) | −2(1) | −5(1) | 2(1) |
| C(22) | 51(1) | 81(2) | 105(2) | 27(2) | 23(1) | 13(1) |
| C(23) | 90(2) | 97(2) | 54(1) | 29(1) | 6(1) | 22(2) |

Form 2 is a crystalline form of the compound of Example 12. Form 2 was characterized by Powder X-ray diffraction (PXRD) shown in FIG. 1. PXRD analysis of Form 2 was conducted using a Bruker AXS D4 Endeavor diffractometer equipped with a Cu radiation source. The divergence slit was set at 0.6 mm while the secondary optics used variable slits. Diffracted radiation was detected by a PSD-Lynx Eye detector. The X-ray tube voltage and amperage were set to 40 kV and 40 mA respectively. Data was collected in the Theta-2Theta goniometer at the Cu (k-alpha average) from 3.0 to 40.0 degrees 2-Theta using a step size of 0.037 degrees and a time per step of 10 seconds. Samples were prepared by placing them in a silicon low background sample holder and rotated during collection.

Data were collected using Bruker DIFFRAC Plus XRD Commander Version 2.6.1 and analysis was performed by EVA diffract plus software (version 4.2.1). The PXRD data file was not processed prior to peak searching. Using the peak search algorithm in the EVA software, peaks selected with a threshold value of 1 were used to make preliminary peak assignments. To ensure validity, adjustments were manually made; the output of automated assignments was visually checked and peak positions were adjusted to the peak maximum. Peaks with relative intensity of ≥3% were generally chosen. The peaks which were not resolved or were consistent with noise were not selected. A typical error associated with the peak position of crystalline material, from PXRD, stated in USP, is up to +/−0.2° 2-Theta (USP-941). Table 9 provides the PXRD peak list for Form 2. Asterisked peak positions represent characteristic peaks of Form 2.

TABLE 9

| Angle 2-Theta | Relative Intensity % |
|---|---|
| 10.1* | 29 |
| 12.8 | 9 |
| 13.3* | 9 |
| 15.1* | 17 |
| 17.8* | 100 |
| 19.0 | 3 |
| 19.8 | 30 |
| 20.2 | 4 |
| 20.5 | 8 |
| 21.3 | 6 |
| 21.4 | 5 |
| 21.9 | 13 |
| 22.7 | 12 |
| 23.0 | 9 |
| 23.5 | 3 |
| 24.5 | 21 |
| 24.7* | 45 |
| 25.0 | 6 |
| 25.3 | 9 |
| 25.5 | 9 |
| 26.0 | 13 |
| 26.8 | 7 |
| 27.3 | 5 |
| 30.5 | 7 |
| 31.1 | 7 |
| 31.7 | 3 |
| 37.1 | 4 |

Figure 3:
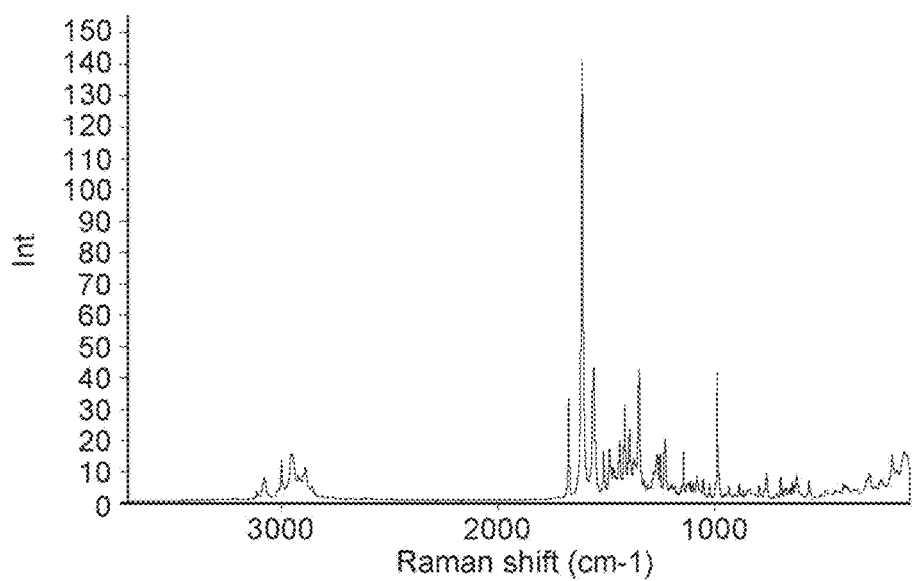
FIG. 3 depicts a characteristic Raman Spectrum of Form 2 carried out on a Nicolet NXR FT-Raman accessory attached to the FT-IR bench. The spectrometer is equipped with a 1064 nm Nd:YVO4 laser and a liquid nitrogen cooled Germanium detector.

Form 2 was also characterized by Raman spectral pattern shown in FIG. 3. Raman spectra were collected using a Nicolet NXR FT-Raman accessory attached to the FT-IR bench. The spectrometer is equipped with a 1064 nm Nd:YVO4 laser and a liquid nitrogen cooled Germanium detector. Prior to data acquisition, instrument performance and calibration verifications were conducted using polystyrene. API samples were analyzed in glass NMR tubes that were static during spectral collection. The spectra were collected using 0.5 W of laser power and 512 co-added scans. The collection range was 3700-100 cm-1. These spectra were recorded using 2 cm-1 resolution and Happ-Genzel apodization. Utilizing the Raman method above, the possible variability associated with a spectral measurement is ±2 cm$^{-1}$. The API samples were collected at ambient conditions (23° C. and between 30%-60% RH). Form 2 may be stored at ambient conditions (15-30° C. and ambient humidities).

The intensity scale was normalized to 1 prior to peak picking. Peaks were manually identified using the Thermo Nicolet Omnic 9.7.46 software. Peak position was picked at the peak maximum, and peaks were only identified as such, if there was a slope on each side; shoulders on peaks were not included. For the neat API an absolute threshold of 0.015 (Form 2) with a sensitivity of 68-88 was utilized during peak picking. For the tablets an absolute threshold of 0.046 to 0.052 with a sensitivity of 64 to 67 was used for peak picking. The peak position has been rounded to the nearest whole number using standard practice (0.5 rounds up, 0.4 rounds down). Peaks with normalized peak intensity between (1-0.75), (0.74-0.30), (0.29-0) were labeled as strong, medium and weak, respectively.

Table 10 provides the full Raman peak list for Form 2. Asterisked peak positions are unique to Form 2.

TABLE 10

| Raman peak position (cm$^{-1}$) | Normalized intensity |
| --- | --- |
| 111 | s |
| 179 | m |
| 200 | w |
| 226 | w |
| 241 | w |
| 277 | w |
| 300 | w |
| 318 | w |
| 339 | w |
| 350 | w |
| 391 | w |
| 432 | w |
| 520 | w |
| 589 | w |
| 604 | w |
| 620 | w |
| 639* | w |
| 703 | w |
| 738 | w |
| 792 | w |
| 815* | m |
| 835 | w |
| 862 | w |
| 875 | w |
| 893 | w |
| 932 | w |
| 1004 | w |
| 1025 | w |
| 1092 | w |
| 1118 | w |
| 1143 | m |
| 1166 | w |
| 1174* | w |
| 1189 | w |
| 1201 | w |
| 1211 | m |
| 1242 | w |
| 1299 | w |
| 1328 | w |
| 1364 | m |
| 1376 | m |
| 1385 | m |
| 1411 | m |
| 1424 | w |
| 1441 | w |
| 1448 | w |
| 1460 | w |
| 1475 | w |
| 1509 | w |
| 1597* | s |
| 1611 | s |
| 1660* | w |
| 2516 | w |
| 2614 | w |
| 2738 | w |
| 2805 | w |
| 2878 | w |
| 2900 | w |
| 2918 | w |
| 2935 | m |
| 2960 | m |
| 2985 | w |

TABLE 10-continued

| Raman peak position (cm$^{-1}$) | Normalized intensity |
| --- | --- |
| 3001 | w |
| 3048 | w |
| 3068 | m |
| 3075 | m |
| 3107 | w |
| 3190 | w |

Figures 5, 6:
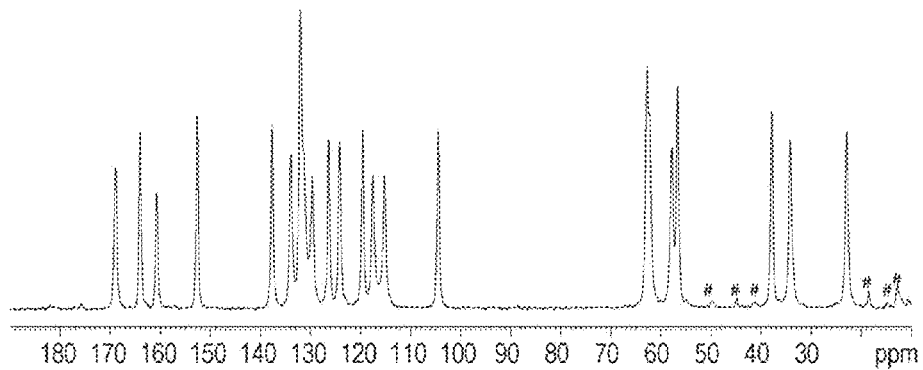
FIG. 5 depicts a characteristic 13C solid state NMR spectrum of Form 2 conducted on a CPMAS probe positioned into a Bruker-BioSpin Avance III 500 MHz ($^1$H frequency) NMR spectrometer.
FIG. 6 is a table summarizing biological and physiochemical data for Examples 11, 8 and 12 and Comparators A-F. The summary includes the kappa opioid receptor potency (KOR Ki), mu opioid receptor potency (MOR Ki), selectivity for KOR over MOR, the percent of kappa opioid receptors necessary to reverse the effects of a kappa opioid agonist, human liver microsome intrinsic clearance (HLM) and the inhibition of cytochrome P450s. Cells containing data that are not in the ideal range for a given assay are highlighted in gray. "NT"=not tested.

Form 2 was also characterized by solid state NMR (ssNMR) as shown in FIG. 5. Solid state NMR (ssNMR) analysis was conducted on a CPMAS probe positioned into a Bruker-BioSpin Avance III 500 MHz ($^1$H frequency) NMR spectrometer. Material was packed into a 4 mm rotor sealed with a standard drive cap. Data was collected at ambient temperature. $^{13}$C ssNMR spectra were collected using a proton decoupled cross-polarization magic angle spinning (CPMAS) experiment. A magic angle spinning rate of 15.0 kHz was used. A phase modulated proton decoupling field of 80-90 kHz was applied during spectral acquisition. The cross-polarization contact time was set to 2 ms and the recycle delay to 40 seconds. The number of scans was adjusted to obtain an adequate signal to noise ratio. The carbon chemical shift scale was referenced using a $^{13}$C CPMAS experiment on an external standard of crystalline adamantane, setting its upfield resonance to 29.5 ppm (as determined from neat TMS).

Automatic peak picking was performed using Bruker-BioSpin TopSpin version 3.5 software. Generally, a threshold value of 5% relative intensity was used for preliminary peak selection. The output of the automated peak picking was visually checked to ensure validity and adjustments were manually made if necessary. Although specific $^{13}$C solid state NMR peak values are reported herein there does exist a range for these peak values due to differences in instruments, samples, and sample preparation. This is common practice in the art of solid state NMR because of the variation inherent in peak positions. A typical variability for a $^{13}$C chemical shift x-axis value is on the order of plus or minus 0.2 ppm for a crystalline solid. The solid state NMR peak heights reported herein are relative intensities. Solid state NMR intensities can vary depending on the actual setup of the CPMAS experimental parameters and the thermal history of the sample. Table 11 provides the $^{13}$C solid state NMR peak list peak list for Form 2. Asterisked peak positions represent characteristic peaks of Form 2.

TABLE 11

| $^{13}$C Chemical Shifts [ppm] | Intensity |
| --- | --- |
| 22.9 | 59 |
| 34.2 | 56 |
| 37.9 * | 67 |
| 56.7 | 75 |
| 57.8 | 54 |
| 62.4 | 65 |
| 62.8 | 81 |
| 104.5 | 60 |
| 115.2 | 44 |
| 117.5 | 45 |
| 119.6 * | 60 |
| 124.2 * | 56 |
| 126.4 * | 56 |
| 129.7 | 44 |
| 131.4 | 53 |
| 132.0 | 100 |

TABLE 11-continued

| $^{13}$C Chemical Shifts [ppm] | Intensity |
|---|---|
| 133.9 | 52 |
| 137.7 | 62 |
| 152.6 * | 65 |
| 160.8 | 39 |
| 164.0 | 59 |
| 168.9 | 47 |

Single Crystal X-Ray Experimental: Form 1

A single crystal of the compound 4-(4-{[(2S)-2-(3-methoxy-1-methyl-1H-pyrazol-4-yl)pyrrolidin-1-yl]methyl}phenoxy)benzamide, single enantiomer (Example 12) was obtained by crystallization from DMSO (designated Form 1) as follows:

Approximately 2 mg of Form 1, was weighed into a reaction vial followed by addition of approximately 20 µL of dimethyl sulfoxide (DMSO). A clear solution was obtained. The reaction vial was then capped. The septum of the reaction vial cap was pierced with a needle, and the solvent was left to slowly evaporate. After several weeks, formation of high quality crystals was observed. The crystalline product was then viewed under polarized light microscope (PLM) to confirm crystallinity and large enough crystals were obtained for single crystal X-ray diffraction (SXRD) analysis.

Data collection was performed on a Bruker D8 Quest diffractometer at room temperature. Data collection consisted of omega and phi scans. The structure was solved by direct methods using SHELX software suite in the Orthorhombic class space group P2$_1$2$_1$2$_1$. The structure was subsequently refined by the full-matrix least squares method. All non-hydrogen atoms were found and refined using anisotropic displacement parameters. The hydrogen atoms located on nitrogen were found from the Fourier difference map and refined with distances restrained. The remaining hydrogen atoms were placed in calculated positions and were allowed to ride on their carrier atoms. The final refinement included isotropic displacement parameters for all hydrogen atoms. Analysis of the absolute structure using likelihood methods (Hooft 2008) was performed using PLATON (Spek 2010). Assuming the sample submitted is enantiopure, the results indicate that the absolute structure has been correctly assigned. The method calculates that the probability that the structure is correctly assigned is 100.0. The Hooft parameter is reported as 0.07 with an Esd of 0.019. The final R-index was 4.8%. A final difference Fourier revealed no missing or misplaced electron density. Pertinent crystal, data collection and refinement are summarized in X-ray table 12. Atomic coordinates, bond lengths, bond angles and displacement parameters are listed in tables 13-15. The absolute stereochemistry of crystalline Form 1 was found to be (S) at the 2 position of the pyrrolidine ring. Thus the single enantiomer of Example 12 was found to be 4-(4-{[(2S)-2-(3-methoxy-1-methyl-1H-pyrazol-4-yl)pyrrolidin-1-yl]methyl}phenoxy) benzamide.

SOFTWARE AND REFERENCES

SHELXTL, Version 5.1, Bruker AXS, 1997
PLATON, A. L. Spek, J. Appl. Cryst. 2003, 36, 7-13.
MERCURY, C. F. Macrae, P. R. Edington, P. McCabe, E. Pidcock, G. P. Shields, R. Taylor, M. Towler and J. van de Streek, J. Appl. Cryst. 39, 453-457, 2006.
OLEX2, Dolomanov, O. V.; Bourhis, L. J.; Gildea, R. J.; Howard, J. A. K.; Puschmann, H., (2009). J. Appl. Cryst., 42, 339-341.
R. W. W. Hooft et al. J. Appl. Cryst. (2008). 41. 96-103.
H. D. Flack, Acta Cryst. 1983, A39, 867-881.

X-RAY TABLE 12

| Crystal data and structure refinement for Form 1. | |
|---|---|
| Identification code | Z768 |
| Crystallization | DMSO |
| Empirical formula | C23 H26 N4 O3 |
| Formula weight | 406.48 |
| Temperature | 296(2) K |
| Wavelength | 1.54178 Å |
| Crystal system | Orthorhombic |
| Space group | P2$_1$2$_1$2$_1$ |
| Unit cell dimensions | a = 4.9599(3) Å, α = 90°. |
| | b = 9.6376(6) Å, β = 90°. |
| | c = 44.314(2) Å, γ = 90°. |
| Volume | 2118.3(2) Å$^3$ |
| Z | 4 |
| Density (calculated) | 1.275 Mg/m$^3$ |
| Absorption coefficient | 0.697 mm$^{-1}$ |
| F(000) | 864 |
| Crystal size | 0.300 × 0.160 × 0.040 mm$^3$ |
| Theta range for data collection | 3.990 to 70.170°. |
| Index ranges | −5 <= h <= 5, −11 <= k <= 11, −53 <= l <= 53 |
| Reflections collected | 23933 |
| Independent reflections | 3982 [R(int) = 0.0915] |
| Completeness to theta = 67.679° | 99.9% |
| Absorption correction | Empirical |
| Refinement method | Full-matrix least-squares on F$^2$ |
| Data/restraints/parameters | 3982/2/280 |
| Goodness-of-fit on F$^2$ | 1.099 |
| Final R indices [I > 2sigma(I)] | R1 = 0.0477, wR2 = 0.1033 |
| R indices (all data) | R1 = 0.0609, wR2 = 0.1099 |
| Absolute structure parameter | 0.01(19) |
| Extinction coefficient | 0.0043(6) |
| Largest diff. peak and hole | 0.161 and −0.140 e · Å$^{-3}$ |

X-RAY TABLE 13

Atomic coordinates (×10⁴) and equivalent isotropic displacement parameters ($Å^2 \times 10^3$) for Form 1. U(eq) is defined as one third of the trace of the orthogonalized $U^{ij}$ tensor.

|  | x | y | z | U(eq) |
|---|---|---|---|---|
| N(1) | 3690(5) | 1511(3) | 8399(1) | 50(1) |
| N(2) | 5624(6) | 3274(2) | 5838(1) | 47(1) |
| N(3) | 3591(6) | 7563(3) | 5910(1) | 49(1) |
| N(4) | 5378(6) | 8114(3) | 5712(1) | 52(1) |
| O(1) | −653(5) | 941(3) | 8343(1) | 69(1) |
| O(2) | 3472(6) | −239(2) | 7013(1) | 65(1) |
| O(3) | 8445(6) | 7094(2) | 5373(1) | 65(1) |
| C(1) | 591(7) | −185(3) | 7761(1) | 52(1) |
| C(2) | 1041(7) | −503(3) | 7462(1) | 56(1) |
| C(3) | 3035(7) | 185(3) | 7307(1) | 46(1) |
| C(4) | 4574(7) | 1182(4) | 7446(1) | 52(1) |
| C(5) | 4142(7) | 1470(3) | 7749(1) | 46(1) |
| C(6) | 2148(6) | 790(3) | 7909(1) | 40(1) |
| C(7) | 1606(6) | 1084(3) | 8234(1) | 44(1) |
| C(8) | 4553(7) | 700(3) | 6806(1) | 49(1) |
| C(9) | 6702(8) | 290(3) | 6639(1) | 59(1) |
| C(10) | 7657(8) | 1146(3) | 6411(1) | 58(1) |
| C(11) | 6478(7) | 2405(3) | 6350(1) | 44(1) |
| C(12) | 4328(8) | 2804(3) | 6526(1) | 54(1) |
| C(13) | 3352(8) | 1960(3) | 6752(1) | 59(1) |
| C(14) | 7472(7) | 3314(3) | 6096(1) | 51(1) |
| C(15) | 5692(10) | 1947(3) | 5679(1) | 71(1) |
| C(16) | 4455(14) | 2236(4) | 5377(1) | 93(2) |
| C(17) | 4699(10) | 3782(4) | 5329(1) | 74(1) |
| C(18) | 6255(8) | 4313(3) | 5606(1) | 50(1) |
| C(19) | 5517(7) | 5752(3) | 5702(1) | 44(1) |
| C(20) | 3622(7) | 6167(3) | 5905(1) | 47(1) |
| C(21) | 6505(7) | 7016(3) | 5590(1) | 44(1) |
| C(22) | 9036(10) | 8463(4) | 5265(1) | 83(1) |
| C(23) | 1888(8) | 8475(4) | 6085(1) | 62(1) |

X-RAY TABLE 14

Bond lengths [Å] and angles [°] for Form 1.

| | | | |
|---|---|---|---|
| N(1)—C(7) | 1.331(4) | C(11)—C(14) | 1.510(4) |
| N(1)—H(1X) | 0.96(2) | C(12)—C(13) | 1.376(5) |
| N(1)—H(1Y) | 0.95(2) | C(12)—H(12) | 0.9300 |
| N(2)—C(15) | 1.460(4) | C(13)—H(13) | 0.9300 |
| N(2)—C(14) | 1.466(4) | C(14)—H(14A) | 0.9700 |
| N(2)—C(18) | 1.469(4) | C(14)—H(14B) | 0.9700 |
| N(3)—C(20) | 1.346(4) | C(15)—C(16) | 1.498(6) |
| N(3)—N(4) | 1.357(4) | C(15)—H(15A) | 0.9700 |
| N(3)—C(23) | 1.446(4) | C(15)—H(15B) | 0.9700 |
| N(4)—C(21) | 1.314(4) | C(16)—C(17) | 1.511(5) |
| O(1)—C(7) | 1.229(4) | C(16)—H(16A) | 0.9700 |
| O(2)—C(3) | 1.383(4) | C(16)—H(16B) | 0.9700 |
| O(2)—C(8) | 1.396(4) | C(17)—C(18) | 1.535(5) |
| O(3)—C(21) | 1.361(4) | C(17)—H(17A) | 0.9700 |
| O(3)—C(22) | 1.434(4) | C(17)—H(17B) | 0.9700 |
| C(1)—C(2) | 1.378(5) | C(18)—C(19) | 1.496(4) |
| C(1)—C(6) | 1.381(4) | C(18)—H(18) | 0.9800 |
| C(1)—H(1) | 0.9300 | C(19)—C(20) | 1.362(4) |
| C(2)—C(3) | 1.375(5) | C(19)—C(21) | 1.404(4) |
| C(2)—H(2) | 0.9300 | C(20)—H(20) | 0.9300 |
| C(3)—C(4) | 1.375(5) | C(22)—H(22A) | 0.9600 |
| C(4)—C(5) | 1.386(4) | C(22)—H(22B) | 0.9600 |
| C(4)—H(4) | 0.9300 | C(22)—H(22C) | 0.9600 |
| C(5)—C(6) | 1.382(4) | C(23)—H(23A) | 0.9600 |
| C(5)—H(5) | 0.9300 | C(23)—H(23B) | 0.9600 |
| C(6)—C(7) | 1.492(4) | C(23)—H(23C) | 0.9600 |
| C(8)—C(9) | 1.356(5) | | |
| C(8)—C(13) | 1.373(5) | C(7)—N(1)—H(1X) | 123(2) |
| C(9)—C(10) | 1.387(5) | C(7)—N(1)—H(1Y) | 117(2) |
| C(9)—H(9) | 0.9300 | H(1X)—N(1)—H(1Y) | 118(3) |
| C(10)—C(11) | 1.374(4) | C(15)—N(2)—C(14) | 112.5(3) |
| C(10)—H(10) | 0.9300 | C(15)—N(2)—C(18) | 104.8(2) |
| C(11)—C(12) | 1.377(5) | C(14)—N(2)—C(18) | 113.3(3) |
| C(20)—N(3)—N(4) | 111.9(3) | C(11)—C(10)—C(9) | 121.6(3) |
| C(20)—N(3)—C(23) | 128.5(3) | C(11)—C(10)—H(10) | 119.2 |
| N(4)—N(3)—C(23) | 119.5(3) | C(9)—C(10)—H(10) | 119.2 |
| C(21)—N(4)—N(3) | 103.2(2) | C(10)—C(11)—C(12) | 117.6(3) |
| C(3)—O(2)—C(8) | 119.2(2) | C(10)—C(11)—C(14) | 121.4(3) |
| C(21)—O(3)—C(22) | 115.6(3) | C(12)—C(11)—C(14) | 121.0(3) |
| C(2)—C(1)—C(6) | 121.1(3) | C(13)—C(12)—C(11) | 121.3(3) |
| C(2)—C(1)—H(1) | 119.4 | C(13)—C(12)—H(12) | 119.3 |
| C(6)—C(1)—H(1) | 119.4 | C(11)—C(12)—H(12) | 119.3 |
| C(3)—C(2)—C(1) | 119.4(3) | C(8)—C(13)—C(12) | 119.7(3) |
| C(3)—C(2)—H(2) | 120.3 | C(8)—C(13)—H(13) | 120.2 |
| C(1)—C(2)—H(2) | 120.3 | C(12)—C(13)—H(13) | 120.2 |
| C(4)—C(3)—C(2) | 120.7(3) | N(2)—C(14)—C(11) | 111.3(3) |
| C(4)—C(3)—O(2) | 123.0(3) | N(2)—C(14)—H(14A) | 109.4 |
| C(2)—C(3)—O(2) | 116.2(3) | C(11)—C(14)—H(14A) | 109.4 |
| C(3)—C(4)—C(5) | 119.4(3) | N(2)—C(14)—H(14B) | 109.4 |
| C(3)—C(4)—H(4) | 120.3 | C(11)—C(14)—H(14B) | 109.4 |
| C(5)—C(4)—H(4) | 120.3 | H(14A)—C(14)—H(14B) | 108.0 |

X-RAY TABLE 14-continued

Bond lengths [Å] and angles [°] for Form 1.

| | | | | |
|---|---|---|---|---|
| C(6)—C(5)—C(4) | 120.7(3) | N(2)—C(15)—C(16) | 104.9(3) |
| C(6)—C(5)—H(5) | 119.6 | N(2)—C(15)—H(15A) | 110.8 |
| C(4)—C(5)—H(5) | 119.6 | C(16)—C(15)—H(15A) | 110.8 |
| C(1)—C(6)—C(5) | 118.7(3) | N(2)—C(15)—H(15B) | 110.8 |
| C(1)—C(6)—C(7) | 119.1(3) | C(16)—C(15)—H(15B) | 110.8 |
| C(5)—C(6)—C(7) | 122.2(3) | H(15A)—C(15)—H(15B) | 108.8 |
| O(1)—C(7)—N(1) | 121.8(3) | C(15)—C(16)—C(17) | 106.0(3) |
| O(1)—C(7)—C(6) | 121.6(3) | C(15)—C(16)—H(16A) | 110.5 |
| N(1)—C(7)—C(6) | 116.7(3) | C(17)—C(16)—H(16A) | 110.5 |
| C(9)—C(8)—C(13) | 120.3(3) | C(15)—C(16)—H(16B) | 110.5 |
| C(9)—C(8)—O(2) | 118.1(3) | C(17)—C(16)—H(16B) | 110.5 |
| C(13)—C(8)—O(2) | 121.4(3) | H(16A)—C(16)—H(16B) | 108.7 |
| C(8)—C(9)—C(10) | 119.4(3) | C(16)—C(17)—C(18) | 104.9(3) |
| C(8)—C(9)—H(9) | 120.3 | C(16)—C(17)—H(17A) | 110.8 |
| C(10)—C(9)—H(9) | 120.3 | C(18)—C(17)—H(17A) | 110.8 |
| C(16)—C(17)—H(17B) | 110.8 | | |
| C(18)—C(17)—H(17B) | 110.8 | | |
| H(17A)—C(17)—H(17B) | 108.8 | | |
| N(2)—C(18)—C(19) | 112.4(2) | | |
| N(2)—C(18)—C(17) | 102.9(3) | | |
| C(19)—C(18)—C(17) | 114.4(3) | | |
| N(2)—C(18)—H(18) | 109.0 | | |
| C(19)—C(18)—H(18) | 109.0 | | |
| C(17)—C(18)—H(18) | 109.0 | | |
| C(20)—C(19)—C(21) | 102.7(3) | | |
| C(20)—C(19)—C(18) | 129.0(3) | | |
| C(21)—C(19)—C(18) | 128.2(3) | | |
| N(3)—C(20)—C(19) | 108.2(3) | | |
| N(3)—C(20)—H(20) | 125.9 | | |
| C(19)—C(20)—H(20) | 125.9 | | |
| N(4)—C(21)—O(3) | 123.1(3) | | |
| N(4)—C(21)—C(19) | 113.9(3) | | |
| O(3)—C(21)—C(19) | 123.0(3) | | |
| O(3)—C(22)—H(22A) | 109.5 | | |
| O(3)—C(22)—H(22B) | 109.5 | | |
| H(22A)—C(22)—H(22B) | 109.5 | | |
| O(3)—C(22)—H(22C) | 109.5 | | |
| H(22A)—C(22)—H(22C) | 109.5 | | |
| H(22B)—C(22)—H(22C) | 109.5 | | |
| N(3)—C(23)—H(23A) | 109.5 | | |
| N(3)—C(23)—H(23B) | 109.5 | | |
| H(23A)—C(23)—H(23B) | 109.5 | | |
| N(3)—C(23)—H(23C) | 109.5 | | |
| H(23A)—C(23)—H(23C) | 109.5 | | |
| H(23B)—C(23)—H(23C) | 109.5 | | |

Symmetry transformations used to generate equivalent atoms:

X-RAY TABLE 15

Anisotropic displacement parameters ($Å^2 \times 10^3$) for Form 1. The anisotropic displacement factor exponent takes the form: $-2\pi^2[h^2 a^{*2}U^{11} + \ldots + 2 h k a^* b^* U^{12}]$

| | $U^{11}$ | $U^{22}$ | $U^{33}$ | $U^{23}$ | $U^{13}$ | $U^{12}$ |
|---|---|---|---|---|---|---|
| N(1) | 37(2) | 68(2) | 44(1) | 1(1) | 4(1) | 0(1) |
| N(2) | 64(2) | 40(1) | 38(1) | 1(1) | 3(1) | −2(1) |
| N(3) | 53(2) | 45(1) | 49(2) | −3(1) | 9(1) | 4(1) |
| N(4) | 61(2) | 43(1) | 51(2) | 4(1) | 5(1) | −1(1) |
| O(1) | 38(1) | 107(2) | 63(2) | −8(1) | 15(1) | −2(1) |
| O(2) | 109(2) | 43(1) | 44(1) | −1(1) | 10(1) | −14(1) |
| O(3) | 76(2) | 56(1) | 62(1) | 14(1) | 28(1) | 1(1) |
| C(1) | 45(2) | 58(2) | 54(2) | 6(2) | 4(2) | −11(2) |
| C(2) | 61(2) | 51(2) | 56(2) | −4(2) | −2(2) | −14(2) |
| C(3) | 60(2) | 35(2) | 43(2) | 4(1) | 2(2) | 2(1) |
| C(4) | 56(2) | 54(2) | 45(2) | 7(2) | 7(2) | −12(2) |
| C(5) | 48(2) | 48(2) | 42(2) | 1(1) | 0(1) | −9(1) |
| C(6) | 32(2) | 41(2) | 46(2) | 6(1) | 1(1) | 3(1) |
| C(7) | 34(2) | 49(2) | 50(2) | 6(1) | 6(1) | 2(1) |
| C(8) | 69(2) | 39(2) | 37(2) | −1(1) | −2(2) | −4(2) |
| C(9) | 81(3) | 39(2) | 56(2) | 4(2) | 1(2) | 15(2) |
| C(10) | 65(2) | 51(2) | 56(2) | 0(2) | 12(2) | 12(2) |
| C(11) | 51(2) | 42(2) | 39(2) | −1(1) | −4(1) | 4(1) |
| C(12) | 64(2) | 41(2) | 56(2) | 7(2) | 3(2) | 13(2) |
| C(13) | 68(2) | 55(2) | 53(2) | 0(2) | 13(2) | 14(2) |
| C(14) | 56(2) | 43(2) | 54(2) | 2(2) | 2(2) | 0(2) |
| C(15) | 112(4) | 43(2) | 59(2) | −6(2) | 3(2) | −5(2) |
| C(16) | 157(5) | 69(3) | 53(2) | −9(2) | −6(3) | −11(3) |
| C(17) | 120(4) | 64(2) | 36(2) | −2(2) | 5(2) | 7(2) |
| C(18) | 65(2) | 42(2) | 43(2) | 1(1) | 14(2) | 6(2) |
| C(19) | 51(2) | 41(2) | 38(2) | 7(1) | 6(1) | 3(1) |
| C(20) | 56(2) | 42(2) | 44(2) | 5(1) | 7(2) | −3(2) |
| C(21) | 49(2) | 46(2) | 38(2) | 5(1) | 5(1) | 2(2) |
| C(22) | 108(4) | 63(2) | 78(3) | 22(2) | 35(3) | −11(2) |
| C(23) | 64(2) | 58(2) | 63(2) | −10(2) | 8(2) | 11(2) |

Figure 2:
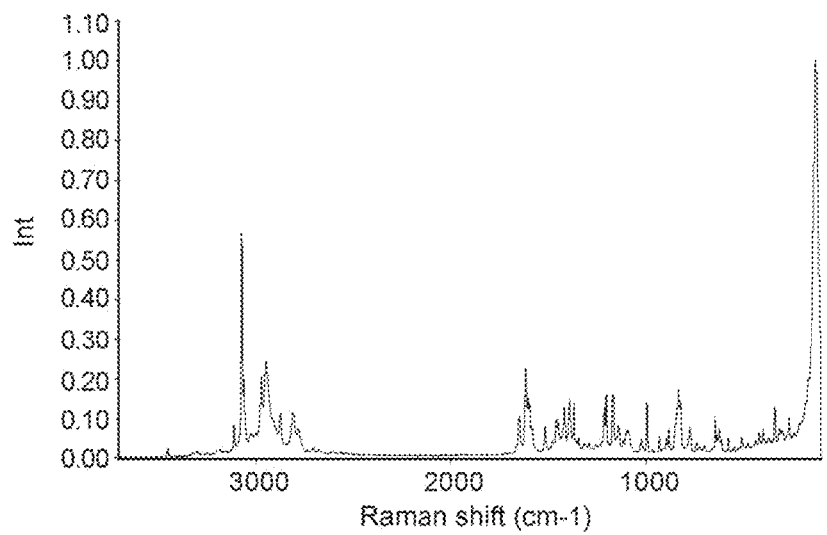
FIG. 2 depicts a characteristic Raman Spectrum of Form 1 carried out on a Nicolet NXR FT-Raman accessory attached to the FT-IR bench. The spectrometer is equipped with a 1064 nm Nd:YVO4 laser and a liquid nitrogen cooled Germanium detector.

Form 1 is a crystalline form of the compound of Example 12. Form 1 was characterized by Raman spectral pattern shown in FIG. 2. Raman spectra were collected using a Nicolet NXR FT-Raman accessory attached to the FT-IR bench. The spectrometer is equipped with a 1064 nm Nd:YVO4 laser and a liquid nitrogen cooled Germanium detector. Prior to data acquisition, instrument performance and calibration verifications were conducted using polystyrene. API samples were analyzed in glass NMR tubes that were static during spectral collection. The spectra were collected using 0.5 W of laser power and 512 co-added scans. The collection range was 3700-100 cm-1. These spectra were recorded using 2 cm-1 resolution and Happ-Genzel apodization. Utilizing the Raman method above, the possible variability associated with a spectral measurement is ±2 cm$^{-1}$. The API samples were collected at ambient conditions (~23° C. and between 30%-60% RH). Form 1 may be stored at ambient conditions (15-30° C. and ambient humidities).

The intensity scale was normalized to 1 prior to peak picking. Peaks were manually identified using the Thermo Nicolet Omnic 9.7.46 software. Peak position was picked at the peak maximum, and peaks were only identified as such, if there was a slope on each side; shoulders on peaks were not included. For the neat API an absolute threshold of 0.012 (Form 1) with a sensitivity of 68-88 was utilized during peak picking. For the tablets an absolute threshold of 0.046 to 0.052 with a sensitivity of 64 to 67 was used for peak picking. The peak position has been rounded to the nearest whole number using standard practice (0.5 rounds up, 0.4 rounds down). Peaks with normalized peak intensity between (1-0.75), (0.74-0.30), (0.29-0) were labeled as strong, medium and weak, respectively.

Table 16 provides the full Raman peak list for Form 1. Asteriked peaks are unique to Form 1.

TABLE 16

| Raman peak position (cm$^{-1}$) | Normalized intensity |
|---|---|
| 125 | s |
| 239 | w |
| 264 | w |
| 298 | w |
| 312 | w |
| 338 | w |
| 370 | w |
| 397 | w |
| 418 | w |
| 435 | w |
| 476 | w |
| 506 | w |
| 547 | w |
| 575 | w |
| 611 | w |
| 621 | w |
| 633 | w |
| 643* | w |
| 699 | w |
| 723 | w |
| 738 | w |
| 772 | w |
| 819* | w |
| 825 | w |
| 832 | w |
| 841 | w |
| 878 | w |
| 891 | w |
| 929 | w |
| 962 | w |
| 990 | w |
| 1019 | w |
| 1090 | w |
| 1098 | w |
| 1113 | w |
| 1135 | w |
| 1165 | w |
| 1169* | w |
| 1199 | w |
| 1209 | w |
| 1248 | w |
| 1287 | w |
| 1300 | w |
| 1342 | w |
| 1365 | w |
| 1387 | w |
| 1413 | w |
| 1447 | w |
| 1454 | w |
| 1474 | w |
| 1512 | w |
| 1583 | w |
| 1594* | w |
| 1600* | w |
| 1611 | w |
| 1645* | w |
| 2599 | w |
| 2670 | w |
| 2703 | w |
| 2780 | w |
| 2809 | w |
| 2872 | w |
| 2945 | w |
| 2968 | w |
| 3001 | w |
| 3024 | w |
| 3057 | w |
| 3069 | w |
| 3108 | w |
| 3192 | w |
| 3299 | w |
| 3449 | w |

Figure 4:
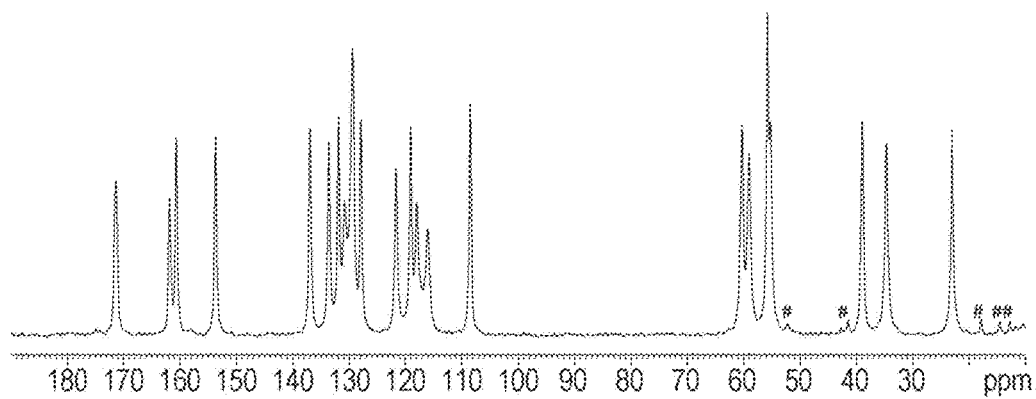
FIG. 4 depicts a characteristic 13C solid state NMR spectrum of Form 1 conducted on a CPMAS probe positioned into a Bruker-BioSpin Avance III 500 MHz ($^1$H frequency) NMR spectrometer.

Form 1 was also characterized by solid state NMR (ssNMR) as shown in FIG. 4. Solid state NMR (ssNMR) analysis was conducted on a CPMAS probe positioned into a Bruker-BioSpin Avance III 500 MHz ($^1$H frequency) NMR spectrometer. Material was packed into a 4 mm rotor sealed with a standard drive cap. Data was collected at ambient temperature. $^{13}$C ssNMR spectra were collected using a proton decoupled cross-polarization magic angle spinning (CPMAS) experiment. A magic angle spinning rate of 15.0 kHz was used. A phase modulated proton decoupling field of 80-90 kHz was applied during spectral acquisition. The cross-polarization contact time was set to 2 ms and the recycle delay to 40 seconds. The number of scans was adjusted to obtain an adequate signal to noise ratio. The carbon chemical shift scale was referenced using a $^{13}$C CPMAS experiment on an external standard of crystalline adamantane, setting its upfield resonance to 29.5 ppm (as determined from neat TMS).

Automatic peak picking was performed using Bruker-BioSpin TopSpin version 3.5 software. Generally, a threshold value of 5% relative intensity was used for preliminary peak selection. The output of the automated peak picking was visually checked to ensure validity and adjustments were manually made if necessary. Although specific $^{13}$C solid state NMR peak values are reported herein there does exist a range for these peak values due to differences in instruments, samples, and sample preparation. This is common practice in the art of solid state NMR because of the variation inherent in peak positions. A typical variability for a $^{13}$C chemical shift x-axis value is on the order of plus or minus 0.2 ppm for a crystalline solid. The solid state NMR peak heights reported herein are relative intensities. Solid state NMR intensities can vary depending on the actual setup of the CPMAS experimental parameters and the thermal history of the sample. Table 17 provides the $^{13}$C solid state NMR peak list for Form 1. Asteriked peak positions represent characteristic peaks.

TABLE 17

| $^{13}$C Chemical Shifts [ppm] | Intensity |
| --- | --- |
| 23.0 | 64 |
| 34.7 | 59 |
| 39.0 * | 66 |
| 55.2 | 66 |
| 55.8 | 100 |
| 59.0 | 56 |
| 60.3 | 65 |
| 108.5 | 72 |
| 116.0 | 33 |
| 118.0 | 41 |
| 119.0 * | 65 |
| 121.6 * | 51 |
| 127.9 * | 67 |
| 129.4 | 89 |
| 130.9 | 42 |
| 131.9 | 68 |
| 133.6 | 60 |
| 137.0 | 64 |
| 153.7 * | 62 |
| 160.7 | 61 |
| 161.8 | 42 |
| 171.3 | 48 |

Examples 13, 14, and 15

(+/−)-4-(4-{[2-(3-Methoxy-1H-pyrazol-4-yl)pyrrolidin-1-yl]methyl}phenoxy)benzamide (13), (−)-4-(4-{[2-(3-Methoxy-1H-pyrazol-4-yl)pyrrolidin-1-yl]methyl}phenoxy)benzamide (ENT-1) (14), and (+)-4-(4-{[2-(3-Methoxy-1H-pyrazol-4-yl)pyrrolidin-1-yl]methyl}phenoxy)benzamide (ENT-2) (15)

room temperature, the reaction was quenched via addition of 1 M aqueous sodium hydroxide solution. The resulting mixture was stirred vigorously for 15 minutes and the aqueous layer was extracted with dichloromethane. The combined organic layers were dried over sodium sulfate, filtered, and concentrated in vacuo. Silica gel chromatography (Gradient: 0% to 10% methanol in ethyl acetate) provided racemate 13 as a gum. Yield of racemate 13: 380 mg, 0.969 mmol, 81%. LCMS m/z 393.3 [M+H]$^+$. $^1$H NMR (400 MHz, CDCl$_3$) δ 7.78 (br d, J=8.8 Hz, 2H), 7.41 (s, 1H), 7.31-7.25 (m, 2H, assumed; partially obscured by solvent peak), 6.99 (br d, J=8.8 Hz, 2H), 6.97 (br d, J=8.6 Hz, 2H), 6.2-5.4 (v br m, 2H), 3.96 (s, 3H), 3.91 (d, J=13.5 Hz, 1H), 3.39 (dd, J=7.8, 7.6 Hz, 1H), 3.14 (d, J=13.1 Hz, 1H), 3.10-3.02 (m, 1H), 2.25-2.11 (m, 2H), 1.95-1.73 (m, 3H).

A portion of 13 (290 mg, 0.739 mmol) was separated into its component enantiomers via supercritical fluid chromatography {Column: Chiral Technologies Chiralcel OJ, 5 μm; Mobile phase: 7:3 carbon dioxide/[methanol containing 0.2% (7 M ammonia in methanol)]}. The first-eluting enantiomer, obtained as a tan solid that exhibited a negative (−) rotation, was designated as 14. Yield: 72 mg, 0.183 mmol, 25% for the separation. LCMS m/z 393.5 [M+H]$^+$. $^1$H NMR (400 MHz, CD$_3$OD) δ 7.86 (br d, J=9.0 Hz, 2H), 7.47 (s, 1H), 7.30 (br d, J=8.6 Hz, 2H), 7.01-6.95 (m, 4H), 3.89 (s, 3H), 3.83 (d, J=12.9 Hz, 1H), 3.46-3.37 (m, 1H), 3.22 (d, J=12.9 Hz, 1H), 3.04-2.96 (m, 1H), 2.34-2.25 (m, 1H), 2.19-2.08 (m, 1H), 1.93-1.75 (m, 3H).

The second-eluting enantiomer, also obtained as a tan solid, exhibited a positive (+) rotation and was designated as 15. Yield: 84 mg, 0.214 mmol, 29% for the separation. LCMS m/z 393.5 [M+H]$^+$. $^1$H NMR (400 MHz, CD$_3$OD) δ 7.86 (br d, J=9.0 Hz, 2H), 7.48 (s, 1H), 7.30 (br d, J=8.6 Hz,

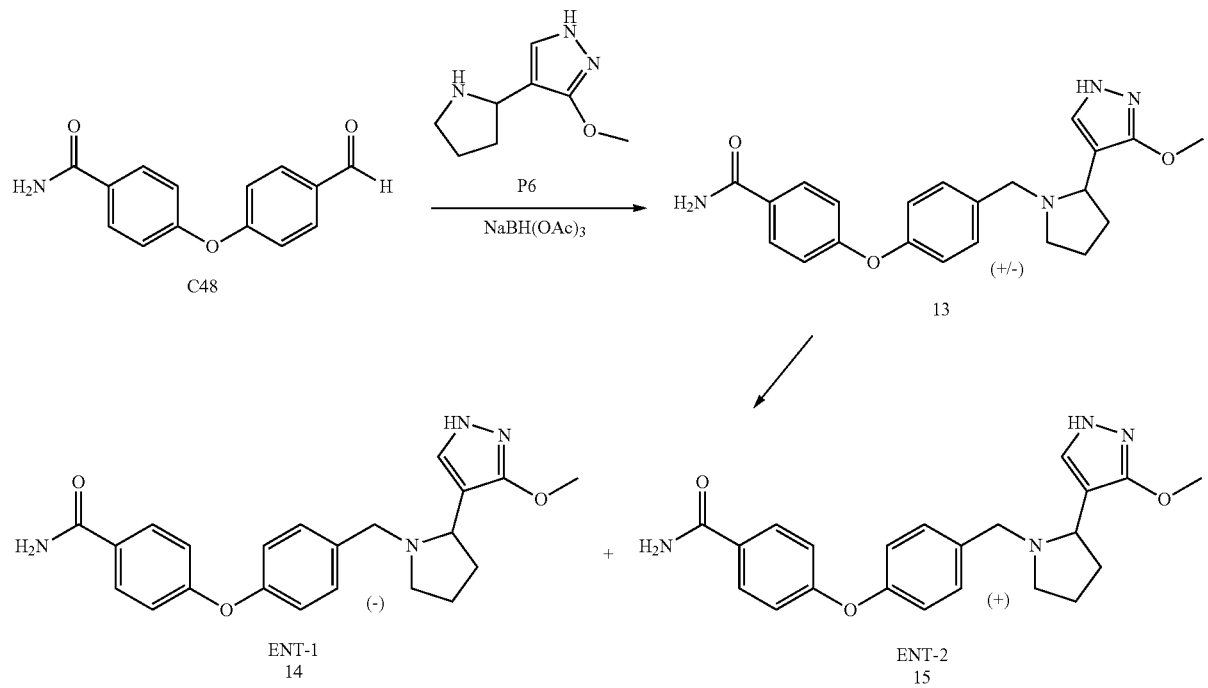

Sodium triacetoxyborohydride (98%, 310 mg, 1.43 mmol) was added to a solution of P6 (200 mg, 1.20 mmol) and C48 (288 mg, 1.19 mmol) in dichloromethane (5 mL). After the reaction mixture had been stirred overnight at 2H), 7.01-6.95 (m, 4H), 3.89 (s, 3H), 3.84 (d, J=12.9 Hz, 1H), 3.47-3.38 (m, 1H), 3.23 (d, J=12.9 Hz, 1H), 3.05-2.96 (m, 1H), 2.36-2.24 (m, 1H), 2.20-2.08 (m, 1H), 1.94-1.76 (m, 3H).

By analytical HPLC [Column: Chiral Technologies Chiralcel OJ, 4.6×150 mm, 5 μm; Mobile phase A: carbon dioxide; Mobile phase B: methanol containing 0.2% (7 M ammonia in methanol); Gradient: 5% B from 0 to 1.00 minute, 5% to 60% B over 8.00 minutes; Flow rate: 3.0 mL/minute], 14 exhibited a retention time of 5.64 minutes. Using the same analytical system, 15 exhibited a retention time of 6.26 minutes.

Examples 16, 17, and 18

(+/−)-4-(4-{[2-(1,3-Dimethyl-1H-pyrazol-4-yl)pyrrolidin-1-yl]methyl}phenoxy)-2-hydroxybenzamide (16), (+)-4-(4-{[2-(1,3-Dimethyl-1H-pyrazol-4-yl)pyrrolidin-1-yl]methyl}phenoxy)-2-hydroxybenzamide (ENT-1) (17), and (−)-4-(4-{[2-(1,3-Dimethyl-1H-pyrazol-4-yl)pyrrolidin-1-yl]methyl}phenoxy)-2-hydroxybenzamide (ENT-2) (18)

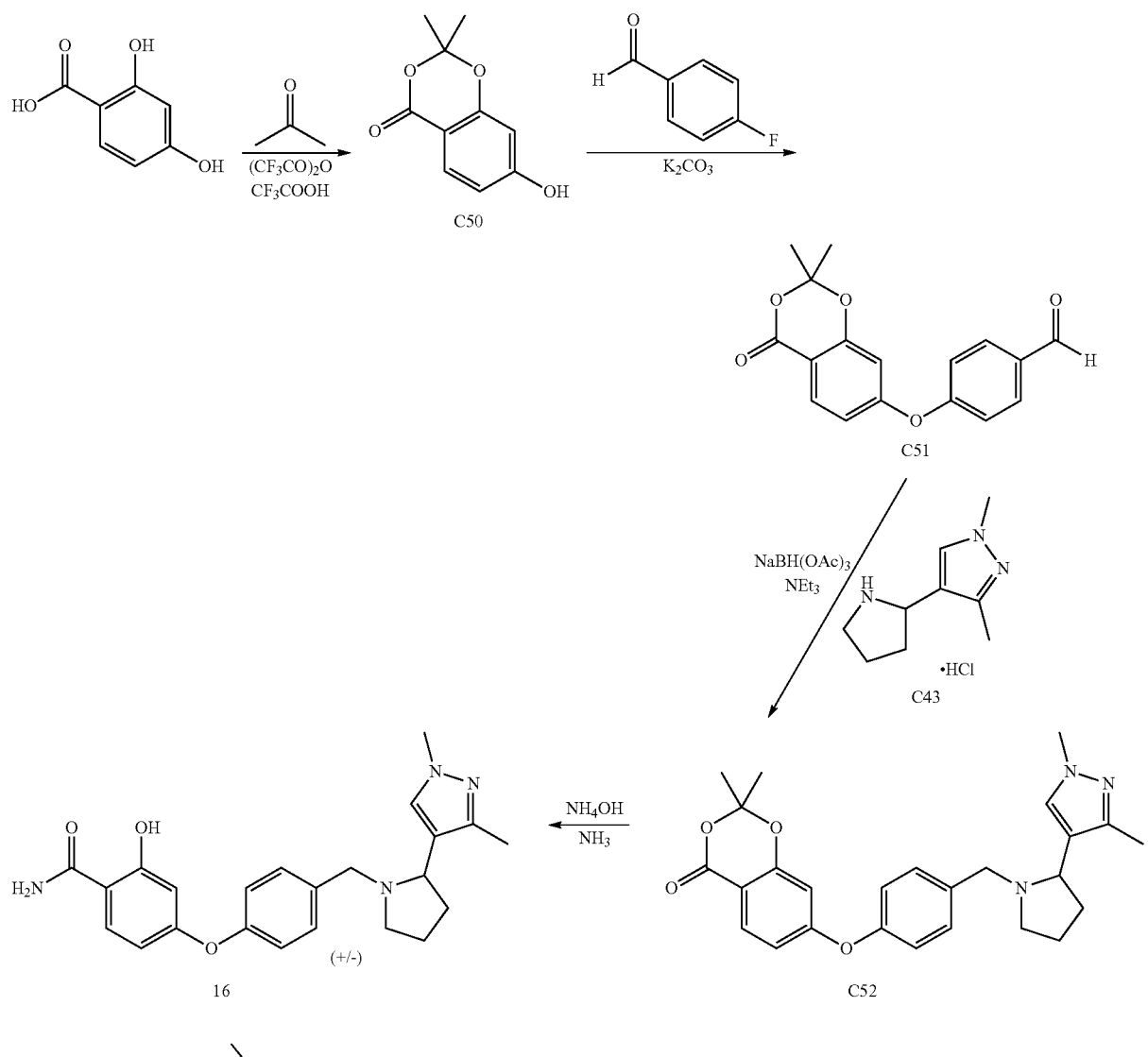

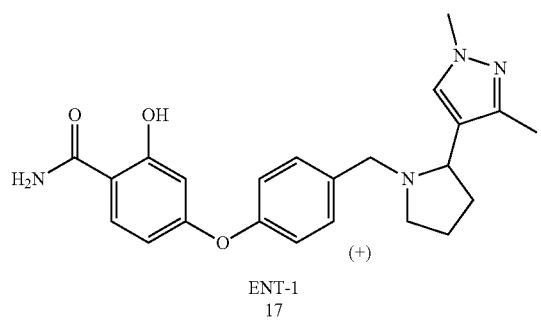
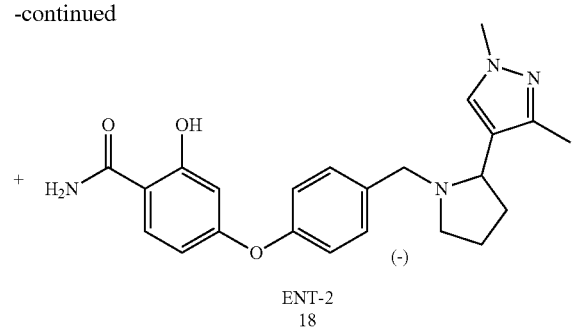

ENT-1 17 (+)
ENT-2 18 (−)

Step 1. Synthesis of 7-hydroxy-2,2-dimethyl-4H-1,3-benzodioxin-4-one (C50)

Trifluoroacetic anhydride (300 mL) and acetone (150 mL) were added drop-wise to a 0° C. suspension of 2,4-dihydroxybenzoic acid (55.0 g, 357 mmol) in trifluoroacetic acid (500 mL) and the reaction mixture was stirred at 25° C. for 3 days. Volatiles were removed in vacuo, the residue was added to saturated aqueous sodium bicarbonate solution (500 mL), and the resulting mixture was extracted with ethyl acetate (3×500 mL). The combined organic layers were washed sequentially with water (500 mL) and with saturated aqueous sodium chloride solution (500 mL), dried over sodium sulfate, filtered, and concentrated under reduced pressure. Trituration with dichloromethane (200 mL) provided the product as a white solid. Yield: 41.0 g, 211 mmol, 59%. LCMS m/z 194.7 [M+H]$^+$. $^1$H NMR (400 MHz, CD$_3$OD) δ 7.73 (d, J=8.5 Hz, 1H), 6.58 (dd, J=8.5, 2.0 Hz, 1H), 6.35 (d, J=2.0 Hz, 1H), 1.69 (s, 6H).

Step 2. Synthesis of 4-[(2,2-dimethyl-4-oxo-4H-1,3-benzodioxin-7-yl)oxy]benzaldehyde (C51)

4-Fluorobenzaldehyde (21.1 g, 170 mmol) was added drop-wise to a 20° C. suspension of C50 (30.0 g, 154 mmol) and potassium carbonate (42.7 g, 309 mmol) in N,N-dimethylformamide (500 mL). The reaction mixture was stirred at 80° C. for 4 days, and then at 100° C. for 16 hours. At this point, it was combined with a similar reaction mixture derived from C50 (1.00 g, 5.15 mmol) and filtered. The filtrate was concentrated to dryness in vacuo, and the residue was dissolved in ethyl acetate (1 L) and washed with saturated aqueous sodium chloride solution (5×300 mL). The organic layer was dried over sodium sulfate, filtered, concentrated under reduced pressure, and purified via chromatography on silica gel (Gradient: 10% to 50% ethyl acetate in petroleum ether), to afford the product as a yellow solid. Combined yield: 32.0 g, 107 mmol, 67%. $^1$H NMR (400 MHz, CDCl$_3$) δ 10.00 (s, 1H), 7.98 (d, J=8.8 Hz, 1H), 7.95 (br d, J=8.8 Hz, 2H), 7.22 (br d, J=8.8 Hz, 2H), 6.78 (dd, J=8.5, 2.3 Hz, 1H), 6.57 (d, J=2.3 Hz, 1H), 1.75 (s, 6H).

Step 3. Synthesis of 7-(4-{[2-(1,3-dimethyl-1H-pyrazol-4-yl)pyrrolidin-1-yl]methyl}phenoxy)-2,2-dimethyl-4H-1,3-benzodioxin-4-one (C52)

Triethylamine (4.84 mL, 34.7 mmol) was added to a mixture of C43 (1.40 g, 6.94 mmol) and C51 (2.28 g, 7.64 mmol) in dichloromethane (25 mL). After the resulting mixture had stirred for 30 minutes at room temperature, it was treated with sodium triacetoxyborohydride (98%, 3.00 g, 13.9 mmol). The reaction mixture was stirred at room temperature overnight, whereupon LCMS analysis revealed a major peak consistent with the product: LCMS m/z 448.3 [M+H]$^+$. The reaction mixture was partitioned between saturated aqueous sodium bicarbonate solution and ethyl acetate. After extraction of the aqueous layer with ethyl acetate, the combined organic layers were dried over sodium sulfate, filtered, and concentrated in vacuo to afford the product as a thick oil. Yield: 3.10 g, 6.93 mmol, quantitative.

Step 4. Synthesis of (+/−)-4-(4-{[2-(1,3-dimethyl-1H-pyrazol-4-yl)pyrrolidin-1-yl]methyl}phenoxy)-2-hydroxybenzamide (16), (+)-4-(4-{[2-(1,3-dimethyl-1H-pyrazol-4-yl)pyrrolidin-1-yl]methyl}phenoxy)-2-hydroxybenzamide (ENT-1) (17), and (−)-4-(4-{[2-(1,3-dimethyl-1H-pyrazol-4-yl)pyrrolidin-1-yl]methyl}phenoxy)-2-hydroxybenzamide (ENT-2) (18)

A mixture of C52 (3.10 g, 6.93 mmol), concentrated ammonium hydroxide (25 mL), and a solution of ammonia in methanol (7 M, 25 mL) was heated at 50° C. overnight. After the reaction mixture had cooled to room temperature, it was concentrated to remove methanol, and then adjusted to neutral pH via addition of concentrated hydrochloric acid. The resulting mixture was extracted with ethyl acetate, and the combined organic layers were dried over sodium sulfate, filtered, and concentrated onto diatomaceous earth. Silica gel chromatography (Gradient: 0% to 5% methanol in dichloromethane) afforded the product as an off-white foam. Yield of racemate 16: 2.70 g, 6.64 mmol, 96%. LCMS m/z 407.3 [M+H]$^+$. $^1$H NMR (400 MHz, CDCl$_3$) δ 12.5-12.2 (v br s, 1H), 7.48 (d, J=8.6 Hz, 1H), 7.29-7.24 (m, 3H, assumed; partially obscured by solvent peak), 6.95 (br d, J=8.6 Hz, 2H), 6.53 (dd, J=8.8, 2.5 Hz, 1H), 6.24 (br d, J=2 Hz, 1H), 3.79 (s, 3H), 3.78 (d, J=12.9 Hz, 1H), 3.35-3.24 (m, 2H), 3.17-3.09 (m, 1H), 2.28-2.11 (m, 2H), 2.22 (s, 3H), 1.96-1.85 (m, 1H), 1.85-1.66 (m, 2H).

Separation of 16 into its component enantiomers was carried out via supercritical fluid chromatography [Column: Chiral Technologies Chiralcel OJ-H, 5 μm; Mobile phase: 85:15 carbon dioxide/(methanol containing 0.2% ammonium hydroxide)]. The first-eluting enantiomer, obtained as a foamy tan solid that exhibited a positive (+) rotation, was designated as 17. Yield: 1.18 g, 2.90 mmol, 44% for the separation. LCMS m/z 407.6 [M+H]$^+$. $^1$H NMR (400 MHz, CDCl$_3$) δ 12.35 (br s, 1H), 7.48 (d, J=8.8 Hz, 1H), 7.33-7.19 (m, 3H, assumed; partially obscured by solvent peak), 7.02-6.91 (m, 2H), 6.53 (dd, J=8.8, 2.4 Hz, 1H), 6.25 (br s, 1H), 3.86-3.72 (m, 1H), 3.79 (s, 3H), 3.37-3.20 (m, 2H), 3.17-3.06 (m, 1H), 2.29-2.10 (m, 2H), 2.22 (s, 3H), 1.97-1.66 (m, 3H). This NMR data was obtained a number of months after isolation of 17, and exhibited broadened signals. A smaller-scale synthesis provided the following data immediately after isolation: LCMS m/z 407.0 [M+H]$^+$. $^1$H NMR (400 MHz, DMSO-d$_6$) δ 13.37 (br s, 1H), 8.34-8.25 (br s, 1H), 7.84 (d, J=9.0 Hz, 1H), 7.84-7.79 (br s, 1H), 7.51 (s, 1H), 7.30 (br d, J=8.5 Hz, 2H), 7.03 (br d, J=8.5 Hz, 2H), 6.44 (dd, J=9.0, 2.5 Hz, 1H), 6.27 (d, J=2.5 Hz, 1H), 3.75 (d, J=13.0 Hz, 1H), 3.71 (s, 3H), 3.27 (dd, J=8.5, 7.5 Hz, 1H), 3.01 (d, J=13.0 Hz, 1H), 2.93-2.85 (m, 1H), 2.15 (s, 3H), 2.12-2.01 (m, 2H), 1.82-1.56 (m, 3H).

The second-eluting enantiomer was further purified via silica gel chromatography (Gradient: 0% to 5% methanol in ethyl acetate), affording this enantiomer as a solid that exhibited a negative (−) rotation. This material was designated as 18. Yield: 1.10 g, 2.71 mmol, 41% for the separation. LCMS m/z 407.3 [M+H]$^+$. $^1$H NMR (400 MHz, CDCl$_3$) δ 7.49 (d, J=9.0 Hz, 1H), 7.28-7.24 (m, 3H, assumed; partially obscured by solvent peak), 6.95 (br d, J=8.6 Hz, 2H), 6.52 (dd, J=9.0, 2.3 Hz, 1H), 6.24 (d, J=2.3 Hz, 1H), 5.75-5.3 (v br s, 2H), 3.78 (d, J=12.9 Hz, 1H), 3.78 (s, 3H), 3.31 (dd, J=8.2, 8.2 Hz, 1H), 3.26 (d, J=12.9 Hz, 1H), 3.15-3.08 (m, 1H), 2.26-2.10 (m, 2H), 2.22 (s, 3H), 1.96-1.84 (m, 1H), 1.84-1.66 (m, 2H).

By analytical HPLC (Column: Chiral Technologies Chiralcel OJ-H, 4.6×250 mm, 5 μm; Mobile phase A: carbon dioxide; Mobile phase B: methanol containing 0.2% ammonium hydroxide; Gradient: 5% B from 0 to 1.00 minute, 5% to 60% B over 8.00 minutes; Flow rate: 3.0 mL/minute), 17 exhibited a retention time of 6.07 minutes. Using the same analytical system, 18 exhibited a retention time of 6.62 minutes.

Example 19

3-Fluoro-4-(4-{[(2S)-2-(1-methyl-1H-pyrazol-3-yl)pyrrolidin-1-yl]methyl}phenoxy) benzamide (19)

Step 1. Synthesis of 3-fluoro-4-[4-(hydroxymethyl)phenoxy]benzamide (C53)

Sodium borohydride (2.92 g, 77.2 mmol) was added portion-wise to a 0° C. solution of C47 (10.0 g, 38.6 mmol) in methanol (200 mL). The reaction mixture was stirred at 25° C. for 30 minutes, whereupon saturated aqueous ammonium chloride solution (50 mL) was added, and methanol was removed via concentration in vacuo. The resulting aqueous suspension was filtered, and the collected solid was washed with water (3×100 mL), providing the product as a white solid. Yield: 9.95 g, 38.1 mmol, 99%. LCMS m/z 261.7 [M+H]$^+$.

Step 2. Synthesis of 4-[4-(chloromethyl)phenoxy]-3-fluorobenzamide (C54)

To a 0° C. solution of C53 (9.95 g, 38.1 mmol) and triethylamine (38.5 g, 380 mmol) in tetrahydrofuran (200 mL) was added methanesulfonyl chloride (43.6 g, 381 mmol) in a drop-wise manner. The reaction mixture was stirred at 25° C. for 18 hours, whereupon it was diluted with water (500 mL) and extracted with ethyl acetate (2×500 mL). The combined organic layers were washed sequentially with water (2×500 mL) and saturated aqueous sodium chloride solution (500 mL), dried over sodium sulfate, filtered, and concentrated in vacuo. Silica gel chromatography (Gradient: 0% to 50% ethyl acetate in petroleum ether) afforded the product as a white solid. Yield: 7.10 g, 25.4 mmol, 67%. $^1$H NMR (400 MHz, CD$_3$OD) δ 7.78 (dd, J=11.5, 2.0 Hz, 1H), 7.70 (ddd, J=8.5, 2.0, 1.0 Hz, 1H), 7.44 (br d, J=8.5 Hz, 2H), 7.11 (dd, J=8.5, 8.0 Hz, 1H), 7.01 (br d, J=8.5 Hz, 2H), 4.65 (s, 2H).

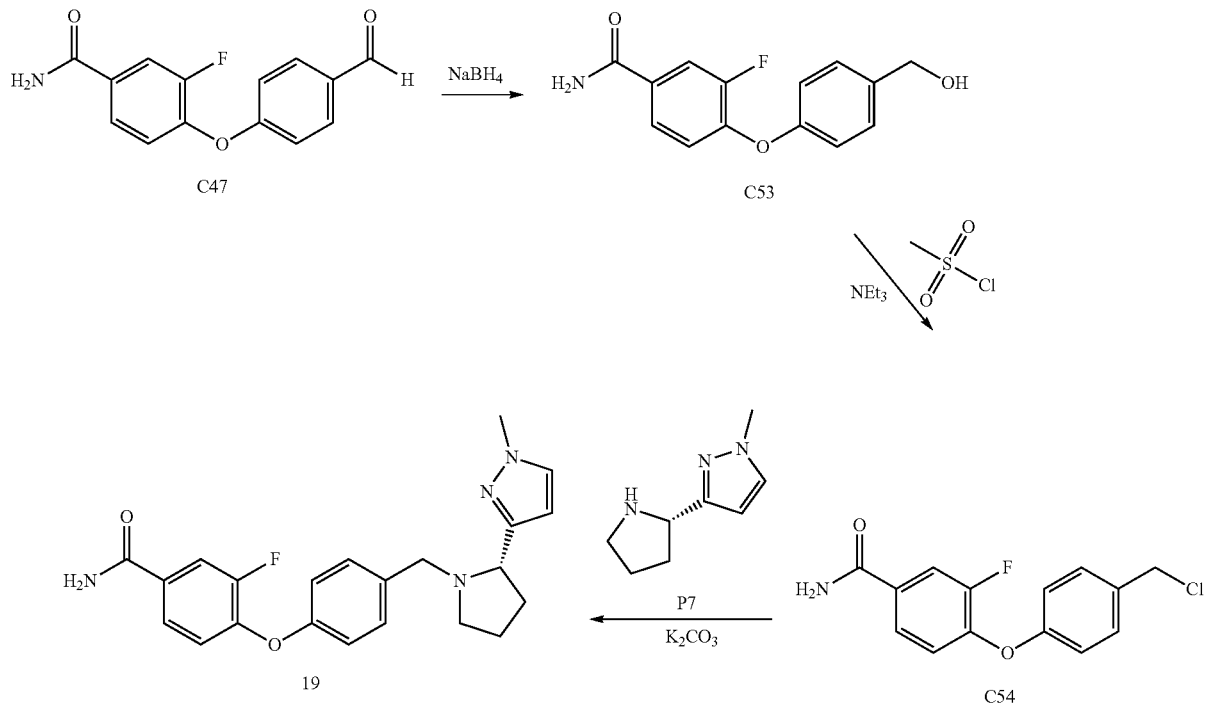

Step 3. Synthesis of 3-fluoro-4-(4-{[(2S)-2-(1-methyl-1H-pyrazol-3-yl)pyrrolidin-1-yl]methyl}phenoxy)benzamide (19)

Potassium carbonate (521 mg, 3.77 mmol) and C54 (548 mg, 1.96 mmol) were added to a solution of P7 (228 mg, 1.51 mmol) in N,N-dimethylformamide (10 mL). After the reaction mixture had been heated at 100° C. for 2 hours, it was filtered. The filtrate was directly subjected to purification via reversed-phase HPLC (Column: Phenomenex Gemini C18, 10 μm; Mobile phase A: 0.225% ammonium hydroxide in water; Mobile phase B: acetonitrile; Gradient: 40% to 70% B) to afford the product as a white solid. Yield: 220 mg, 0.558 mmol, 37%. LCMS m/z 395.1 [M+H]$^+$. $^1$H NMR (400 MHz, CD$_3$OD) δ 7.76 (dd, J=11.5, 2.0 Hz, 1H), 7.67 (ddd, J=8.5, 2.0, 1.0 Hz, 1H), 7.53 (d, J=2.0 Hz, 1H), 7.28 (br d, J=8.5 Hz, 2H), 7.03 (dd, J=8.5, 8.5 Hz, 1H), 6.95 (br d, J=8.5 Hz, 2H), 6.33 (d, J=2.5 Hz, 1H), 3.86 (s, 3H), 3.80 (d, J=12.6 Hz, 1H), 3.53-3.46 (m, 1H), 3.19 (d, J=13.0 Hz, 1H), 3.07-2.99 (m, 1H), 2.33-2.24 (m, 1H), 2.22-2.11 (m, 1H), 1.95-1.78 (m, 3H).

TABLE 18

Method of preparation, structure, and physicochemical data for Examples 20-46.

| Ex. No. | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 20 | Example 3$^{1,2}$; C10, C47 | 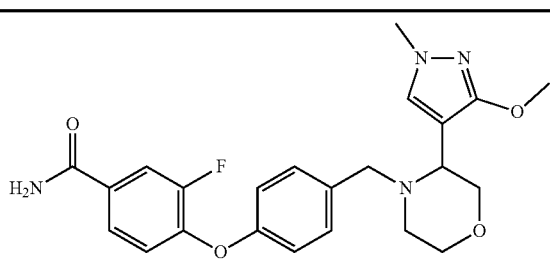 ENT-1 | 3.52 minutes$^2$; 441.2 |
| 21 | Example 3$^{3,4,5}$; C10, C48 | 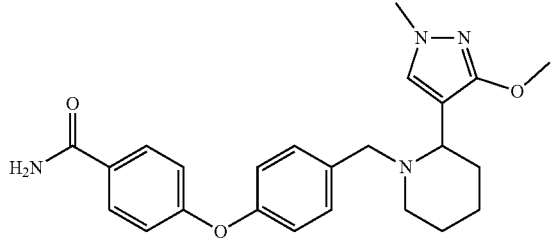 ENT-1 | 2.72 minutes$^5$; 421.4 |
| 22 | Example 3$^{3,1,6}$; C10, C45 | 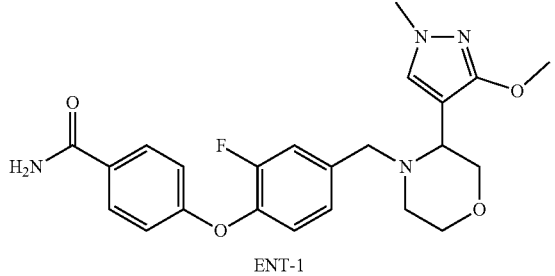 [SMILES: COc1nn(C)cc1C1COCCN1Cc1ccc(Oc2ccc(C(N)=O)cc2)c(F)c1] ENT-1 | 4.07 minutes$^6$; 441.3 |
| 23 | Example 3$^{1,7}$; C48 | 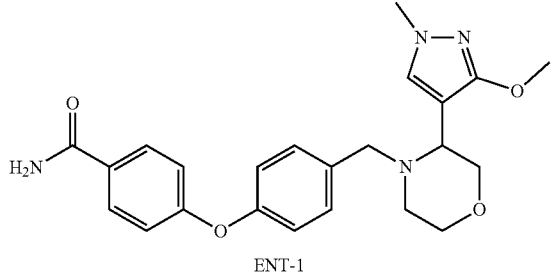 [SMILES: COc1nn(C)cc1C1COCCN1Cc1ccc(Oc2ccc(C(N)=O)cc2)cc1] ENT-1 | 4.30 minutes$^7$; 423.2 |

TABLE 18-continued

Method of preparation, structure, and physicochemical data for Examples 20-46.

| Ex. No. | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 24 | Example 3[8,9]; C10, C32 | Isomer 2<br>Assumed racemic, either cis or trans | 4.71 minutes[9]; 425.2 |
| 25 | Example 3[10]; C48, P8 | Isomer 1 | $^1$H NMR (500 MHz, CDCl$_3$) δ 7.79 (br d, J = 8.8 Hz, 2H), 7.41 (d, J = 2.0 Hz, 1H), 7.27 (br d, J = 8.3 Hz, 2H), 7.00 (br d, J = 8.8 Hz, 2H), 6.98 (br d, J = 8.6 Hz, 2H), 6.2-5.4 (v br m, 2H), [5.02-4.97 (m) and 4.91-4.86 (m), J$_{HF}$ = 54 Hz, 1H], 3.92 (d, J = 13.2 Hz, 1H), 3.85 (s, 3H), 3.29 (dd, J = 27.1, 4.2 Hz, 1H), 3.18-3.12 (m, 1H), 3.03 (d, J = 13.0 Hz, 1H), 2.38-2.24 (m, 1H), 2.29 (s, 3H), 2.19-2.04 (m, 2H); 409.3 |
| 26 | Example 3[10]; C48, P8 | Isomer 2 | $^1$H NMR (500 MHz, CDCl$_3$) δ 7.79 (br d, J = 8.6 Hz, 2H), 7.41 (d, J = 1.7 Hz, 1H), 7.30-7.26 (m, 2H, assumed; partially obscured by solvent peak), 7.00 (br d, J = 8.6 Hz, 2H), 6.99 (br d, J = 8.3 Hz, 2H), 6.15-5.35 (v br m, 2H), [5.03-4.98 (m) and 4.91-4.87 (m), J$_{HF}$ = 55 Hz, 1H], 3.92 (d, J = 13.2 Hz, 1H), 3.85 (s, 3H), 3.29 (dd, J = 27.1, 3.9 Hz, 1H), 3.20-3.12 (m, 1H), 3.03 (d, J = 13.2 Hz, 1H), 2.38-2.24 (m, 1H), 2.30 (s, 3H), 2.20-2.04 (m, 2H) |
| 27 | Example 19[11]; C51 | 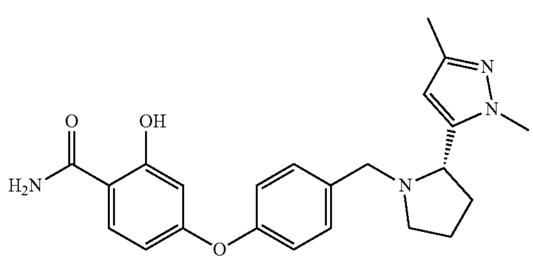 [SMILES: Cc1cc([C@@H]2CCCN2Cc2ccc(Oc3ccc(C(N)=O)c(O)c3)cc2)n(C)n1] | 12.34 (s, 1H), 7.51 (d, J = 8.5 Hz, 1H), 7.31-7.24 (m, 2H, assumed; partially obscured by solvent peak), 6.96 (br d, J = 8.5 Hz, 2H), 6.54 (dd, J = 9.0, 2.5 Hz, 1H), 6.19 (br s, 1H), 5.99 (s, 1H), 3.79-3.73 (m, 1H), 3.78 (s, 3H), 3.58-3.49 (m, 1H), 3.45-3.35 (m, 1H), 3.21-3.12 (m, 1H), 2.36-2.14 (m, 2H), 2.20 (s, 3H), 2.00-1.75 (m, 3H); 406.9 |

TABLE 18-continued

Method of preparation, structure, and physicochemical data for Examples 20-46.

| Ex. No. | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 28 | Example 8$^{12,13}$; C10, C47 | Isomer 1 | 7.67 (dd, J = 11.2, 2.2 Hz, 1H), 7.51 (ddd, J = 8.6, 2.0, 1.2 Hz, 1H), 7.29 (br d, J = 8.6 Hz, 2H), 7.16 (s, 1H), 7.01-6.96 (m, 1H), 6.96 (br d, J = 8.6 Hz, 2H), 6.1-5.55 (v br m, 2H), 3.93-3.86 (m, 1H), 3.92 (s, 3H), 3.72 (s, 3H), 3.44 (dd, J = 9.8, 6.6 Hz, 1H), 3.13 (d, J = 13.3 Hz, 1H), 2.64 (dd, J = 9.4, 3.5 Hz, 1H), 2.39 (dd, J = 9.4, 8.6 Hz, 1H), 2.32 (ddd, J = 12.0, 8.1, 6.6 Hz, 1H), 2.27-2.14 (m, 1H), 1.40 (ddd, J = 11.9, 9.8, 7.2 Hz, 1H), 1.07 (d, J = 6.6 Hz, 3H); 439.3 |
| 29 | Example 8$^{12,13}$; C10, C47 | Isomer 2 | 7.67 (dd, J = 11.0, 2.0 Hz, 1H), 7.50 (ddd, J = 8.4, 2.0, 1.2 Hz, 1H), 7.27 (br d, J = 8.6 Hz, 2H), 7.15 (s, 1H), 6.97 (dd, J = 8.4, 8.2 Hz, 1H), 6.96 (br d, J = 8.4 Hz, 2H), 6.1-5.4 (v br m, 2H), 3.93 (s, 3H), 3.89 (d, J = 13.1 Hz, 1H), 3.73 (s, 3H), 3.42 (dd, J = 8.2, 8.2 Hz, 1H), 3.15 (dd, J = 9.0, 7.2 Hz, 1H), 3.10 (d, J = 12.9 Hz, 1H), 2.38-2.23 (m, 1H), 2.02 (ddd, J = 12.6, 9.8, 8.8 Hz, 1H), 1.77 (dd, J = 9.0, 9.0 Hz, 1H), 1.71 (ddd, J = 12.5, 8, 5.5 Hz, 1H), 1.01 (d, J = 6.6 Hz, 3H); 439.3 |
| 30 | Example 8$^{12,13}$; C10, C47 | Isomer 3 | 7.67 (dd, J = 11.2, 2.2 Hz, 1H), 7.51 (ddd, J = 8.6, 2.1, 1.1 Hz, 1H), 7.29 (br d, J = 8.6 Hz, 2H), 7.16 (s, 1H), 6.99 (dd, J = 8.2, 8.2 Hz, 1H), 6.96 (br d, J = 8.6 Hz, 2H), 6.15-5.55 (v br m, 2H), 3.94-3.86 (m, 1H), 3.92 (s, 3H), 3.72 (s, 3H), 3.44 (dd, J = 9.8, 6.5 Hz, 1H), 3.13 (d, J = 13.5 Hz, 1H), 2.64 (dd, J = 9.4, 3.9 Hz, 1H), 2.39 (dd, J = 9.2, 8.8 Hz, 1H), 2.32 (ddd, J = 12.1, 8.2, 6.5 Hz, 1H), 2.27-2.14 (m, 1H), 1.40 (ddd, J = 12.1, 9.8, 7.3 Hz, 1H), 1.08 (d, J = 6.6 Hz, 3H); 439.3 |
| 31 | Example 8$^{12,13}$; C10, C47 | Isomer 4 | 7.67 (dd, J = 11.2, 2.2 Hz, 1H), 7.50 (ddd, J = 8.5, 2.1, 1.1 Hz, 1H), 7.27 (br d, J = 8.6 Hz, 2H), 7.15 (s, 1H), 6.97 (dd, J = 8.4, 8.0 Hz, 1H), 6.96 (br d, J = 8.6 Hz, 2H), 6.1-5.4 (v br m, 2H), 3.93 (s, 3H), 3.89 (d, J = 13.1 Hz, 1H), 3.73 (s, 3H), 3.42 (dd, J = 8.4, 8.2 Hz, 1H), 3.15 (dd, J = 9.1, 7.1 Hz, 1H), 3.10 (d, J = 13.1 Hz, 1H), 2.38-2.23 (m, 1H), 2.02 (ddd, J = 12.5, 9.8, 8.6 Hz, 1H), 1.77 (dd, J = 9.0, 9.0 Hz, 1H), 1.71 (ddd, J = 12.6, 8.0, 5.5 Hz, 1H), 1.01 (d, J = 6.8 Hz, 3H); 439.3 |

TABLE 18-continued

Method of preparation, structure, and physicochemical data for Examples 20-46.

| Ex. No. | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 32 | Example 14[14]; C13, C45 | ENT-2 | 3.53 minutes[14]; 425.3 |
| 33 | Example 10[15,16]; C51, C13 | ENT-2 | 7.39 (d, J = 8.5 Hz, 1H), 7.29 (br d, J = 8.5 Hz, 2H), 7.15 (s, 1H), 6.97 (br d, J = 8.5 Hz, 2H), 6.51 (dd, J = 8.5, 2.5 Hz, 1H), 6.36 (d, J = 2.5 Hz, 1H), 3.91 (s, 3H), 3.85 (d, J = 12.6 Hz, 1H), 3.72 (s, 3H), 3.36-3.29 (m, 1H), 3.22 (d, J = 13.0 Hz, 1H), 3.10-3.02 (m, 1H), 2.25-2.08 (m, 2H), 1.93-1.71 (m, 3H); 423.2 |
| 34 | Example 27; C51, P7 | 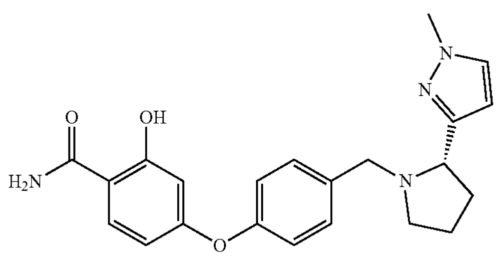 [SMILES: Cn1ccc([C@@H]2CCCN2Cc2ccc(Oc3ccc(C(N)=O)c(O)c3)cc2)n1] | $^1$H NMR (400 MHz, CD$_3$OD) δ 8.46 (br s, 1H), 7.76 (d, J = 8.8 Hz, 1H), 7.61 (d, J = 2.0 Hz, 1H), 7.42 (br d, J = 8.3 Hz, 2H), 7.07 (br d, J = 8.5 Hz, 2H), 6.49 (dd, J = 8.8, 2.3 Hz, 1H), 6.37-6.32 (m, 2H), 4.29-4.19 (m, 2H), 3.94-3.85 (m, 1H), 3.91 (s, 3H), 3.42-3.32 (m, 1H), 3.06-2.95 (m, 1H), 2.48-2.37 (m, 1H), 2.22-2.03 (m, 3H); 392.9 |
| 35 | Example 10[17,18]; C47, P9 | ENT-1 | 7.67 (dd, J = 11.0, 2.0 Hz, 1H), 7.50 (br d, J = 8.5 Hz, 1H), 7.46 (s, 1H), 7.25 (br d, J = 8.5 Hz, 2H), 6.99-6.92 (m, 3H), 6.2-5.6 (v br m, 2H), 3.84 (d, J = 13.0 Hz, 1H), 3.78 (s, 3H), 3.26 (dd, J = 8, 8 Hz, 1H), 3.09-3.01 (m, 1H), 2.98 (d, J = 12.6 Hz, 1H), 2.28 (s, 3H), 2.18-2.05 (m, 2H), 1.95-1.7 (m, 3H, assumed; partially obscured by water peak); 409.0 |
| 36 | Example 3; C48, P9 | (+/−) | 1.81 minutes[19]; 391.3 |

TABLE 18-continued

Method of preparation, structure, and physicochemical data for Examples 20-46.

| Ex. No. | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 37 | Example 14[20]; C47 | 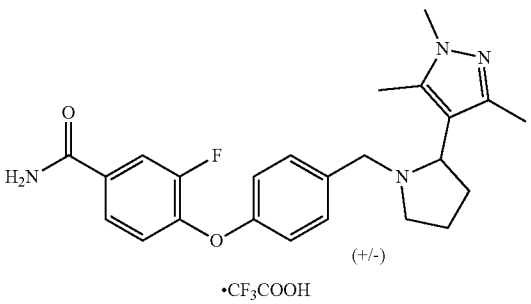 [SMILES: Cc1nn(C)c(C)c1C1CCCN1Cc1ccc(Oc2ccc(C(N)=O)cc2F)cc1 ; "·CF3COOH"] (+/-) •CF$_3$COOH | 1.75 minutes[19]; 423.3 |
| 38 | Example 14[21,22]; C48 | 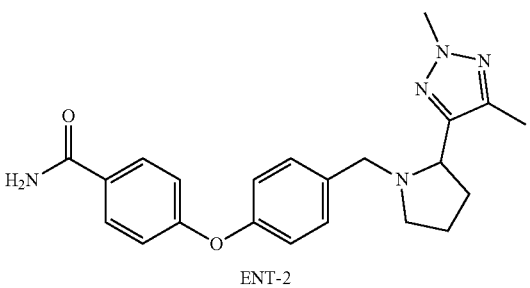 [SMILES: Cc1nn(C)nc1C1CCCN1Cc1ccc(Oc2ccc(C(N)=O)cc2)cc1] ENT-2 | 4.20 minutes[22]; 392.1 |
| 39 | Example 14[21,23]; C45 | 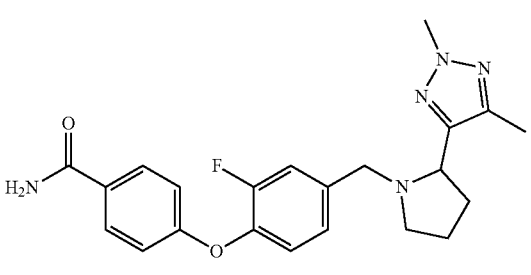 ENT-2 | 3.44 minutes[23]; 410.4 |
| 40 | C47[24] | 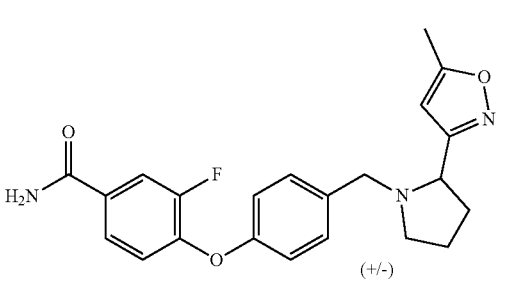 [SMILES: Cc1cc(C2CCCN2Cc2ccc(Oc3ccc(C(N)=O)cc3F)cc2)no1] (+/-) | 1.33 minutes[25]; 396.1 |
| 41 | C48[26,27,28] | 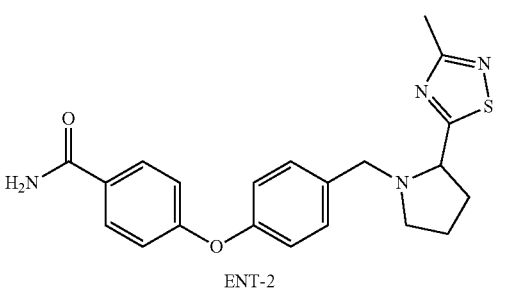 [SMILES: Cc1nsc(C2CCCN2Cc2ccc(Oc3ccc(C(N)=O)cc3)cc2)n1] ENT-2 | 7.80 (br d, J = 9.0 Hz, 2H), 7.38 (br d, J = 8.5 Hz, 2H), 7.06-6.98 (m, 4H), 6.2-5.55 (v br m, 2H), 4.17 (dd, J = 9.5, 4.0 Hz, 1H), 4.07 (d, J = 13.0 Hz, 1H), 3.55 (d, J = 13.0 Hz, 1H), 3.16-3.08 (m, 1H), 2.65 (s, 3H), 2.47-2.35 (m, 2H), 1.98-1.83 (m, 3H); 394.9 |

TABLE 18-continued

Method of preparation, structure, and physicochemical data for Examples 20-46.

| Ex. No. | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 42 | Example 40; C47 | 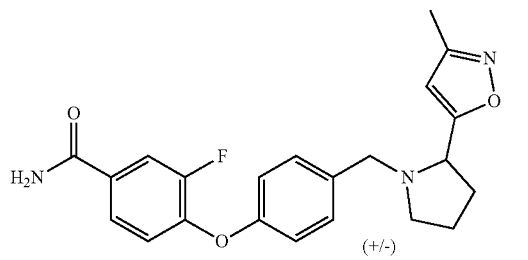 [SMILES: Cc1cc(C2CCCN2Cc2ccc(Oc3ccc(C(N)=O)cc3F)cc2)on1] | 1.31 minutes[25]; 396.1 |
| 43 | P10, C47[29,24,30] | 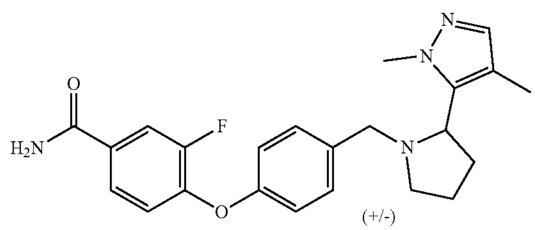 | $^1$H NMR (400 MHz, CD$_3$OD), characteristic peaks: δ 7.80 (br d, J = 11 Hz, 1H), 7.75 (br d, J = 8.5 Hz, 1H), 7.47-7.36 (m, 2H), 7.32 (s, 1H), 7.17 (dd, J = 8.0, 8.0 Hz, 1H), 7.03 (br d, J = 8.0 Hz, 2H), 4.48-4.23 (m, 2H), 3.75 (br s, 3H), 3.69-3.42 (m, 2H), 2.64-2.52 (m, 1H), 2.52-2.21 (m, 3H), 2.19 (br s, 3H); 409.0 |
| 44 | C47[24] | 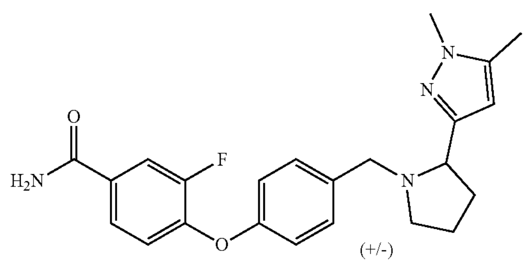 | $^1$H NMR (400 MHz, CD$_3$OD) δ 8.43 (s, 1H), 7.79 (dd, J = 11.5, 2.0 Hz, 1H), 7.72 (ddd, J = 8.5, 2.0, 1.0 Hz, 1H), 7.42 (br d, J = 8.5 Hz, 2H), 7.15 (dd, J = 8.5, 8.0 Hz, 1H), 7.04 (br d, J = 8.5 Hz, 2H), 6.15 (s, 1H), 4.34-4.25 (m, 2H), 3.98 (d, J = 12.6 Hz, 1H), 3.79 (s, 3H), 3.44-3.35 (m, 1H), 3.17-3.07 (m, 1H), 2.49-2.38 (m, 1H), 2.31 (s, 3H), 2.25-2.06 (m, 3H); 409.2 |
| 45 | Example 19; C54 | 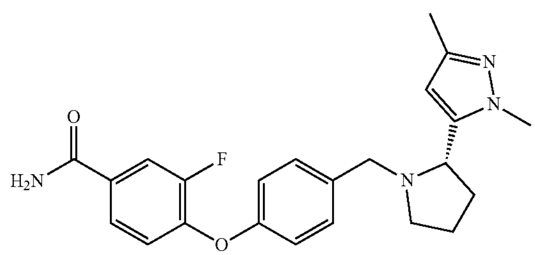 [SMILES: Cc1cc([C@@H]2CCCN2Cc2ccc(Oc3ccc(C(N)=O)cc3F)cc2)n(C)n1] | $^1$H NMR (400 MHz, CD$_3$OD) δ 7.76 (dd, J = 11.5, 2.0 Hz, 1H), 7.67 (br d, J = 8.5 Hz, 1H), 7.29 (br d, J = 8.5 Hz, 2H), 7.02 (dd, J = 8.5, 8.0 Hz, 1H), 6.96 (br d, J = 8.5 Hz, 2H), 6.05 (s, 1H), 3.79 (s, 3H), 3.79 (d, J = 12.6 Hz, 1H), 3.60 (dd, J = 8.5, 8.0 Hz, 1H), 3.26 (d, J = 12.6 Hz, 1H), 3.10-3.03 (m, 1H), 2.35-2.20 (m, 2H), 2.18 (s, 3H), 1.97-1.71 (m, 3H); LCMS m/z 431.0 [M + Na$^+$] |
| 46 | Example 11[31,32]; C48 | 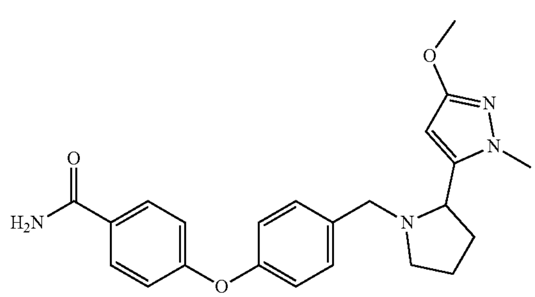 | 7.79 (br d, J = 8.8 Hz, 2H), 7.31-7.25 (m, 2H, assumed; partially obscured by solvent peak), 7.00 (br d, J = 8.8 Hz, 2H), 6.99 (br d, J = 8.4 Hz, 2H), 6.2-5.3 (v br m, 2H), 5.66 (s, 1H), 3.92 (d, J = 13.1 Hz, 1H), 3.87 (s, 3H), 3.78 (s, 3H), 3.49 (dd, J = 8.2, 7.8 Hz, 1H), 3.17 (d, J = 12.9 Hz, 1H), 3.13-3.05 (m, 1H), 2.25-2.14 (m, 2H), 1.99-1.78 (m, 3H)[33]; 407.4 |

1. tert-Butyl 3-methoxymorpholine-4-carboxylate was prepared via anodic oxidation of tert-butyl morpholine-4-carboxylate in methanol, in the presence of tetraethylammonium p-toluenesulfonate (see K. J. Frankowski et al., *Angew. Chem., Int. Ed.* 2015, 54, 10555-10558). Reaction with (3-methoxy-1-methyl-1H-pyrazol-4-yl)lithium (derived from treatment of C10 with n-butyllithium) in the presence of copper(I) bromide-dimethyl sulfide complex and boron trifluoride diethyl etherate (see S. Hanessian et al., *J. Org. Chem.* 2002, 67, 4261-4274) afforded tert-butyl 3-(3-methoxy-1-methyl-1H-pyrazol-4-yl)morpholine-4-carboxylate. This material was subjected to hydrogen chloride to provide the requisite 3-(3-methoxy-1-methyl-1H-pyrazol-4-yl)morpholine, hydrochloride salt.

2. The racemic product was separated into its enantiomers via supercritical fluid chromatography (Column: Phenomenex Lux Cellulose-1, 5 μm; Mobile phase: 85:15 carbon dioxide/methanol). Example 20 was the first-eluting enantiomer. On analytical HPLC (Column: Phenomenex Lux Cellulose-1, 4.6×100 mm, 5 μm; Mobile phase: 3:1 carbon dioxide/methanol; Flow rate: 1.5 mL/minute), Example 20 exhibited a retention time of 3.52 minutes. The enantiomer of Example 20, 3-fluoro-4-(4-{[3-(3-methoxy-1-methyl-1H-pyrazol-4-yl)morpholin-4-yl]methyl}phenoxy)benzamide, ENT-2, had a retention time of 3.78 minutes under the same conditions. The enantiomer of Example 20, LCMS m/z 441.2 [M+H]$^+$, exhibited the following biological data: hKOR $K_i$ 145 nM; hMOR $K_i$>564 nM.

3. In this case, excess acetic acid was used in the reaction, rather than N,N-diisopropylethylamine.

4. 2-(3-Methoxy-1-methyl-1H-pyrazol-4-yl)piperidine, hydrochloride salt, was synthesized using the method described in footnote 1, but using tert-butyl piperidine-1-carboxylate as starting material.

5. The racemic product was separated into its enantiomers via supercritical fluid chromatography [Column: Chiral Technologies Chiralpak AD-H, 5 μm; Mobile phase: 4:1 carbon dioxide/(methanol containing 0.2% ammonium hydroxide)]. Example 21 was the first-eluting enantiomer. On analytical HPLC [Column: Chiral Technologies Chiralpak AD-H, 4.6×100 mm, 5 μm; Mobile phase: 7:3 carbon dioxide/(methanol containing 0.2% ammonium hydroxide)]; Flow rate: 1.5 mL/minute), Example 21 exhibited a retention time of 2.72 minutes. The enantiomer of Example 21, 4-(4-{[2-(3-methoxy-1-methyl-1H-pyrazol-4-yl)piperidin-1-yl]methyl}phenoxy)benzamide, ENT-2, had a retention time of 3.00 minutes under the same conditions. The enantiomer of Example 21, LCMS m/z 421.4 [M+H]$^+$, exhibited the following biological data: hKOR $K_i$ 15.5 nM; hMOR $K_i$ 135 nM.

6. This Example was synthesized as a racemate; the racemic product was separated into its enantiomers via supercritical fluid chromatography (Column: Phenomenex Lux Cellulose-1, 5 μm; Mobile phase: 4:1 carbon dioxide/methanol). Example 22 was the first-eluting enantiomer. On analytical HPLC (Column: Phenomenex Lux Cellulose-1, 4.6×100 mm, 5 μm; Mobile phase: 7:3 carbon dioxide/methanol; Flow rate: 1.5 mL/minute), Example 22 exhibited a retention time of 4.07 minutes. The enantiomer of Example 22, 4-(2-fluoro-4-{[3-(3-methoxy-1-methyl-1H-pyrazol-4-yl)morpholin-4-yl]methyl}phenoxy)benzamide, ENT-2, had a retention time of 4.50 minutes under the same conditions. The enantiomer of Example 22, LCMS m/z 441.2 [M+H]$^+$, exhibited the following biological data: hKOR $K_i$ 263 nM; hMOR $K_i$>564 nM.

7. This Example was synthesized as a racemate; the racemic product was separated into its enantiomers via supercritical fluid chromatography (Column: Phenomenex Lux Cellulose-1, 5 μm; Mobile phase: 85:15 carbon dioxide/methanol). Example 23 was the first-eluting enantiomer. On analytical HPLC (Column: Phenomenex Lux Cellulose-1, 4.6×100 mm, 5 μm; Mobile phase: 3:1 carbon dioxide/methanol; Flow rate: 1.5 mL/minute), Example 23 exhibited a retention time of 4.30 minutes. The enantiomer of Example 23, 4-(4-{[3-(3-methoxy-1-methyl-1H-pyrazol-4-yl)morpholin-4-yl]methyl}phenoxy)benzamide, ENT-2, had a retention time of 4.82 minutes under the same conditions. The enantiomer of Example 23, LCMS m/z 423.2 [M+H]$^+$, exhibited the following biological data: hKOR $K_i$ 223 nM; hMOR $K_i$>564 nM.

8. Compounds C10 and C32 were reacted and further transformed, using the methods described in Preparation P8, to afford the requisite 4-(4-fluoropyrrolidin-2-yl)-3-methoxy-1-methyl-1H-pyrazole.

9. This Example was synthesized as a racemic mixture of cis and trans isomers; NMR data for this mixture: $^1$H NMR (500 MHz, CDCl$_3$) δ 7.78 (br d, J=8.8 Hz, 2H), 7.33-7.27 (m, 3H), 7.02-6.95 (m, 4H), [5.03-4.97 (m) and 4.91-4.86 (m), $J_{HF}$=55 Hz, total 1H], 6.2-5.5 (v br m, 2H), 3.96-3.91 (m, 1H), 3.94 (s, 3H), 3.76 (s, 3H), 3.40-3.30 (m, 1H), 3.16-3.08 (m, 2H), 2.35-2.21 (m, 1H), 2.18-2.04 (m, 2H). This material was separated into its component racemic isomers via supercritical fluid chromatography [Column: Phenomenex Lux Cellulose-4, 5 μm; Mobile phase: 65:35 carbon dioxide/(0.2% ammonium hydroxide in methanol)], providing Example 24 as the second-eluting isomer. Example 24 was assumed to be either the cis or the trans racemic product, but was not stereochemically assigned. On analytical HPLC [Column: Phenomenex Lux Cellulose-4, 4.6×100 mm, 5 μm; Mobile phase: 1:1 carbon dioxide/(0.2% ammonium hydroxide in methanol); Flow rate: 1.5 mL/minute], Example 24 exhibited a retention time of 4.71 minutes. The racemic isomer of Example 24 had a retention time of 3.71 minutes under the same conditions. The isomer of Example 24, LCMS m/z 425.2 [M+H]$^+$, exhibited the following biological data: hKOR $K_i$ 36.3 nM; hMOR $K_i$ 1210 nM.

10. Examples 25 and 26 were synthesized as a presumed racemic mixture of cis and trans isomers. Separation was carried out via supercritical fluid chromatography [Column: Chiral Technologies Chiralcel OJ-H, 5 μm; Mobile phase: 85:15 carbon dioxide/(methanol containing 0.3% ammonium hydroxide)], but only two of the 4 possible isomers were isolated. Example 25 eluted prior to Example 26.

11. Reduction of C51 with sodium borohydride provided 7-[4-(hydroxymethyl)phenoxy]-2,2-dimethyl-4H-1,3-benzodioxin-4-one, which was converted to 7-(4-{[(2S)-2-(1,3-dimethyl-1H-pyrazol-5-yl)pyrrolidin-1-yl]methyl}phenoxy)-2,2-dimethyl-4H-1,3-benzodioxin-4-one using the general methods described in Example 19. Subsequent reaction with aqueous ammonium hydroxide in 1,4-dioxane at elevated temperature provided Example 27.

12. 4-Hydroxy-4-methylpyrrolidin-2-one was converted to tert-butyl 4-methyl-2-oxo-2,5-dihydro-1H-pyrrole-1-carboxylate via treatment with di-tert-butyl dicarbonate and 4-(dimethylamino)pyridine. Reduction with sodium borohydride and nickel(II) chloride then afforded tert-butyl 4-methyl-2-oxopyrrolidine-1-carboxylate, which was reacted with C10 and further transformed, using the general methods described in Preparation P8, to provide the requisite 3-methoxy-1-methyl-4-(4-methylpyrrolidin-2-yl)-1H-pyrazole.

13. Examples 28 through 31 were synthesized as a racemic mixture of geometric isomers. The four components were separated via supercritical fluid chromatography [Column: Phenomenex Lux Cellulose-3, 5 μm; Mobile phase: 4:1 carbon dioxide/(ethanol containing 0.2% ammonium hydroxide)].

On analytical HPLC (Column: Phenomenex Lux Cellulose-3, 4.6×250 mm, 5 μm; Mobile phase A: carbon dioxide; Mobile phase B: ethanol containing 0.2% ammonium hydroxide; Gradient: 5% B for 1.0 minute, then 5% to 60% B over 8.0 minutes; Flow rate: 3.0 mL/minute), Example 28 exhibited a retention time of 5.29 minutes, and Example 31 had a retention time of 4.88 minutes.

A mixture of Examples 29 and 30 eluted between Examples 28 and 31; this mixture was separated using supercritical fluid chromatography {Column: Princeton Methanesulfonamide, 5 μm; Mobile phase: 9:1 carbon dioxide/[methanol containing 0.2% (7 M ammonia in methanol)]}. The first-eluting isomer from this column was Example 29, which was followed by Example 30. On analytical HPLC [Column: Princeton Methanesulfonamide, 4.6×150 mm, 5 μm; Mobile phase A: carbon dioxide; Mobile phase B: methanol containing 0.2% (7 M ammonia in methanol); Gradient: 5% B for 1.0 minute, then 5% to 60% B over 8.0 minutes; Flow rate: 3.0 mL/minute], Example 29 exhibited a retention time of 5.12 minutes, and Example 30 had a retention time of 5.34 minutes.

14. This Example was synthesized as a racemate; the racemic product was separated into its enantiomers via supercritical fluid chromatography [Column: Chiral Technologies Chiralpak IC, 5 μm; Mobile phase: 85:15 carbon dioxide/(methanol containing 0.2% ammonium hydroxide)]. Example 32 was the second-eluting enantiomer. On analytical HPLC [Column: Chiral Technologies Chiralpak AD-H, 4.6×100 mm, 5 μm; Mobile phase: 3:1 carbon dioxide/ (methanol containing 0.2% ammonium hydroxide); Flow rate: 1.5 mL/minute], Example 32 exhibited a retention time of 3.53 minutes. The enantiomer of Example 32, 4-(2-fluoro-4-{[2-(3-methoxy-1-methyl-1H-pyrazol-4-yl)pyrrolidin-1-yl]methyl}phenoxy)benzamide, ENT-1, had a retention time of 3.13 minutes under the same conditions. The enantiomer of Example 32, LCMS m/z 425.3 [M+H]$^+$, exhibited the following biological data: hKOR $K_i$ 0.629 nM; hMOR $K_i$ 13.7 nM.

15. The penultimate compound in the synthesis, 7-(4-{ [2-(3-methoxy-1-methyl-1H-pyrazol-4-yl)pyrrolidin-1-yl] methyl}phenoxy)-2,2-dimethyl-4H-1,3-benzodioxin-4-one, was deprotected via treatment with ammonia in methanol to afford the racemate of Example 33.

16. This Example was synthesized as a racemate; the racemic product was separated into its enantiomers via supercritical fluid chromatography [Column: Chiral Technologies Chiralcel OJ, 5 μm; Mobile phase: 7:3 carbon dioxide/(ethanol containing 0.1% ammonium hydroxide)]. Example 33 was the second-eluting enantiomer. On analytical HPLC [Column: Chiral Technologies Chiralcel OJ, 5 μm; Mobile phase: 7:3 carbon dioxide/(methanol containing 0.05% diethylamine)], Example 33 exhibited a retention time of 5.38 minutes. The enantiomer of Example 33, 2-hydroxy-4-(4-{[2-(3-methoxy-1-methyl-1H-pyrazol-4-yl) pyrrolidin-1-yl]methyl}phenoxy)benzamide, ENT-1, had a retention time of 4.88 minutes under the same conditions. The enantiomer of Example 33, LCMS m/z 423.2 [M+H]$^+$, exhibited the following biological data: hKOR $K_i$ 28.7 nM; hMOR $K_i$ 308 nM.

17. In this case, titanium(IV) isopropoxide was used in place of sodium acetate for the reductive amination.

18. The racemic product was separated into its enantiomers via supercritical fluid chromatography [Column: Chiral Technologies Chiralpak AD, 10 μm; Mobile phase: 45:55 carbon dioxide/(ethanol containing 0.05% ammonium hydroxide)]. Example 35 was the first-eluting enantiomer. On analytical HPLC (Column: Chiral Technologies Chiralpak AD-3, 4.6×50 mm, 3 μm; Mobile phase A: carbon dioxide; Mobile phase B: 0.05% diethylamine in 2-propanol; Gradient: 5% B for 0.2 minutes, then 5% to 40% B over 1.4 minutes, then hold at 40% B; Flow rate: 4 mL/minute), Example 35 exhibited a retention time of 1.77 minutes. The enantiomer of Example 35, 4-(4-{[2-(1,5-dimethyl-1H-pyrazol-4-yl)pyrrolidin-1-yl]methyl}phenoxy)-3-fluorobenzamide, ENT-2, had a retention time of 1.91 minutes under the same conditions. The enantiomer of Example 35, LCMS m/z 409.0 [M+H]$^+$, exhibited the following biological data: hKOR 92.8 $K_i$ nM; hMOR $K_i$ 245 nM.

19. Conditions for analytical HPLC. Column: Waters Atlantis dC18, 4.6×50 mm, 5 μm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes; Flow rate: 2 mL/minute.

20. A mixture of tert-butyl pyrrolidine-1-carboxylate and (1S,2S)—N,N'-bis(3,3-dimethylbutyl)-N,N'-dimethylcyclohexane-1,2-diamine was treated with s-butyllithium. Subsequent addition of zinc chloride afforded the zincate species, which was reacted with 4-bromo-1,3,5-trimethyl-1H-pyrazole in the presence of bis(tri-tert-butylphosphine) palladium(0). Removal of the protecting group with trifluoroacetic acid afforded the requisite 1,3,5-trimethyl-4-(pyrrolidin-2-yl)-1H-pyrazole.

21. 4-Bromo-2,5-dimethyl-2H-1,2,3-triazole was lithiated with n-butyllithium and reacted with tert-butyl 2-oxopyrrolidine-1-carboxylate, providing tert-butyl [4-(2,5-dimethyl-2H-1,2,3-triazol-4-yl)-4-oxobutyl]carbamate. Treatment with hydrogen chloride effected deprotection and cyclization to afford 4-(3,4-dihydro-2H-pyrrol-5-yl)-2,5-dimethyl-2H-1,2,3-triazole, which was taken directly into the reductive amination with the appropriate aldehyde.

22. The racemic product was separated into its enantiomers via supercritical fluid chromatography [Column: Chiral Technologies Chiralpak AD-H, 5 μm; Mobile phase: 3:1 carbon dioxide/(methanol containing 0.2% ammonium hydroxide)]. Example 38 was the second-eluting enantiomer. On analytical HPLC [Column: Chiral Technologies Chiralpak AD-H, 4.6×100 mm, 5 μm; Mobile phase: 7:3 carbon dioxide/(methanol containing 0.2% ammonium hydroxide); Flow rate 1.5 mL/minute], Example 38 exhibited a retention time of 4.20 minutes. The enantiomer of Example 38, 4-(4-{[2-(2,5-dimethyl-2H-1,2,3-triazol-4-yl) pyrrolidin-1-yl]methyl}phenoxy)benzamide, ENT-1, had a retention time of 3.54 minutes under the same conditions. The enantiomer of Example 38, LCMS m/z 392.4 [M+H]$^+$, exhibited the following biological data: hKOR $K_i$>119 nM; hMOR $K_i$ 252 nM.

23. The racemic product was separated into its enantiomers via supercritical fluid chromatography, using the same conditions as those described in footnote 22. Example 39 was the second-eluting enantiomer. On analytical HPLC, using the same HPLC system employed in footnote 22, Example 39 exhibited a retention time of 3.44 minutes. The enantiomer of Example 39, 4-(4-{[2-(2,5-dimethyl-2H-1,2, 3-triazol-4-yl)pyrrolidin-1-yl]methyl}-2-fluorophenoxy) benzamide, ENT-1, had a retention time of 2.99 minutes under the same conditions. The enantiomer of Example 39, LCMS m/z 410.4 [M+H]$^+$, exhibited the following biological data: hKOR $K_i$ 74.5 nM; hMOR $K_i$ 132 nM.

24. In this case, the reductive amination was carried out using sodium cyanoborohydride and acetic acid.

25. Conditions for analytical HPLC. Column: Restek C18, 2.1×30 mm, 3 µm; Mobile phase A: 0.05% formic acid in water (v/v); Mobile phase B: acetonitrile (v/v); Gradient: 2% B for 0.75 minutes, then 2% to 10% B over 0.25 minutes, then 10% to 98% B over 1.0 minute; Flow rate: 1.5 mL/minute).

26. Reaction of tert-butyl 2-carbamoylpyrrolidine-1-carboxylate with Lawesson's reagent (2,4-bis(4-methoxyphenyl)-1,3,2,4-dithiadiphosphetane-2,4-dithione) provided tert-butyl 2-carbamothioylpyrrolidine-1-carboxylate, which was treated with 1,1-dimethoxy-N,N-dimethylethanamine to afford tert-butyl 2-{[(1E)-1-(dimethylamino) ethylidene]carbamothioyl}pyrrolidine-1-carboxylate. Subsequent reaction with hydroxyl amine-O-sulfonic acid, followed by protecting group removal with hydrogen chloride in 1,4-dioxane, yielded the requisite 3-methyl-5-(pyrrolidin-2-yl)-1,2,4-thiadiazole.

27. In this case, the reductive amination was carried out using sodium cyanoborohydride with added triethylamine and magnesium sulfate.

28. The racemic product was separated into its enantiomers via supercritical fluid chromatography [Column: Chiral Technologies Chiralcel OJ-H, 5 µm; Mobile phase: 3:1 carbon dioxide/(ethanol containing 0.1% ammonium hydroxide)]. Example 41 was the second-eluting enantiomer. On analytical HPLC (Column: Chiral Technologies Chiralpak AD-3, 4.6×100 mm, 3 µm; Mobile phase A: carbon dioxide; Mobile phase B: 0.05% diethylamine in methanol; Gradient: 5% to 40% B over 4.5 minutes, then 40% B for 2.5 minutes; Flow rate: 2.8 mL/minute), Example 41 exhibited a retention time of 6.00 minutes. The enantiomer of Example 41, 4-(4-{[2-(3-methyl-1,2,4-thiadiazol-5-yl)pyrrolidin-1-yl]methyl}phenoxy)benzamide, ENT-1, had a retention time of 5.43 minutes under the same conditions. The enantiomer of Example 41, LCMS m/z 394.9 [M+H]$^+$, exhibited the following biological data: hKOR $K_i$>388 nM; hMOR $K_i$>558 nM.

29. Deprotection of P10 was effected using hydrogen chloride in ethyl acetate and methanol, prior to carrying out the reductive amination.

30. Example 43 was isolated via reversed-phase HPLC (Column: Dikma Technologies Diamonsil, 4 µm; Mobile phase A: 0.225% formic acid in water; Mobile phase B: acetonitrile; Gradient: 17% to 37% B). The indicated regiochemistry of the methyl groups in the product was supported by NOE studies.

31. The requisite 3-methoxy-1-methyl-5-(pyrrolidin-2-yl)-1H-pyrazole was synthesized from methyl 2-methyl-5-oxo-2,5-dihydro-1H-pyrazole-3-carboxylate, using the method described in Preparation P6 for conversion of C18 to C25. In this case, the final removal of the benzyloxycarbonyl group was effected with palladium on carbon and triethylsilane.

32. The racemic product was separated into its enantiomers via supercritical fluid chromatography [Column: Chiral Technologies Chiralcel OJ-H, 5 µm; Mobile phase: 87:13 carbon dioxide/(methanol containing 0.2% ammonium hydroxide)]. Example 46 was the second-eluting enantiomer. On analytical HPLC [Column: Phenomenex Lux Cellulose-3, 4.6×100 mm, 5 µm; Mobile phase: 4:1 carbon dioxide/(methanol containing 0.2% ammonium hydroxide); Flow rate: 1.5 mL/minute], Example 46 exhibited a retention time of 3.57 minutes. The enantiomer of Example 46, 4-(4-{[2-(3-methoxy-1-methyl-1H-pyrazol-5-yl)pyrrolidin-1-yl]methyl}phenoxy)benzamide, ENT-1, had a retention time of 3.03 minutes under the same conditions. The enantiomer of Example 46, LCMS m/z 407.2 [M+H]$^+$, exhibited the following biological data: hKOR $K_i$ 111 nM; hMOR $K_i$ 120 nM.

33. This NMR data was obtained on the racemate of Example 46.

The following assays were used to generate the biological data as provided in Tables 6-11 provided herein below.

Kappa and Mu Radioligand Binding Assay:

Binding assays on membranes from CHO cells expressing human kappa or mu opioid receptors were performed according to standard procedures. Frozen cell paste was homogenized in 50 mM Tris HCl buffer (pH 7.4 @ 4 degrees C.) containing 2.0 mM $MgCl_2$ using a Polytron and spun in a centrifuge at 40,000 g for ten minutes. The final pellet was resuspended in assay buffer (50 mM Tris HCl buffer, pH 7.4, containing 1 mM EDTA, 5 mM $MgCl_2$). Incubations were initiated by the addition of membranes to 96-well plates containing test drugs and [$^3$H]diprenorphine (0.6 nM final concentration for kappa opioid receptor and 0.5 nM final concentration for mu) in a final volume of 250 µl. Nonspecific binding was determined by radioligand binding in the presence of a saturating concentration of naltrexone (10 µM). After a one hour incubation period at room temperature, assay samples were rapidly filtered through PEI coated, GF/B fired Unifilter plates (PerkinElmer) and rinsed with ice-cold 50 mM Tris buffer (pH 7.4). Membrane bound [$^3$H]diprenorphine levels were determined by liquid scintillation counting of the filterplates in Ecolume scintillation fluid. The $IC_{50}$ value (concentration at which 50% inhibition of specific binding occurs) was calculated using a logistic 4 parameter fit model of the concentration-response data. $K_i$ values were calculated according to the Cheng Prusoff equation, $K_i=IC_{50}/(1+(L/K_d))$, where L is the concentration of the radioligand used in the experiment and the $K_d$ value is the dissociation constant for the radioligand (determined previously by saturation analysis).

Animals

Adult male C576BL/J6 mice from Jackson Labs (Bar Harbor, Me.) were group housed on individually-vented cage racks, in environmentally-controlled animal quarters (light/dark-6:00 am/6:00 µm) for a minimum of 7 days prior to use. For progressive ratio studies, mice were food-restricted to 80-85% of their body weight before testing began. All animal procedures were approved by the Pfizer Inc. IACUC and conducted in accordance with the NIH Guide for the Care and Use of Laboratory Animals.

Progressive Ratio Responding:

Motivation and food-reinforced operant behavior were assessed in the progressive ratio assay. Adult male C576BL/J6 mice were food-restricted to 80-85% of their body weight over a period of one week and kept in their home cages. Mice were trained to nose-poke for a food reward. Food reward pellets were delivered on a progressive ration scheduling, such that while one nose-poke resulted in the first reward, the second reward was only delivered after 3 nose-pokes, the third after seven nose-pokes, and so on. Mice were assessed in a 60 minute session, where the number of rewards obtained was used as a surrogate of the level of motivation. Once mice had reached a stable level of responding, mice were dosed with the kappa opioid receptor agonist, spiradoline (3.2 mg/kg s.c.), to induce a deficit in motivation. Mice were co-administered increasing doses of the kappa opioid receptor antagonists (0.0032-3.2 mg/kg s.c.) to assess their ability to antagonize the spiradoline-induced deficit.

In Vivo Receptor Occupancy

In vivo receptor occupancy was assessed in adult male C57BL6/J mice. Mice were administered increasing doses (0.001-32 mg/kg s.c.) 30 min prior to administration of the kappa opioid receptor ligand, [$^3$H]GR103545 (100 µCi/kg, intraorbital). Animals were euthanized 10 min later using cervical dislocation and the brains dissected. One hemisphere was stored at −40° C. for subsequent measurement of compound concentration, the other was homogenized in chilled Tris-HCl buffer (50 mM, pH 7.4; 1:10 w/v) for twenty seconds. Samples of brain homogenate were filtered through 0.3 to 0.5% PEI-soaked GF/B filters, and the filters washed twice with chilled buffer before radioactivity was counted overnight using a scintillation counter. Binding of the ligand in cerebellum was used to determine non-specific binding.

Determination of In Vitro Intrinsic Clearance in Human Liver Microsomes:

Compounds were prepared as solutions in methanol. The final concentration of methanol in the incubation media was 0.2% (v/v). In vitro $t_{1/2}$ of each compound was determined in triplicate in an incubation containing substrate (2 µM) within human liver microsomes (P450 concentration, 0.25 µM) in 0.1 M potassium phosphate buffer (pH 7.4) at 37° C. The total incubation volume was 1 mL. The reaction mixture was pre-warmed at 37° C. for 2 min before adding NADPH (1.2 mM). Aliquots (75 µL) of the reaction mixture at 0, 5, 10, 15, and 30 min were added to acetonitrile (200 µL) containing internal standard (terfenadine)(0.05 µg/mL), and the samples were centrifuged at 2500 g for 5 min prior to liquid chromatography/tandem mass spectrometry (LC/MS-MS) analysis of each compound using multiple reaction monitoring (MRM). For control experiments, NADPH was omitted from these incubations.

The microsomal half-life ($t_{1/2}$) was obtained from a log-linear plot of the substrate depletion vs incubation time and was scaled to hepatic intrinsic clearance ($CL_{int}$) using the following equation, in which the term $t_{1/2}$ refers to the in vitro half-life:

$$CL_{int,app,scaled} = 0.693 \cdot \frac{1}{T_{1/2}(\min)} \cdot \frac{\text{g liver weight}}{\text{kg body weight}} \cdot \frac{\text{mL incubation}}{\text{mg microsomal protein}} \cdot \frac{45 \text{ mg microsomal protein}}{\text{g liver}}$$

Multi-Point Cocktail DDI $IC_{50}$ Assay Conditions:

Standard marker activity substrates were incubated with pooled human liver microsomes (HL-MIX-102) in the presence of NADPH (1.2 mM) in 100 mM KH$_2$PO$_4$, pH 7.4 containing 3.3 mM MgCl$_2$ at 37° C. The incubation volume was 0.1 mL, utilizing a 384-well plate format. The microsomal protein concentrations (0.1 mg/mL) and P450 concentration (0.035 µM) was used for each probe substrate at the following concentrations [tacrine (1A2) 2 uM; diclofenac (2C9) 5 µM; dextromethorphan (2D6) 5 µM; midazolam (3A4) 2 µM; taxol (2C8) 5 µM; S-mephenytoin (2C19) 40 µM]. Substrate concentrations were near $K_m$ values that had been previously determined and incubation times were selected based on determinations of reaction velocity linearity. Each test compound/prototypical inhibitors was tested at a concentration range of 0-30 µM in triplicate, in final vehicle solvent concentrations of 0.9% acetonitrile and 0.1% DMSO. Incubations were initiated with the addition of NADPH. At the end of the incubation period, termination solvent containing internal standard was added, the terminated incubation mixture was centrifuged to precipitate microsomal protein. Samples were directly injected on an HPLC-MS/MS system. A Biomek FX workstation was used for liquid handling and sample incubation.

Single Point Time Dependent Inhibition (SPTDI) Assay:

Zimmerlin et al. *Drug Metabolism and Disposition* 39(6), 1039-1046 (2011)

The objective of this study was to investigate the potential of a series of carboxamides to be time dependent inactivators of CYP3A isozymes, in vitro, using midazolam and testosterone as probe substrates for CYP 3A4/5 activity incubated with pooled human liver microsomes (HLM). Pooled HLMs (0.1-1.0 mg/ml) were pre-incubated with individual carboxamides at initial substrate concentrations of 6 or 10 µM in the presence and absence of NADPH (1.3 mM). Pre-incubations (n=2/compound) were performed for 30 min at 37° C. After pre-incubation, a 10-fold dilution of the incubate (0.02 ml) was added to the probe substrate incubate (0.18 ml) containing the respective probe P450 isozyme substrate (midazolam or testosterone for CYP3A, 1 uM), and was incubated at 37° C. The combined incubation reactions were terminated and analyzed for marker substrate activity (Ex: hydroxyl metabolite of midazolam and 6β hydroxy testesterone) as described previously (Walsky and Obach, 2004; Obach et al., 2007). Terminated incubation mixtures were filtered and analyzed by liquid chromatography (LC)-tandem mass spectrometry (MS/MS) for metabolites as described previously (Walsky and Obach, 2004). To determine $k_{obs,app}$ values, the decrease in natural logarithm of the activity over time was plotted for each inactivator concentration, and $k_{obs,app}$ values were described as the negative slopes of the lines. Inactivation kinetic parameters were determined using nonlinear regression of the data to the expression in eq. 1:

$$k_{obs,app} = k_{obs,app,[1]=0} + \frac{k_{inact} \times [1]}{K_1 + [1]}$$

Statistical significance of $k_{obs}$ between solvent and test incubations was inferred using analysis performed by Yates et al. (Yates P, Eng H, Di L, Obach R S. Drug Metab Dispos 2012; 40:2289-96).

Transformed Human Liver Endothelial (THLE) Assay:

ATP depletion was measured after 72 hours of exposure to a particular concentration of the chemical. In detail, THLE-2 (transformed human liver epithelial) cells were obtained from ATCC (CRL-2706 or CRL-10149) and cultured according to ATCC's recommendation. Media consisted of basal medium (BEGM Bullet Kit, Lonza Cat#: CC-3170), supplemented with 10% fetal bovine serum (Sigma Cat#: F4135) and 2.5 ng/l hEFG (BD Biosciences Cat#: 356052) and 700 ng/L phosphoethanolamine (Sigma Cat#: p-0503). Cells were cultured in T175 Human fibronectin/collagen/bovine serum albumin coated flasks. For each experiment, cells were plated onto 384-well plates (Human fibronectin/collagen/bovine serum albumin coated 384, custom order, BD Biosciences Cat#: 359298) at a cell density of 2.5×103/well in a total medium volume of 25 µl/well. Plates were incubated for 24 hours at 37° C., 5% CO$_2$.

Compound test plates were prepared using a 10 dose, 2.0 fold dilution protocols with a final assay concentration range of 300-0.058 µM. All compounds were initially solubilized in 100% DMSO. This dosing scheme contained 32 compounds per plate. Stock plates were prepared using 1 µl aliquots of 100× compound/well (30 mM-0.058 mM). The plates were prepared for dosing by adding 99 μl of cell culture media and mixing. Test compounds were added to cell culture plates by aspirating overnight culture media and replacing with 25 μL/well of media containing test compound using the layout outlined below. The final concentration of DMSO in each well was 1.0%. Following the 72 hour exposure to test articles, cell viability in each well iwass determined by measuring the concentration of cellular ATP using the Lonza Vialight™ Plus Cell Proliferation/Cytoxicity Kit (Lonza cat: LT07-121) according to the manufacturer's protocol. The ATP concentration was determined by reading luminescence using a Wallac Envision plate reader (Perkin Elmer, Waltham, Mass., USA). Percent of viable cells relative to no-drug treated controls was determined for each well. Final data output was a calculated LC50 value describing the dose projected to kill 50% of the cells following a 72 hour exposure.

HepG2_Glu ATP Viability 72 hr IC50:

This assay was run in a similar manner to the assay as described in Marroquin et al. *Toxicological Sciences* 97(2), 539-547 (2007) with a modification such that the instant assay was run for a 72 hour period as described below.

The aim of this assay was to measure cytotoxicity of a compound by measuring cell viability. In order to quantify cell viability, the amount of ATP present was measured, indicating that there were metabolically active cells. The reagent used to quantify the ATP present was Promega Cell Titer-Glo. This reagent works by catalyzing luciferin by luciferase in the presence of $Mg^{2+}$, ATP, and molecular oxygen, thus emitting a luminescent signal, which was proportional to the amount of ATP present in the sample.

HepG2 cells grown in glucose-supplemented media were plated in 384 well plates at a density of 1000 cells/well for the 72 hour assay in a total medium volume of 25 μl/well. Plates were then incubated for 24 hours at 37° C., 95% humidity, and 5% $CO_2$ before compound dosing.

After 24 hours to allow cells to attach to the plate, HepG2 cells were exposed to test compounds in an 11-point dose response format with a 1:2 serial dilution, ranging from 300 uM to 0.029 uM for 72 hours. All compounds were tested in triplicate. Following the 72 hour exposure to test compounds, cell viability was determined by measuring the concentration of cellular ATP by adding Promega Cell Titer-Glo according to the manufacturer's directions. The plates were then read on a fluorescent plate reader and data is analyzed using ActivityBase software. Final data output was a calculated $IC_{50}$ value describing the dose predicted to kill 50% of the cells following a 72 hour exposure.

Respirometric Screening Technology (RST) Assay:

This assay was carried out substantially as described in Hynes et al. *Toxicological Sciences* 91(1), 186-200 (2006). More specifically, the assay conditions were similar to those described for the "Fluorescence-based assay of mitochondrial respiration" at page 188-189 of the Hynes reference.

Shake Flask Log D (SF Log D) Determination:

The Log D determinations were carried out in a similar manner as described by Hay et al. *Drug Metabolism and Disposition* 37(9), 1864-1870, 2009, the procedure of which is generally described below.

Log $D_{(7.4)}$ Determination. The distribution coefficient of the test compounds between octan-1-ol and 0.1 M sodium phosphate buffer, pH 7.4, was determined by the shake flask methodology in an automated manner. 0.3 mg of compound was dissolved in 300 μL of octan-1-ol and aliquoted in duplicate into a 96-well block. Three hundred microliters of presaturated buffer (2 liters of buffer presaturated with 10 mL of octan-1-ol) was added to the wells, and the solution was vigorously mixed. After centrifugation, the two phases were separated. Ten microliters of a 1:200 dilution of the octan-1-ol layer and 10 μL of a 1:20 dilution of the buffer layer were directly injected onto the high-performance liquid chromatography (HPLC) (for example using an appropriate C18 column, isocratic elution with 90% methanol, 10% water, 2 mM ammonium acetate, and 0.03% formic acid at flow rate of 2 mL/min). The peak areas were corrected for the dilution factors, and the following calculation was applied to determine the mean log D value at pH 7.4 (log $D_{(7.4)}$):

$$\mathrm{Log}D_{(7.4)} = \log^{10}\frac{(\text{peak area for octan-1-ol sample})}{(\text{peak area for buffer sample})}.$$

TABLE 19

IUPAC Name and Biological Activity for Examples 1-46.

| Example Number | IUPAC Name | hKOR binding assay $K_i$ (nM)[a] | hMOR binding assay $K_i$ (nM)[a] |
|---|---|---|---|
| 1 | (+/−)-4-(4-{[2-(1,3-dimethyl-1H-pyrazol-4-yl)pyrrolidin-1-yl]methyl}-2-fluorophenoxy)benzamide | 0.871 | 20.2 |
| 2 | (+)-4-(4-{[2-(1,3-dimethyl-1H-pyrazol-4-yl)pyrrolidin-1-yl]methyl}-2-fluorophenoxy)benzamide (ENT-1) | 3.95 | 27.8 |
| 3 | (−)-4-(4-{[2-(1,3-dimethyl-1H-pyrazol-4-yl)pyrrolidin-1-yl]methyl}-2-fluorophenoxy)benzamide (ENT-2) | 0.461[b] | 16.9[b] |
| 4 | (+/−)-4-(4-{[2-(1,3-dimethyl-1H-pyrazol-4-yl)pyrrolidin-1-yl]methyl}phenoxy)-3-fluoro benzamide | N.D.[c] | N.D. |
| 5 | 4-(4-{[2-(1,3-dimethyl-1H-pyrazol-4-yl)pyrrolidin-1-yl]methyl}phenoxy)-3-fluoro benzamide, ENT-1 | 16.8 | 73.6 |
| 6 | 4-(4-{[2-(1,3-dimethyl-1H-pyrazol-4-yl)pyrrolidin-1-yl]methyl}phenoxy)-3-fluoro benzamide, ENT-2 | 1.06 | 40.7 |

TABLE 19-continued

IUPAC Name and Biological Activity for Examples 1-46.

| Example Number | IUPAC Name | hKOR binding assay $K_i$ (nM)[a] | hMOR binding assay $K_i$ (nM)[a] |
|---|---|---|---|
| 7 | (+/−)-3-fluoro-4-(4-{[2-(3-methoxy-1-methyl-1H-pyrazol-4-yl)pyrrolidin-1-yl]methyl}phenoxy)benzamide | 5.71 | 196 |
| 8 | (−)-3-fluoro-4-(4-{[2-(3-methoxy-1-methyl-1H-pyrazol-4-yl)pyrrolidin-1-yl]methyl}phenoxy)benzamide (ENT-1) | 2.56 | 98.7 |
| 8, (L)-Lactate salt | 3-fluoro-4-(4-{[2-(3-methoxy-1-methyl-1H-pyrazol-4-yl)pyrrolidin-1-yl]methyl}phenoxy)benzamide, ENT-1, (L)-lactate salt | N.D. | N.D. |
| 9 | (+)-3-fluoro-4-(4-{[2-(3-methoxy-1-methyl-1H-pyrazol-4-yl)pyrrolidin-1-yl]methyl}phenoxy)benzamide (ENT-2) | 22.5 | >352 |
| 10 | 4-(4-{[(2S)-2-(5-methyl-1,2,4-thiadiazol-3-yl)pyrrolidin-1-yl]methyl}phenoxy)benzamide | 4.00 | 218 |
| 11 | 4-(4-{[(2S)-2-(1,3-dimethyl-1H-pyrazol-4-yl)pyrrolidin-1-yl]methyl}phenoxy)benzamide | 1.21 | 51 |
| 12 | 4-(4-{[2-(3-methoxy-1-methyl-1H-pyrazol-4-yl)pyrrolidin-1-yl]methyl}phenoxy)benzamide (single enantiomer, synthesized from P4); determined to be 4-(4-{[(2S)-2-(3-methoxy-1-methyl-1H-pyrazol-4-yl)pyrrolidin-1-yl]methyl}phenoxy)benzamide | 1.47 | 46.2 |
| 13 | (+/−)-4-(4-{[2-(3-methoxy-1H-pyrazol-4-yl)pyrrolidin-1-yl]methyl}phenoxy)benzamide | N.D. | N.D. |
| 14 | (−)-4-(4-{[2-(3-methoxy-1H-pyrazol-4-yl)pyrrolidin-1-yl]methyl}phenoxy)benzamide (ENT-1) | 6.08 | 31.3 |
| 15 | (+)-4-(4-{[2-(3-methoxy-1H-pyrazol-4-yl)pyrrolidin-1-yl]methyl}phenoxy)benzamide (ENT-2) | 23.2 | 150 |
| 16 | (+/−)-4-(4-{[2-(1,3-dimethyl-1H-pyrazol-4-yl)pyrrolidin-1-yl]methyl}phenoxy)-2-hydroxybenzamide | 9.67 | 159 |
| 17 | (+)-4-(4-{[2-(1,3-dimethyl-1H-pyrazol-4-yl)pyrrolidin-1-yl]methyl}phenoxy)-2-hydroxybenzamide (ENT-1) | 27.0 | 108 |
| 18 | (−)-4-(4-{[2-(1,3-dimethyl-1H-pyrazol-4-yl)pyrrolidin-1-yl]methyl}phenoxy)-2-hydroxybenzamide (ENT-2) | 1.76 | 63.6 |
| 19 | 3-fluoro-4-(4-{[(2S)-2-(1-methyl-1H-pyrazol-3-yl)pyrrolidin-1-yl]methyl}phenoxy)benzamide | 0.999 | 13.5 |
| 20 | 3-fluoro-4-(4-{[3-(3-methoxy-1-methyl-1H-pyrazol-4-yl)morpholin-4-yl]methyl}phenoxy)benzamide, ENT-1 | 5.86 | 165 |
| 21 | 4-(4-{[2-(3-methoxy-1-methyl-1H-pyrazol-4-yl)piperidin-1-yl]methyl}phenoxy)benzamide, ENT-1 | 0.567 | 14.6 |
| 22 | 4-(2-fluoro-4-{[3-(3-methoxy-1-methyl-1H-pyrazol-4-yl)morpholin-4-yl]methyl}phenoxy)benzamide, ENT-1 | 4.52 | 95.1 |
| 23 | 4-(4-{[3-(3-methoxy-1-methyl-1H-pyrazol-4-yl)morpholin-4-yl]methyl}phenoxy)benzamide, ENT-1 | 3.22 | 73.3 |
| 24 | 4-(4-{[4-fluoro-2-(3-methoxy-1-methyl-1H-pyrazol-4-yl)pyrrolidin-1-yl]methyl}phenoxy)benzamide, Isomer 2, assumed racemic, either cis or trans | 2.21 | 252 |
| 25 | 4-(4-{[2-(1,3-dimethyl-1H-pyrazol-4-yl)-4-fluoropyrrolidin-1-yl]methyl}phenoxy)benzamide, Isomer 1 | 2.70 | 391 |
| 26 | 4-(4-{[2-(1,3-dimethyl-1H-pyrazol-4-yl)-4-fluoropyrrolidin-1-yl]methyl}phenoxy)benzamide, Isomer 2 | 10.5 | >526 |
| 27 | 4-(4-{[(2S)-2-(1,3-dimethyl-1H-pyrazol-5-yl)pyrrolidin-1-yl]methyl}phenoxy)-2-hydroxybenzamide | 2.07 | 121 |
| 28 | 3-fluoro-4-(4-{[2-(3-methoxy-1-methyl-1H-pyrazol-4-yl)-4-methylpyrrolidin-1-yl]methyl}phenoxy)benzamide, Isomer 1 | 4.88 | 77.9 |
| 29 | 3-fluoro-4-(4-{[2-(3-methoxy-1-methyl-1H-pyrazol-4-yl)-4-methylpyrrolidin-1-yl]methyl}phenoxy)benzamide, Isomer 2 | 0.498 | 10.6 |

TABLE 19-continued

IUPAC Name and Biological Activity for Examples 1-46.

| Example Number | IUPAC Name | hKOR binding assay $K_i$ (nM)$^a$ | hMOR binding assay $K_i$ (nM)$^a$ |
|---|---|---|---|
| 30 | 3-fluoro-4-(4-{[2-(3-methoxy-1-methyl-1H-pyrazol-4-yl)-4-methylpyrrolidin-1-yl]methyl}phenoxy)benzamide, Isomer 3 | 0.417 | 9.59 |
| 31 | 3-fluoro-4-(4-{[2-(3-methoxy-1-methyl-1H-pyrazol-4-yl)-4-methylpyrrolidin-1-yl]methyl}phenoxy)benzamide, Isomer 4 | 4.99 | 51.7 |
| 32 | 4-(2-fluoro-4-{[2-(3-methoxy-1-methyl-1H-pyrazol-4-yl)pyrrolidin-1-yl]methyl}phenoxy)benzamide, ENT-2 | 2.47 | 112 |
| 33 | 2-hydroxy-4-(4-{[2-(3-methoxy-1-methyl-1H-pyrazol-4-yl)pyrrolidin-1-yl]methyl}phenoxy)benzamide, ENT-2 | 1.69 | 52.2 |
| 34 | 2-hydroxy-4-(4-{[(2S)-2-(1-methyl-1H-pyrazol-3-yl)pyrrolidin-1-yl]methyl}phenoxy)benzamide | 0.508 | 3.98 |
| 35 | 4-(4-{[2-(1,5-dimethyl-1H-pyrazol-4-yl)pyrrolidin-1-yl]methyl}phenoxy)-3-fluorobenzamide, ENT-1 | 2.90 | 18.4 |
| 36 | (+/−)-4-(4-{[2-(1,5-dimethyl-1H-pyrazol-4-yl)pyrrolidin-1-yl]methyl}phenoxy)benzamide | 8.53 | 20.9 |
| 37 | (+/−)-3-fluoro-4-(4-{[2-(1,3,5-trimethyl-1H-pyrazol-4-yl)pyrrolidin-1-yl]methyl}phenoxy)benzamide | 13.3 | 12.5 |
| 38 | 4-(4-{[2-(2,5-dimethyl-2H-1,2,3-triazol-4-yl)pyrrolidin-1-yl]methyl}phenoxy)benzamide, ENT-2 | 0.688 | 116 |
| 39 | 4-(4-{[2-(2,5-dimethyl-2H-1,2,3-triazol-4-yl)pyrrolidin-1-yl]methyl}-2-fluorophenoxy)benzamide, ENT-2 | 0.367 | 40.9 |
| 40 | 3-fluoro-4-(4-{[2-(5-methyl-1,2-oxazol-3-yl)pyrrolidin-1-yl]methyl}phenoxy)benzamide | 139 | 299 |
| 41 | 4-(4-{[2-(3-methyl-1,2,4-thiadiazol-5-yl)pyrrolidin-1-yl]methyl}phenoxy)benzamide, ENT-2 | 85.8 | 2730 |
| 42 | 3-fluoro-4-(4-{[2-(3-methyl-1,2-oxazol-5-yl)pyrrolidin-1-yl]methyl}phenoxy)benzamide | 54.7 | 318 |
| 43 | 4-(4-{[2-(1,4-dimethyl-1H-pyrazol-5-yl)pyrrolidin-1-yl]methyl}phenoxy)-3-fluorobenzamide, formate salt | 16.8 | 56.2 |
| 44 | 4-(4-{[2-(1,5-dimethyl-1H-pyrazol-3-yl)pyrrolidin-1-yl]methyl}phenoxy)-3-fluorobenzamide, formate salt | 14.5 | 127 |
| 45 | 4-(4-{[(2S)-2-(1,3-dimethyl-1H-pyrazol-5-yl)pyrrolidin-1-yl]methyl}phenoxy)-3-fluorobenzamide | 1.70 | 108 |
| 46 | 4-(4-{[2-(3-methoxy-1-methyl-1H-pyrazol-5-yl)pyrrolidin-1-yl]methyl}phenoxy)benzamide, ENT-2 | 0.657 | 25 |

$^a$Values represent the geometric mean of 2-6 determinations, unless otherwise indicated.
$^b$Value represents the geometric mean of ≥7 determinations.
$^c$Not determined.

Tables 20-24 below provide biological data for the compounds of Examples 11, 8, 12, 45, 10 as well as Comparators A-F. Comparator compounds A, B and D are Examples 345, 343 and 344 from U.S. Pat. No. 7,560,463 (corresponding to WO 2004026305), Comparator compounds C and F are Examples 18 and 24 from Mitch et al. *J. Med. Chem.* 2011, 54, 8000-8012, and Comparator E is Example 1A from U.S. Pat. No. 7,709,522 B2; these Comparator compounds can be prepared as described therein.

Table 20, below, provides human kappa opioid receptor (hKOR) radioligand binding Ki's, human mu opioid receptor (hMOR) radioligand binding Ki's, and selectivity ratios calculated by dividing the hMOR Ki by the hKOR Ki. The structures are provided below for Examples 11, 8, 12, 45, 10, 35, 37, 38, 40-44, 46 and literature comparators A-F.

Potency and Selectivity Comparators:

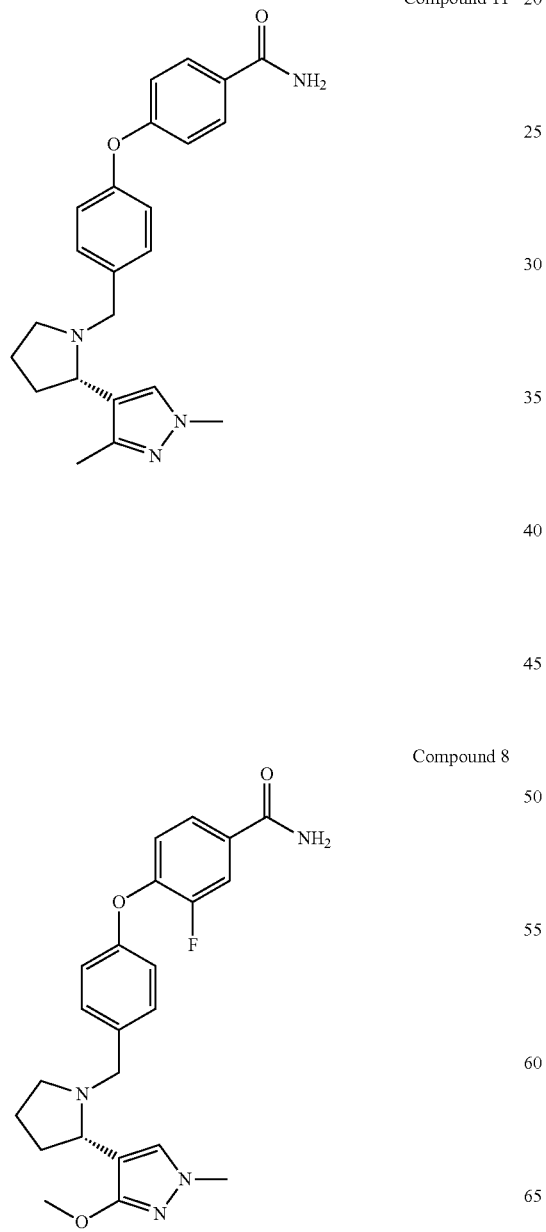

Compound 11

Compound 8

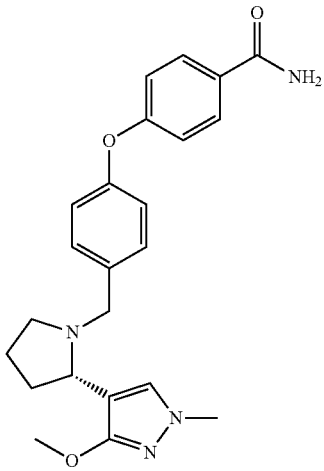

Compound 12

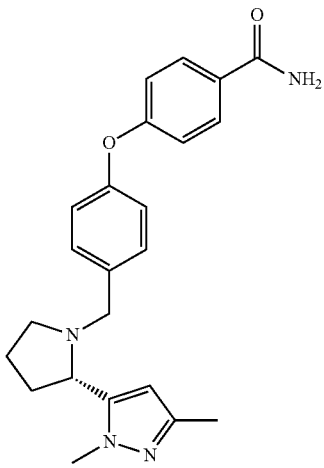

Compound 45

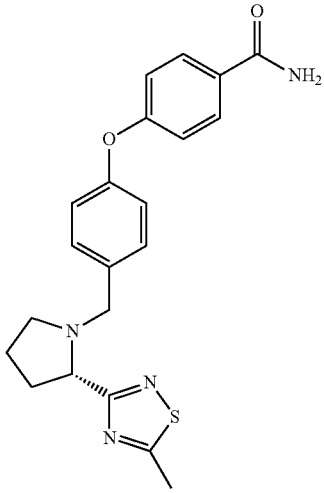

Compound 10

Compound 38
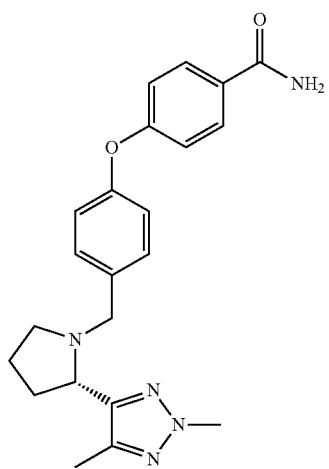
Compound 43
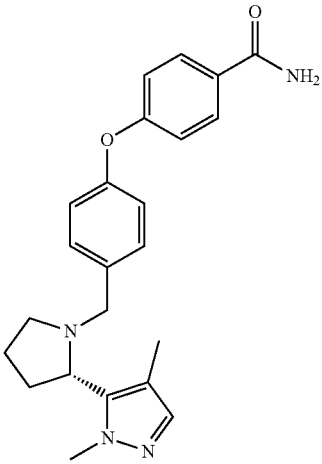
Compound 35
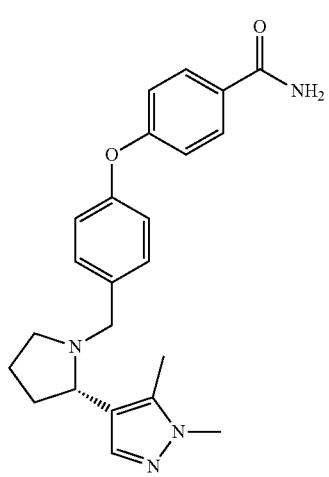
Compound 44
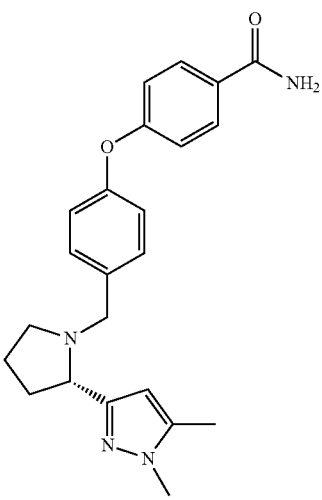
Compound 37
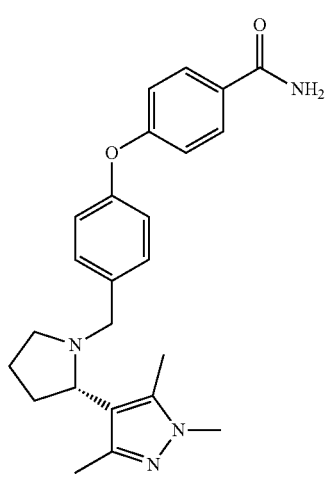
Compound 41
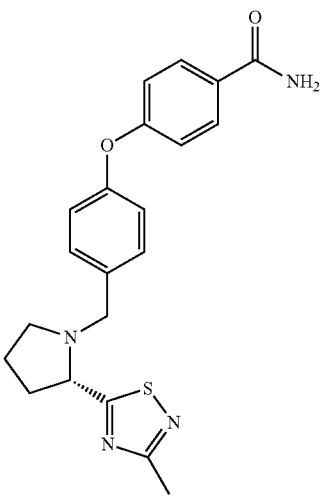

Compound 42
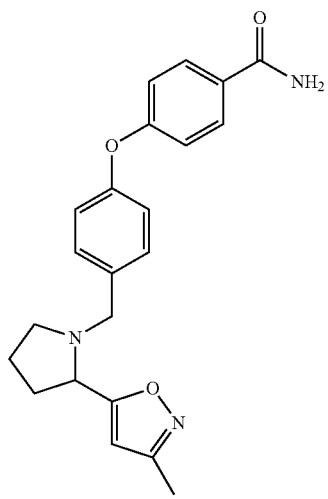
Compound 40
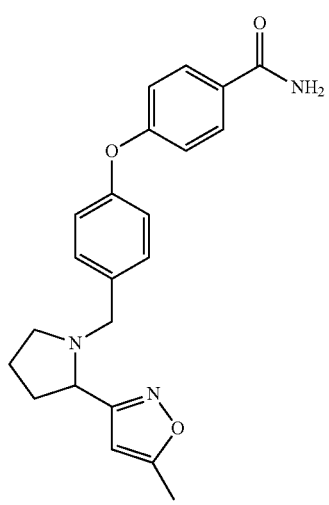
Comparator A
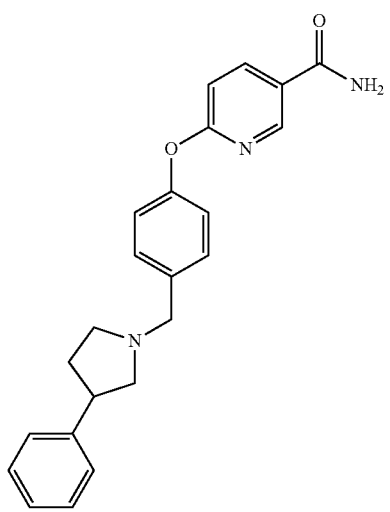
Comparator B
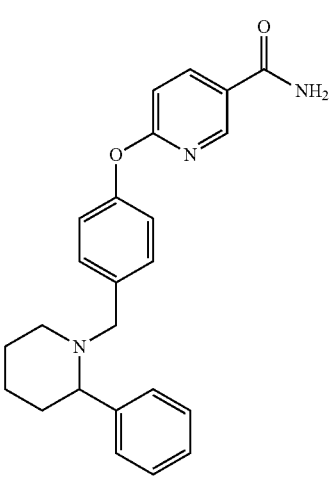
Compound 46
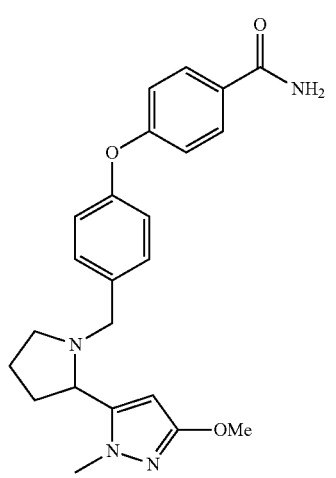
Comparator C
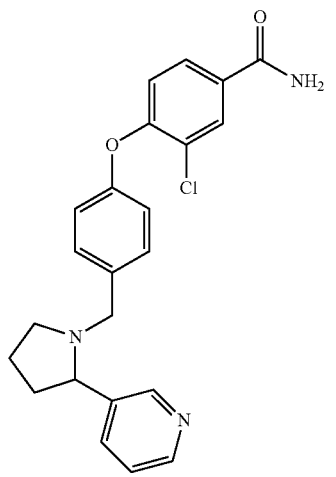

-continued

Comparator D

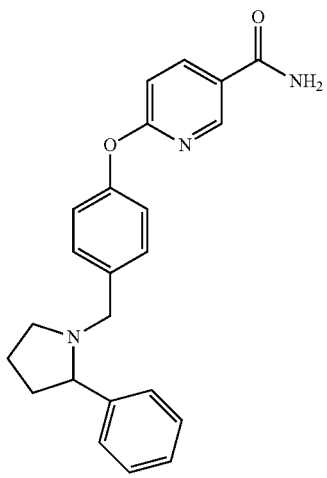

Comparator E

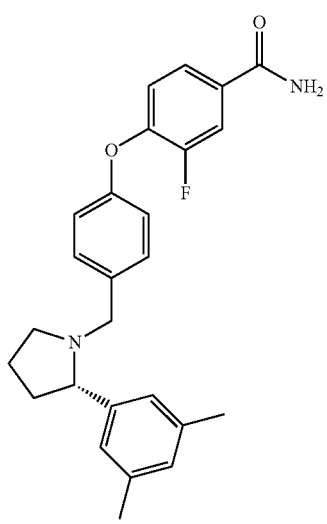

Comparator F

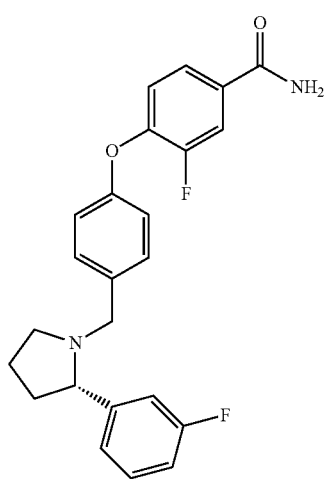

TABLE 20

Human kappa opioid receptor (hKOR) radioligand binding Ki's, human mu opioid receptor (hMOR) radioligand binding Ki's, and selectivity ratios calculated by dividing the hMOR Ki by the hKOR Ki. The data are provided below for Examples 11, 8, 12, 45, 10, 35, 37, 38, 40-44, 46 and literature comparators A-F.

| Compound | hKOR binding assay Ki (nM) | hMOR binding assay Ki (nM) | Selectivity hMOR/hKOR |
| --- | --- | --- | --- |
| 11 | 1.2 | 51 | 42 |
| 8 | 2.6 | 99 | 37 |
| 12 | 1.5 | 46 | 31 |
| 45 | 1.7 | 108 | 64 |
| 10 | 4 | 218 | 54 |
| 38 | 0.7 | 116 | 168 |
| 35 | 2.9 | 18.4 | 6.4 |
| 37 | 13.3 | 12.5 | 0.9 |
| 43 | 16.8 | 56.2 | 3 |
| 44 | 14.5 | 127 | 9 |
| 41 | 85.8 | 2730 | 32 |
| 42 | 54.7 | 318 | 5.8 |
| 40 | 139 | 299 | 2.2 |
| Comparator A | 3.1 | 0.1 | 0.03 |
| Comparator B | 12 | 18 | 9.8 |
| 46 | 0.657 | 25 | 38 |
| Comparator C | 1.2 | 21 | 17 |
| Comparator D | 5.8 | 163 | 28 |
| Comparator E | 0.2 | 7.8 | 39 |
| Comparator F | 1.1 | 37.5 | 35 |

Uncontrolled release of dynorphins, which are endogenous agonists of the kappa opioid receptor (KOR), can lead to symptoms of anxiety, poor emotional regulation, anhedonia, and loss of cognition. These symptoms contribute to the psychopathology of a number of CNS disorders including Alzheimer's Disease, Parkinson's Disease, substance abuse disorder, and depression. Blocking the activation of the kappa opioid receptor with an antagonist can be used to ameliorate the symptoms caused by excess dynorphin; however, concomitant blocking of the mu opioid receptor (MOR) with an antagonist should be avoided or there can be adverse side effects including nausea, vomiting, other gastrointestinal effects, and dizziness. Mu opioid receptor antagonist adverse events have been associated with human receptor occupancy of approximately 50%. In order to maintain a receptor occupancy at KOR at over 80% while keeping MOR receptor occupancy consistently below 50%, those skilled in the art appreciate that a >25-fold selectivity for KOR binding over mu binding is desirable. Additionally, those skilled in the art appreciate that acceptable potency for a highly brain penetrant GPCR antagonist targeting the central nervous system should have a potency of less than 10 nM for the target receptor. Surprisingly, there are significant differences in potency and selectivity in pyrazole-containing compounds with respect to the regioisomer of the methyl and methoxy substituents. Examples 11, 8, and 12 have a 1,3,4-substitution pattern and have excellent potency (1-3 nM) and selectivity (31-42 fold); the regioisomers of these compounds, Examples 35 and 37, are surprisingly less selective for KOR over MOR, with selectivity for KOR over MOR of only 2.5-fold and 0.9-fold respectively. Example 45 is an example of a 1,3,5-substituted regioisomer of the pyrazole that also has excellent potency and selectivity over MOR, while related Comparators 43 and 44 surprisingly and unexpectedly have unacceptably lower levels of selectivity (MOR/KOR). The criticality of the regioisomeric pattern of substitution on the pyrazole for acceptable levels of KOR potency and selectivity over MOR is clearly demonstrated.

Few other heterocycles were found that are as effective at maintaining potency and selectivity as some patterns of disubstituted pyrazoles. Example 10 shows that one regioisomer of the thiadiazole has good potency and selectivity, but a different regioisomer, Example 41, surprisingly and unexpectedly has a KOR potency of >100 nM. Similarly, Examples 42 and 40 also has low KOR potency. It is also surprising and unexpected that Examples 11, 8, 12, 45, 10 and 38 are more selective than the phenyl examples, Comparators A and B. Those skilled in the art will appreciate the potential impact of selectivity on adverse side effects derived from MOR occupancy over 50%.

Compounds 11, 8, and 12 are potent kappa opioid receptor antagonists with greater than 30-fold binding selectivity over mu opioid receptor.

Table 21, below, provides mouse in vivo receptor occupancy (IVRO) EC50's and progressive ratio results for compounds 11, 8, 12, 45 and Comparator E.

Example 11

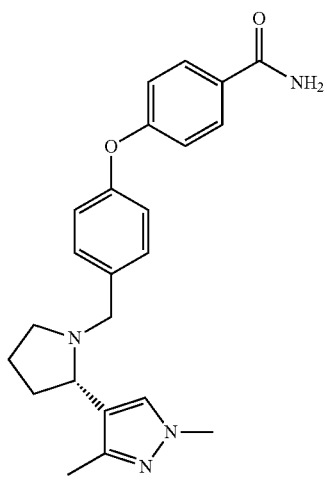

Example 8

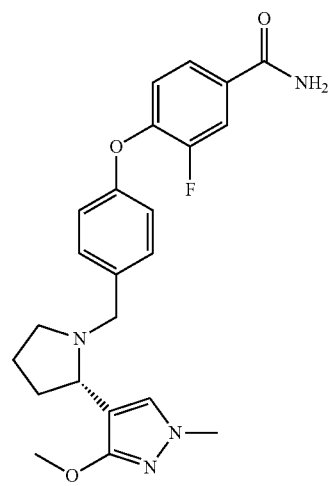

Example 12

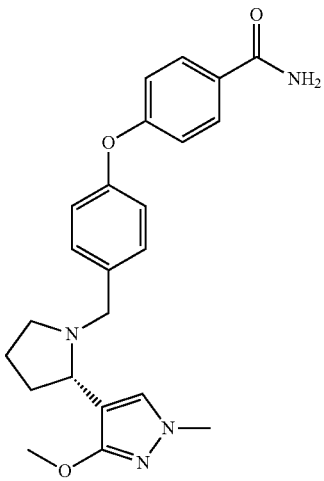

Example 45

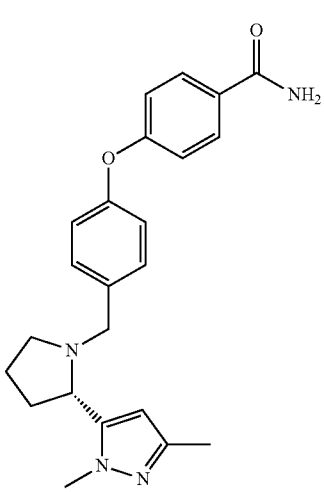

Comparator E

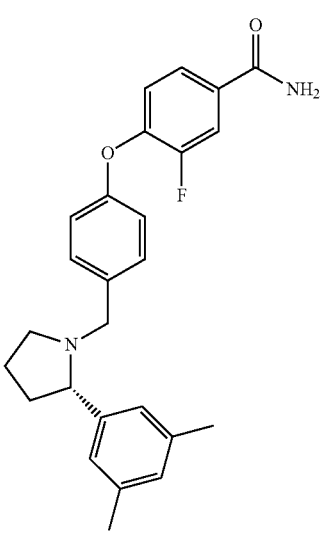

TABLE 21

Progressive ratio (PR) and in vivo receptor occupancy (IVRO), as measured by displacement of KOR agonist ligand, [$^3$H]GR103545, data for Examples 11, 8, 12, 45 and Comparator E.

| Compound | Mouse KOR IVRO unbound brain IC50 (nM) | % KOR IVRO to achieve 50% PR reversal |
|---|---|---|
| 11 | 2.5 | 30 |
| 8 | 0.69 | 25 |
| 12 | 2.5 | 30 |
| 45 | 0.25 | 85 |
| Comparator E | 0.015 | 70 |

Measurement of in vivo KOR occupancy after subcutaneous dosing of Examples 11, 8, 12, 45 and Comparator E in mice showed that all five compounds displaced KOR agonist radioligand ([$^3$H]GR103545) binding in the brain in an exposure-dependent manner. The ability of these compounds to antagonize the effect of a KOR agonist in vivo was also measured using the progressive ratio assay, a behavioral assay that measures the motivation of food restricted mice to work for a food reward. Animals must progressively work more for each food reward they receive and the number of rewards they are willing to work for before they stop responding (the "break point") is used as a surrogate measure of their level of motivation. The KOR agonist, spiradoline, produces a robust decrease in the number of rewards mice work for. The KOR antagonist compounds in Table 21 were co-administered with spiradoline to antagonize the deficit in motivation caused by spiradoline. While all five compounds produce dose-dependent reversal of the effect of spiradoline, Examples 11, 8, and 12 are able to achieve 50% reversal with only 25-30% receptor occupancy (as measured by displacement of [$^{11}$C] GR103545 in a separate group of animals), but Example 45 and Comparator E need >70% receptor occupancy to achieve the same degree of antagonism. Compounds 11, 8, and 12 function to antagonize spiradoline in this in vivo mouse assay at significantly lower receptor occupancy than does Comparator E. One skilled in the art will appreciate the potential for this difference in RO necessary to reverse the effects of an exogenous KOR agonist could extend to lower RO necessary to reverse the effects of an endogenous KOR agonist for compounds 11, 8, and 12.

Table 22 below provides human liver microsomal intrinsic clearance (HLM CL$_{int}$), potential for reversible inhibition of CYP450 isozymes, and kinetic constants of single point time dependent inhibition (SPTDI) at CYP3A4 data for Examples 11, 8, 12 and 46 and Comparators A-F.

Clearance, DDI, and TDI Comparators:

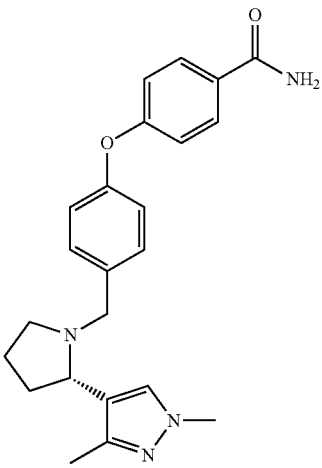

Compound 11

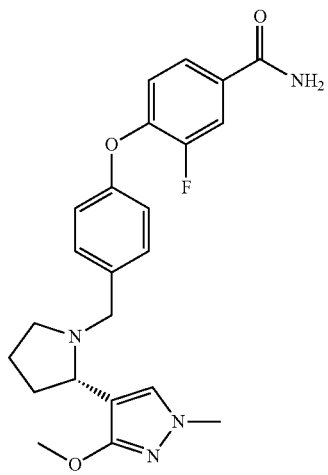

Compound 8

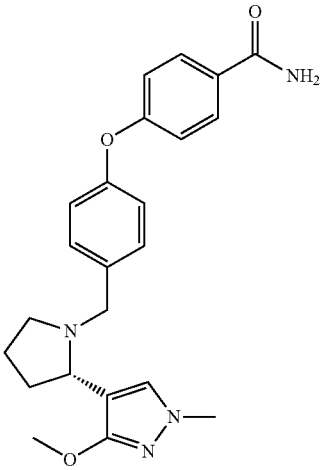

Compound 12

Compound 46
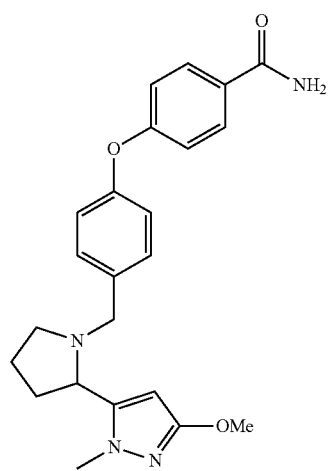
Comparator C
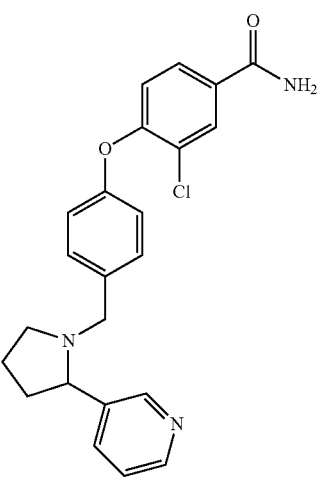
Comparator A
Comparator D
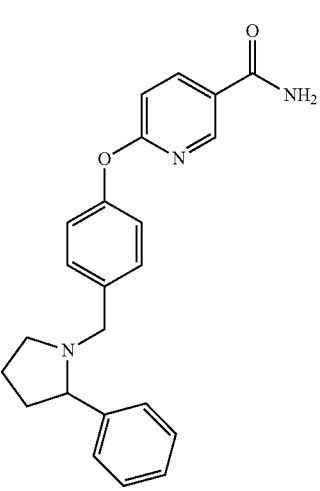
Comparator B
Comparator E
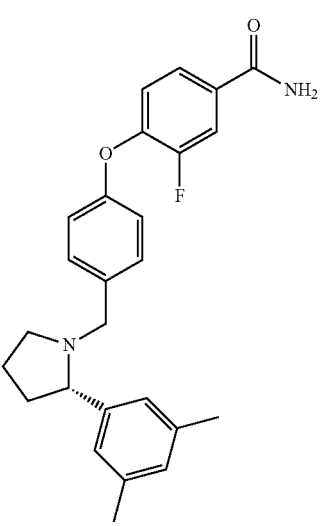

-continued

Comparator F

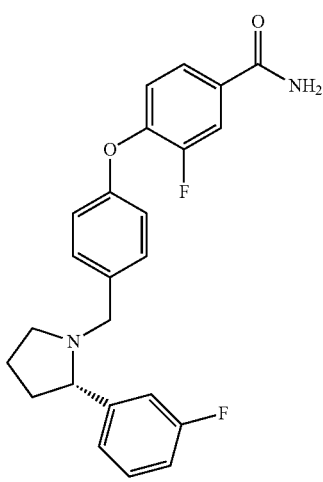

TABLE 22

Human liver microsomal intrinsic clearance (HLM $CL_{int}$), potential for reversible inhibition of CYP450 isozymes, and kinetic constants of single point time dependent inhibition (SPTDI) at CYP3A4 data for Examples 11, 8, 12 and 46 and Comparators A-F.

| Compound | HLM CLint (mL/min/kg) | >25% reversible inhibition of CYP activity at 3 μM (CYP) | SPTDI CYP3A4 $k_{obs}$ (min−1)[1] |
|---|---|---|---|
| 11 | 20 | no | 0.0055 |
| 8 | 12 | no | 0.0044 |
| 12 | 8 | no | 0.0042 |
| 46 | 105 | no | NT |
| Comparator A | 20 | no | NT |
| Comparator B | 89 | no | 0.0041 |
| Comparator C | 320 | yes (2C8, 2C9, 3A4, 2D6) | NT |
| Comparator D | 45 | yes (2D6) | 0.0065 |
| Comparator E | 30 | yes (2C8) | 0.0113[2] |
| Comparator F | 36 | no | 0.0133 |

[1]Most compounds were tested at a single high dose of 10 μM.
[2]Comparator E was tested at a single dose of 6 μM.

The hepatic clearance of KOR antagonists is an important consideration for the selection of viable drug candidates. Those skilled in the art will appreciate the negative impact of higher clearance compounds on projected human dose, dosing regimen, and potential liabilities associated with metabolites and increased body burden. In general, basic amines, which are predominantly cleared via hepatic metabolism with low to moderate clearance ($CL_{int}$<20 mL/min/kg) in human liver microsomes are more desirable than compounds that undergo rapid clearance. From the data presented above it will be apparent to those skilled in the art that Examples 11, 8 and 12 each possess an advantageously low hepatic clearance profile with a $CL_{int}$<20 mL/min/kg. It is surprising and unexpected that these examples have advantageous low metabolic clearance compared to the higher metabolic clearance of the regioisomeric methoxy pyrazole Example 46. Comparators B and C also demonstrate high hepatic clearance as measured by the human liver microsomal assay. The low hepatic clearance values exhibited by the compounds of Examples 11, 8, and 12 should allow for acceptable dosages and dosing regimens in humans.

CYP450 isozymes catalyze the oxidative metabolism of a majority of endogenous compounds and more than 80% of marketed drugs; therefore, inhibition of this family of enzymes can lead to pharmacokinetic drug-drug interactions (DDIs). Inhibition of CYP450 isozymes can follow reversible, competitive kinetics or irreversible, time dependent kinetics. Inhibition of major CYP450 isozymes is of particular concern due to the potential for altering the pharmacokinetics of concomitant substrates that are predominantly eliminated via metabolism by CYP3A4/5, CPY2D6, CPY2C8, and CYP2C19. Those skilled in the art will appreciate the desire to minimize or preferentially eliminate the potential to inhibit major CYP450 isozymes in a viable clinical candidate. Compounds in Table 22 were assessed to determine both reversible and irreversible CYP inhibitory potential.

Reversible CYP450 inhibitory potential for each compound was assessed using the CYP450 DDI cocktail assay, measuring the inhibition of the metabolism of a known probe substrate of each of the major CYP isozymes at 3 μM concentration. Those skilled in the art appreciate that a percent inhibition of a given CYP450 enzyme of >25% at 3 μM concentration indicates a medium to high risk for DDI. As shown in Table 22, Examples 11, 8, and 12 display no significant risk of reversible inhibition at 3 μM for all major CYP450 isozymes. Comparators C, D, and E each show a risk for reversible DDI at CYP450 isozymes 2C8, 2C9, 3A4, and/or 2D6.

Irreversible inhibition, or time-dependent inhibition (TDI) of cytochrome P450s (CYPs) is generally characterized by an increase in enzyme inhibition with respect to time and inhibitor concentration (Grimm 2009). In cases where enzyme inhibition requires metabolic turnover, the mechanism generally involves the formation of a reactive inhibitory intermediate that may irreversibly inactivate CYPs; this mechanism could cause clinical drug-drug interactions due to inhibition of the relevant CYP responsible for metabolizing the victim drug (Grimm 2009; Rowland Yeo 2011). Hazard assessment for irreversible CYP450 inhibitory potential of CYP3A was performed for several compounds in Table 22 using the single point time dependent inhibition (SPTDI) assay, which measures the pseudo-first order rate constant of inactivation ($k_{obs}$) at a single high concentration (6-10 μM) of a test compound (Zimmerlin 2011). Based on the analysis performed by Yates (2008), compounds showing a $k_{obs}$ of >0.008 min$^{-1}$ in this assay are considered to have a potential for TDI, and $k_{obs}$<0.008 min$^{-1}$ are negative or may have a very weak potential for TDI at CYP3A4. Examples 11, 8, and 12 all have $k_{obs}$ values of <0.008 min$^{-1}$ (tested at 10 μM) and therefore have a low to no significant risk for TDI at CYP3A4. However, Comparators E and F have $k_{obs}$ values of 0.011 min$^{-1}$ (tested at 6 μM) and 0.0133 min$^{-1}$ (tested at 10 μM) indicating a potential risk of CYP3A4 TDI (Zimmerlin 2011; Yates 2012).

Compounds 11, 8, and 12 have surprisingly low intrinsic metabolic turnover rates in human liver microsomes. Compounds 11, 8 and 12 show no significant risk of reversible inhibition at the major CYP isozymes, and are not time dependent inactivators of CYP3A4.

Table 23 below provides in vitro cell toxicity data for Examples 11, 8 and 12 and Comparators A-F. Data provided are from the transformed human liver endothelial (THLE) assay, the HepG2 Glu 72 hour assay, respirometric screening technology (RST) and the SFLog D assay.

Cell Toxicity Comparators:
Compound 11
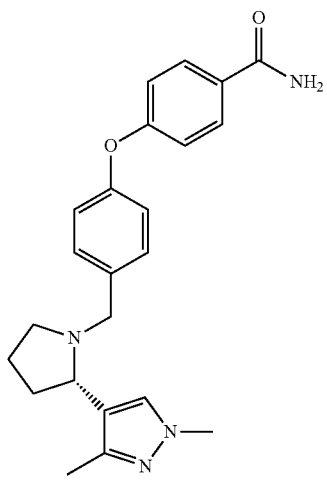
Compound 8
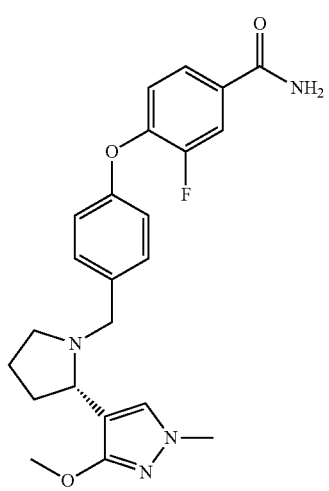
Compound 12
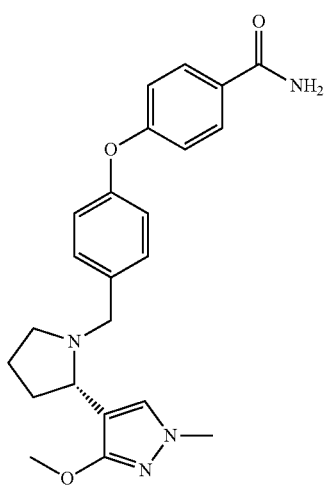
-continued
Comparator A
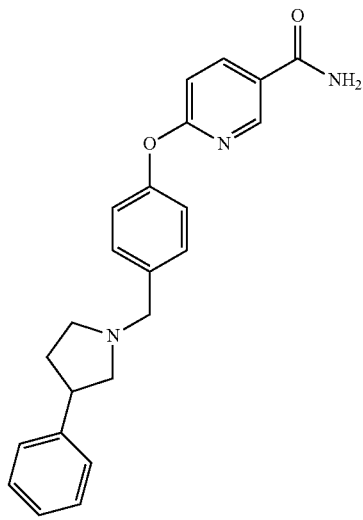
Comparator B
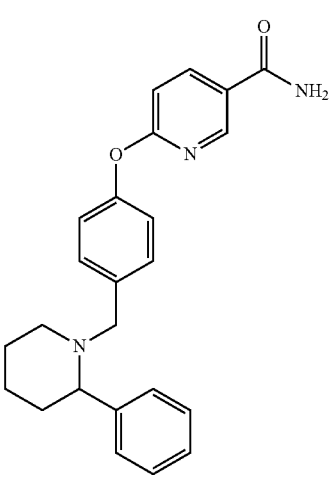
Comparator C
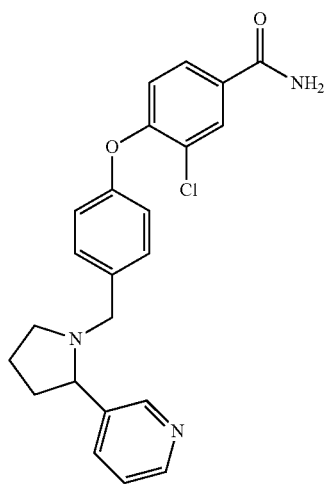

Comparator D

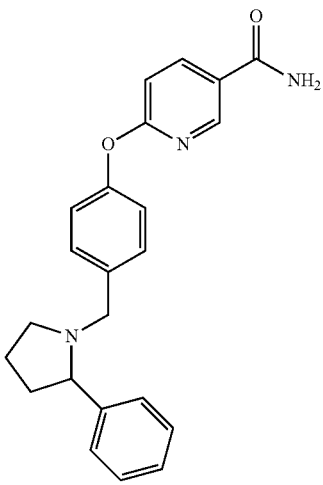

Comparator E

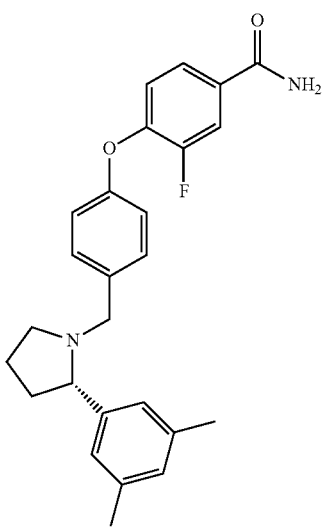

Comparator F

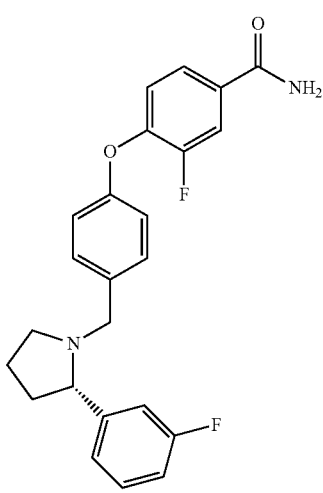

TABLE 23

In vitro cell toxicity data for Examples 11, 8 and 12 and Comparators A-F. Data provided are from the transformed human liver endothelial (THLE) assay, the HepG2 Glu 72 hour assay, respirometric screening technology (RST) and the SFLogD assay.

| Compound | THLE (uM) | HepG2 Glu 72 hr (uM) | RST inhibitory (uM) | ClogP | SFLogD |
|---|---|---|---|---|---|
| 11 | >300 | 267 | No effect | 3.3 | 1.9 |
| 8 | >300 | >300 | No effect | 3.4 | 1.9 |
| 12 | >300 | >300 | No effect | 3.3 | 1.4 |
| Comparator A | >300 | 174 | NT | 3.9 | 1.8 |
| Comparator B | 224 | 112 | No effect | 4.7 | 2.7 |
| Comparator C | 177 | 72 | 21 | 4.1 | 3.2 |
| Comparator D | 179 | 69 | No effect | 4.1 | 2.3 |
| Comparator E | 26 | 43 | 19 | 6.1 | 4.6 |
| Comparator F | 37 | 56 | 66 | 5.2 | 3.7 |

The potential clinical hepatotoxicity or drug induced liver injury (DILI) is one of the major reasons for the withdrawal of compounds from the market (Holt and Ju, 2010). Those skilled in the art will appreciate that generalized cell toxicity is an early indicator of potential adverse outcomes both in preclinical safety models (Shah 2014, Green 2010, Benbow 2010) and in the clinic (Shah 2015, Thompson 2012). Two common assays for understanding the extent of generalized cell toxicity are the THLE and the HepG2 assays. These assays measure cell viability by measuring cellular ATP content following incubation of test compounds for 72 hours in transformed human liver endothelial (THLE) and human hepatoma (HepG2) cell lines. Those skilled in the art appreciate that if the $LD_{50}$s of a compound in one or both of the THLE or HepG2 assays are <50 µM, there is a greater risk of the compound to cause DILI or other adverse outcomes in animal studies and/or human clinical studies. Table 23 provides cell viability data for Examples 11, 8, and 12 and Comparator compounds A-F. Examples 11, 8 and 12 show little to no cytotoxicity in either of these cell lines, which is advantageous as it reduces the potential risk for DILI in taking these compounds forward to the clinic. However, Comparator compounds E and F produce cytotoxicity at lower concentrations, and may pose a potential risk for DILI or other organ toxicities in the clinic if higher than anticipated compound concentrations are needed to drive efficacy resulting in a lower margin of safety.

From a mechanistic standpoint, mitochondrial dysfunction has been shown to be one of the critical mechanisms in DILI (Aleo 2014). Mitochondrial dysfunction has also been noted as a characteristic feature of many chronic illnesses, including bipolar disorder, Parkinson's disease, schizophrenia, depression, autism, and chronic fatigue syndrome (Morris 2015). Mitochondrial dysfunction can be assessed by measuring mitochondrial oxygen consumption in isolated rat mitochondria using luminescent oxygen-sensitive probes in a respirometric screening technology (RST) assay (Hynes 2006); both inhibition and uncoupling of oxidative phosphorylation in the RST assay were measured for compounds in Table 23. While Examples 11, 8, and 12 showed no significant activity in the RST assay, Comparator compounds C and E showed µM inhibitory activity.

An analysis of 812 drugs from four major pharmaceutical companies (Waring 2015) showed a statistically significant difference in lipophilicity between compounds that progress to Phase II studies compared to those that were terminated due to safety reasons in Phase I, with the average c Log P of 3.1 and 3.8 for those progressing and failed compounds, respectively. There was a similar trend noted in c Log D, with average values of 2.1 and 2.8 for progressing and failed compounds, respectively. Examples 11, 8, and 12 have c Log P and Log D values much more in line with drugs that progress to Phase II, while Comparators B-F have significantly higher c Log P values and Comparators E and F have significantly higher Log D values. It is generally acknowledged by those skilled in the art that compounds with lower lipophilicity are less likely to have toxicology-based attrition in the clinic.

Compounds 11, 8, and 12 are clean in cell toxicity assays, and have physiochemical properties consistent with a decreased probability of toxicology-based attrition in the clinic.

Overall, Examples 11, 8 and 12 have a surprising and unexpected alignment of favorable properties and biological data (FIGS. 6 and 7). Examples 11, 8, and 12 have favorable kappa opioid receptor potency, selectivity over mu opioid receptor, and the percent of kappa opioid receptors necessary to reverse the effects of a kappa opioid agonist, which is important for receptor engagement, safety, and pharmacodynamic effect. Examples 11, 8, and 12 have favorable human liver microsome intrinsic clearance and have low potential for either reversible or irreversible inhibition of cytochrome P450s, which is important for dosing regimen and avoidance of pharmacokinetic drug-drug interactions. Compounds 11, 8, and 12 are also clean in cell toxicity assays (THLE, HepG2, and RST) and have favorable physiochemical properties, which are consistent with a decreased probability of toxicology-based attrition in the clinic. FIGS. 6 and 7 highlight the surprising and unexpected nature of this alignment for compounds 11, 8, and 12 by noting that the literature comparators do not share this favorable alignment.

REFERENCES

N. Green et al. Using an in vitro cytotoxicity assay to aid in compound selection for in vivo safety studies, BMCL, 2010, 5308.
J. Benbow et al. Predicting safety toleration of pharmaceutical chemical leads: Cytotoxicity correlations to exploratory toxicity studies, Toxicology Letters, 2010, 175.
F. Shah et al. Chemotypes sensitivity and predictivity of in vivo outcomes for cytotoxic assays in THLE and HepG3 cell lines, BMCL, 2014, 2753.
R. A. Thompson et al. In vitro approach to assess the potential for risk of idiosyncratic adverse reactions caused by candidate drugs, Chemical research in Toxicology, 2012, 1616.
F. Shah et al. Setting clinical exposure levels of concern for drug-induced liver injury (DILI) using mechanistic in vitro assays, Toxicology Sciences, 147(2), 2015, 500.
M. Waring et al. An analysis of the attrition of drug candidates from four major pharmaceutical companies, Nature Reviews Drug Discovery, 2015, 475.
M Holt and C Ju. Drug induced livery injury, Handb. Exp. Pharmacol., 2010, 3.
M Aleo et al. Human Drug-Induced Liver Injury Severity Is Highly Associated with Dual Inhibition of Liver Mitochondrial Function and Bile Salt Export Pump. Hepatology vol 60, no 3, 2014.
G Morris and M Berk The many roads to mitochondrial dysfunction in neuroimmune and neuropsychiatric disorders. BMC Medicine (2015) 13:68
J Hynes et al. Investigation of Drug-Induced Mitochondrial Toxicity Using Flourescence_Based Oxygen-Sensitive Probes. Toxicological Sciences 91(1), 186-200 (2006).
S. W. Grimm et al. The Conduct of in Vitro Studies to Address Time-Dependent Inhibition of Drug-Metabolizing Enzymes: A Perspective of the Pharmaceutical Research and Manufacturers of America. Drug Metabolism and Deposition, 37 (7), 1355 (2009)
K. Rowland Yeo et al. Prediction of Time-Dependent CYP3A4 Drug-Drug interactions by Physiologically Based Pharmacokinetic Modelling: Impact of Inactivation Parameters and Enzyme Turnover. European Journal of Pharmaceutical Sciences, 43 (3), 160 (2011)
A. Zimmerlin et al. CYP3A Time-Dependent Inhibition Risk Assessment Validated with 400 Reference Drugs. Drug Metabolism and Deposition, 39 (6), 1039 (2011)
P. Yates et al. Statistical Methods for Analysis of Time-Dependent Inhibition of Cytochrome P450 Enzymes. Drug Metabolism and Deposition, 40 (12), 2289 (2012)
Obach, R. S.; Walsky, R. L.; Venkatakrishnan, K. Mechanism Based Inactivation of Human Cytochrome P450 Enzymes and the Prediction of Drug Drug Interactions. Drug Metab. Dispos. 2007, 35, 246-55
Berry L.; Zhao, Z. An Examination of IC50 and IC50-Shift Experiments in Assessing Time-Dependent Inhibition of CYP3A4, CYP2D6 and CYP2C9 in Human Liver Microsomes. Drug Metabolism Letters, 2008, 2, 51-59
Hay T.; Jones R.; Beaumont K.; Kemp M. Modulation of the partition coefficient between octanol and buffer at pH 7.4 and pKa to achieve the optimum balance of blood clearance and volume of distribution for a series of tetrahydropyran histamine type 3 receptor antagonists. Drug Metab. Dispos. 2009, 37(9), 1864-1870.

Various modifications of the invention, in addition to those described herein, will be apparent to those skilled in the art from the foregoing description. Such modifications are also intended to fall within the scope of the appendant claims. Each reference (including all patents, patent applications, journal articles, books, and any other publications) cited in the present application is hereby incorporated by reference in its entirety.

What is claimed is:

1. A compound of Formula I

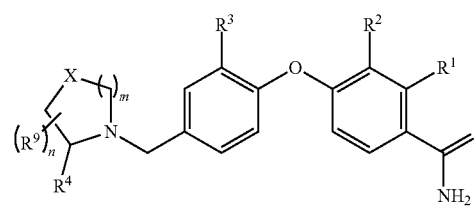

or a pharmaceutically acceptable salt thereof;
wherein
$R^1$ is hydrogen, fluoro or hydroxy;
$R^2$ and $R^3$ are each independently hydrogen or fluoro;
X is $CR^5R^6$ or O;
m is 1 or 2;
n is 0, 1 or 2;

$R^4$ is selected from the group consisting of

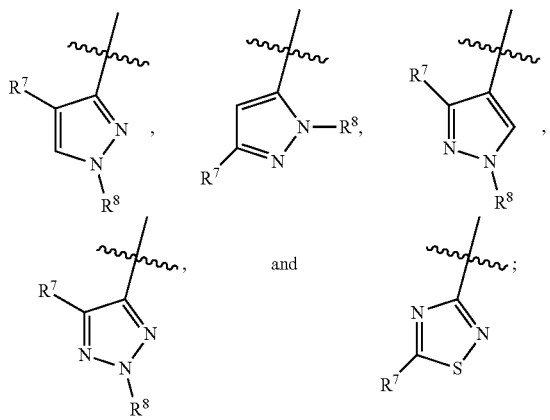

$R^5$ and $R^6$ are each independently selected from the group consisting of hydrogen, fluoro, hydroxy, $C_1$-$C_3$alkyl and $C_1$-$C_3$alkoxy;

$R^7$ and $R^8$ are each independently selected from the group consisting of hydrogen, $C_1$-$C_6$alkyl and $C_1$-$C_6$alkoxy; wherein the $C_1$-$C_6$alkyl and $C_1$-$C_6$alkoxy are optionally substituted with one to three fluoro; and $R^9$ at each occurrence is independently selected from fluoro, $C_1$-$C_3$alkyl and $C_r$-$C_6$alkoxy, wherein the $C_1$-$C_3$alkyl and $C_1$-$C_6$alkoxy are optionally substituted with one to three fluoro.

2. The compound of claim 1 wherein
m is 1;
X is $CR^5R^6$;
$R^5$ and $R^6$ are each independently selected from the group consisting of hydrogen, fluoro and methyl;
$R^7$ is selected from the group consisting of hydrogen, methyl and methoxy; and
$R^8$ is methyl or hydrogen;
or a pharmaceutically acceptable salt thereof.

3. The compound of claim 2 of the Formula Ia

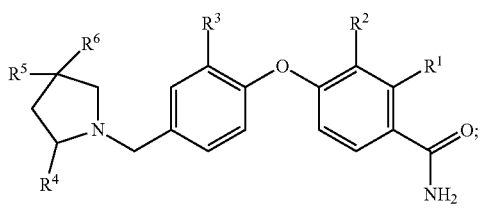

Ia or a pharmaceutically acceptable salt thereof.

4. The compound of claim 3 wherein
$R^4$ is

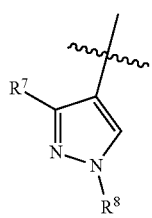 or 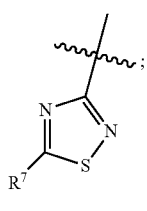 ;

$R^5$ and $R^6$ are each hydrogen and
$R^7$ is methyl or methoxy;
or a pharmaceutically acceptable salt thereof.

5. The compound of claim 1 wherein
m is 2;
or a pharmaceutically acceptable salt thereof.

6. The compound of claim 5 wherein
X is O;
or a pharmaceutically acceptable salt thereof.

7. The compound of claim 6 of the Formula Ib

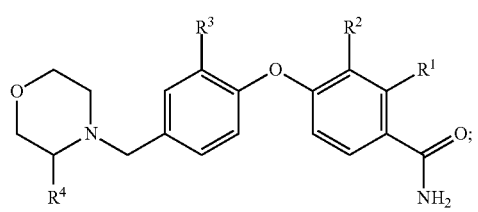

Ib wherein
$R^4$ is

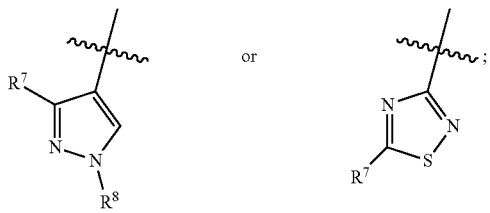

$R^7$ is methyl or methoxy; and
$R^8$ is methyl or hydrogen;
or a pharmaceutically acceptable salt thereof.

8. The compound of claim 5 wherein
X is $CR^5R^6$;
or a pharmaceutically acceptable salt thereof.

9. The compound of claim 8 of the Formula Ic

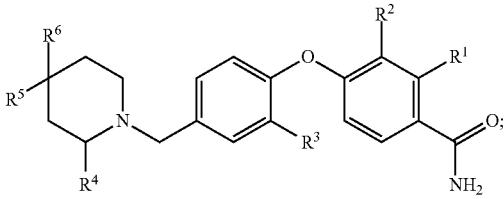

Ic wherein
$R^4$ is

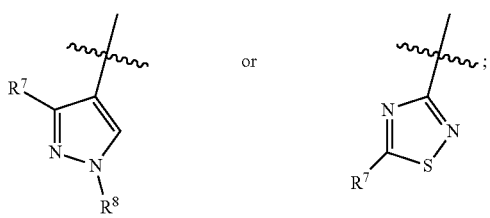

R⁵ and R⁶ are each hydrogen;
R⁷ is methyl or methoxy; and
R⁸ is methyl or hydrogen;
or a pharmaceutically acceptable salt thereof.

10. A compound of claim 1 selected from the group consisting of
(+/−)-4-(4-{[2-(1,3-dimethyl-1H-pyrazol-4-yl)pyrrolidin-1-yl]methyl}-2-fluorophenoxy)benzamide;
(+)-4-(4-{[2-(1,3-dimethyl-1H-pyrazol-4-yl)pyrrolidin-1-yl]methyl}-2-fluorophenoxy) benzamide;
(−)-4-(4-{[2-(1,3-dimethyl-1H-pyrazol-4-yl)pyrrolidin-1-yl]methyl}-2-fluorophenoxy) benzamide;
(+/−)-4-(4-{[2-(1,3-dimethyl-1H-pyrazol-4-yl)pyrrolidin-1-yl]methyl}phenoxy)-3-fluorobenzamide;
4-(4-{[2-(1,3-dimethyl-1H-pyrazol-4-yl)pyrrolidin-1-yl]methyl}phenoxy)-3-fluorobenzamide, ENT-1;
4-(4-{[2-(1,3-dimethyl-1H-pyrazol-4-yl)pyrrolidin-1-yl]methyl}phenoxy)-3-fluorobenzamide, ENT-2;
(+/−)-3-fluoro-4-(4-{[2-(3-methoxy-1-methyl-1H-pyrazol-4-yl)pyrrolidin-1-yl]methyl}phenoxy)benzamide;
(−)-3-fluoro-4-(4-{[2-(3-methoxy-1-methyl-1H-pyrazol-4-yl)pyrrolidin-1-yl]methyl}phenoxy)benzamide;
(+)-3-fluoro-4-(4-{[2-(3-methoxy-1-methyl-1H-pyrazol-4-yl)pyrrolidin-1-yl]methyl}phenoxy)benzamide;
4-(4-{[(2S)-2-(5-methyl-1,2,4-thiadiazol-3-yl)pyrrolidin-1-yl]methyl}phenoxy) benzamide;
4-(4-{[(2S)-2-(1,3-dimethyl-1H-pyrazol-4-yl)pyrrolidin-1-yl]methyl}phenoxy) benzamide;
4-(4-{[(2S)-2-(3-methoxy-1-methyl-1H-pyrazol-4-yl)pyrrolidin-1-yl]methyl}phenoxy) benzamide;
(+/−)-4-(4-{[2-(3-methoxy-1H-pyrazol-4-yl)pyrrolidin-1-yl]methyl}phenoxy) benzamide;
(+4-(4-{[2-(3-methoxy-1H-pyrazol-4-yl)pyrrolidin-1-yl]methyl}phenoxy) benzamide;
(+)-4-(4-{[2-(3-methoxy-1H-pyrazol-4-yl)pyrrolidin-1-yl]methyl}phenoxy) benzamide;
(+/−)-4-(4-{[2-(1,3-dimethyl-1H-pyrazol-4-yl)pyrrolidin-1-yl]methyl}phenoxy)-2-hydroxybenzamide;
(+)-4-(4-{[2-(1,3-dimethyl-1H-pyrazol-4-yl)pyrrolidin-1-yl]methyl}phenoxy)-2-hydroxybenzamide;
(−)-4-(4-{[2-(1,3-dimethyl-1H-pyrazol-4-yl)pyrrolidin-1-yl]methyl}phenoxy)-2-hydroxybenzamide;
3-fluoro-4-(4-{[(2S)-2-(1-methyl-1H-pyrazol-3-yl)pyrrolidin-1-yl]methyl}phenoxy) benzamide;
3-fluoro-4-(4-{[3-(3-methoxy-1-methyl-1H-pyrazol-4-yl)morpholin-4-yl]methyl} phenoxy)benzamide, ENT-1;
4-(4-{[2-(3-methoxy-1-methyl-1H-pyrazol-4-yl)piperidin-1-yl]methyl}phenoxy) benzamide, ENT-1;
4-(2-fluoro-4-{[3-(3-methoxy-1-methyl-1H-pyrazol-4-yl)morpholin-4-yl]methyl} phenoxy)benzamide, ENT-1;
4-(4-{[3-(3-methoxy-1-methyl-1H-pyrazol-4-yl)morpholin-4-yl]methyl}phenoxy) benzamide, ENT-1;
4-(4-{[4-fluoro-2-(3-methoxy-1-methyl-1H-pyrazol-4-yl)pyrrolidin-1-yl]methyl} phenoxy)benzamide, Isomer 2, assumed racemic, either cis or trans;
4-(4-{[2-(1,3-dimethyl-1H-pyrazol-4-yl)-4-fluoropyrrolidin-1-yl]methyl}phenoxy) benzamide, Isomer 1;
4-(4-{[2-(1,3-dimethyl-1H-pyrazol-4-yl)-4-fluoropyrrolidin-1-yl]methyl}phenoxy) benzamide, Isomer 2;
4-(4-{[(2S)-2-(1,3-dimethyl-1H-pyrazol-5-yl)pyrrolidin-1-yl]methyl}phenoxy)-2-hydroxybenzamide;
3-fluoro-4-(4-{[2-(3-methoxy-1-methyl-1H-pyrazol-4-yl)-4-methylpyrrolidin-1-yl] methyl}phenoxy)benzamide, Isomer 1;
3-fluoro-4-(4-{[2-(3-methoxy-1-methyl-1H-pyrazol-4-yl)-4-methylpyrrolidin-1-yl] methyl}phenoxy)benzamide, Isomer 2;
3-fluoro-4-(4-{[2-(3-methoxy-1-methyl-1H-pyrazol-4-yl)-4-methylpyrrolidin-1-yl] methyl}phenoxy)benzamide, Isomer 3;
3-fluoro-4-(4-{[2-(3-methoxy-1-methyl-1H-pyrazol-4-yl)-4-methylpyrrolidin-1-yl] methyl}phenoxy)benzamide, Isomer 4;
4-(2-fluoro-4-{[2-(3-methoxy-1-methyl-1H-pyrazol-4-yl)pyrrolidin-1-yl]methyl} phenoxy)benzamide, ENT-2;
2-hydroxy-4-(4-{[2-(3-methoxy-1-methyl-1H-pyrazol-4-yl)pyrrolidin-1-yl]methyl} phenoxy)benzamide, ENT-2;
2-hydroxy-4-(4-{[(2S)-2-(1-methyl-1H-pyrazol-3-yl)pyrrolidin-1-yl]methyl}phenoxy) benzamide;
4-(4-{[2-(2,5-dimethyl-2H-1,2,3-triazol-4-yl)pyrrolidin-1-yl]methyl}phenoxy) benzamide, ENT-2;
4-(4-{[2-(2,5-dimethyl-2H-1,2,3-triazol-4-yl)pyrrolidin-1-yl]methyl}-2-fluorophenoxy)benzamide, ENT-2;
4-(4-{[(2S)-2-(1,3-dimethyl-1H-pyrazol-5-yl)pyrrolidin-1-yl]methyl}phenoxy)-3-fluorobenzamide; and
a pharmaceutically acceptable salt thereof.

11. The compound 4-(4-{[2-(3-methoxy-1-methyl-1H-pyrazol-4-yl)pyrrolidin-1-yl]methyl}phenoxy)benzamide; or a pharmaceutically acceptable salt thereof.

12. The compound 4-(4-{[(2S)-2-(3-methoxy-1-methyl-1H-pyrazol-4-yl)pyrrolidin-1-yl]methyl}phenoxy)benzamide; or a pharmaceutically acceptable salt thereof.

13. A pharmaceutical composition comprising a therapeutically effective amount of a compound of claim 1, or a pharmaceutically acceptable salt thereof together with a pharmaceutically acceptable vehicle, diluent or carrier.

14. A crystalline form of 4-(4-{[(2S)-2-(3-methoxy-1-methyl-1H-pyrazol-4-yl)pyrrolidin-1-yl]methyl}phenoxy) benzamide (Form 2), wherein said crystalline form has an analytical parameter selected from the group consisting of:
a solid state NMR spectrum comprising 13C chemical shifts (ppm) at 124.2±0.2, 126.4±0.2, and 152.6±0.2;
a powder X-ray diffraction pattern comprising peaks at diffraction angles (2θ) of 17.8±0.2, 10.1±0.2, and 15.1±0.2; and
a Raman spectrum comprising Raman peak shifts (cm-1) at 1660±2, 1597±2, and 815±2.

15. The crystalline form of 4-(4-{[(2S)-2-(3-methoxy-1-methyl-1H-pyrazol-4-yl)pyrrolidin-1-yl]methyl}phenoxy) benzamide (Form 2) of claim 14, wherein said crystalline form has a solid state NMR spectrum further comprising a 13C chemical shift (ppm) at 37.9±0.2.

16. The crystalline form of 4-(4-{[(2S)-2-(3-methoxy-1-methyl-1H-pyrazol-4-yl)pyrrolidin-1-yl]methyl}phenoxy) benzamide (Form 2) of claim 14, wherein said crystalline form has a solid state NMR spectrum further comprising a 13C chemical shift (ppm) at 119.6±0.2.

17. The crystalline form of 4-(4-{[(2S)-2-(3-methoxy-1-methyl-1H-pyrazol-4-yl)pyrrolidin-1-yl]methyl}phenoxy) benzamide (Form 2) of claim 14, wherein said crystalline form has a powder X-ray diffraction pattern further comprising a peak at a diffraction angle (2θ) of 13.3±0.2.

18. The crystalline form of 4-(4-{[(2S)-2-(3-methoxy-1-methyl-1H-pyrazol-4-yl)pyrrolidin-1-yl]methyl}phenoxy) benzamide (Form 2) of claim 14, wherein said crystalline form has powder X-ray diffraction pattern further comprising a peak at a diffraction angle (2θ) of 24.7±0.2.

19. The crystalline form of 4-(4-{[(2S)-2-(3-methoxy-1-methyl-1H-pyrazol-4-yl)pyrrolidin-1-yl]methyl}phenoxy)

benzamide (Form 2) of claim 14, wherein said crystalline form has a Raman spectrum further comprising a Raman peak shift (cm-1) at 639±2.

20. The crystalline form of 4-(4-{[(2S)-2-(3-methoxy-1-methyl-1H-pyrazol-4-yl)pyrrolidin-1-yl]methyl}phenoxy) benzamide (Form 2) of claim 14, wherein said crystalline form has a Raman spectrum further comprising a Raman peak shift (cm-1) at 1174±2.

21. A pharmaceutical composition comprising the crystalline form of 4-(4-{[(2S)-2-(3-methoxy-1-methyl-1H-pyrazol-4-yl)pyrrolidin-1-yl] methyl}phenoxy)benzamide (Form 2) of claim 14 in a therapeutically effective amount in admixture with at least one pharmaceutically acceptable excipient.

22. A method of antagonizing kappa opioid receptors, the method comprising administering to a patient a therapeutically effective amount of the crystalline form of claim 14.

23. A method of treating a neurological disorder or a psychiatric disorder in which the kappa opioid receptor is involved in a patient having said disorder, the method comprising administering to the patient a therapeutically effective amount of the crystalline form of claim 14.

24. A crystalline form according to claim 14, or a pharmaceutically acceptable salt thereof for use in antagonizing kappa opioid receptors.

25. A crystalline form according to claim 14, or a pharmaceutically acceptable salt thereof for use in treatment of a neurological disorder or a psychiatric disorder in which the kappa opioid receptor is involved in a patient having said disorder.

* * * * *

UNITED STATES PATENT AND TRADEMARK OFFICE
CERTIFICATE OF CORRECTION

PATENT NO. : 10,316,021 B2
APPLICATION NO. : 15/820679
DATED : June 11, 2019
INVENTOR(S) : Kablaoui et al.

It is certified that error appears in the above-identified patent and that said Letters Patent is hereby corrected as shown below:

In the Claims

In Claim 1, Column 173, Line 29, replace "$C_r C_6 alkoxy$" with "$C_1-C_6 alkoxy$".

Signed and Sealed this
Third Day of September, 2019

Andrei Iancu
*Director of the United States Patent and Trademark Office*